US009913863B2

(12) United States Patent
Tedder et al.

(10) Patent No.: US 9,913,863 B2
(45) Date of Patent: Mar. 13, 2018

(54) REGULATORY B CELLS AND THEIR USES

(71) Applicant: DUKE UNIVERSITY, Durham, NC (US)

(72) Inventors: Thomas F. Tedder, Durham, NC (US); Koichi Yanaba, Tokyo (JP); Jean-David Bouaziz, Paris (FR)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/165,844

(22) Filed: May 26, 2016

(65) Prior Publication Data

US 2016/0375059 A1   Dec. 29, 2016

Related U.S. Application Data

(62) Division of application No. 12/989,468, filed as application No. PCT/US2009/002560 on Apr. 27, 2009.

(60) Provisional application No. 61/125,680, filed on Apr. 25, 2008.

(51) Int. Cl.

| A61K 38/00 | (2006.01) |
| C12N 5/00 | (2006.01) |
| C12N 5/02 | (2006.01) |
| A61K 35/17 | (2015.01) |
| C07K 16/28 | (2006.01) |
| C12N 5/0781 | (2010.01) |
| A61K 35/12 | (2015.01) |
| A61K 39/00 | (2006.01) |

(52) U.S. Cl.
CPC .......... *A61K 35/17* (2013.01); *C07K 16/2887* (2013.01); *C12N 5/0087* (2013.01); *C12N 5/0635* (2013.01); *A61K 2035/122* (2013.01); *A61K 2035/124* (2013.01); *A61K 2039/505* (2013.01); *C07K 2317/732* (2013.01); *C07K 2317/734* (2013.01); *C12N 2501/52* (2013.01)

(58) Field of Classification Search
None
See application file for complete search history.

(56) References Cited

U.S. PATENT DOCUMENTS

| 7,438,907 | B2 | 10/2008 | Schuurman | |
| 7,534,772 | B2 | 5/2009 | Weiner | |
| 7,695,716 | B2 | 4/2010 | Drachman | |
| 2004/0265315 | A1 | 12/2004 | Dingivan | |
| 2005/0234073 | A1* | 10/2005 | Blumberg | A61K 31/445 514/256 |
| 2009/0074711 | A1 | 3/2009 | Glennie | |
| 2009/0123467 | A1 | 5/2009 | Bedi et al. | |
| 2010/0266680 | A1 | 10/2010 | Andre et al. | |
| 2011/0135666 | A1 | 6/2011 | Tedder et al. | |
| 2012/0183535 | A1 | 7/2012 | Buggy | |
| 2013/0136754 | A1 | 5/2013 | Tedder et al. | |
| 2013/0309244 | A1 | 7/2013 | Tedder et al. | |
| 2014/0065118 | A1 | 3/2014 | Tedder et al. | |

FOREIGN PATENT DOCUMENTS

| WO | WO 2005000901 | 1/2005 |
| WO | WO 2006/121852 | 11/2006 |
| WO | WO 2008025848 | 3/2008 |
| WO | WO 2009047270 | 4/2009 |
| WO | WO 2010132659 | 11/2010 |

OTHER PUBLICATIONS

Morshed et al (Eur. J Immunol., 2002,v.32, p. 2551-2561.*
Zupo et al ( Eur. J of Immunol, 1994, v.24 pp. 1426-1433.*
Mishima et al ( Gastroenterology, 2007, v.132, No. 4, sup.2 p. A399.*
Philips et al ( Immunol. and cell Biol., 1998, v.76, pp. 332-342).*
Anolik, J. H. et al., "New treatments for SLE: Cell-depleting and anti-cytokine therapies," 2005 Best Practice & Research Clinical Rheumatology 19(5):859-878.
Asadullah, K. et al., "Interleukin-10 therapy—Review of a new approach," 2003 Pharmacol. Rev. 55:241-269.
Blair, P.A. et al., "CD19+CD24hiCD38h cells exhibit regulatory capacity in healthy individuals but are functionally impaired in systemic lupus erythematosus patients," 2010 Immunity 32:129-140.
Bouaziz et al. "Regulatory B cells as inhibitors of immune responses and inflammation," 2008 Immunol. Rev. 224:201-214.
Brummel, R. et al., "Activation of Marginal Zone B Cells from Lupus Mice with Type A(D) CpG-Oligodeoxynucleotides 1," 2005 J. Immunol. 174:2429-34.
Brutkiewicz, R.R. et al., "TAP-independent, β2-Microglobulin-dependent surface expression of functional mouse CD1.1," 1995 J. Exp. Med. 182:1913-1919.
Cang, S., et al., Novel CD20 monoclonal antibodies for lymphoma therapy, Journal of Hematology and Oncology, 2012, 5:64.
Colgan, S.P. et al., "Ligation of intestinal epithelial CD1d induces bioactive IL-10: Critical role of the cytoplasmic tail in autocrine signaling," 1999, PNAS, 96(24):13938-13943.
Colliou, N. et al., "Long-Term Remissions of Severe Pemphigus After Rituximab Therapy Are Associated with Prolonged Failure of Desmoglein B Cell Response," Science Translational Medicine 5, 175ra30 (2013).

(Continued)

*Primary Examiner* — Michail Belyavskyi
(74) *Attorney, Agent, or Firm* — Andrus Intellectual Property Law, LLP

(57) ABSTRACT

The present invention relates to a phenotypically distinct $CD1d^{high}CD5^+$ B cell subset that regulates T cell mediated inflammatory responses through the secretion of interleukin-10 (IL-10). The invention also relates to the use of these IL-10 producing regulatory B cells in the manipulation of immune and inflammatory responses, and in the treatment of disease. Therapeutic approaches involving adoptive transfer of these regulatory B cells, or expansion of their endogenous levels for controlling autoimmune or inflammatory diseases and conditions are described. Ablation of this subset of regulatory B cells, or inhibition of their IL-10 production can be used to upregulate immunodeficient conditions, and/or to treat tumors/cancer. Diagnostic applications also are encompassed.

20 Claims, 48 Drawing Sheets

(56) References Cited

OTHER PUBLICATIONS

Figures 1A, 1B, 1C, 1D:
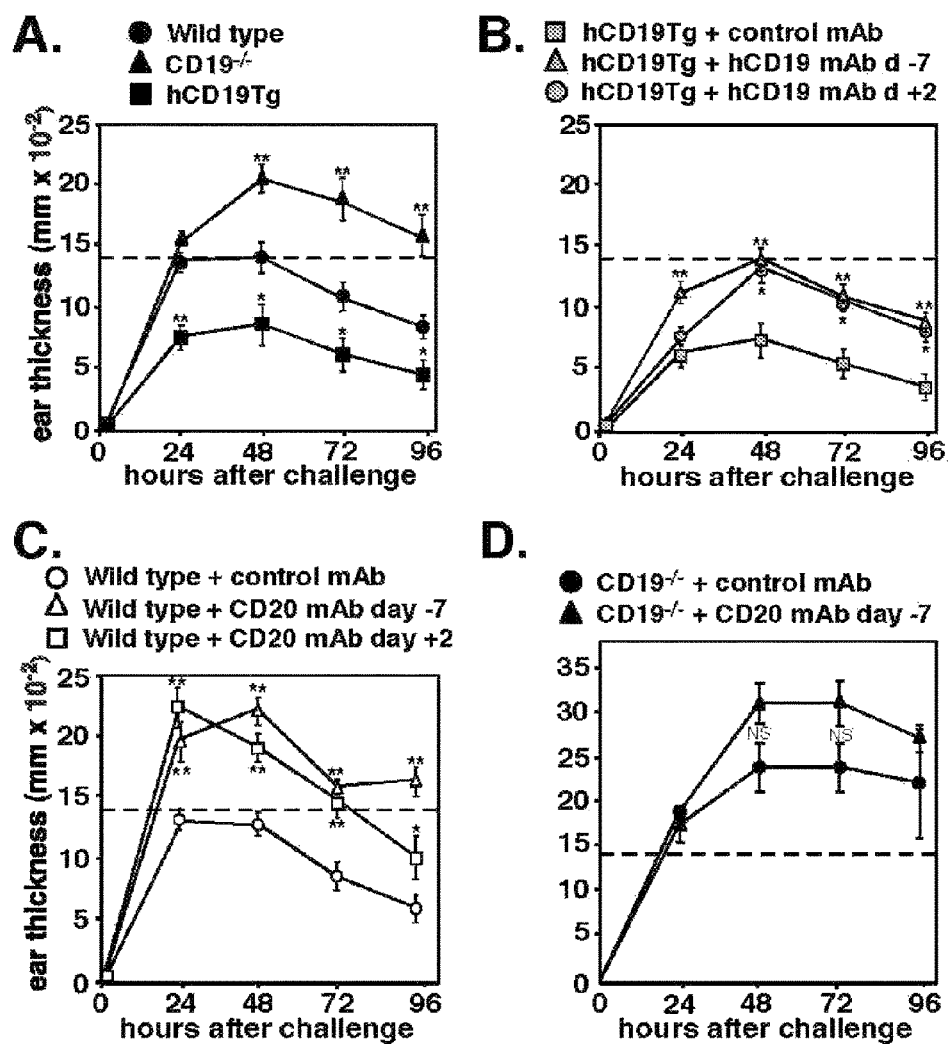

Cuss, A.K. et al., "Expansion of functionally immature transitional B cells is associated with human-immunodeficient states characterized by impaired humoral immunity," 2006 J. Immunol. 176:1506-1516).
Dalwadi, H. et al., "B cell developmental requirement for the Gαi2 Gene1," 2003 J. Immunol. 170:1707-1715.
DiLillo, D. J. et al., "B10 cells and regulatory B cells balance immune responses during inflammation, autoimmunity, and cancer," Ann. N. Y. Acad. Sci. 1183, 38-57 (2010).
Duan, B. et al., "Lupus resistance is associated with marginal zone abnormalities in an NZM murine model,"2007, Lab. Invest. 87:14-28.
El Zouhairi, M., et al., Molecularly targeted therapy for metastatic colon cancer: proven treatments and promising new agents, Gastrointest Cancer Res., 2011, 15-21, 4:1.
Evans, J.G. et al., "Novel suppressive function of transitional 2 B Cells in experimental arthritis," 2007 J. Immunol. 178:7868-78.
Federico, et al., Chronic inflammation and oxidative stress in human carcinogenesis, International Journal of Cancer, 2007; pp. 2381-2386, vol. 121.
Ferguson, T.A. et al., "Regulation of contact hypersensitivity by interleukin 10," (1994) J. Exp. Med. 179:1597-1604.
Fillatreau, S. et al., "B cells regulate autoimmunity by provision of IL-10," Nat. Immunol. 3, 944-950 (2002).
Fillatreau, S., "Novel regulatory functions for Toll-like receptor-activated B cells during intracellular bacterial infection," Immunol. Rev. 240, 52-71 (2011).
Goodnow, C.C. et al., Altered immunoglobulin expression and functional silencing of self-reactive B lymphocytes in transgenic mice, Nature, 1988, pp. 676-682, vol. 334.
Gray, M. et al., "Apoptotic cells protect mice from autoimmune inflammation by the induction of regulatory B cells," 2007, Proc. Natl. Acad. Sci. USA 104:14080-5.
Haas, K. M. et al., "B-1a and B-1b cells exhibit distinct developmental requirements and have unique functional roles in innate and adaptive immunity to S. pneumoniae," 2005, Immunity 23:7-18.
Haas, K. M. et al., "Protective and pathogenic roles for B cells during systemic autoimmunity in NZB/W F1 mice," J. Immunol. 184, 4789-4800 (2010).
Hasegawa, M. et al., "B-lymphocyte depletion reduces skin fibrosis and autoimmunity in the tight-skin mouse model for systemic sclerosis," 2006, Am. J. Pathol. 169:954-66.
Harris, D.P. et al., "Reciprocal regulation of polarized cytokine production by effector B and T cells," 2000, Nat. Immunol. 1:475-82.
Hayakawa, I. et al., "B-lymphocyte depletion ameliorates Sjogren's syndrome in Id3 knockout mice," 2007, Immunology 122:73-9.
Hernandez, H.J. et al., "In infection with Schistosoma mansoni, B cells are required for T helper type 2 cell responses but not for granuloma formation," 1997 J. Immunology 158:4832-4837.
Horikawa, M. et al., "Regulatory B cell production of IL-10 inhibits lymphoma depletion during CD20 immunotherapy in mice," J. Clin. Invest. 121, 4268-4280 (2011).
Huggins, J. et al., "CpG DNA activation and plasma-cell differentiation of CD27_naïve human B cells," Blood 109(4):1611-1619 (2007).
Inoue, S. et al., "Inhibitory effects of B cells on antitumor immunity," 2006 Cancer Res. 66:7741-7747.
Iwata, Y. et al., "Characterization of a rare IL-10-competent B cell subset in humans that parallels mouse regulatory B10 cells," Blood 117, 530-541 (2011).
Jiang, S. et al., "Regulatory T cells and transplantation tolerance," 2006 Human Immunol. 67:765-776.
Kansas, G.S. et al., Transmembrane signals generated through MHC class II, CD19, CD20, CD39 and CD40 antigens induce LFA-1-dependent and -independent adhesion in human B cells through a tyrosine kinase-dependent pathway. J Immunol. 1991; 147: 4094-4102.

Klein, U. et al., "Human immunoglobulin (Ig)M+IgD+ peripheral blood B cells expressing the CD27 cell surface antigen carry somatically mutated variable region genes: CD27 as a general marker for somatically mutated (Memory) B Cells," 1998 J. Exp. Med. 188:1679-1689.
van Krieken, J.H.J.M. et al., "Splenic marginal zone lymphocytes and related cells in the lymph node: A morphologic and immunohistochemical study," 1989 Hum. Pathol. 20:320-325.
Kurosaki, T., "Paradox of B cell-targeted therapies," 2008 J. Clin. Inv. 118(10):3260-3263.
Lampropoulou, V. et al., "TLR-activated B cells suppress T cell-mediated autoimmunity," 2008 J. Immunol. 180:4763-4773.
Lebien, T. W., and Tedder, T. F., B-lymphocytes: How they develop and function. Blood, 2008, pp. 1570-1579, vol. 112.
Levesque, M.C. et al., "B cell-directed therapies for autoimmune disease and correlates of disease response and relapse," 2008 J. Allergy Clin. Immunol. 121:13-21.
Lund, et al., "Cytokine-producing B lymphocytes—key regulators of immunity," 2008 Curr. Op. Immunol. 20(3):332-338.
Lyons, J.-A. et al., "B cells are critical to induction of experimental allergic encephalomyelitis by protein but not by a short encephalitogenic peptide," 1999 Eur. J. Immunol. 29:3432-3439.
Maini, R.N., et. al., How does infliximab work in rheumatoid arthritis, Arthritis Res., 2002, 4 Supp 2:S22-8.
Makowska, A. et al., "CD1high B cells: A population of mixed origin," 1999 Eur. J. Immunol. 29:3285-3294.
Mann, M. et al., "B cell regulation of CD4+CD25+ T regulatory cells and IL-10 via B7 is essential for recovery from experimental autoimmune encephalomyelitis 1," 2007 J. Immunol. 178:3447-3456.
Martin, F. et al., Marginal zone and B1 B cells unite in the early response against T-independent blood-borne particulate antigens, Immunity, 2001, pp. 617-629, vol. 14.
Maseda, D. et al., "Regulatory B10 cells differentiate into antibody-secreting cells after transient IL-10 production in vivo," J. Immunol. 188, 1036-1048 (2012).
Matsushita, et al., "Inhibitory role of CD19 in the progrssion of experimental autoimmune encephalomyelitis by regulating cytokine response," 2006 Am. J. Path., 168(3):812-821.
Matsushita, T. et al., "Regulatory B cells inhibit EAE initiation in mice while other B cells promote disease progression,". J. Clin. Invest. 118, 3420-3430 (2008).
Office Action for U.S. Appl. No. 12/989,468 dated Mar. 31, 2015 (9 pages).
Office Action for U.S. Appl. No. 12/989,468 dated Feb. 26, 2016 (10 pages).
Matsushita, et al., "B-lymphocyte depletion for the treatment of multiple sclerosis: Now things really get interesting," 2009 Expert Rev. Neurotherapeutics 9(3):309-312.
Matsushita, T. et al., "Regulatory B cells (B10 cells) and regulatory T cells have independent roles in controlling EAE initiation and late-phase immunopathogenesis," J. Immunol. 185, 2240-2252 (2010).
Matsushita, T. et al., "Identifying regulatory B cells (B10 cells) that produce IL-10," Methods Mol. Biol. 677, 99-111 (2011).
Mauri, C. et al., Therapeutic activity of agonsitic monoclonal antibodies against CD40 in a chronic autoimmune inflammatory process, Nat Med, 2000, pp. 673-679, vol. 6.
Mauri et al., "Prevention of arthritis by interleukin-10-producing B cells," 2003, J. Exp. Med. 197:489-501.
Mauri, C. et al., "The 'short' history of regulatory B cells," 2008, TRENDS in Immunol. 29: 34-40.
Mauri C., "Regulation of immunity and autoimmunity by B cells," Curr. Opin. Immunol. 22, 761-7657 (2010).
Minard-Colin, V. et al., "Lymphoma depletion during CD20 immunotherapy in mice is mediated by macrophage FcγRI, FcγRIII, and FcγRIV," 2008 Blood 112:1205-1213.
Mizoguchi, A. et al., "Chronic intestinal inflammatory condition generates IL-10-producing regulatory B cell subset characterized by CD1d upregulation," 2002 Immunity 16:219-30.
Mizoguchi, A. et al., "A case for regulatory B cells," 2006, J. Immunol. 176:705-710.

(56) References Cited

OTHER PUBLICATIONS

O'Garra, A. et al., "Lyl B (B-1) cells are the main source of B cell-derived interleukin 10," 1992 Eur. J. Immunol. 22:711-717.
Paciorkowski, N. et al., "Primed Peritoneal B lymphocytes are sufficient to transfer protection against Brugia pahangi infection in mice," 2003 Infection and Immunity 71(3):1370-1378.
Pallier, A. et al., Patients with drug-free long-term graft function display increased numbers of peripheral B cells with a memory and inhibitory phenotype, Kidney International 78:503-513 (2010).
Parsonnet, J., Bacterial infection as cause of cancer, Environ Health Perspectives, 1995, pp. 263-268, Supp. 8.
Poe, et al., CD22 regulates B lymphocyte function in vivo through both ligand-dependent and ligand-independent mecahnaisms, Nat Immunol, 2004, pp. 1078-1087, vol. 5.
Poe, J. C. et al., "Amplified B lymphocyte CD40 signaling drives regulatory B10 cell expansion in mice," PLoS ONE 6, e22464 (2011).
Roncarolo, M.G. et al., "Regulatory T-cell immunotherapy for tolerance to self antigens and alloangens in humans," 2007 Nature Reviews Immunol. 7:585-598.
Sanz, I. et al., "Phenotypic and functional heterogeneity of human memory B cells," 2008 Sem. Immunol. 20:67-82.
Sato, S. et al., "CD19 regulates B lymphocyte signaling thresholds critical for the development of B-1 lineage cells and autoimmunity," J. Immunol. 157, 4371-4378 (1996).
Schwarz, A. et al., "In vivo effects of interleukin-10 on contact hypersensitivity and delayed-type hypersensitivity reactions," 1994, J. Invest. Dermatol. 103:211-16.
Sims, G.P. et al., "Identification and characterization of circulating human transitional B cells," 2005 Blood 105:4390-4398.
Spencer, N.F. et al., "IL-12 directly stimulates expression of IL-10 by CD5+ B cells and IL-6 by both CD5+ and CD5− B cells: Possible involvement in age-associated cytokine dysregulation," 1997, Int. Immunol. 9:745-54.
Sonoda, K.-H. et al., "CD1d on antigen-transporting APC and splenic marginal zone B cells promotes NKT cell-dependent tolerance," 2002 Eur. J. Immunol. 32:848-857.
Tangye, S.G. et al., "Identification of functional human splenic memory B cells by expression of CD148 and CD27," 1988 J. Exp. Med. 188:1691-1703.
Tian, J. et al. Lipopolysaccharide-activated B cells down-regulate Th1 immunity and prevent autoimmune diabetes in nonobese diabetic mice, 2001 J. Immunol. 167:1081-1089.
Uchida, J. et al, "The innate mononuclear phagocyte network depletes B lymphocytes through Fc receptor-dependent mechanisms during anti-CD20 antibody immunotherapy," 2004 J. Exp. Med. 199:1659-1669.
Velupillai, P. et al., "B-1 cell (CD5+B220+) outgrowth in murine schistosomiasis is genetically restricted and is largely due to activation by polylactosamine sugars," 1997 J. of Immunology 158:338-344.
Watanabe, R. et al., "CD19 expression in B cells is important for suppression of contact hypersensitivity," 2007 American J. of Pathol. 171(2):560-570.
Wehr, C., et al., A new CD21low B cell population in the peripheral blood of patients with SLE, Clin. Immunol., 2004, pp. 161-171, vol. 113.2.
Wei, B. et al., "Mesenteric B cells centrally inhibit CD4+ T cell colitis through interaction with regulatory T cell subsets," 2005 PNAS 102(6):2010-2015.
Weitzman, S.A. and Gordon, L.I, et al., Inflammation and cancer: role of phagocyte-generated oxidants in carcinogenesis, Blood, 1990, pp. 655-663, vol. 76.
Wolf, S.D. et al., "Experimental autoimmune encephalomyelitis induction in genetically B cell-deficient mice," 1996 J. Exp. Med. 184:2271-2278.
Xiu, Y. et al., "B lymphocyte depletion by CD20 monoclonal antibody prevents diabetes in nonobese diabetic mice despite isotype-specific differences in Fc$\gamma$R effector funcitons," 2008, J. Immunol. 180:2863-75.
Yanaba, K. et al., "B cell depletion delays collagen-induced arthritis in mice: Arthritis induction requires synergy between humoral and cell-mediated immunity," 2007, J. Immunol. 179:1369-80.
Yanaba, K. et al., "A regulatory B cell subset with a unique CD1dhiCD5+ phenotype controls T cell-dependent inflammatory responses," Immunity 28, 639-650 (2008).
Yanaba, K. et al., "The development and function of regulatory B cells expressing IL-10 (B10 cells) requires antigen receptor diversity and TLR signals," J. Immunol. 182, 7459-7472 (2009).
Yanaba, K. et al., "Regulatory B cells," 2009 Jap. Soc. Clin. Immunol. 32(3):135-141 (Abstract).
Yokoyama, S. et al., "Expression of the Blast-1 activation/adhesion molecule and its identification as CD48," 1991 J. Immunol. 146:2192-2200.
Zhang, X. et al., "Type I interferons protect neonates from acute inflammation through interleukin 10-producing B cells," 2007 J. of Experimental Medicine 204(5): 1107-1118.
International Search Report and Written Opinion in International Patent Application No. PCT/US2009/002560 dated Jul. 20, 2010 (10 pages).
International Search Report and Written Opinion in International Patent Application No. PCT/US2011/046643 dated Mar. 14, 2012 (11 pages).
Office Action for U.S. Appl. No. 12/989,468 dated Apr. 12, 2012 (7 pages).
Office Action for U.S. Appl. No. 12/989,468 dated Aug. 20, 2012 (9 pages).
Written Opinion for Singapore Patent Application No. 201007776-6 dated Apr. 4, 2013 (9 pages).
Office Action for U.S. Appl. No. 12/989,468 dated Sep. 26, 2013 (9 pages).
International Search Report and Written Opinion in International Patent Application No. PCT/US2013/058484 dated Jan. 10, 2014 (10 pages).
International Preliminary Report on Patentability in International Patent Application No. PCT/US2013/058484 dated Mar. 19, 2015 (8 pages).
Office Action for U.S. Appl. No. 12/989,468 dated Aug. 29, 2014 (8 pages).

\* cited by examiner

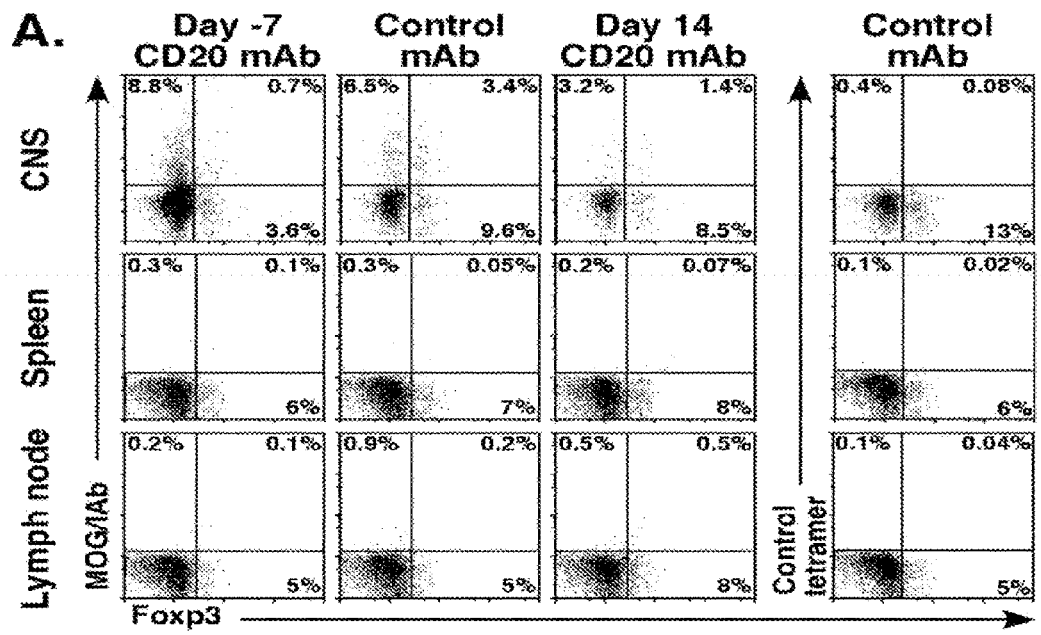
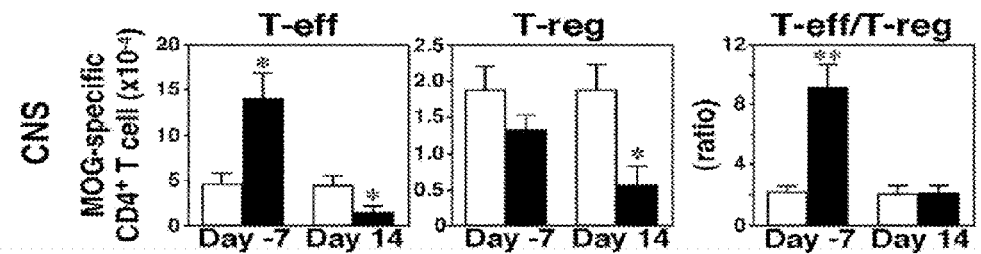
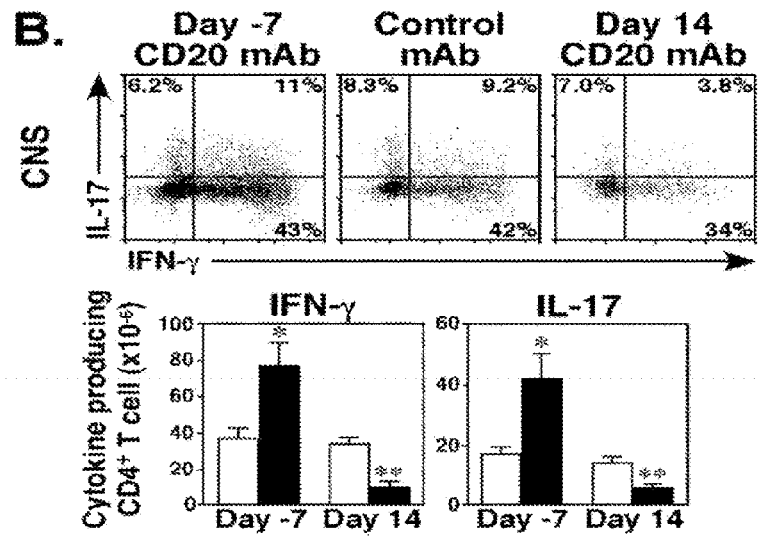
Fig. 11A – 11B

Fig. 31A – 31B
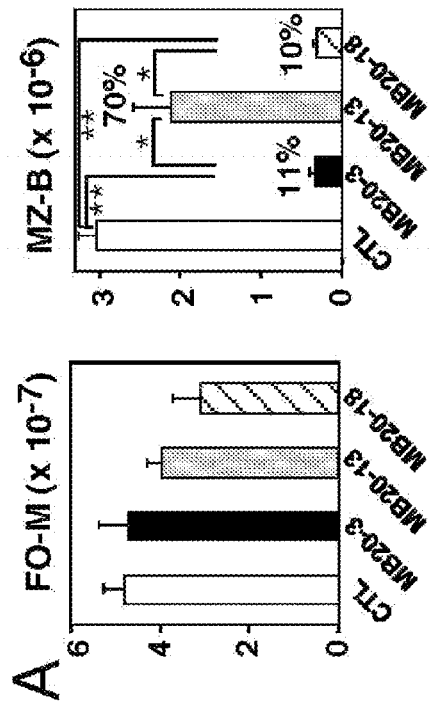
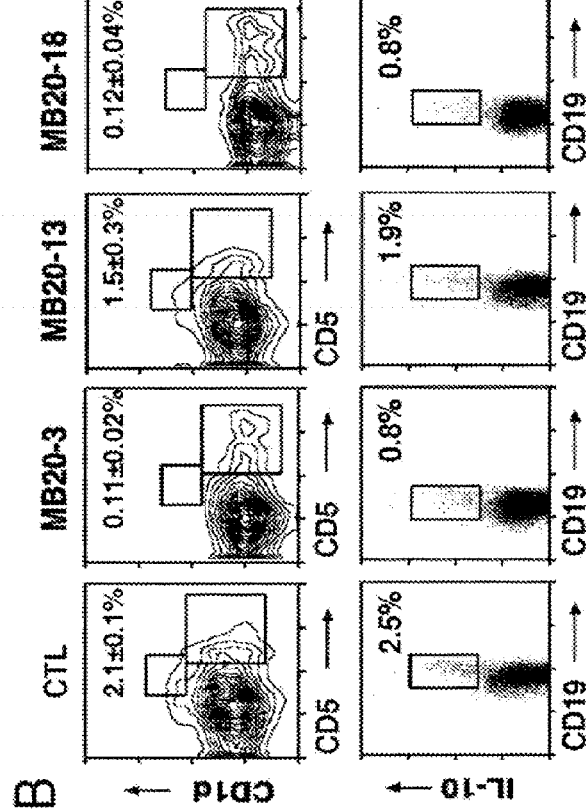
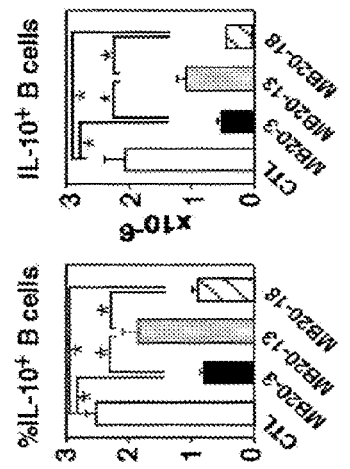
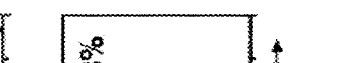

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic: Sense IL-10 primer

<400> SEQUENCE: 1
ggttgccaag ccttatcgga                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic: Antisense IL-10 primer

<400> SEQUENCE: 2
acctgctcca ctgccttgct                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic:  sense GAPDH primer

<400> SEQUENCE: 3
ttcaccacca tggagaaggc                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic: antisense GAPDH primer

<400> SEQUENCE: 4
ggcatggact gtggtcatga                                          20

<210> SEQ ID NO 5
<211> LENGTH: 21
<212> TYPE: PRT
<213> ORGANISM: Artificial Sequence
<220> FEATURE:
<223> OTHER INFORMATION: Synthetic: MOG35-55 peptide

<400> SEQUENCE: 5

Met Glu Val Gly Trp Tyr Arg Ser Pro Phe Ser Arg Val Val His Leu
1               5                   10                  15

Tyr Arg Asn Gly Lys
            20
```

REGULATORY B CELLS AND THEIR USES

This application is a divisional of U.S. application Ser. No. 12/989,468, filed Oct. 25, 2010 and now issued as U.S. Pat. No. 9,669,057, which is a national stage filing under 35 U.S.C. § 371 if International Application No. PCT/US2009/002560, filed Apr. 27, 2009, which claims and is entitled to priority of U.S. Provisional Patent Application No. 61/125,680, filed on Apr. 25, 2008, each of which is incorporated by reference herein in its entirety. This application includes an electronically submitted Sequence Listing in .txt format. The .txt file contains a sequence listing entitled "2016-09-01 5667-00215_ST25.txt" created on Sep. 1, 2016 and is 1,548 bytes in size. The Sequence Listing contained in this .txt file is part of the specification and is hereby incorporated by reference herein in its entirety.

1. INTRODUCTION

The present invention relates to a phenotypically distinct $CD1d^{high}CD5^+$ B cell subset that regulates T cell mediated inflammatory responses through the secretion of interleukin-10 (IL-10). The invention also relates to the use of these IL-10 producing regulatory B cells in the manipulation of immune and inflammatory responses, and in the treatment of disease. Therapeutic approaches involving adoptive transfer of these regulatory B cells, or expansion of their endogenous levels for controlling autoimmune or inflammatory diseases and conditions are described. Ablation of this subset of regulatory B cells, or inhibition of their IL-10 production can be used to upregulate immunodeficient conditions, and/or to treat tumors/cancer. Diagnostic applications are also encompassed.

2. BACKGROUND

The immune response can loosely be divided into two components: the humoral immune response which involves antibody formation, and the cell-mediated immune response which involves the activation of macrophages, natural killer (NK) cells, antigen-specific cytotoxic T-lymphocytes, and the release of various cytokines in response to antigen. Typically, B lymphocytes (B cells) are characterized by their role in antibody production; whereas T lymphocytes (T cells) are characterized by their role in cell-mediated immunity. However, B cells possess additional immune functions, including the production of cytokines, and the ability to function as antigen presenting cells (APCs).

Once generated, immune responses need to be regulated to prevent the responding effector cells from causing harmful effects. Immunoregulation has traditionally been thought of as a function of T cells. Functionally distinct regulatory T cell subsets have been identified and clearly defined. For example, helper T cells that up-regulate the immune response include T helper type 1 (Th1) cells that regulate cell-mediated immune responses, and T helper type 2 (Th2) cells that regulate the humoral immune response. Suppressor T cells crucial for the maintenance of immunological tolerance, currently referred to as T regulatory cells, include IL-10-producing T regulatory 1 (Tr1) cells, and TGF-β1-producing T helper type 3 (Th3) cells. Recent studies of autoimmune conditions gave rise to the notion that B cells may also participate in immunoregulation. However, regulatory B cell subsets have not been clearly defined.

Multiple roles for B cells have been implicated in autoimmune diseases. B cells, a major immune cell population, can play a pathogenic role in acquired immune responses by producing autoantibodies that drive the development of autoimmune diseases. Certain therapies developed for treating autoimmunity are aimed at depleting pathogenic B cells. However, the tools currently available are not specific for the pathogenic B cells and deplete most B cells. For example, B cell depletion in humans using CD20 monoclonal antibody (mAb) can be effective in treating patients with various autoimmune disorders, such as rheumatoid arthritis and lupus (Edwards et al., 2001, Rheumatol. 40:205-11; Edwards et al., 2005, Rheumatol. 44:151-56; El Tal et al., 2006, J. Am. Acad. Dermatol. 55:449-59; Anolik et al., 2004, Arth. Rheum. 50:3580-90; Stasi et al., 2007, Blood 110:2924-30). CD20 is a B cell-specific marker that is first expressed on the cell surface during the pre-B to immature B cell transition, but is lost upon plasma cell differentiation (Tedder & Engel, 1994, Immunol. Today 15:450-54; Uchida et al., 2004, Int. Immunol. 16:119-29). A recent phase II trial using anti-CD20 antibodies indicates clinical efficacy in multiple sclerosis (MS) patients (Hauser et al., 2008, N. Engl. J. Med. 358:676-88). However, the mechanisms underlying the effect of B cell depletion on disease activity remains unknown. On the flip side, B cell depletion may exacerbate disease. Indeed, B cell depletion was recently found to exacerbate ulcerative colitis in human clinical trials (Goetz et al., 2007, Inflamm Bowel Dis. 13:1365-8) and may contribute to the development of psoriasis (Dass et al., 2007, Arthritis Rheum. 56:2715-8).

Over a decade ago, Janeway and colleagues (Wolf et al., 1996, J. Exp. Med. 184: 2271-2278) described studies designed to assess the role of B cells in the course of autoimmune disease by inducing acute experimental autoimmune encephalomyelitis (EAE) in B cell-deficient mice. EAE is an autoimmune disease of the central nervous system (CNS) that models human multiple sclerosis. Results showed that elimination of B cells did not prevent induction of autoimmunity. Instead, the lack of B cells seemed to exacerbate disease outcome, in that the B cell deficient mice did not fully recover as compared to wild-type mice. Thus, while B cells supply the autoantibodies thought to be responsible for disease, these investigators concluded that B cells are not required for activation of disease, and instead, that their presence is required to enhance recovery. More recently, it was reported that B cell IL-10 production correlated with recovery from EAE, a Th1-mediated autoimmune disease (Fillatreau et al., 2002, Nature Immunol. 3: 944-950). IL-10 is an immunoregulatory cytokine produced by many cell populations. IL-10 has been shown to suppress cell-mediated immune and inflammatory responses.

Other recent studies in mouse models indicate that B cells and IL-10 play a protective role in T cell-mediated inflammation, e.g., in Th2-mediated inflammatory bowel disease (Mizoguchi et al., 2002, Immunity 16:216-219), and in contact hypersensitivity (CHS) responses—a cutaneous inflammatory immune reaction that is mediated by T cells in sensitized individuals following subsequent contact with the sensitizing antigen (Enk, 1997, Mol. Med. Today 3:423-8). In particular, mice with B cells deficient for CD19 expression ($CD19^{-/-}$) have augmented CHS responses (Watanabe et al., 2007, Am. J. Pathol. 171:560-70). IL-10 must be involved in protection since neutralizing IL-10 through mAb treatment enhances CHS responses, while systemic IL-10 administration reduces CHS responses (Ferguson et al., 1994, J. Exp. Med. 179:1597-1604; Schwarz et al., 1994, J. Invest. Dermatol. 103:211-16).

On the basis of these and other studies, it has been proposed that, like their T cell counterparts, B cells can be divided into functionally distinct regulatory subsets capable of inhibiting inflammatory responses and inducing immune tolerance by mechanisms that include IL-10 and TGF-β production, secondary antigen presentation, and interactions with other immune cells either directly or through secreted antibodies. (For reviews on the subject, see Mauri & Ehrenstein, 2007, TRENDS in Immunol. 29: 34-40; and Mizoguchi & Bhan, 2006, J. Immunol. 176:705-710).

However, it remains unclear whether regulatory B cells represent a unique regulatory lineage tasked with maintaining self-tolerance the way that naturally occurring regulatory T cells are. The generation of regulatory B cells has been reported in multiple mouse models of chronic inflammation, although their existence in normal mice remains unknown (Mizoguchi & Bhan, 2006, J. Immunol. 176:705-10). Despite the identification of a regulatory B cell subset generated in these mouse models, no definitive murine phenotype has been established and, in fact, only a general list of cell-surface markers envisioned to potentially associate with regulatory B cells exists (Mauri & Ehrenstein, 2007, Trends Immun 29:34-40). Furthermore, the existence of regulatory B cells in humans remains a matter of speculation, and the potential phenotypic markers for human regulatory B cells are unknown (Mauri & Ehrenstein, 2007, Trends Immun 29:34-40). A role for CD40 in the generation of regulatory B cells and the induction of IL-10 production by these cells has been postulated (Inoue et al., 2006 Cancer Res. 66:7741-7747). Nonetheless, it has yet to be proven whether CD40 can be directly targeted, i.e., with anti-CD40 antibodies, as a means to generate regulatory B cells in vivo (Mauri & Ehrenstein, 2007, Trends Immun 29:34-40).

Further complicating these issues, during immune responses, IL-10 is also secreted by multiple cell types, including T cells, monocytes, macrophages, mast cells, eosinophils, and keratinocytes, and can suppress both Th1 and Th2 polarization and inhibit antigen presentation and proinflammatory cytokine production by monocytes and macrophages (Asadullah et al., 2003, Pharmacol. Rev. 55:241-69). Clearly, it is unknown whether multiple B cell populations or a novel B cell subset regulates inflammatory responses, whether regulatory B cells produce IL-10 or other cytokines directly, whether regulatory B cells have potent activities in vivo, whether humans possess regulatory B cells, how regulatory B cells can be activated and/or expanded, and the role of regulatory B cells in disease. To advance therapeutic application, subsets of immunoregulatory B cells need to be better defined and their phenotype will need to be more closely correlated with their function in vivo.

3. SUMMARY

The present invention relates to a phenotypically distinct $CD1d^{high}CD5^+$ B cell subset that regulates T cell mediated inflammatory and immune responses through secretion of IL-10. The invention also relates to harnessing this regulatory B cell subset for the manipulation of immune and inflammatory responses in humans and other mammals. Treatments for diseases associated with diminished IL-10 levels, such as inflammatory and autoimmune diseases are described, as well as treatments for diseases associated with elevated IL-10 levels, such as immunosuppression and cancer.

Cellular compositions enriched for the $CD1d^{high}CD5^+$ B cell subset, and methods for their preparation are described. The invention relates, in part, to the discovery that a cellular composition that has been enriched by selection using both $CD1d^{high}$ and CD5 as cellular markers will contain a higher percentage of IL-10 producing B cells than a population enriched using only one of these markers. These cellular compositions can be expanded and used to treat inflammatory and/or autoimmune conditions or diseases by adoptive transfer. In an alternative approach, therapeutic regimens designed to expand the endogenous population of the $CD1d^{high}CD5^+$ B cell subset in subjects in need of such treatment can be used to treat inflammatory and/or autoimmune conditions or diseases. In this approach, antibodies that activate and/or stimulate expansion of the regulatory B cell subset, or increase their production of IL-10 can be used.

In an alternative embodiment, methods are described for treating diseases and/or conditions involving immunosuppression or cancer by depleting or ablating the $CD1d^{high}CD5^+$ regulatory B cell subset in subjects in need thereof. In this approach, antibodies that kill the regulatory B cell subset, or inhibit their proliferation or their production of IL-10 can be used.

In yet another embodiment, methods for identifying the regulatory B cell subset in patients and/or patient samples are described for diagnosing the immune status of affected individuals.

The invention is based, in part, on the identification of a rare regulatory B cell subset that controls T cell-mediated immune and inflammatory responses in vivo. The principles of the invention are illustrated in animal models in the studies described in the examples, infra, and resolve previously unexplained contradictions reported in the literature for the role of B cells in disease models such as EAE, arthritis, and inflammatory bowel disease. The examples described infra demonstrate:

- a phenotypically unique B cell subset with potent regulatory activities in vivo;
- a reliable method of intracellular cytokine staining that clearly identifies $CD1d^{high}CD5^+$ regulatory B cells as the IL-10-producing B cell subset;
- adoptive transfer of this $CD1d^{high}CD5^+$ cell subset has potent IL-10-dependent regulatory functions during inflammation in vivo, which can apply to other T cell-mediated inflammatory or autoimmune diseases;
- expansion of the unique regulatory B cell subset in human CD19 transgenic mice results in a decreased inflammatory response;
- the absence of this unique B cell subset in CD19-deficient mice results in augmented T cell-mediated inflammation; and
- the presence of this unique IL-10-producing B cell subset in healthy wild type mice (1-2% of spleen B cells) and expansion of the population during contact hypersensitivity responses.

The phenotypic markers described herein were identified in murine models; a cognate human regulatory B cell subset that produces IL-10 is encompassed by the invention. This regulatory B cell subset will be phenotypically distinct from other B cell populations, and may be identified by transcription factors responsible for displaying the same cell surface markers; i.e., $CD1d^{high}CD5^+$.

4. DESCRIPTION OF THE FIGURES

FIG. 1A-FIG. 1D: B cell regulation of T cell-mediated inflammatory responses. CHS responses in (FIG. 1A) wild type, hCD19Tg, and CD19$^{-/-}$ mice, (FIG. 1B) hCD19Tg mice treated with hCD19 or isotype control mAb 7 days before or 2 days after initial oxazolone sensitization, and (FIG. 1C) wild type or (FIG. 1D) CD19$^{-/-}$ mice treated with CD20 or isotype control mAb 7 days before or 2 days after first sensitization with oxazolone. The increase in ear thickness was measured at various time points after oxazolone challenge. Values represent means (±SEM) from ≥4 mice of each group. Horizontal dashed lines representing the average increase in ear thickness at 48 hours after oxazolone challenge in wild type mice is shown for comparison. Significant differences between sample means are indicated; *p<0.05; **p<0.01, NS, differences between means were not significant. Similar results were obtained in at least two independent experiments.

Figures 2A, 2B, 2C, 2D:
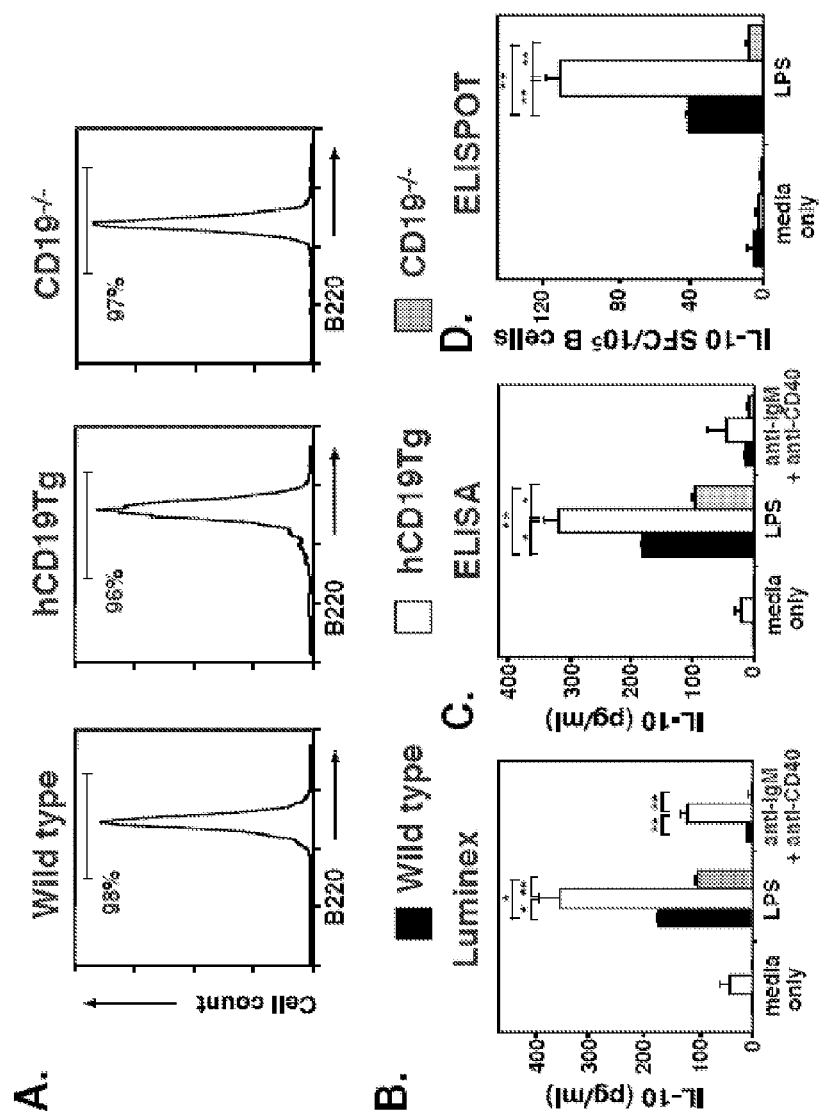

FIG. 2A-FIG. 2D: IL-10 production by spleen B cells from wild type, hCD19Tg, and CD19$^{-/-}$ mice. (FIG. 2A) Representative flow cytometry histograms showing B cell purities after B220-mAb coated microbead isolation. (FIG. 2B) Luminex and (FIG. 2C) ELISA determinations of secreted IL-10 protein levels by purified B220$^+$ cells cultured in media alone or containing LPS, or anti-CD40 mAb plus anti-IgM antibody. Values are means (±SEM) from ≥3 mice of each group. (FIG. 2D) Frequency of IL-10-secreting B cells determined by ELISPOT assay. Purified B220$^+$ cells were incubated in the absence or presence of LPS for 24 h. Values represent mean numbers (±SEM) of spot-forming colonies per 10$^5$ B220$^+$ cells from ≥3 mice of each group. FIG. 2B-2D). Significant differences between sample means are indicated; *p<0.05, **p<0.01. Results represent one of two independent experiments producing similar results.

Figure 3A:
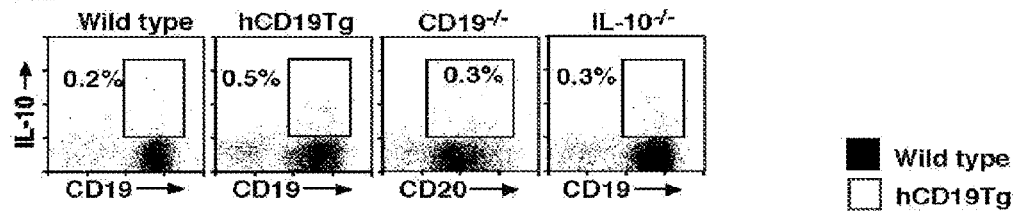
Figure 3B:
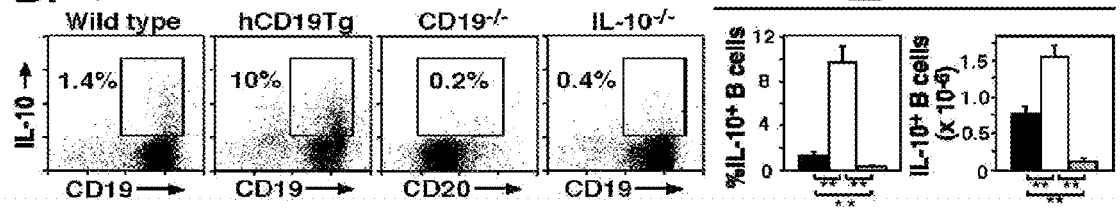
Figure 3C:
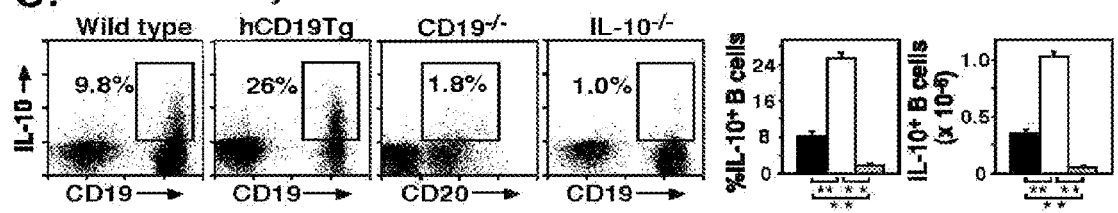
Figure 3D:
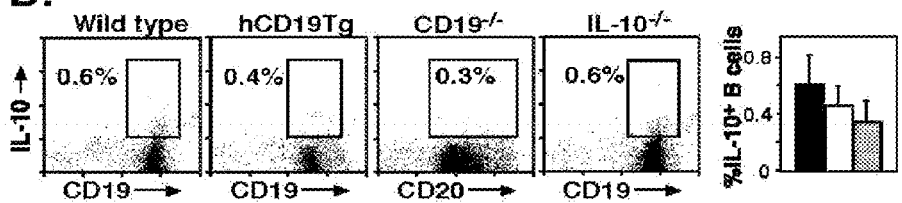
Figure 3E:
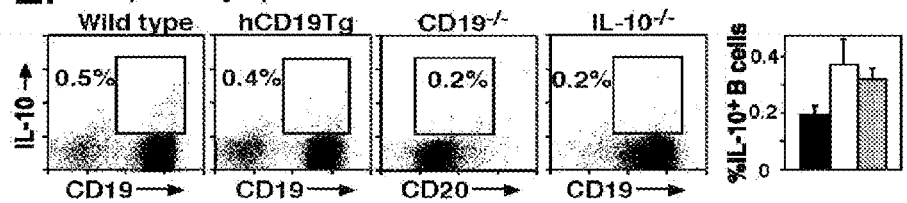
Figure 3F:
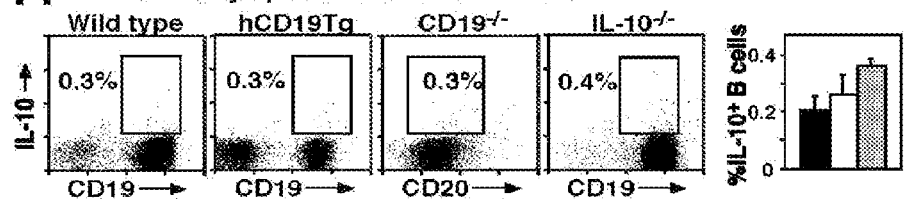
Figure 3G:
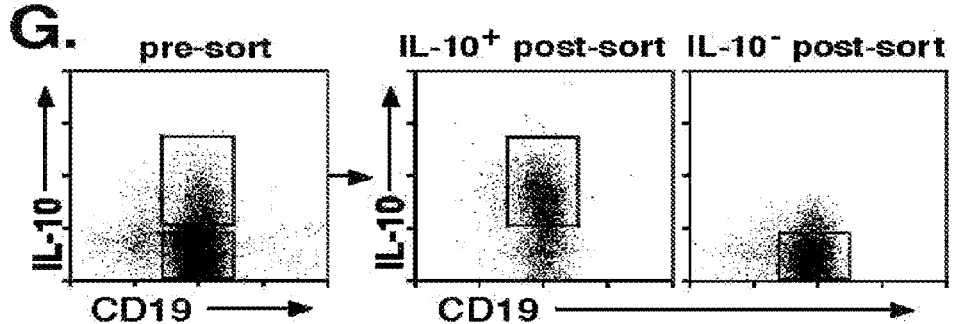

FIG. 3A-FIG. 3H: Cytokine production by B cells from wild type, hCD19Tg, and CD19$^{-/-}$ mice. (FIG. 3A) Splenocytes without stimulation, or (FIG. 3B) spleen, (FIG. 3C) peritoneal cavity, (FIG. 3D) blood, (FIG. 3E) peripheral lymph node, and (FIG. 3F) mesenteric lymph node lymphocytes after culture with LPS, PMA, ionomycin, and monensin for 5 h. The cells were stained with B220 mAb (except peritoneal cavity) and/or CD19 or CD20 mAbs to identify B cells. After permeabilization, the cells were stained with anti-IL-10 mAb. During flow cytometry analysis, B220 staining was used as the initial gate for identifying B cells (except peritoneal cavity). All data are representative of 3 independent experiments with 3 mice in each group. Representative results for one mouse are shown demonstrating the frequency of IL-10-producing cells among total B cells within the indicated gates. Bar graphs indicate mean (±SEM) percentages and numbers of B cells that produced IL-10 in the one representative experiment. Significant differences between sample means are indicated: , p<0.01. (FIG. 3G) Representative isolation of IL-10 secreting B cells. Purified splenic B220$^+$ cells from three hCD19Tg mice were pooled and stimulated with LPS, PMA, and ionomycin for 5 hours before staining for IL-10 secretion and CD19 expression (left panel). IL-10$^+$ and IL-10$^-$ B cells were isolated by cell sorting using the indicated gates and subsequently reassessed for IL-10 secretion and CD19 expression (right panels). (FIG. 3H) Microarray analysis of cytokine gene expression by IL-10-secreting B cells versus B cells not secreting IL-10 after purification as in (FIG. 3G). Mean fold-differences (±SEM) in cytokine transcript expression levels from three independent experiments are shown. Values of 1 indicate no difference. Significant differences between IL-10$^+$ and IL-10$^-$ cells sample means are indicated: , p<0.005.

Figure 4:
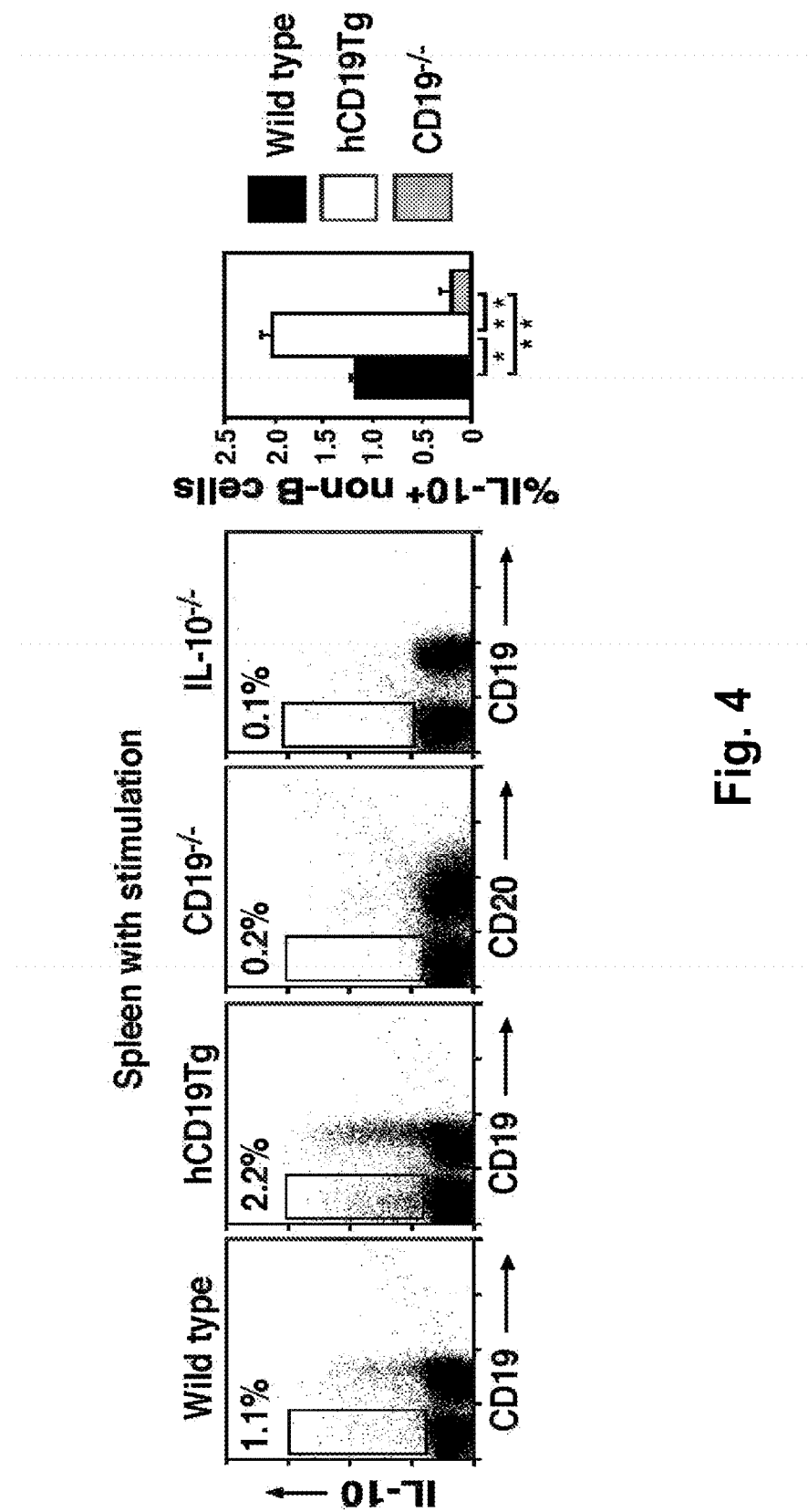

FIG. 4: IL-10 production by non-B cells from wild type, hCD19Tg, and CD19$^{-/-}$ mice. Splenocytes were cultured with LPS, PMA, ionomycin, and monensin for 5 hours before staining with CD19 or CD20 mAbs to identify B cells. After permeabilization, the cells were stained with anti-IL10 mAb and assessed by flow cytometry. Representative histograms show results with single mice while the bar graph indicates results for all samples. Values represent the percentage of IL-10-producing cells among total non-B cells. All data are representative of 3 independent experiments with 3 mice in each group.

FIG. 5A-FIG. 5E: Phenotype of IL-10-producing B cells. (FIG. 5A) CD1d and CD5 expression on CD19$^+$ B220$^+$ splenocytes from wild type and hCD19Tg mice does not change following LPS, PMA, ionomycin, and monensin treatments, and permeabilization. CD1d and CD5 expression on CD19$^+$ B220$^+$ cells before (thin line) or after 5 hour incubation with LPS, PMA, ionomycin, monensin, and permeabilization (thick line) was determined by immunofluorescence staining with flow cytometry analysis. (FIG. 5B) IL-10-producing spleen B cells from wild type and hCD19Tg mice expressed both CD1d and CD5. Purified CD19$^+$ splenocytes were cultured with LPS, PMA, ionomycin, and monensin for 5 hours before permeabilization and staining using CD1d, CD5, B220, and IL-10 mAbs, with four-color flow cytometry analysis. (FIG. 5C) Spleen IL-10-producing B cells represent a CD1d$^{high}$CD5$^+$ subset distinct from B-1a cells in wild type and hCD19Tg mice. Histograms demonstrate cytoplasmic IL-10 expression by permeabilized CD1d$^{high}$CD5$^+$, CD1d$^{low}$CD5$^+$, and CD1d$^-$CD5$^-$ B cells from wild type and hCD19Tg mice after LPS, PMA, and ionomycin stimulation. CD1d and CD5 expression by B cells from CD19$^{-/-}$ and IL-10$^{-/-}$ mice is also shown. Percentages indicate mean (±SEM) CD1d$^{high}$CD5$^+$ cell, or IL-10$^+$ cell frequencies among CD1d$^{high}$CD5$^+$ B cells as indicated for each group of three mice. (FIG. 5D) Stimulation does not induce the CD1d$^{high}$CD5$^+$ phenotype of IL-10 secreting B cells. Splenic CD1d$^{high}$CD5$^+$ or CD1d$^{low}$CD5$^-$ B cells were purified from three wild type or hCD19Tg mice by cell sorting and pooled before LPS, PMA, and ionomycin stimulation for 5 h, with subsequent assessment for cytoplasmic IL-10 production by immunofluorescence staining. Percentages indicate IL-10$^+$ cell frequencies. (FIG. 5E) IgM, IgD, CD5, CD1d, CD21, CD24, CD23, CD11b, CD43, and B220 expression by IL-10$^+$ (thick line) or IL-10$^-$ (dashed line) B cells from wild type and hCD19Tg mice. CD19$^+$ splenocytes were cultured with LPS, PMA, ionomycin, and monensin for 5 hours before permeabilization and staining for IL-10. Thin lines represent isotype-matched control mAb staining. FIG. 5A-FIG. 5D). All results represent ≥2 independent experiments with 3 mice in each group.

FIG. 6A-FIG. 6E: IL-10 production by CD1d$^{high}$CD5$^+$ B cells correlates with suppression of T cell-mediated inflammation. (FIG. 6A) IL-10 production by wild type, hCD19Tg, and CD19$^{-/-}$ B cells during CHS responses. B220$^+$ cells were purified from the spleen and draining lymph nodes of naive mice (filled bars) or 2 days following oxazolone challenge (open bars). (FIG. 6B) Splenic CD1d$^{high}$CD5$^+$ or non-CD1d$^{high}$CD5$^+$ B cells were purified from naïve or oxazolone challenged wild type mice (as in FIG. 6A) by cell sorting. (FIG. 6A, FIG. 6B) Values represent relative mean IL-10 transcripts normalized to GAPDH transcript levels (±SEM) in triplicate samples of pooled RNA from 3 mice as quantified by real-time PCR analysis. Results are representative of at least 2 independent experiments with 3 mice in each group. Significant differences between sample means are indicated; *p<0.05, **p<0.01. (FIG. 6C) CHS responses in hCD19Tg mice treated with anti-IL-10 receptor or isotype control mAb 1 hour before and 47 hours after oxazolone challenge. (FIG. 6D) CHS responses in wild type and IL-10$^{-/-}$ mice after B cell depletion. Mice were treated with CD20 or isotype control mAb 7 days before the first sensitization with oxazolone. (FIG. 6C-FIG. 6D) Ear thickness was measured after oxazolone challenge as indicated. Values represent mean (±SEM) increases in ear thickness for ≥4 mice of each group. Significant differences between the mean CHS responses between groups and control mAb-treated wild type mice are indicated; *p<0.05; **p<0.01. (FIG. 6E) IL-10 production by circulating B cells from wild type mice during CHS responses. Blood mononuclear cells from three mice were pooled and cultured with LPS, PMA, ionomycin, and monensin for 5 hours before the cells were stained with B220 and/or CD19 or CD20 mAbs to identify B cells. After permeabilization, the cells were stained with anti-IL-10 mAb. Values represent the percentage of IL-10-producing cells among total B cells with results from IL-10$^{-/-}$ mice shown as a control.

Figures 7A, 7B, 7C:
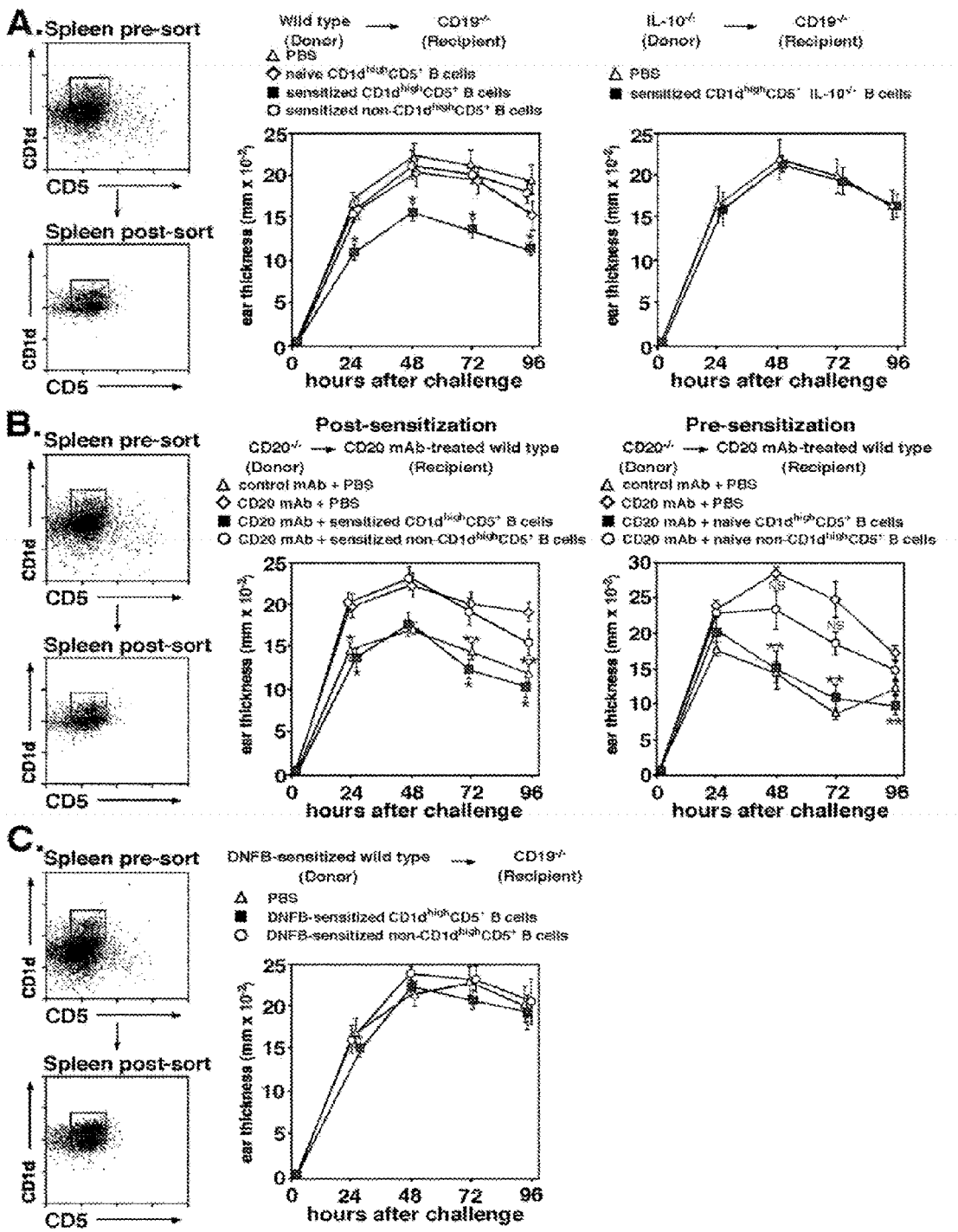
Figures 8A, 8B, 8C, 8D:
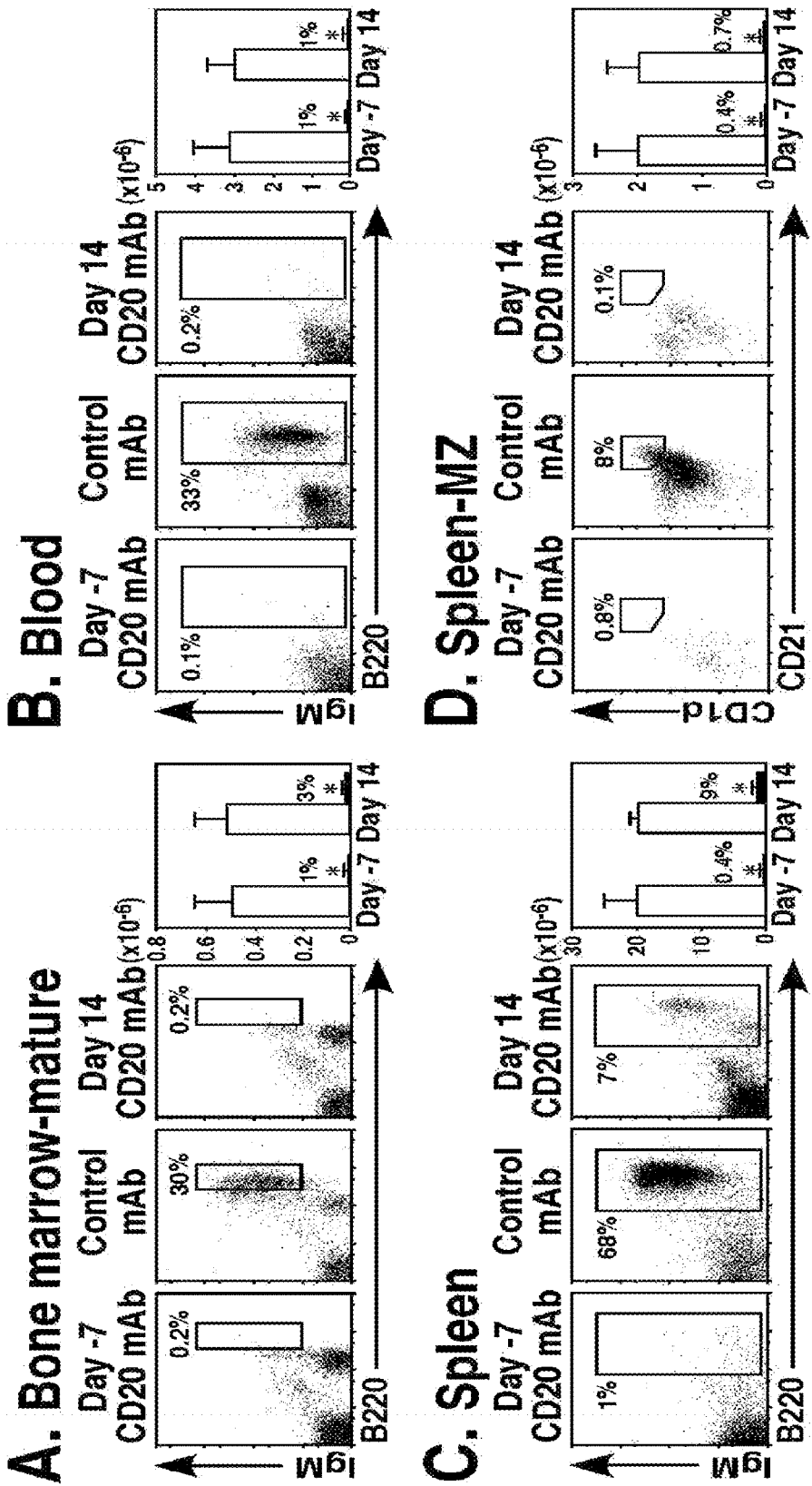
Figures 8E, 8F, 8G, 8H:
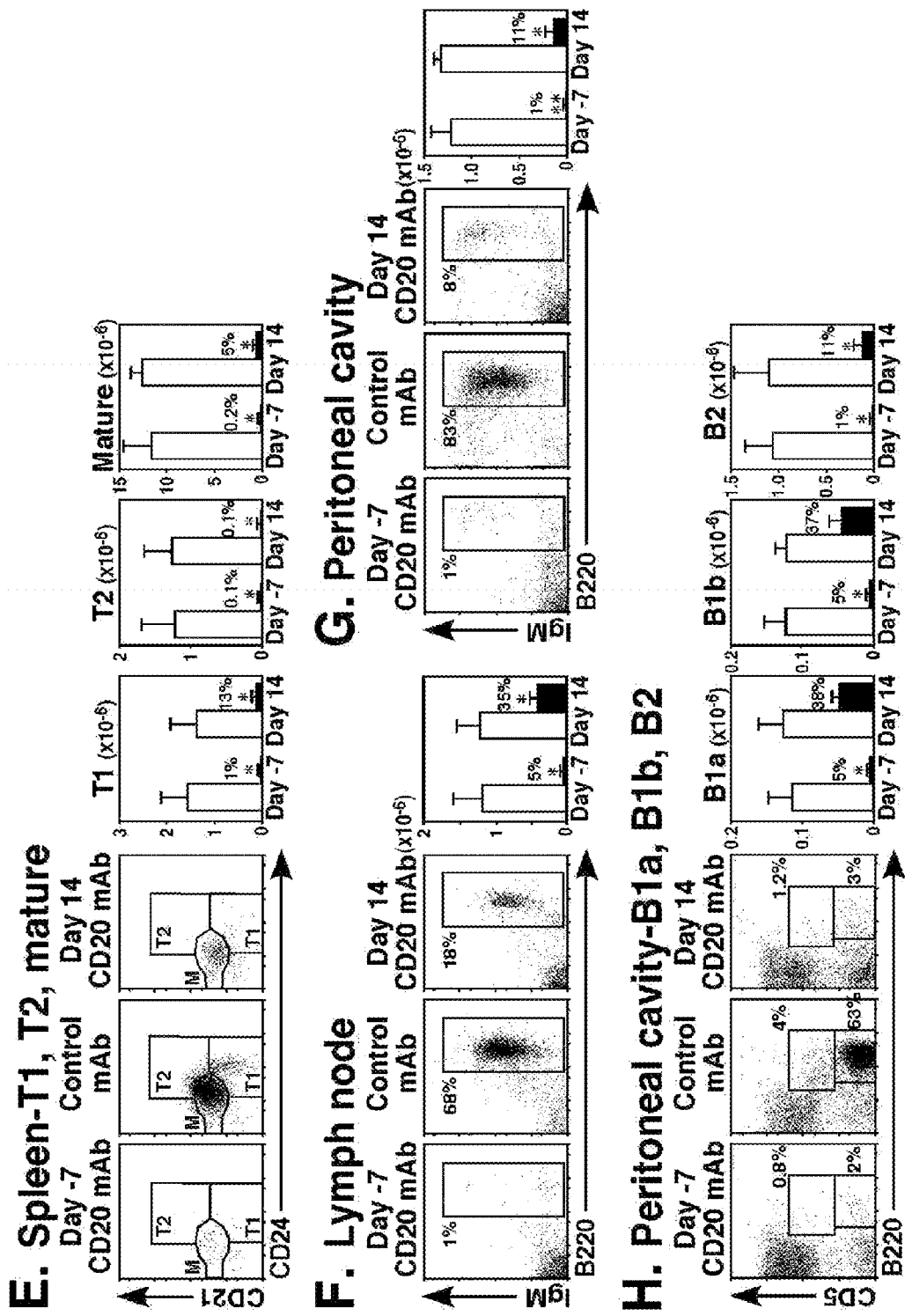

FIG. 7A-FIG. 7C: CD1d$^{high}$CD5$^+$ B cells exert an inhibitory role during T cell-mediated inflammatory responses. (FIG. 7A) Splenic CD1d$^{high}$CD5$^+$ or non-CD1d$^{high}$CD5$^+$ B cells from sensitized or naive mice were purified (representative results, left panel). Purified cells from wild type (middle panel) or IL-10$^{-/-}$ (right panel) mice were transferred into oxazolone-sensitized CD19$^{-/-}$ mice. Recipient mice were challenged 48 hours after transfer with increased ear thickness measured. Significant differences between mean CHS responses in control mice versus mice adoptively transferred with CD1d$^{high}$CD5$^+$ B cells are indicated; *p<0.05. (FIG. 7B) CD1d$^{high}$CD5$^+$ or non-CD1d$^{high}$CD5$^+$ splenic B cells were purified from sensitized or naive CD20$^{-/-}$ mice and transferred into sensitized or naive wild type mice, respectively, that had been treated with CD20 or control mAb 7 days earlier using the same procedures as in (FIG. 7A). For sensitized mice, the adoptive transfer was performed 2 days before challenge (middle panel). For naive mice, the adoptive transfer was performed 2 days before initial sensitization (right panel). Significant differences between CD20 mAb-treated control mice versus other groups are indicated; *p<0.05; **p<0.01. (FIG. 7C) Adoptive transfer of CD1d$^{high}$CD5$^+$ or non-CD1d$^{high}$CD5$^+$ B cells purified from DNFB-sensitized mice does not alter CHS responses in CD19-/- recipients. The same procedures were used as in (FIG. 7A) except the donor mice were sensitized with DNFB. FIG. 7A-FIG. 7C). Values represent means (±SEM) from ≥4 mice of each group.

FIG. 8A-FIG. 8H: CD20 mAb-induced B cell depletion in EAE mice. Mice were treated with CD20 (closed bars) or control (open bars) mAb (250 µg) 7 days before or 14 days after MOG immunization. Representative depletion of B cells from the bone marrow (FIG. 8A), blood (FIG. 8B), spleen (FIG. 8C-FIG. 8E), peripheral lymph nodes (FIG. 8F), and peritoneal cavity (FIG. 8G and FIG. 8H) on day 18. Bar graphs indicate the numbers of blood (per ml) and tissue B cells (mean±SEM, n≥4, *p<0.05, **<0.01). Percentages indicated within the bar graphs represent relative B cell number in CD20 mAb-treated mice compared to control mAb-treated littermates.

Figure 9A:
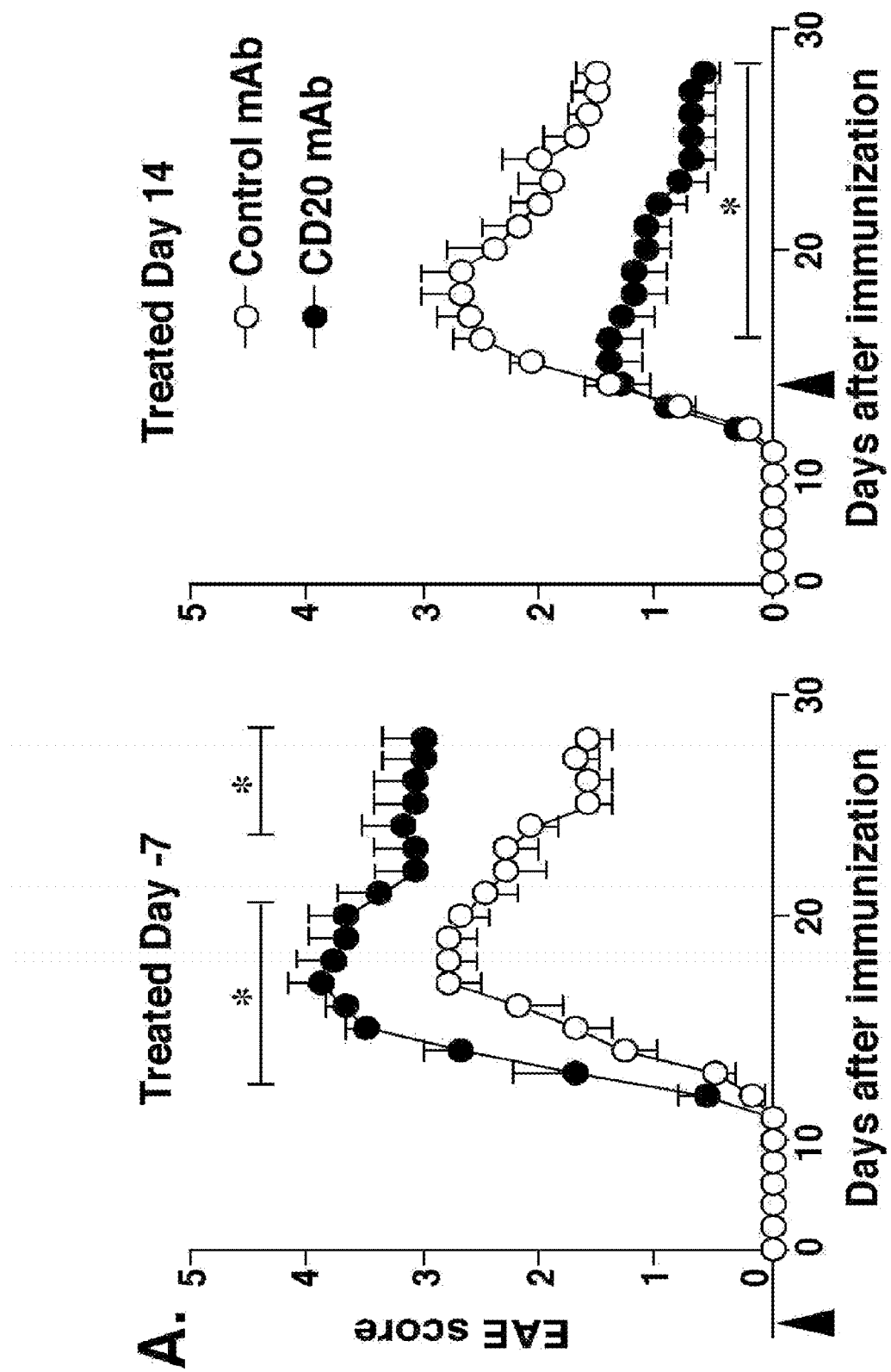
Figures 9B, 9C:
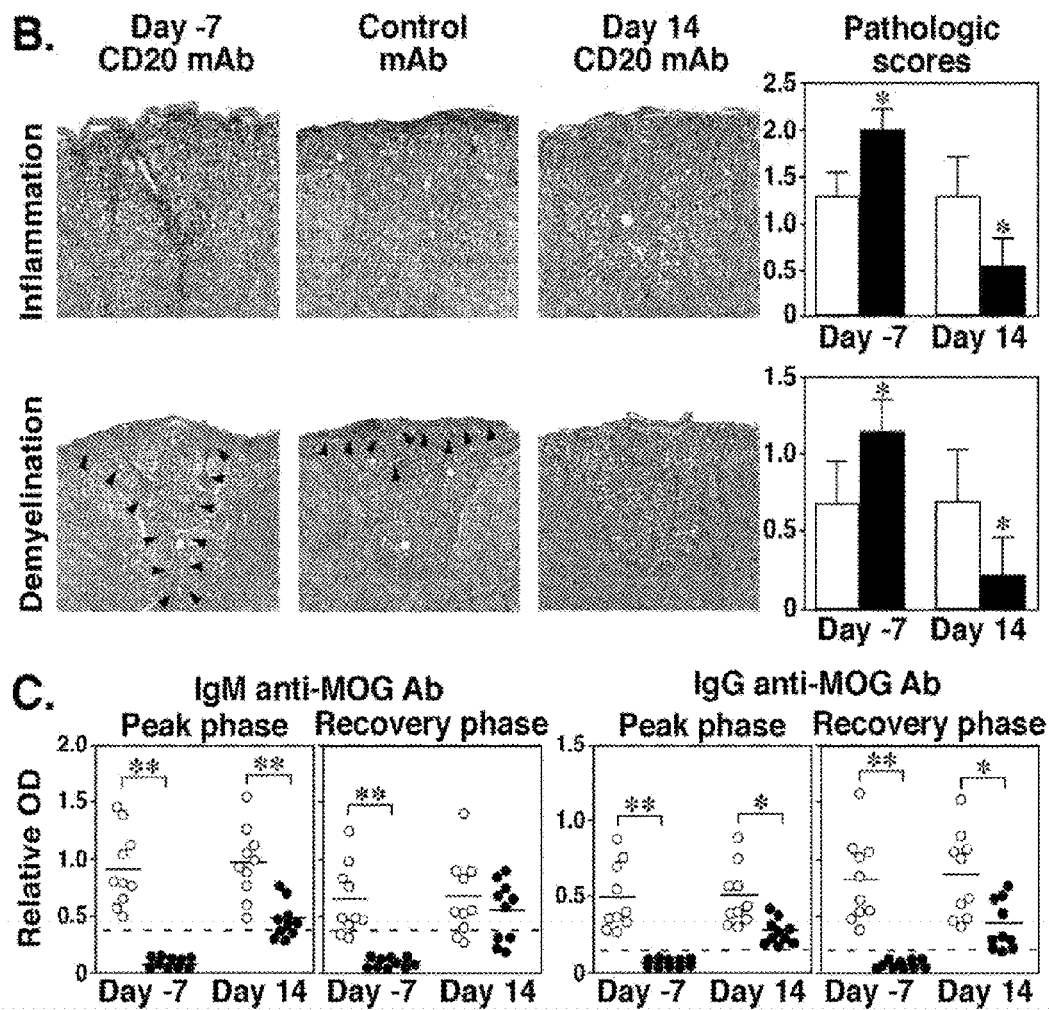

FIG. 9A-FIG. 9C: B cells regulate EAE severity. Mice were treated with CD20 (closed circles/bars) or control (open circles/bars) mAb (250 µg) 7 days before or 14 days after MOG immunization. (FIG. 9A) Arrowheads indicate mAb injection. Values represent EAE clinical scores (mean±SEM, n=10, *p<0.05). (FIG. 9B) Spinal cord tissues harvested on day 18 (mean±SEM, n≥4, *p<0.05). Arrowheads indicate focal demyelination. Original magnification: ×200. (FIG. 9C) B cell depletion attenuates MOG-specific antibody production on day 18 (peak phase) and day 28 (recovery phase). Dashed lines indicate mean values for unimmunized mice (n=6). *p<0.01, **p<0.001.

Figures 10A, 10B, 10C:
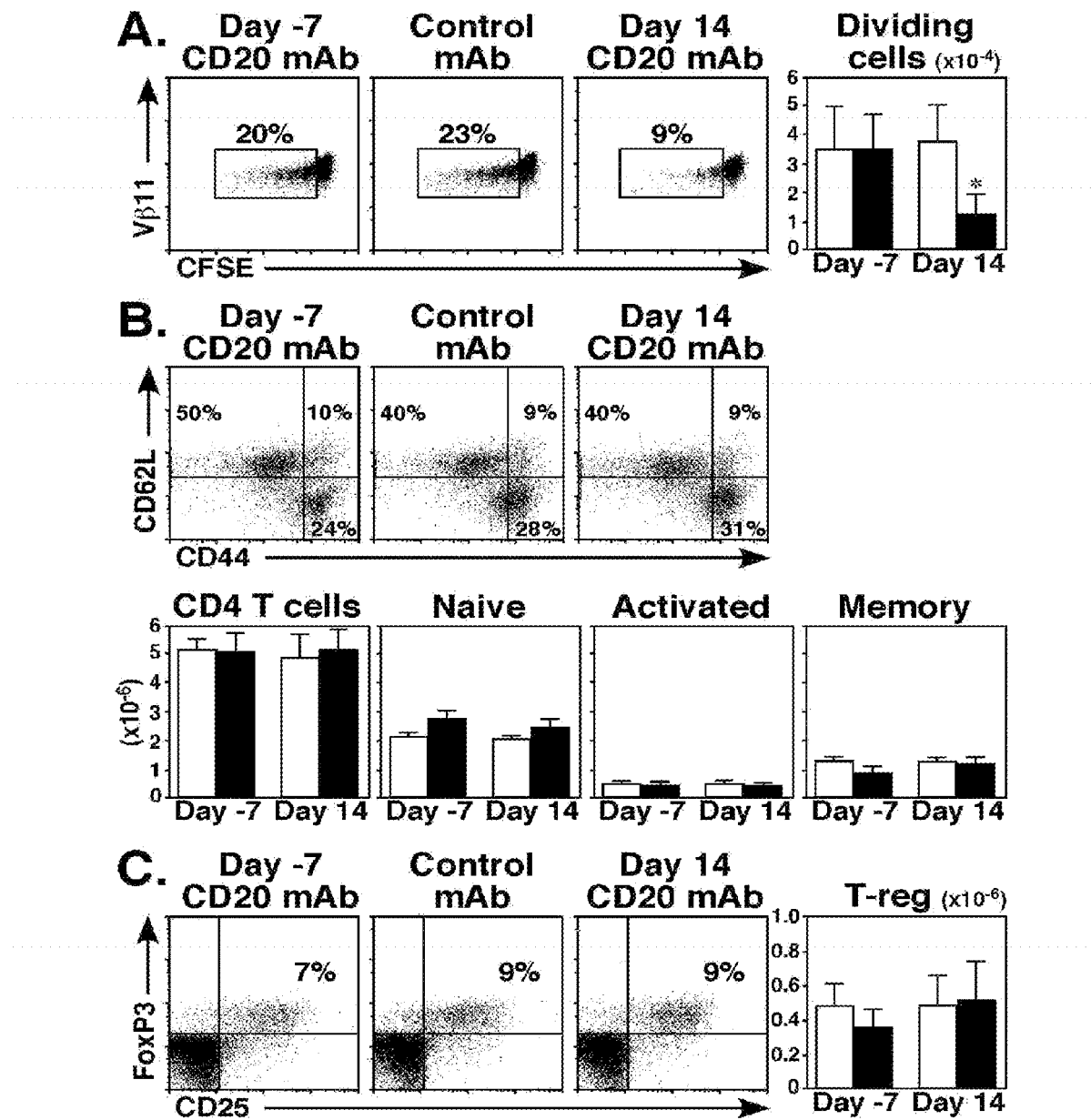

FIG. 10A-FIG. 10C: B cells regulate MOG-specific CD4$^+$ T cell expansion in vivo. Mice were treated with CD20 (closed bars) or control (open bars) mAb (250 µg) 7 days before or 14 days after MOG immunization. (FIG. 10A) CFSE-labeled TCR$^{MOG}$ CD4$^+$ T cells were transferred into mice on day 17. Four days later, lymph node cells were analyzed for CFSE division (gated on CD4$^+$Vβ11$^+$CFSE$^+$ cells). Bar graphs indicate the numbers of dividing cells (mean±SEM, n≥4, *p<0.001). (FIG. 10B) CD4$^+$ T cell subsets and (FIG. 10C) regulatory T cells (T-reg) on day 18 (mean±SEM, n≥4).

FIG. 11A-FIG. 11B: B cells regulate CNS-infiltrating CD4$^+$ T cell numbers and activation during EAE. Mice were treated with CD20 (closed bars) or control (open bars) mAb (250 µg) 7 days before or 14 days after MOG immunization. (FIG. 11A) MOG-specific effector T cell (T-eff; MOG/IAb-tetramer$^+$CD4$^+$FoxP3$^-$) and regulatory T cell (T-reg; MOG/IAb-tetramer$^+$CD4$^+$FoxP3$^+$) on day 18. Bar graphs indicate the numbers and the ratio of T-eff/T-reg (mean±SEM, n≥4, *p≤0.05). (FIG. 11B) IL-17 and IFN-γ production by CNS-infiltrating CD4$^+$ T cells on day 18. Bar graphs indicate numbers of IL-17$^+$ and IFN-γ$^+$CD4$^+$ T cells (mean±SEM, n≥4, *p<0.05, **p<0.01).

Figures 12A, 12B:
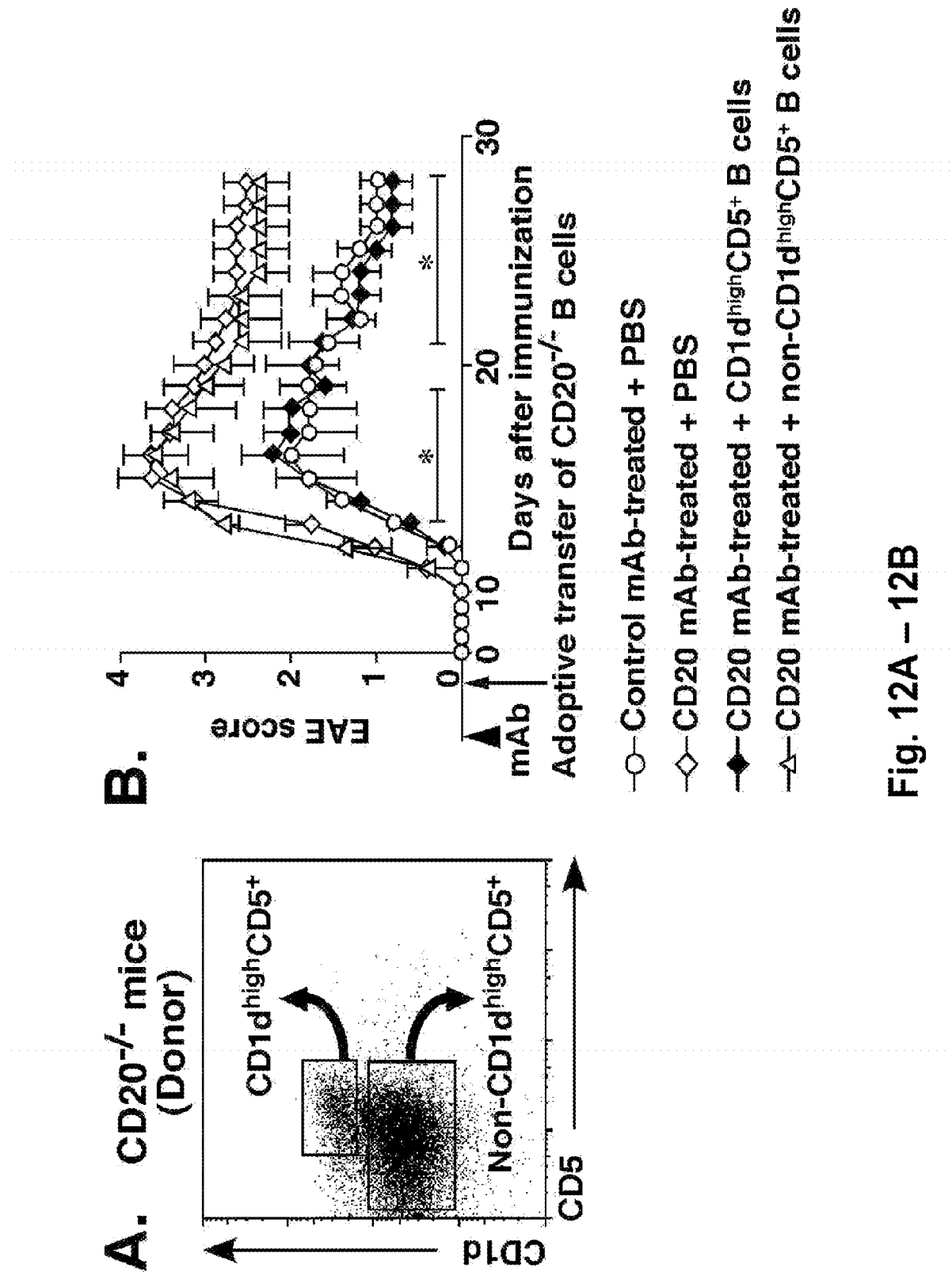

FIG. 12A-FIG. 12B: Regulatory CD1d$^{high}$CD5$^+$ B cells suppress disease symptoms in EAE. (FIG. 12A) Splenic CD19$^+$ B cells from CD20$^{-/-}$ mice, sorted into regulatory CD1d$^{high}$CD5$^+$ and non-regulatory CD1d$^{high}$CD5$^+$ B cell subsets. (FIG. 12B) CD1d$^{high}$CD5$^+$ or non-CD1d$^{high}$CD5$^+$ B cells (2×10$^6$) from CD20$^{-/-}$ mice were transferred into wild type mice that had been treated with CD20 or control mAb 5 days earlier (arrowhead). Recipient mice were immunized with MOG 2 days after transfer (day 0). Values represent EAE clinical scores (mean±SEM, n≥5). Significant differences between mice treated with CD20 mAb versus CD20 mAb plus CD1d$^{high}$CD5$^+$ B cells: *p<0.05.

Figure 13:
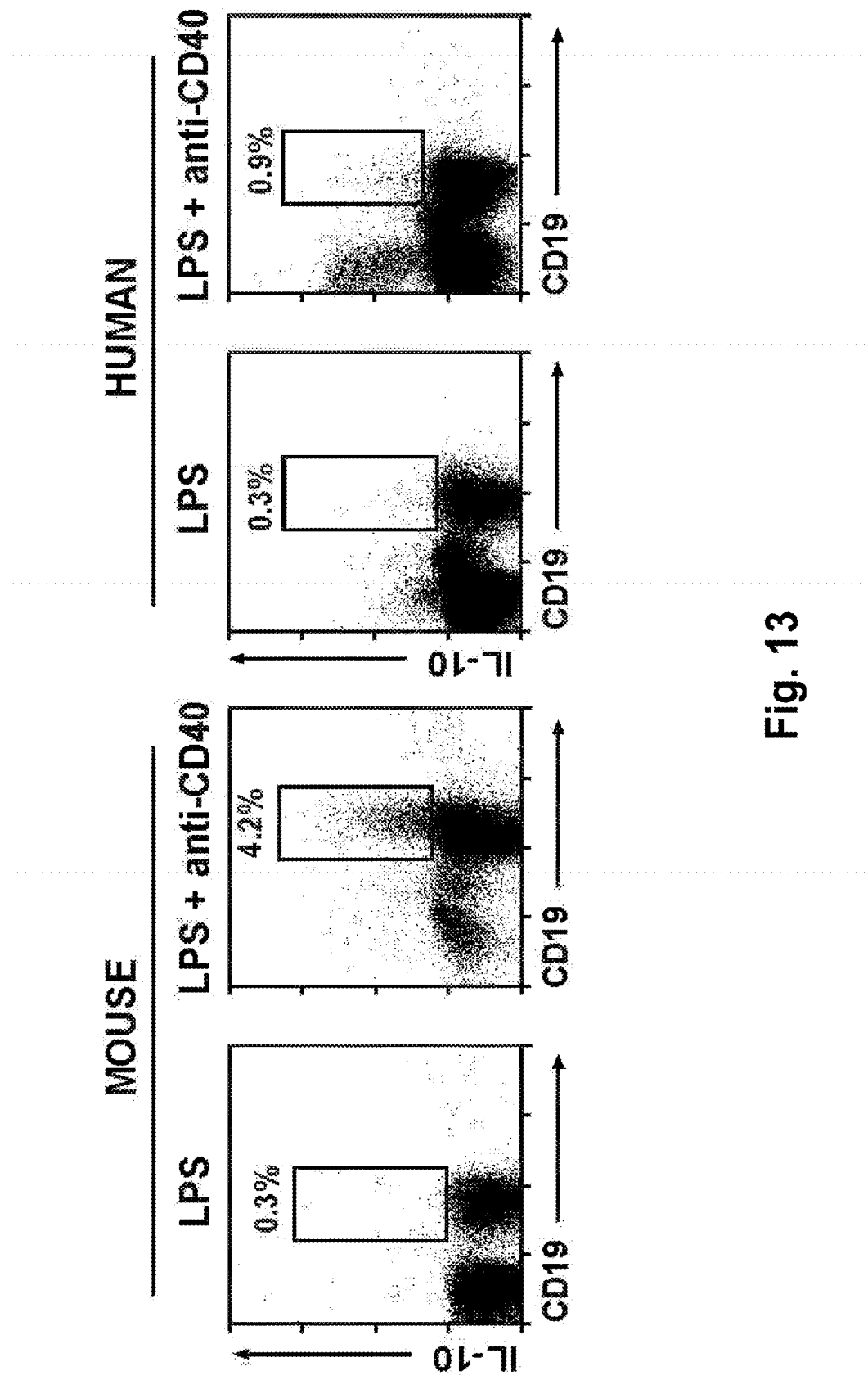

FIG. 13: CD40 stimulation induces IL-10 production by human and mouse blood B cells. Blood mononuclear cells were cultured with LPS, PMA, ionomycin, and monensin for 5 hours, or were cultured with CD40 mAb for 48 hours with LPS, PMA, ionomycin, and monensin added during the final 5 hours of culture. The cells were stained with CD19 mAb to identify B cells. After permeabilization, the cells were stained with anti-IL-10 mAb. Values represent the percentage of IL-10-producing cells among total B cells and are representative of three independent experiments.

Figure 14:

FIG. 14: IL-10 producing B cells in blood samples from healthy human donors. Peripheral blood mononuclear cells (PBMC) were isolated from four healthy human donors and activated in vitro in RPMI 1640 media containing 10% fetal bovine serum (FBS), 10 µg/ml of LPS, 50 ng/ml of PMA, 500 ng/ml of ionomycin, and monensin for 5 hours. IL-10$^+$ and IL-10$^-$ B cells were identified by immunofluorescence staining with flow cytometry analysis. The relative frequencies of IL-10$^+$ cells in the indicated gates are shown, with background cytoplasmic staining shown for an isotype control mAb.

Figures 15A, 15B, 15C:
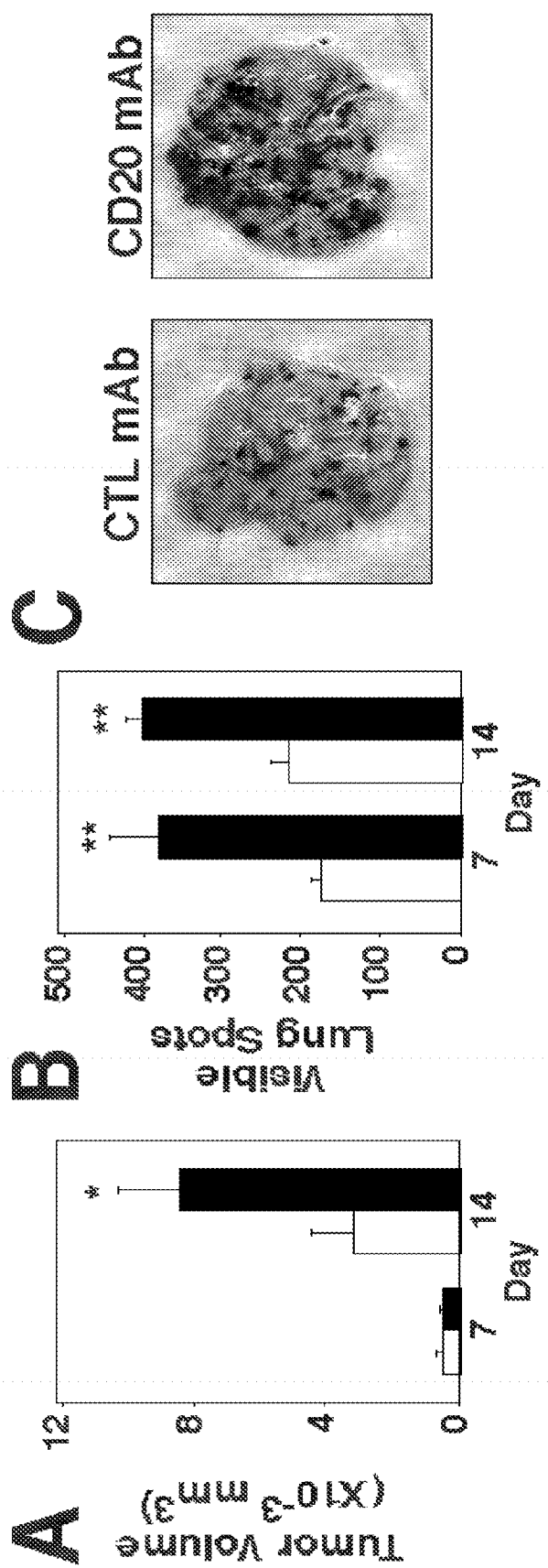

FIG. 15A-FIG. 15C: B cell depletion with CD20 mAb enhances the growth and metastasis of melanoma tumors. FIG. 15A. Mice were treated with control mAb (open bars) or CD20 mAb (filled bars) seven days before subcutaneous injection of B16 melanoma cells. Values represent the mean (±SEM) tumor volume on the indicated day. FIG. 15B. Mice were treated with mAb as in (FIG. 15A), and injected intravenously with B16 melanoma cells. Values represent the mean (±SEM) number of lung metastasis spots on the indicated day. FIG. 15A-B. Differences between sample values were statistically significant: *, p<0.05; **, p<0.01.

FIG. 15C. Representative pictures of lungs from control and CD20 mAb-treated mice 14 days after receiving an intravenous injection of B16 melanoma cells.

Figures 16A, 16B, 16C:
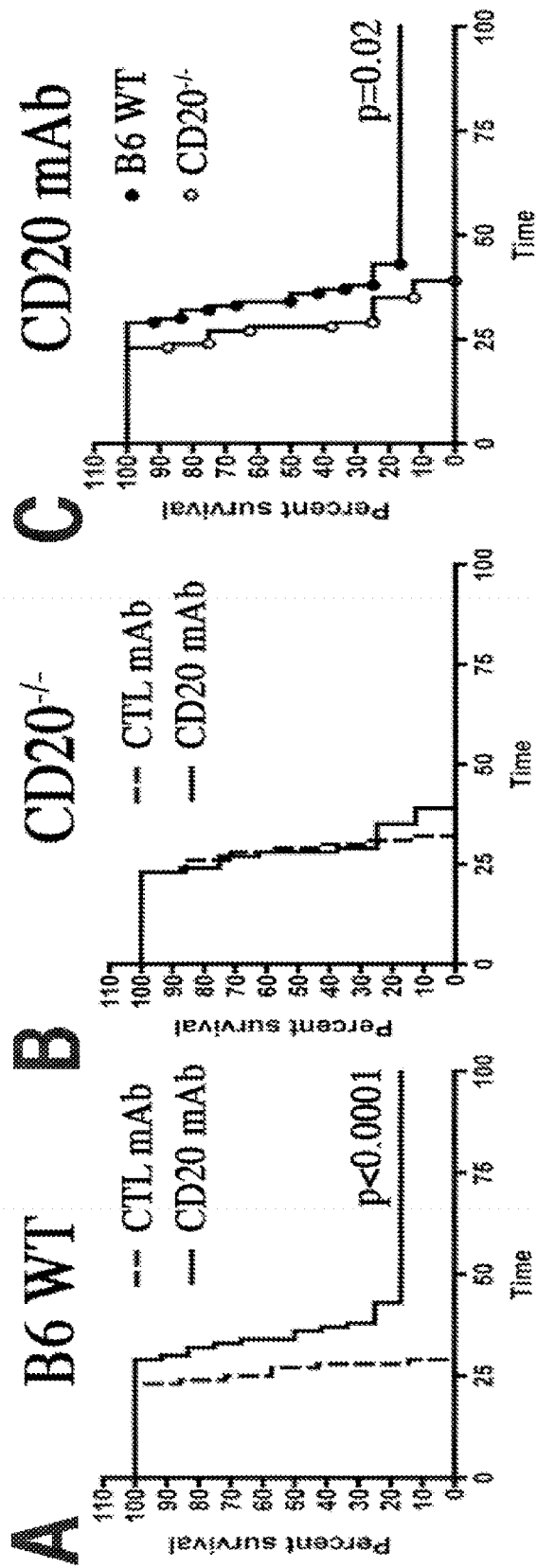

FIG. 16A-FIG. 16C: Survival of lymphoma-bearing CD20 mAb-treated mice is enhanced when endogenous B cells are depleted. B6 wild type (FIG. 16A) or $CD20^{-/-}$ (FIG. 16B) mice were injected subcutaneously with $CD20^+$ syngeneic lymphoma cells derived from a C57BL/6 Eμ-cMyc transgenic mouse on day 0, and then received 250 μg of control or CD20 mAb on day 1 and day 7. Mice were monitored daily for survival. FIG. 16C. Percent survival comparison between CD20 mAb-treated lymphoma-bearing B6 WT and $CD20^{-/-}$ mice.

Figures 17A, 17B:
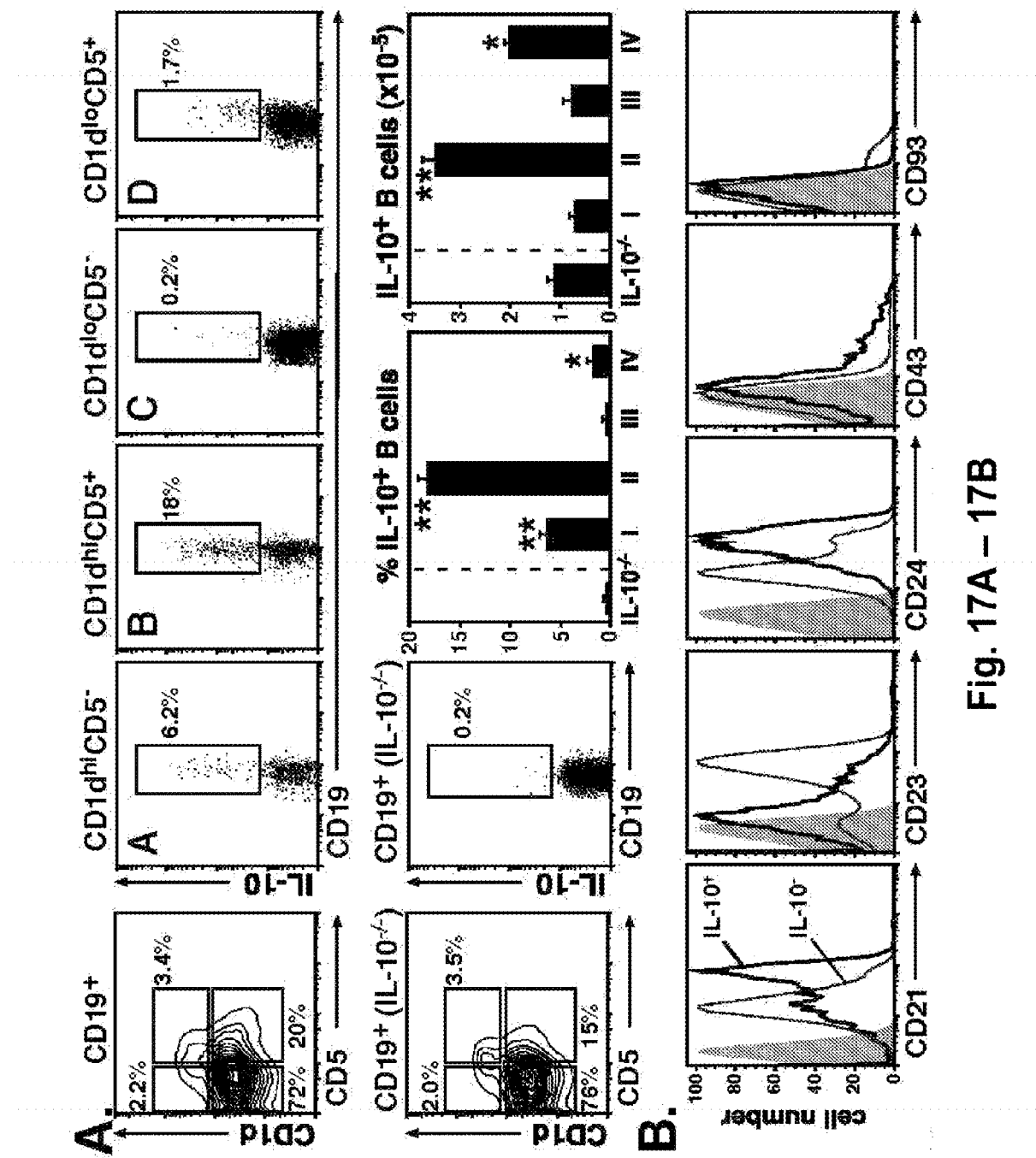
Figures 17C, 17D, 17E:
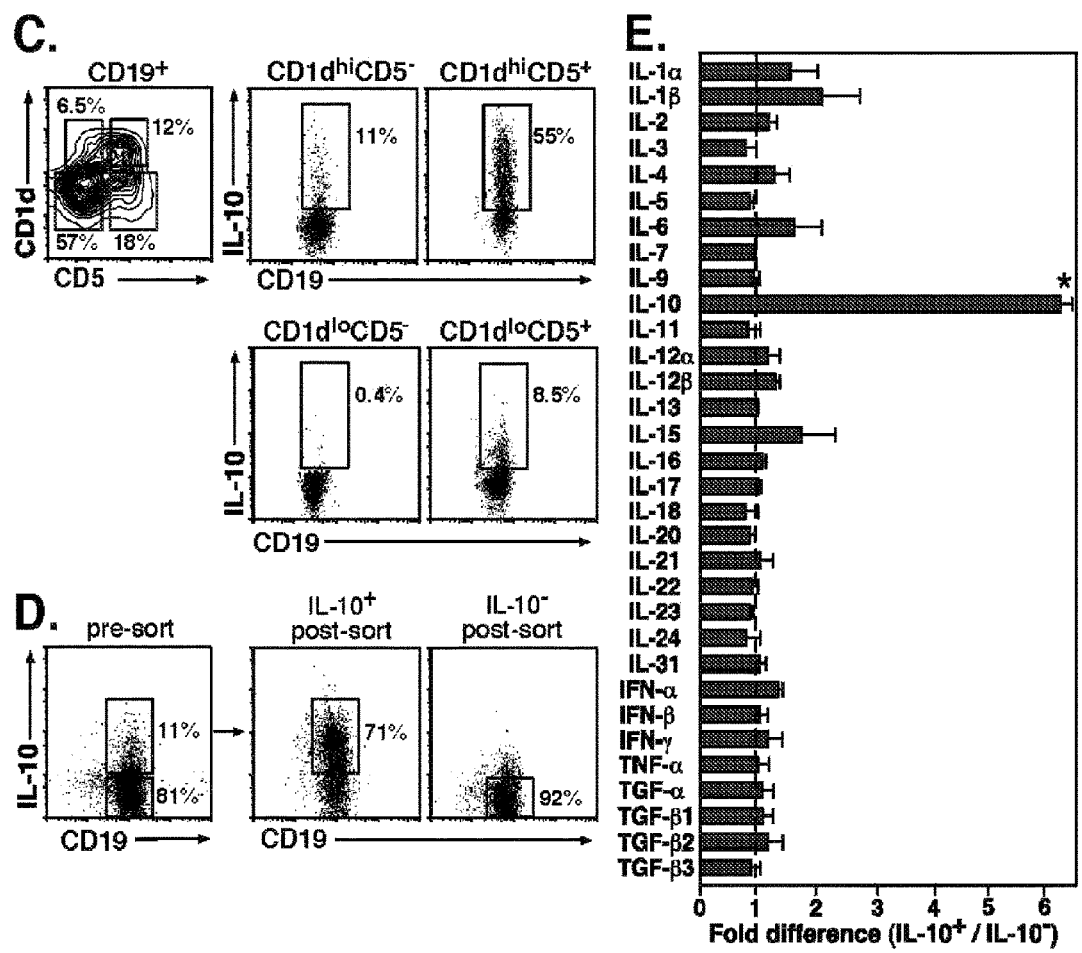

FIG. 17A-FIG. 17E. B10 cells preferentially secrete IL-10. (FIG. 17A) IL-10-producing B cells were predominantly found within the $CD1d^{hi}CD5^+CD19^+$ B cell subset. Splenocytes from wild type and $IL-10^{-/-}$ mice were cultured with L+PIM for 5 h, then stained with CD1d, CD5, and CD19 mAb before permeabilization and staining using IL-10 mAb. Percentages and bar graphs indicate mean (±SEM) B cell subset frequencies and numbers among $CD19^+$ splenocytes or $IL-10^+$ cell frequencies among the indicated B cell subsets (FIG. 17Aa, $CD1d^{hi}CD5^-$; FIG. 17Ab, $CD1d^{hi}CD5^+$; FIG. 17Ac, $CD1d^{lo}CD5^-$; FIG. 17Ad, $CD1d^{lo}CD5^+$) from 3 mice as determined by flow cytometry analysis. Values significantly different from background frequencies or numbers for $IL-10^{-/-}$ mice are indicated: *, p<0.05; , p<0.01. (FIG. 17B) CD21, CD23, CD24, CD43, and CD93 expression by IL-10-producing (thick line) and $IL-10^-$ (thin line) $CD19^+$ spleen B cells from wild type mice cultured with L+PIM for 5 h, then stained for cell surface antigens before permeabilization and cytoplasmic IL-10 staining. Gray histograms represent isotype-matched control mAb staining. Results are representative of those obtained with B cells from ≥3 mice as determined by flow cytometry analysis. (FIG. 17C) IL-10-producing B cells from hCD19Tg mice are predominantly found within the $CD1d^{hi}CD5^+CD19^+$ B cell subset Staining and analysis was as described in (FIG. 17A). (FIG. 17D) Representative isolation of IL-10-secreting B cells. Splenic $B220^+$ cells purified from three hCD19Tg mice were pooled and cultured with L+PI for 5 hours before staining for CD19 and secreted IL-10 capture (left panel). Cytoplasmic $IL-10^+$ and $IL-10^-$ B cells were isolated by cell sorting using the indicated gates and subsequently reassessed for IL-10 secretion and CD19 expression (right panels). (FIG. 17E) Cytokine gene expression by IL-10-secreting and non-secreting B cells purified as in (FIG. 17D). Mean fold-differences (±SEM) in cytokine transcript levels ($IL-10^+/IL-10^-$ cells) from 3 independent experiments are shown. Values of 1 (dashed line) indicate no difference in cytokine expression between the $IL-10^+$ and $IL-10^-$ B cells, with significant differences indicated: , p<0.005.

Figures 18A, 18B, 18C:
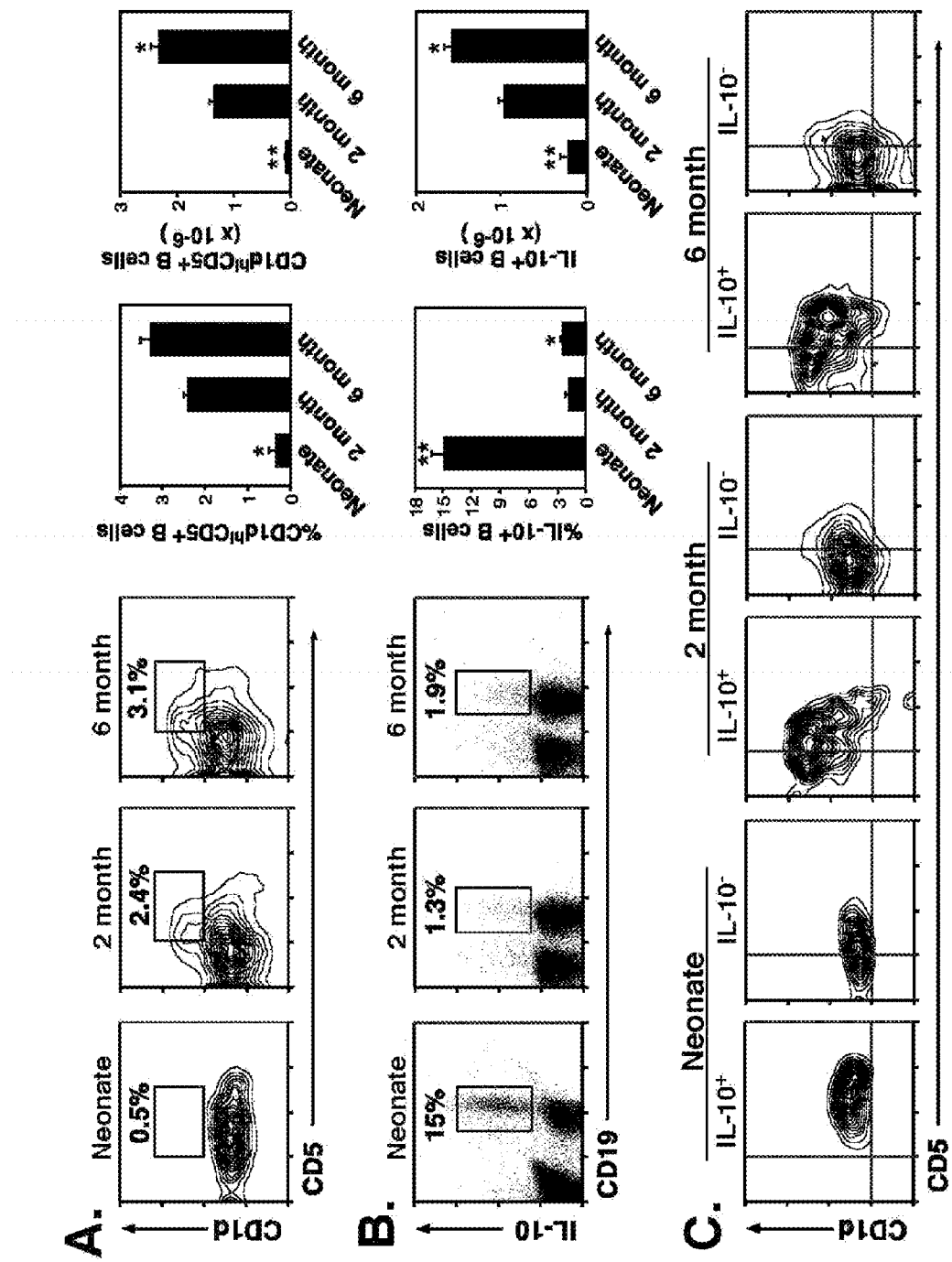

FIG. 18A-FIG. 18C. B10 cell development in neonatal and 2- or 6-mo-old wild type B6 mice. (FIG. 18A) Representative CD1d and CD5 expression by $CD19^+$ B cells. Splenocytes were stained with CD1d, CD5, and CD19 mAbs with flow cytometry analysis of cells. Results represent one mouse indicating the frequency of $CD1d^{hi}CD5^+$ B cells among total B cells within the indicated gates. Bar graphs indicate mean (±SEM) percentages and numbers of $CD1d^{hi}CD5^+$ B cells in one of two independent experiments with three mice in each group. (FIG. 18B) IL-10 production by B cells. Splenocytes were cultured with L+PIM for 5 h, then stained with CD19 mAb to identify B cells, permeabilized, and stained using IL-10 mAb with flow cytometry analysis. Representative results demonstrate the frequency of IL-10-producing cells among total $CD19^+$ B cells within the indicated gates. Bar graphs indicate mean (±SEM) percentages and numbers of B cells that produced IL-10 in one of two independent experiments with three mice in each group. (FIG. 18A, FIG. 18B) Significant differences between sample means are indicated: *p<0.05, **, p<0.01. (FIG. 18C) Representative CD1d and CD5 expression by $IL-10^+$ or $IL-10^-$ B cells from neonatal mice. Horizontal and vertical gates delineate background staining using unreactive isotype-matched control mAbs.

Figures 19A, 19B, 19C:
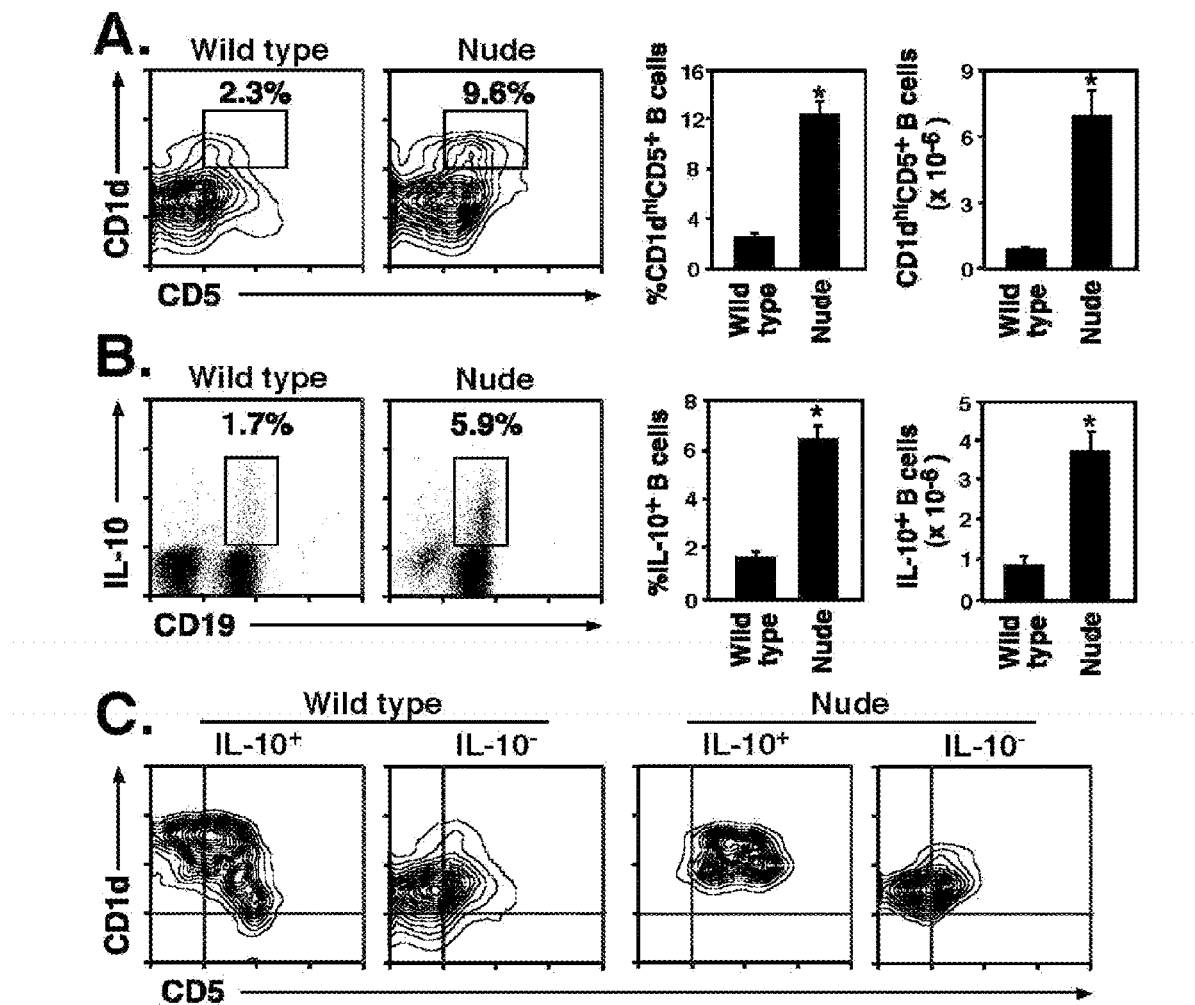

FIG. 19A-FIG. 19F. B10 cell development in T cell-deficient and gnotobiotic mice. (FIG. 19A) CD1d and CD5 expression by spleen $CD19^+$ B cells from 2 mo-old wild type and nude mice. Results represent one mouse indicating the frequency of $CD1d^{hi}CD5^+$ B cells within the indicated gates among total B cells. Bar graphs indicate mean (±SEM) percentages and numbers of $CD1d^{hi}CD5^+$ B cells in one of two independent experiments with three mice in each group. (FIG. 19B) IL-10 production by B cells from wild type and nude mice. Splenocytes were cultured with L+PIM for 5 h, stained with CD19 mAb, permeabilized, and stained using IL-10 mAb with flow cytometry analysis. Representative results demonstrate the frequency of IL-10-producing cells within the indicated gates among total $CD19^+$ B cells. Bar graphs indicate mean (±SEM) percentages and numbers of B cells that produced IL-10 in one of two independent experiments with three mice in each group. (FIG. 19C) CD1d and CD5 expression by $IL-10^+$ or $IL-10^-$ B cells from wild type and nude mice. Data are representative of 2 independent experiments with three mice in each group. Horizontal and vertical gates delineate background staining using unreactive isotype-matched control mAbs. (FIG. 19D) The presence of T cells during in vitro cultures does not influence B cell IL-10 production. Wild type splenocytes or purified $B220^+$ B cells were cultured with L+PIM for 5 h, then stained with CD19 mAb, permeabilized, and stained using IL-10 mAb with flow cytometry analysis. Representative results demonstrate the frequency of IL-10-producing cells within the indicated gates among total $CD19^+$ B cells. Bar graphs indicate mean (±SEM) percentages and numbers of B cells that produced IL-10 in one of two independent experiments with three mice in each group. (FIG. 19E) CD1d and CD5 expression by spleen $CD19^+$ B cells from specific pathogen free (SPF) and gnotobiotic mice. Bar graphs indicate mean (±SEM) percentages and numbers of $CD1d^{hi}CD5^+$ B cells in three mice. (FIG. 19F) IL-10 production by B cells from specific-pathogen-free (SPF) and gnotobiotic mice cultured as in (FIG. 19B). Bar graphs indicate mean (±SEM) percentages and numbers of B cells that produced IL-10 in three mice. (FIG. 19A, FIG. 19B, FIG. 19D-FIG. 19F) Significant differences between sample means are indicated: *p<0.05, **, p<0.01.

Figures 20A, 20B:
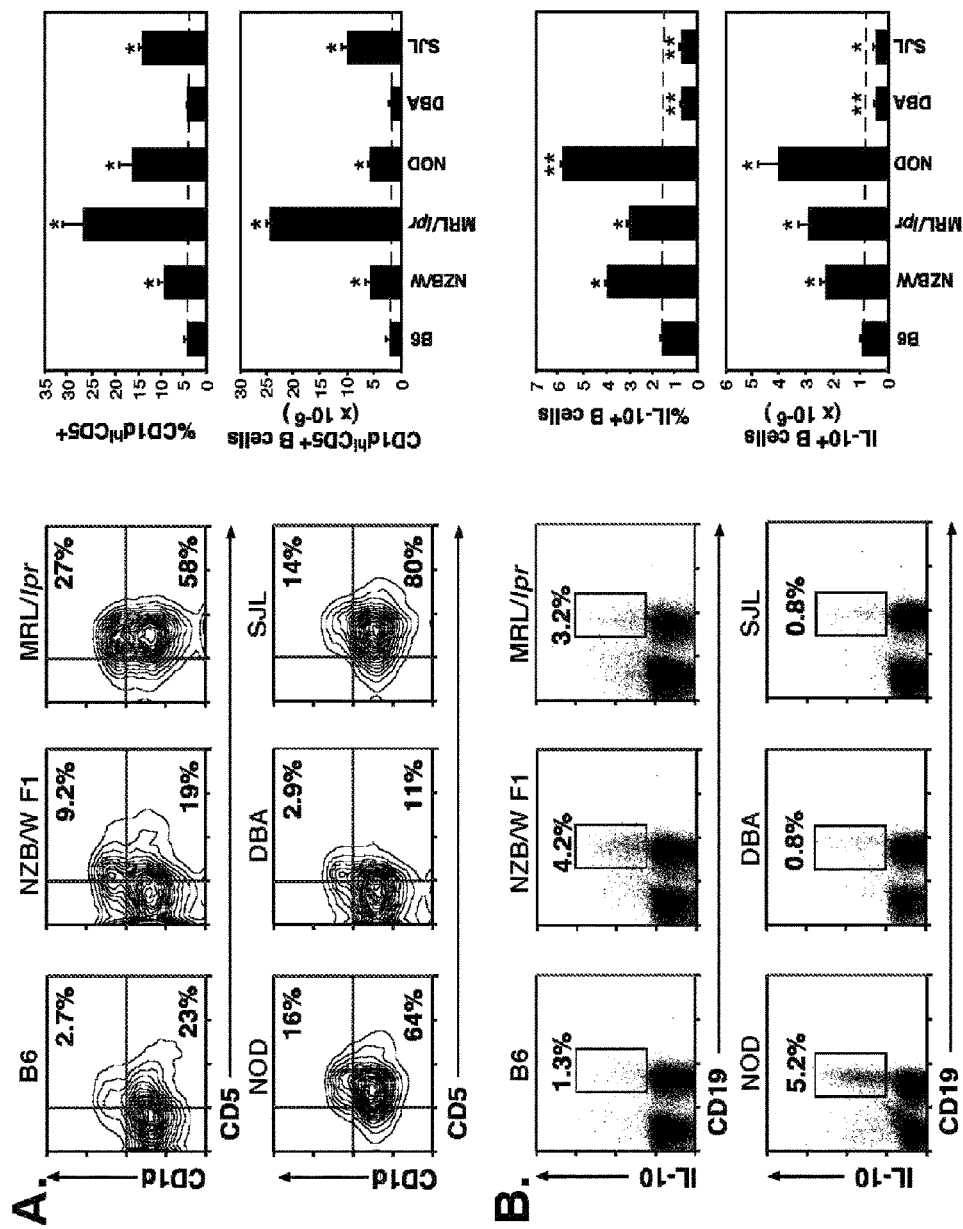
Figure 20C:
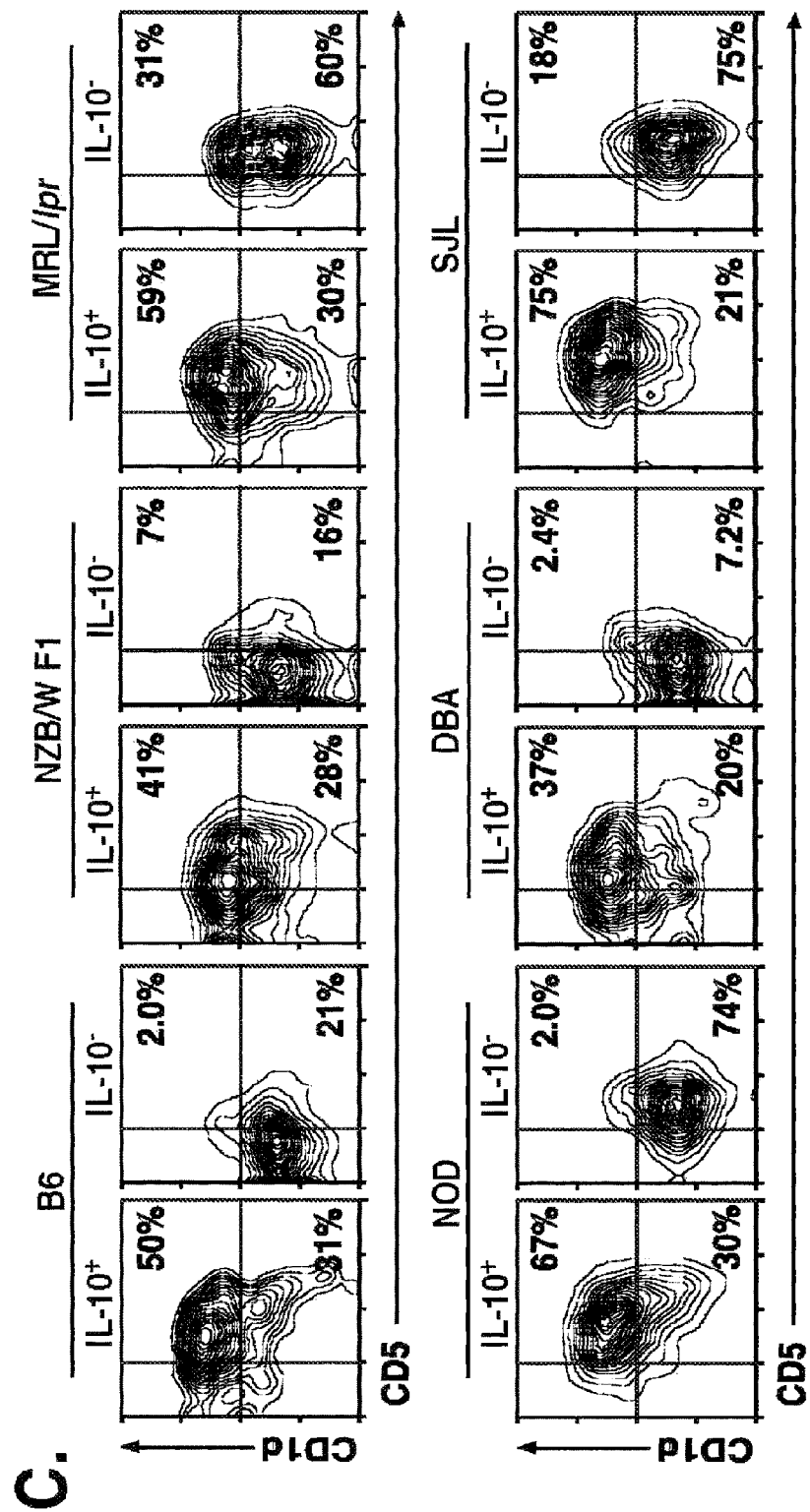

FIG. 20A-FIG. 20C. Autoimmunity promotes B10 cell expansion. (FIG. 20A) CD1d and CD5 expression by spleen B cells from 2 mo-old wild type B6, NZB/W F1, MRL/lpr, NOD, DBA/1, and SJL/J mice. Representative results demonstrate the frequency of $CD1d^{hi}CD5^+$ B cells within the indicated gates among total $CD19^+$ B cells. Horizontal and vertical gates are set to delineate the $CD1d^{hi}CD5^+$ B cell subset. Bar graphs indicate mean (±SEM) percentages and numbers of $CD1d^{hi}CD5^+$ B cells in one of two independent experiments with 3 mice in each group. (FIG. 20B) IL-10 production by B cells. Splenocytes were cultured with L+PIM for 5 h, then stained with CD19 mAb, permeabilized, and stained using IL-10 mAb with flow cytometry analysis. Representative results demonstrate the frequency of IL-10-producing cells within the indicated gates among total B cells. Bar graphs indicate mean (±SEM) percentages and numbers of B cells that produced IL-10 in one of two independent experiments with 3 mice in each group. (FIG. 20A, FIG. 20B) Significant differences between sample means are indicated: *p<0.05, **, p<0.01. (FIG. 20C) CD1d and CD5 expression by IL-10$^+$ or IL-10$^-$ B cells. Horizontal and vertical gates are set to delineate the CD1d$^{hi}$CD5$^+$ B cell subset as in (FIG. 20A). Data are representative of 2 independent experiments with 3 mice in each group.

Figure 21A:
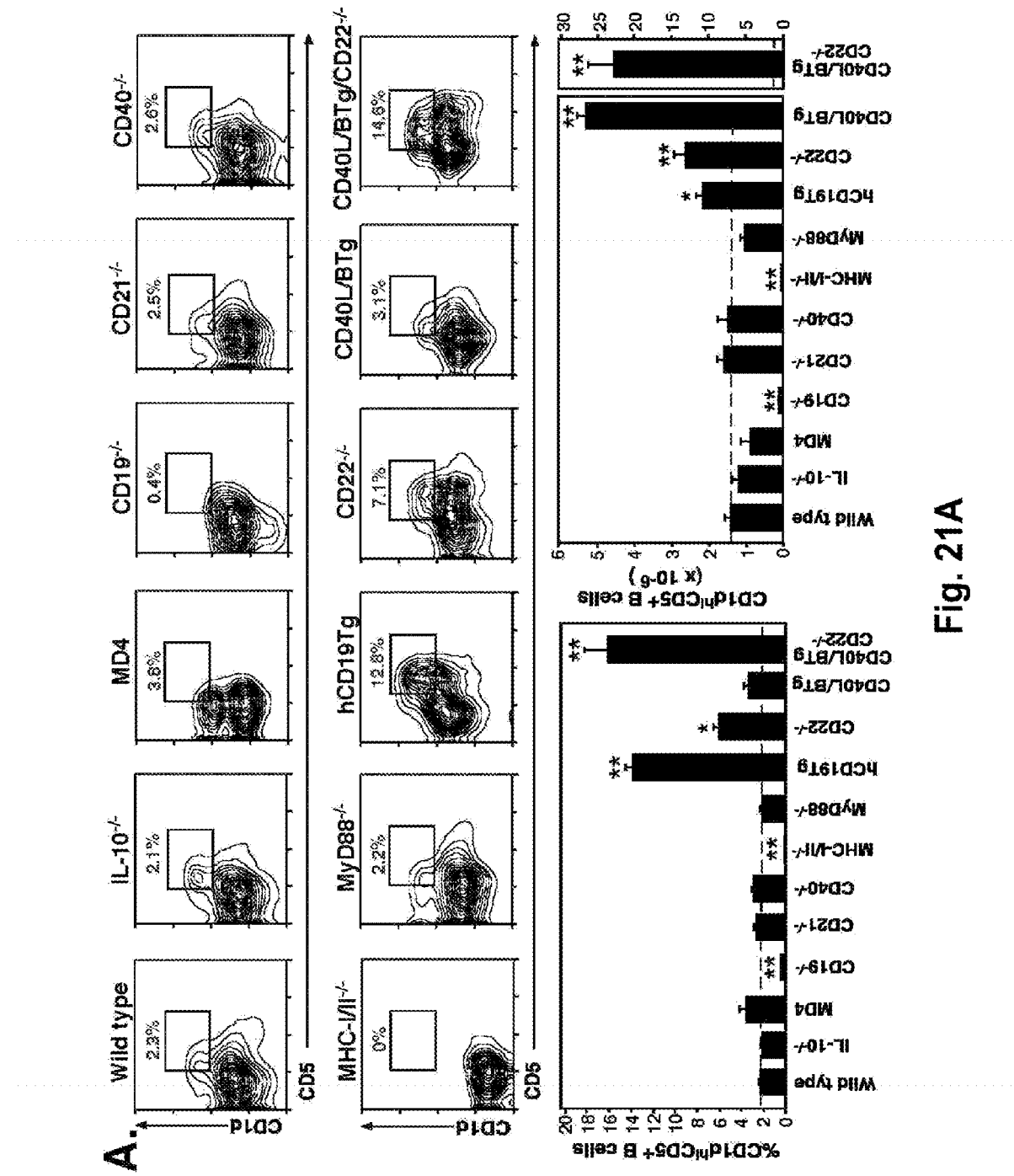
Figure 21B:
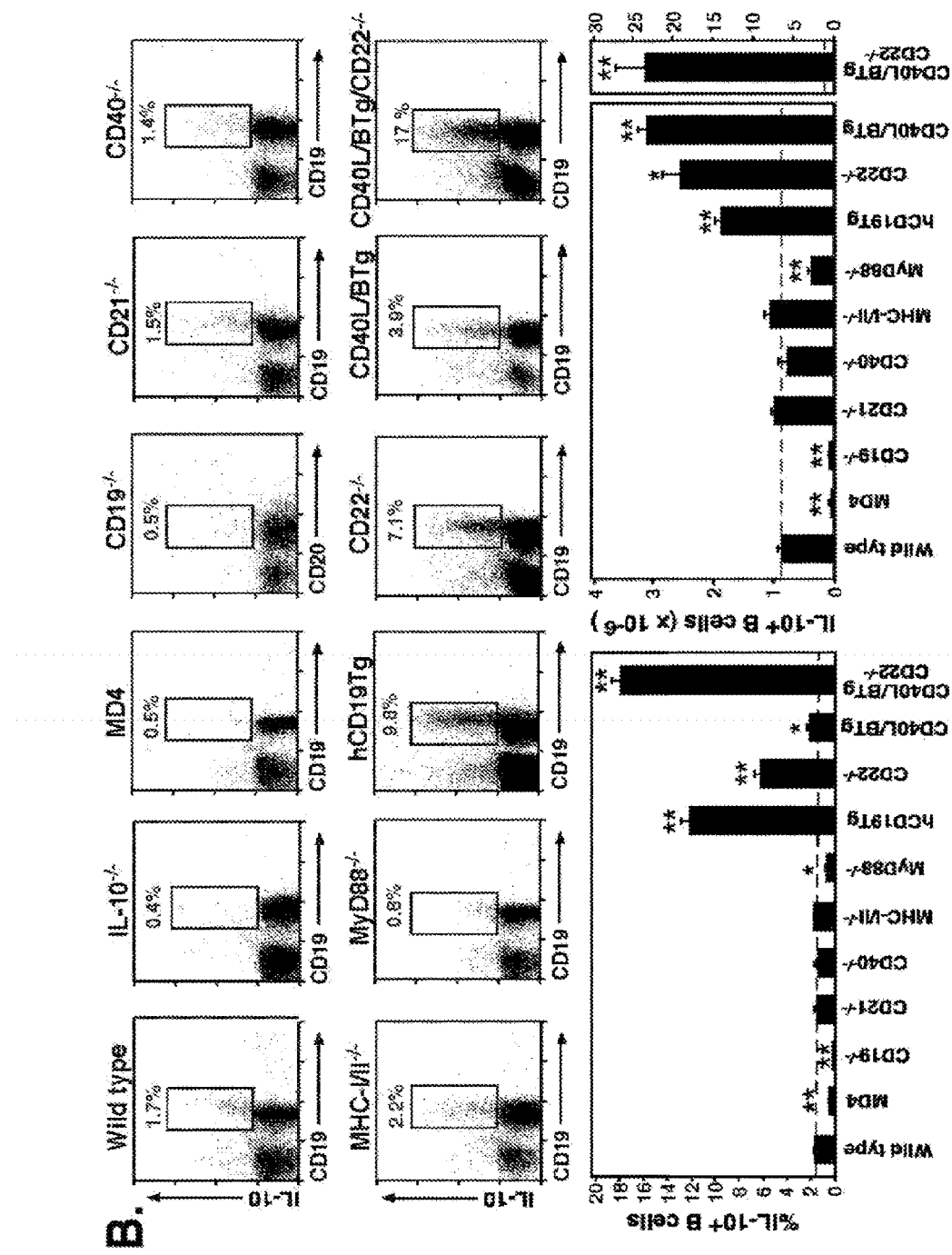

FIG. 21A-FIG. 21B. Cell surface molecules that regulate B10 cell development in vivo. (FIG. 21A) CD1d and CD5 expression by spleen B cells from wild type, IL-10$^{-/-}$, MD4, CD19$^{-/-}$, CD21$^{-/-}$, CD40$^{-/-}$, MyD88$^{-/-}$, hCD19Tg, CD22$^{-/-}$, CD40L/BTg, and CD40L/BTg/CD22$^{-/-}$ mice. Splenocytes were stained with CD1d, CD5, and CD19 or CD20 mAbs (for CD19$^{-/-}$ mice). Representative results demonstrate the frequency of CD1d$^{hi}$CD5$^+$ B cells within the indicated gates among total CD19$^+$ or CD20$^+$ B cells. Bar graphs indicate mean (±SEM) percentages and numbers of CD1d$^{hi}$CD5$^+$ B cells in one of two independent experiments with 3 mice in each group. The horizontal dashed line is provided for reference to wild type mice. (FIG. 21B) IL-10 production by B cells. Splenocytes were cultured with L+PIM for 5 h, stained with CD19 or CD20 mAb, permeabilized, and stained using IL-10 mAb with flow cytometry analysis. Representative frequencies of IL-10-producing cells within the indicated gates among total CD19$^+$ or CD20$^+$ B cells. Bar graphs indicate mean (±SEM) percentages and numbers of B cells that produced IL-10 in one of two independent experiments with 3 mice in each group. The horizontal dashed line is for reference.

FIG. 22A-FIG. 22D. In vitro B cell stimulation induces IL-10 production and secretion. CD19$^+$ splenocytes were purified from (FIG. 22A, FIG. 22B) wild type mice, or (FIG. 22C, FIG. 22D) wild type (filled bars) and MyD88$^{-/-}$ (open bars) littermates. Purified B cells were cultured with media alone, LPS, L+PIM, agonistic CD40 mAb, mitogenic anti-IgM Ab, or various combinations of these stimuli for the times indicated. For cytoplasmic IL-10 staining, PIM was added as indicated during the last 5 hours of all cultures before the cells were isolated, stained with CD19 mAb, permeabilized, and stained with IL-10 mAb for flow cytometry analysis. (FIG. 22A) Values within representative histograms indicate the percentage of IL-10-producing cells within the gates shown among total B cells. Monensin was added for 5 hours to media-only and LPS-only cultures. (FIG. 22B, FIG. 22D) For measuring secreted IL-10, culture supernatant fluid was harvested from cultured cells at the times indicated, with IL-10 concentrations determined by ELISA. Bar graphs indicate mean (±SEM) percentages or mean IL-10 (±SEM) concentrations from (FIG. 22A, FIG. 22B) one of 3 independent experiments with 3 mice in each group, or (FIG. 22C, FIG. 22D) one experiment with 3 mice in each group. (FIG. 22A-FIG. 22D) Significant differences between sample means are indicated: *p<0.05, **, p<0.01.

Figures 23A, 23B:
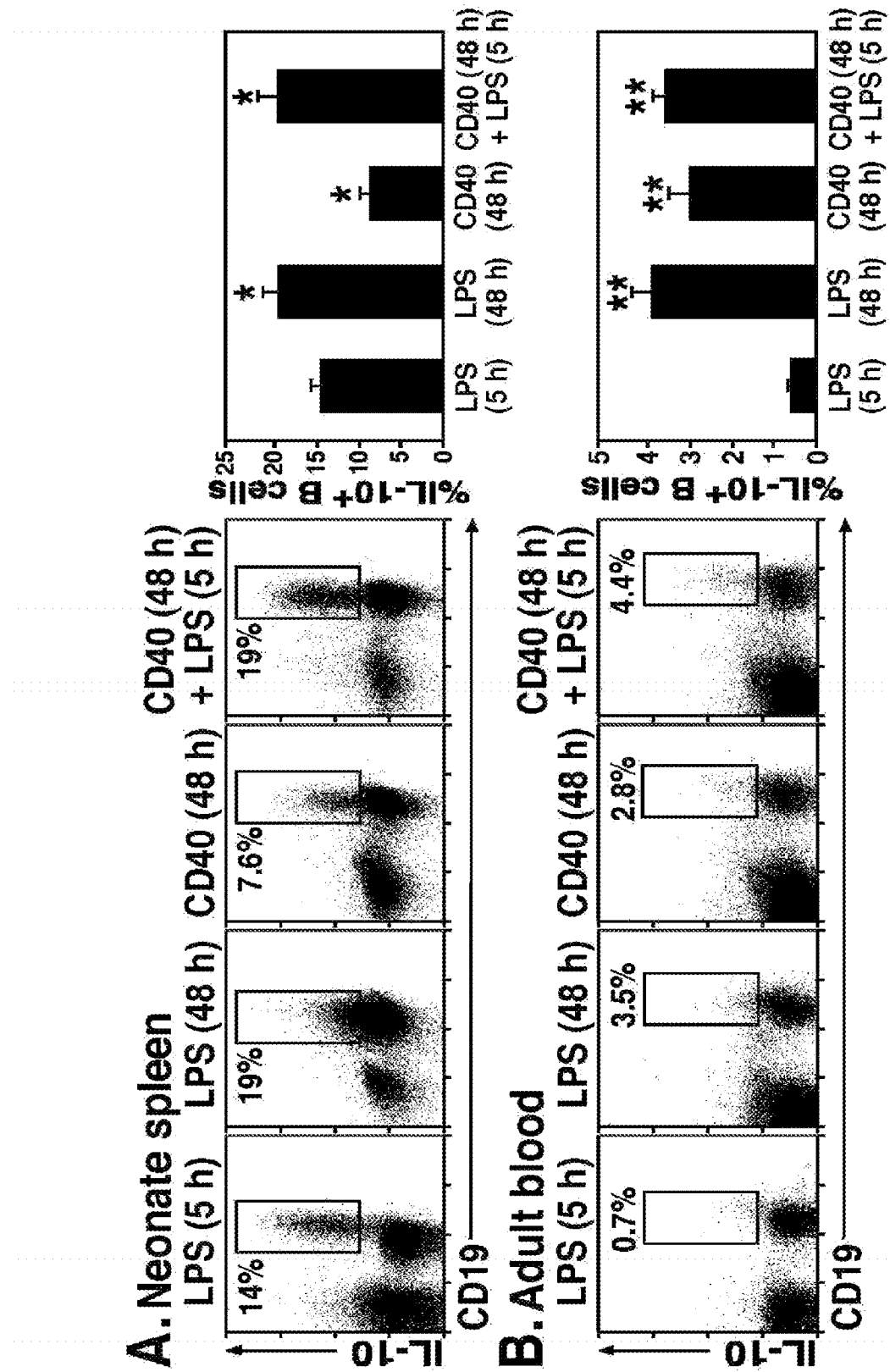
Figure 23C:
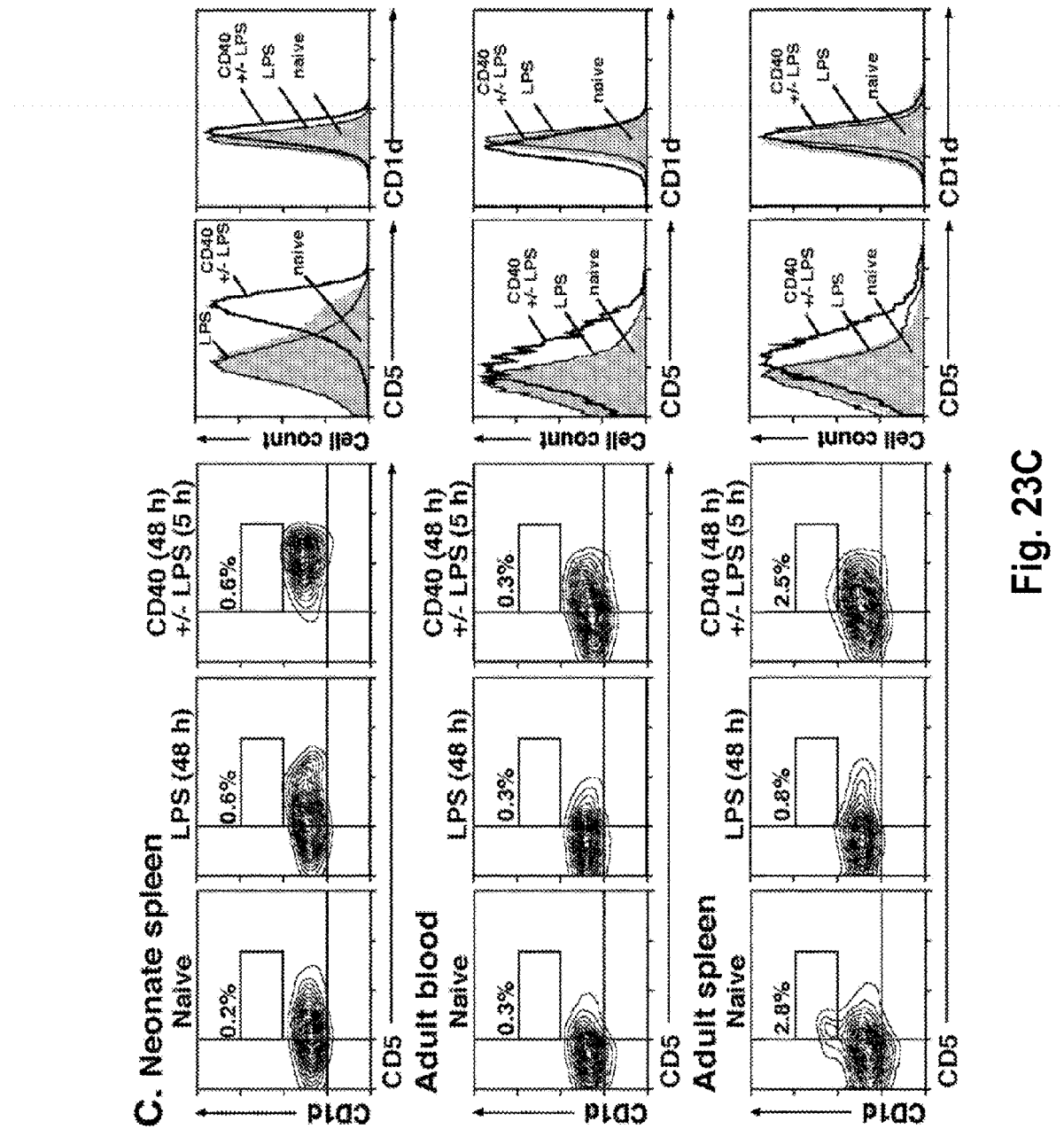

FIG. 23A-FIG. 23C. LPS and CD40 signals induce the maturation of B10 progenitor cells. LPS and CD40 mAb induce IL-10 production by (FIG. 23A) neonatal spleen or (FIG. 23B) adult blood B cells from wild type mice. (FIG. 23A-FIG. 23B) Cells were cultured with LPS, agonistic CD40 mAb, or both for the times indicated, with PIM added during the last 5 hours of each culture. The cultured cells were isolated, stained with CD19 mAb, permeabilized, and stained using IL-10 mAb with flow cytometry analysis. Values within representative histograms indicate the percentage of IL-10-producing cells among CD19$^+$ B cells within the gates shown. Bar graphs indicate mean (±SEM) percentages of IL-10 producing B cells in one of two independent experiments with 3 mice in each group. Significant differences between sample means are indicated: *p<0.05, **, p<0.01. (FIG. 23C) CD40 stimulation induces B cell CD5 expression. Cell surface CD1d and CD5 expression by wild type CD19$^+$ cells was determined by immunofluorescence staining. Neonatal splenocytes, or adult blood and spleen B cells were freshly isolated, or cultured for 48 hours with LPS or agonistic CD40 mAb (plus or minus LPS for the last 5 hours of culture). Values indicate the percentage of CD1d$^{hi}$CD5$^+$ B cells among total B cells within the indicated gates. Single color histograms are representative of two independent experiments with 3 mice in each group.

Figure 24A:
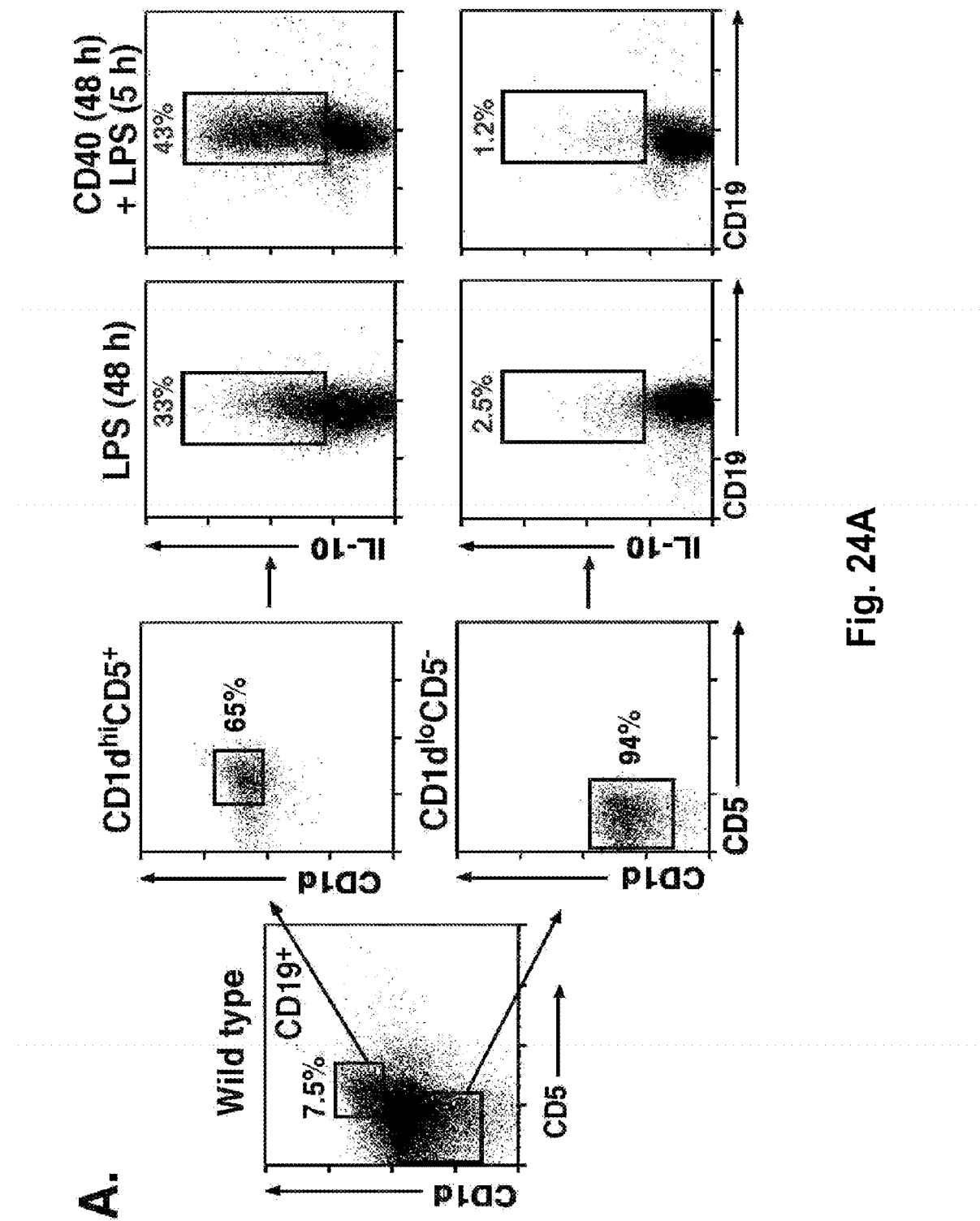
Figures 24B, 24C:
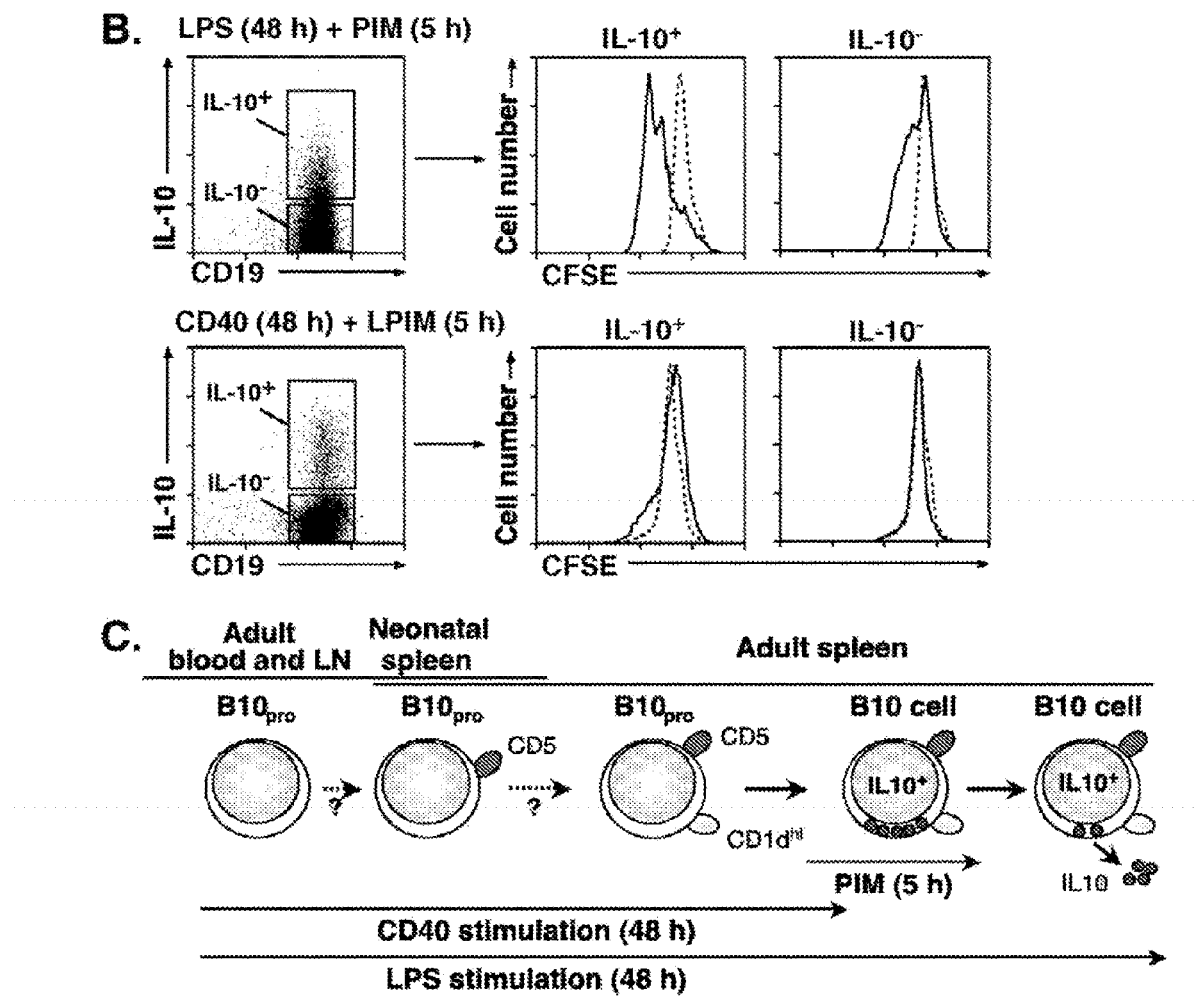

FIG. 24A-FIG. 24C. Effect of LPS or CD40 ligation on IL-10 production, proliferation, and the phenotype of CD1d$^{hi}$CD5$^+$ B cells. (FIG. 24A) LPS and CD40 mAb-induced cytoplasmic IL-10 production are restricted to CD1d$^{hi}$CD5$^+$ B cells. CD1d$^{hi}$CD5$^+$ or CD1d$^{lo}$CD5$^-$ B220$^+$ B cells were purified from pooled splenocytes of three wild type mice by cell sorting and reassessed for CD1d and CD5 expression (middle panels). The purified B cell subsets were cultured with LPS or CD40 mAb for 48 h, with L+PIM added for the last 5 hours of culture before permeabilization, staining for IL-10, and flow cytometry analysis (right panels). The frequencies of IL-10$^+$ cells among the sorted CD1d$^{hi}$CD5$^+$ or CD1d$^{lo}$CD5$^-$ B cell subsets are shown for one of two independent experiments. (FIG. 24B) Clonal expansion of IL-10-producing B cells after LPS but not CD40 stimulation in vitro for 48 h. Wild type CD19$^+$ splenocytes were labeled with CFSE and cultured with LPS or CD40 mAb for 48 h, with L+PIM added for the last 5 hours of culture. Histograms (right) represent CFSE expression by the IL-10$^+$ or IL-10$^-$ B cell subsets. Dashed lines represent CFSE staining of unstimulated B cells. (FIG. 24A-FIG. 24B) Data are representative of 2 independent experiments. (FIG. 24C) Potential B10 developmental pathway leading to the generation of the IL-10 secreting B10 cell subset. Dashed arrows and question marks represent potential maturation steps based on CD5 and CD1d expression patterns.

FIG. 25A-FIG. 25E. B cell depletion enhances lymphoma killing by CD20 mAb in vivo. (FIG. 25A) CD20 and CD154 expression by primary BL3750 lymphoma cells. BL3750 cells (thick line) and spleen B220$^+$ cells from Eμ-cMy-cTG$^{+/-}$ mice (thin line) were assessed by three-color immunofluorescence staining with flow cytometry analysis. Background staining using a control (CTRL) mAb is shown (dashed line). Results are representative of two independent experiments. (FIG. 25B) CD20$^{-/-}$ mice are resistant to B cell depletion by CD20 mAb. Representative circulating IgM$^+$ B220$^+$ B cells in wild type or CD20$^{-/-}$ mice 6 days after CD20 mAb treatment. All mice were given 10$^6$ BL3750 cells subcutaneously 1 day before mAb treatment. Identical results were obtained in mice not given tumor cells. Percentages indicate the relative frequencies of cells within the gates. Results are representative of four independent experiments. (FIG. 25C) B cell depletion prolongs overall mouse survival. Wild type or CD20$^{-/-}$ mice were given 10$^5$ (n=9-10 mice/group; left panels) or 10$^6$ (n=10-18 mice/group; right panels) BL3750 cells on day 0 with CD20 (●) or control (○) mAb (250 μg/mouse) given on day 1 or days 1 and 7 (arrowheads) in ≥3 independent experiments. Statistical comparisons of survival used the Log-Rank test. (FIG. 25D) Representative dorsal tumors resected from control or CD20 mAb-treated wild type or CD20$^{-/-}$ mice 16 days after receiving 10$^6$ BL3750 cells. Line graphs indicate tumor volumes (±SEM) for wild type or CD20$^{-/-}$ mice given CD20 (●) or control (○) mAb (250 μg/mouse) on days 1 and 7 following 10$^6$ BL3750 cell transfer. Values represent mean (±SEM) tumor volumes observed in 3-6 mice for each group from 2 independent experiments. (FIG. 25E) Representative frequencies of IL-10 producing B cells among total spleen CD19$^+$ B cells in wild type mice or littermates given 10$^5$ BL3750 cells 28 days earlier, in comparison with B cells from CD20$^{-/-}$ and IL-10$^{-/-}$ mice, and BL3750 cells. Bar graphs indicate mean (±SEM) percentages of IL-10$^+$ cells among CD19$^+$ B cells in wild type mice (open bars) or littermates given BL3750 cells (filled bars) either 14 or 28 days earlier, with three mice in each group. (FIG. 25D-FIG. 25E) Significant differences between means are indicated; *p<0.05, **p<0.01.

Figures 26A, 26B:
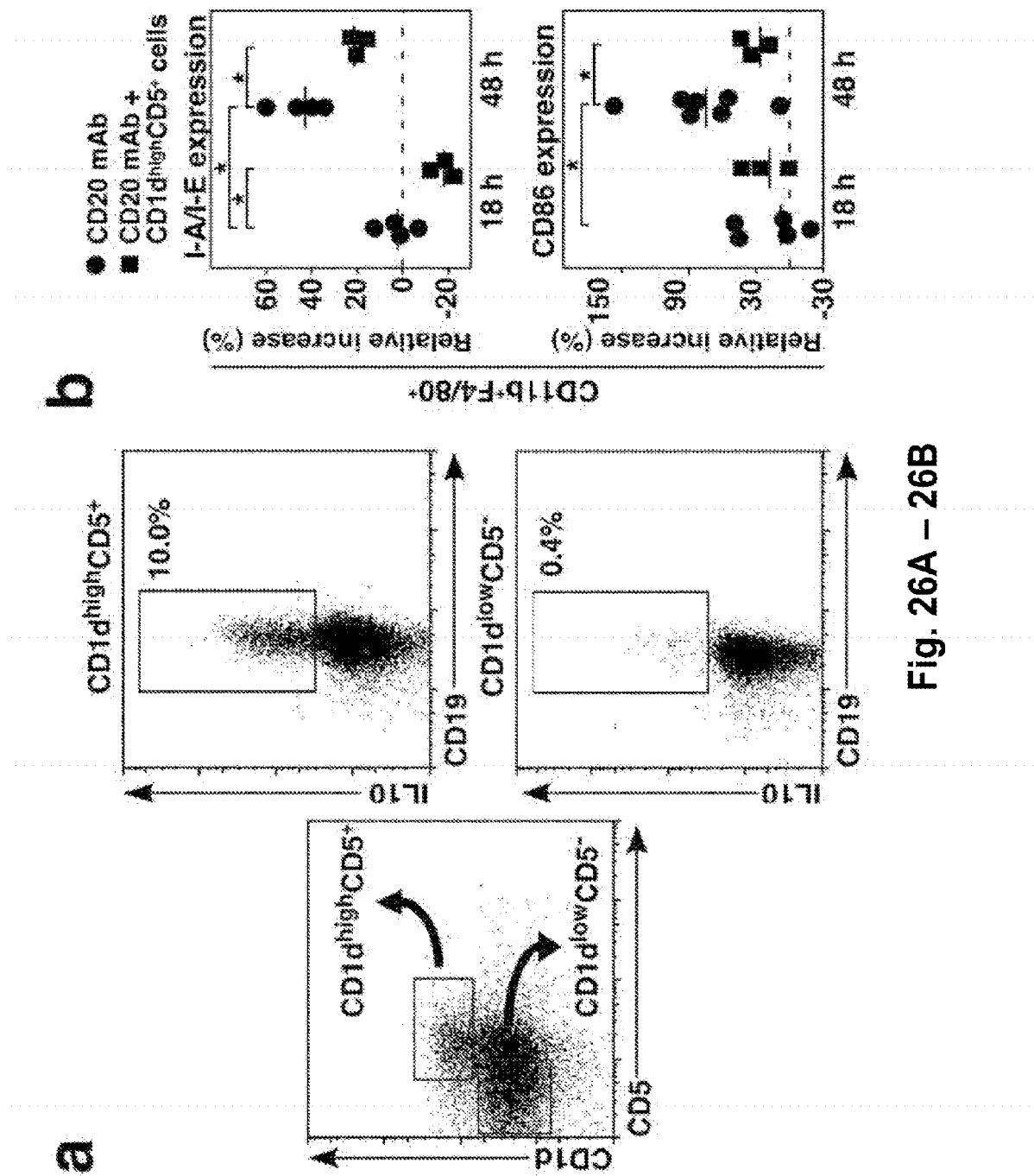
Figure 26C:
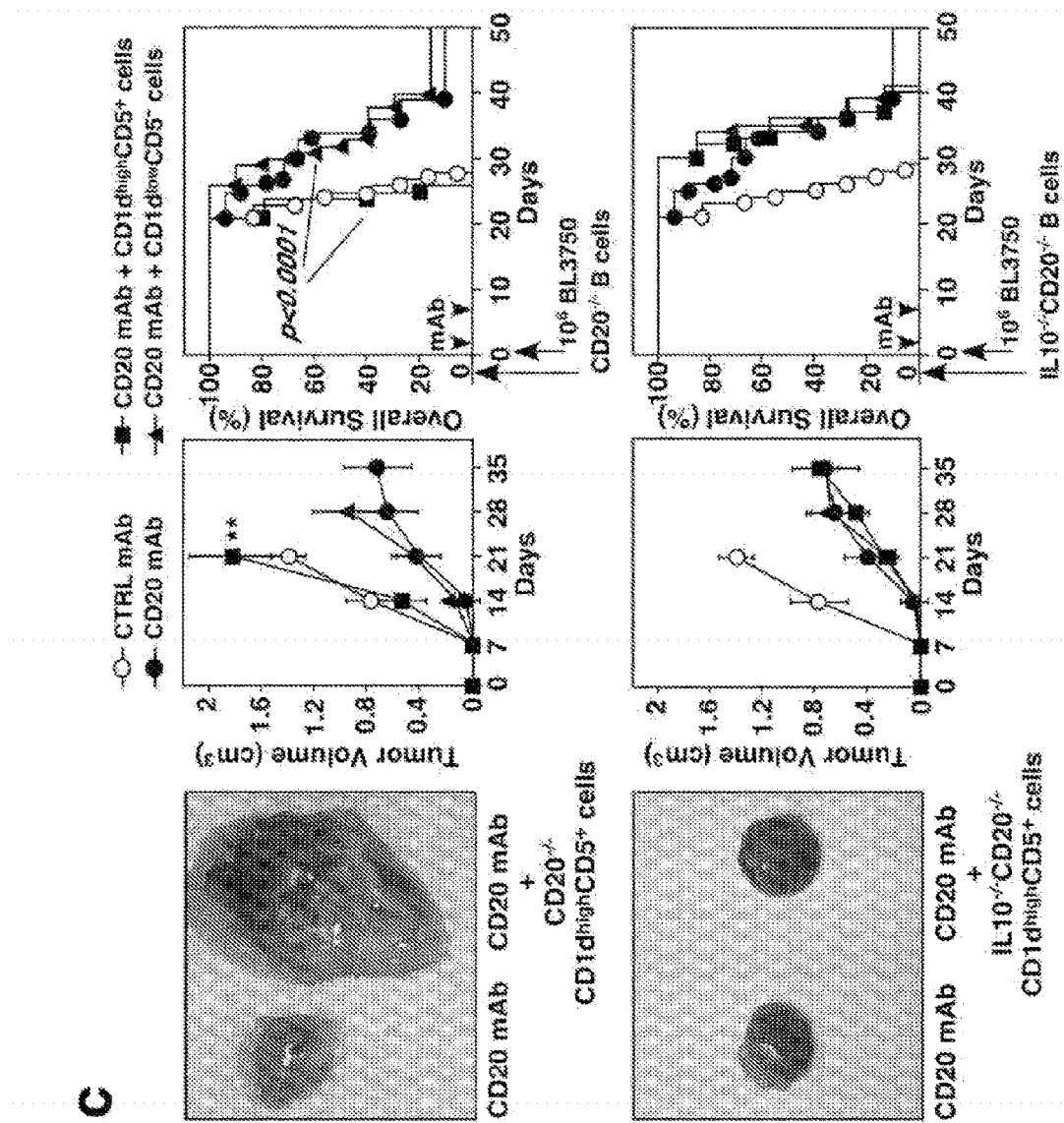

FIG. 26A-FIG. 26C. Regulatory CD1d$^{high}$CD5$^+$ B cells inhibit lymphoma killing by CD20 mAb in vivo through IL-10 dependent mechanisms. (FIG. 26A) Representative purification of splenic CD19$^+$ B cells from CD20$^{-/-}$ mice into CD1d$^{high}$CD5$^+$ and non-CD1d$^{high}$CD5$^+$ subsets. Percentages indicate IL-10$^+$ cell frequencies among the indicated B cell subsets as determined by flow cytometry analysis. (FIG. 26B) CD1d$^{high}$CD5$^+$ B cells inhibit macrophage activation in vivo. Wild type mice were untreated (●) or given CD1d$^{high}$CD5$^+$ B cells from CD20$^{-/-}$ mice (■, 2×10$^6$/mouse) one day before CD20 mAb treatment. Spleen CD11b$^+$F4/80$^+$ macrophages were isolated 18 and 48 hours after CD20 mAb treatment and assessed for MHC class II (I-A/I-E) and CD86 expression by immunofluorescence staining. Graphs indicate an increase (%) in mean fluorescence staining intensities relative to wild type mice treated with control mAb (dashed horizontal line). Values represent individual mice, with horizontal bars indicating means. (FIG. 26C) CD1d$^{high}$CD5$^+$ B cells inhibit lymphoma killing by CD20 mAb through IL-10 production. B cell subsets purified from CD20$^{-/-}$ or IL-10$^{-/-}$CD20$^{-/-}$ mice were given to wild type recipients (2×10$^6$/mouse) one day before receiving 10$^6$ BL3750 tumor cells on day 0. CD20 or control mAbs (250 μg/injection, arrowheads) were given on days 1 and 7. Representative dorsal tumors were resected from mice on day 16. Tumor volumes (±SEM) and overall mouse survival were quantified after tumor challenge and control (○), CD20 mAb (●), CD20 mAb plus CD1d$^{high}$CD5$^+$ B cells (■), or CD20 mAb plus non-CD1d$^{high}$CD5$^+$ B cell (▲) treatments (n=10-18 mice/group) as indicated. Results represent pooled data from 4 independent experiments. (FIG. 26B-FIG. 26C) Significant differences between means are indicated, *p<0.05, **p<0.01.

Figures 27A, 27B, 27C:
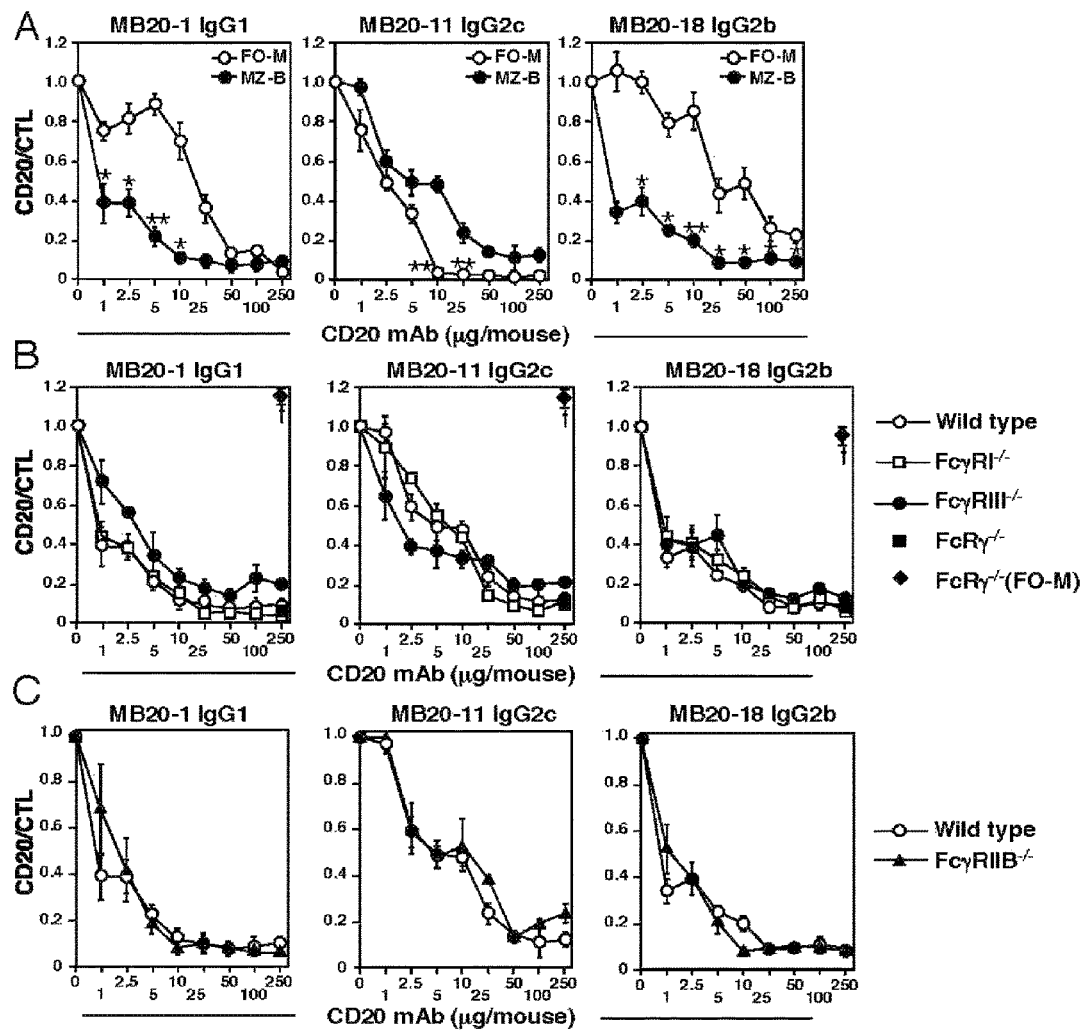

FIG. 27A-FIG. 27C. Mouse CD20 Ab-mediated marginal zone B cell depletion is independent of Fc receptor expression. FIG. 27A) Spleen follicular mature B cell (FO-M, CD21$^+$CD24$^+$ B220$^+$) and marginal zone B cell (MZ-B, CD21$^{high}$CD1d$^{high}$B220$^+$) numbers were determined 7 days after MB20-1 IgG1, MB20-11 IgG2c, MB20-18 IgG2b, or isotype-matched control (CTL) mAb treatment of C57BL/6 mice. FIG. 27B) Marginal zone B cell depletion in wild type mice (open circles), FcγRI$^{-/-}$ mice (open squares), FcγRIII$^{-/-}$ mice (filled circles), and FcRγ$^{-/-}$ mice (filled squares). Follicular mature B cell depletion in FcRγ$^{-/-}$ mice is shown by filled diamonds. FIG. 27C) Marginal zone B cell depletion in wild type mice (open circles) and FcγRIIB$^{-/-}$ mice (filled triangles). FIG. 27A-FIG. 27C) Values (±SEM) represent the percentage of B cells present in CD20 mAb-treated mice (n=3) relative to control mAb-treated littermates (n=3) at each mAb dose evaluated. Significant differences between sample means are indicated (*, p<0.05; **, p<0.01; †, p<0.01).

Figure 28A:
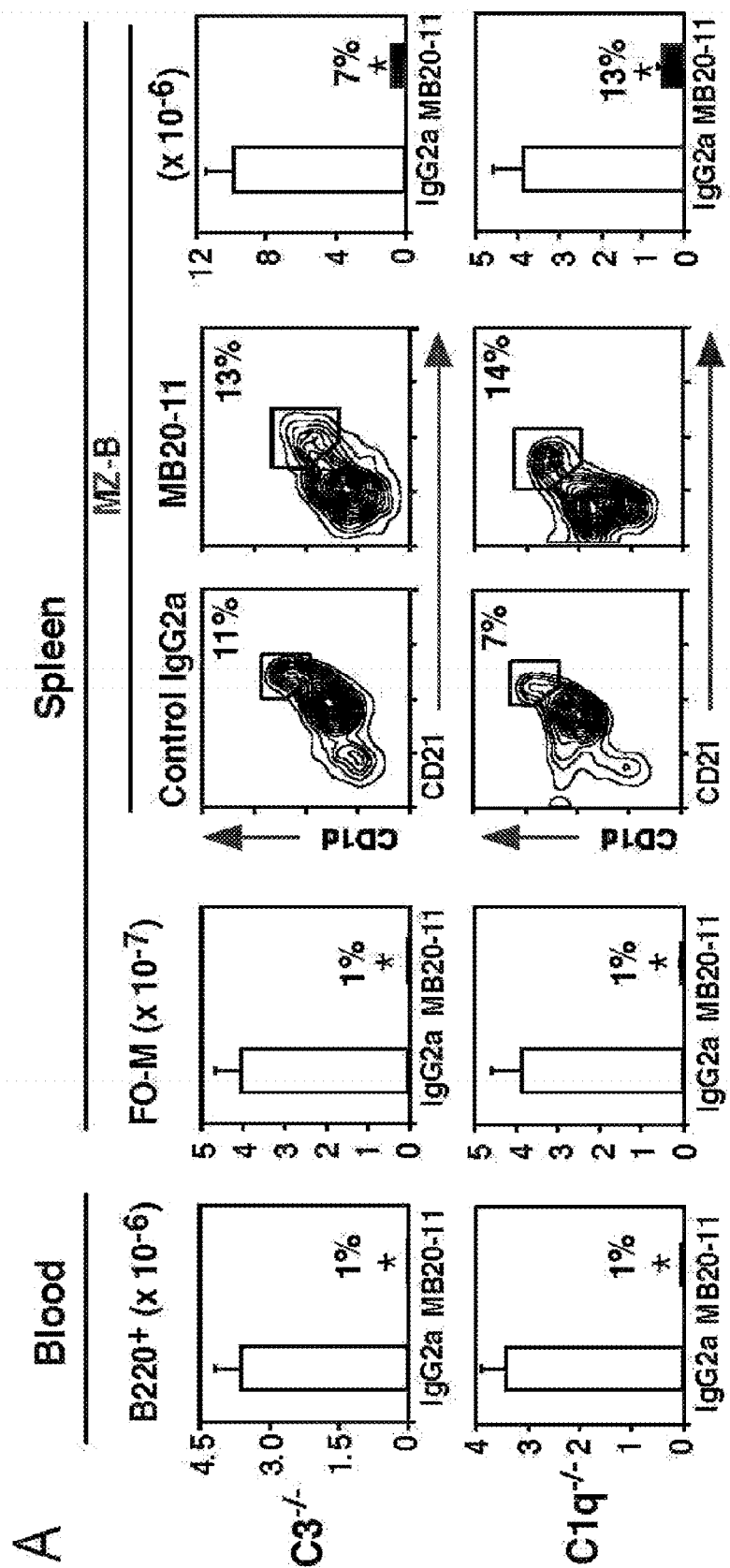
Figure 28B:
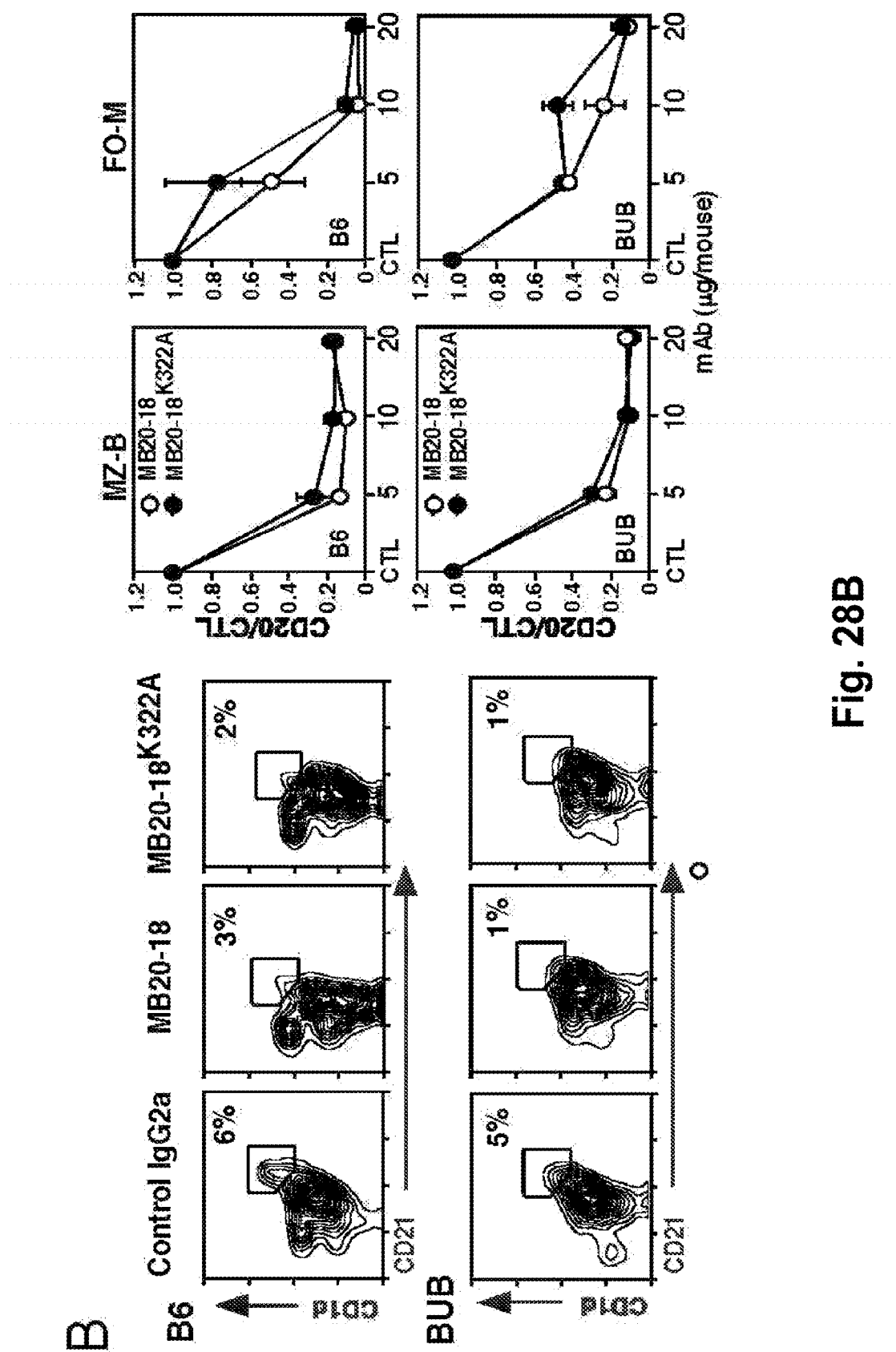

FIG. 28A-FIG. 28B. Mouse CD20 mAb-mediated marginal zone B cell depletion is complement-independent pathway. FIG. 28A) Blood (B220$^+$), spleen FO-M, and spleen MZ-B cell depletion in C3$^{-/-}$ or C1q$^{-/-}$ mice treated with MB20-11 CD20 mAb or control Ab (250 μg/mouse). Values (±SEM) indicate mean B cell numbers 7 days after mAb treatment (n=3). FIG. 28B) MB20-18 IgG2a (open squares) or MB20-18 IgG2a$_{K322A}$ (filled squares) mAb depletion of FO-M and MZ-B cells in C57BL/6 (B6) and BUB mice. B cell numbers were determined 7 days after mAb treatment at the indicated mAb doses. Values (±SEM) represent percentages of B cells present in mAb-treated mice relative to control mAb treated littermates (n=3).

Figure 29A:
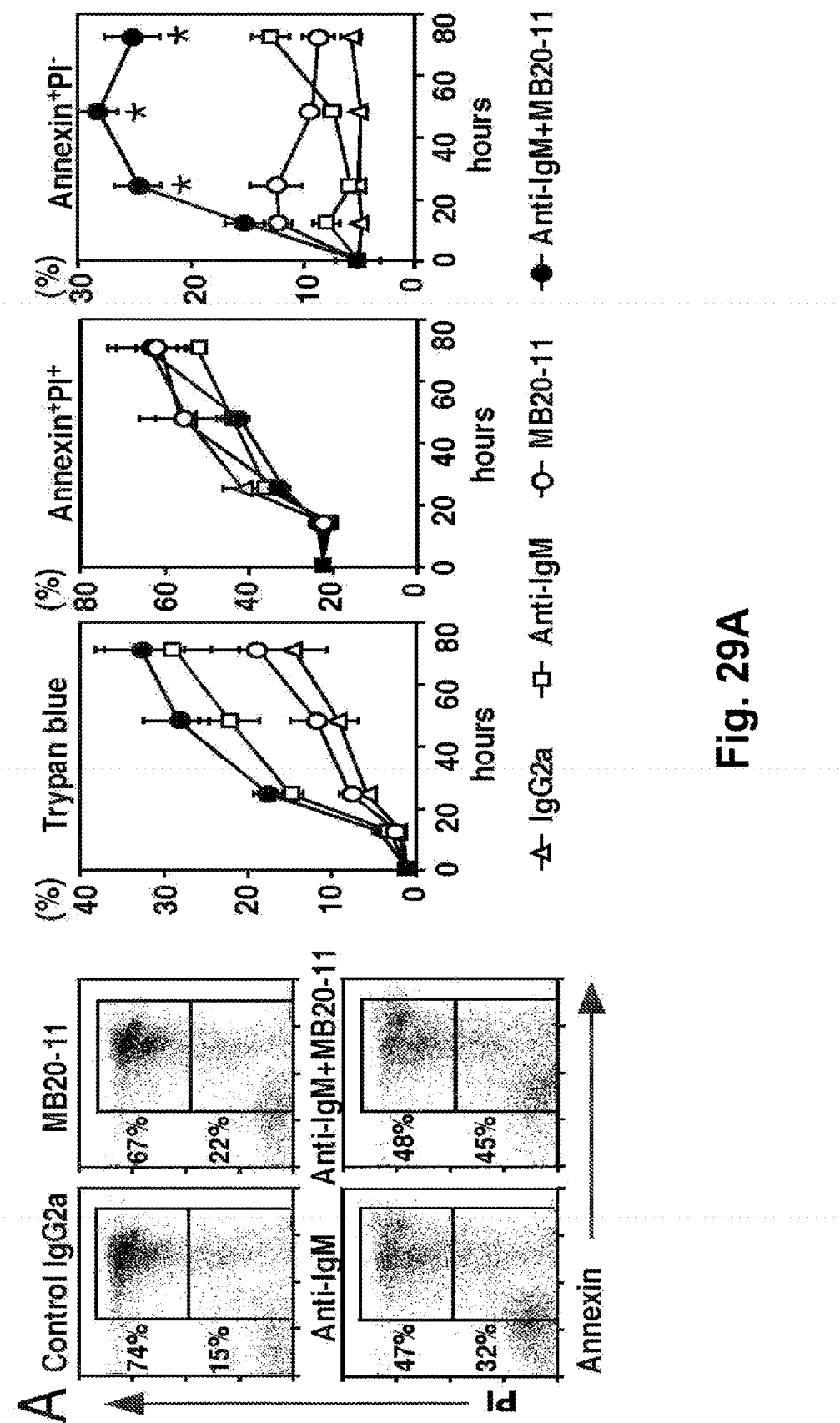
Figure 29B:
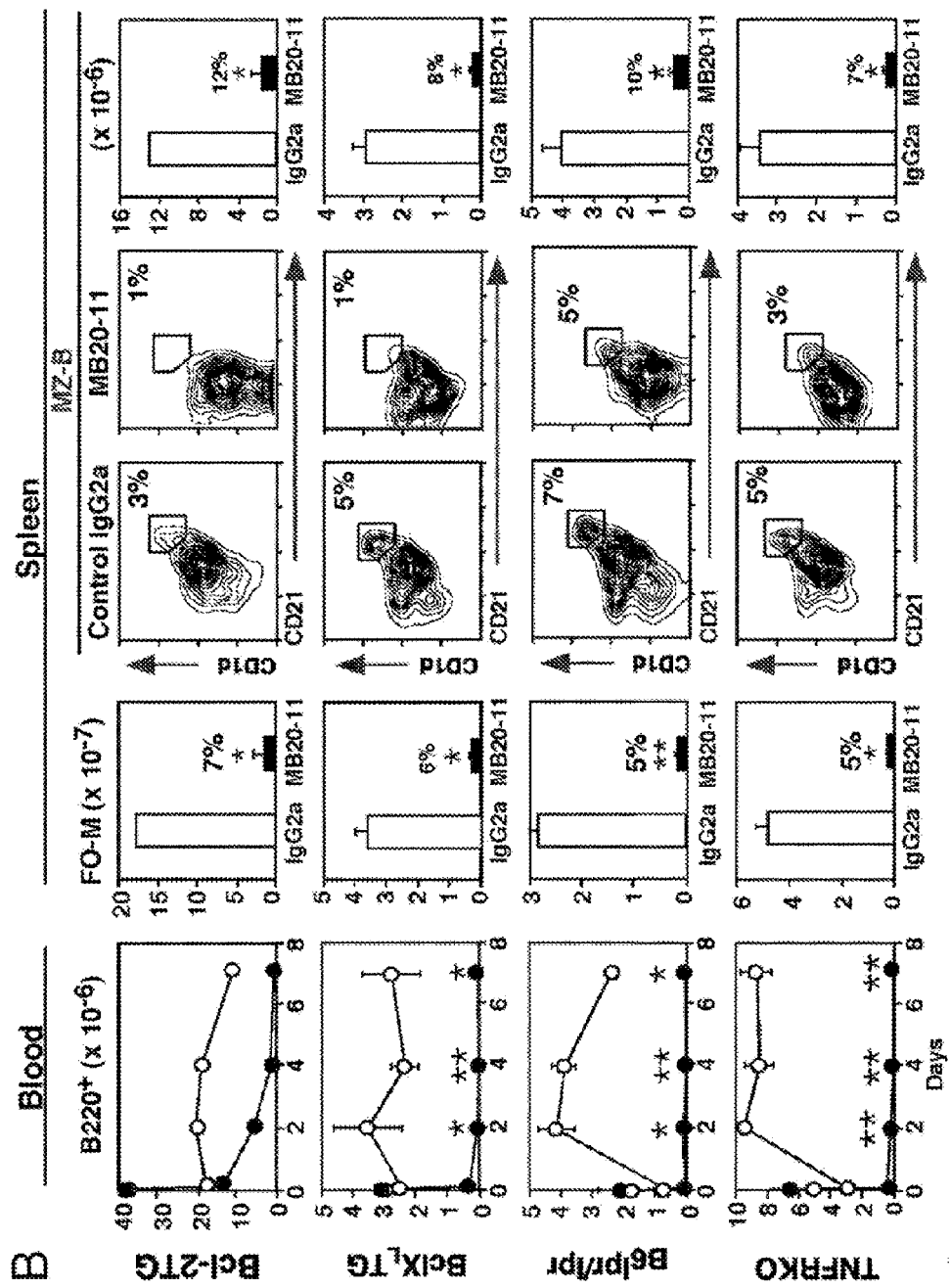
Figure 29C:
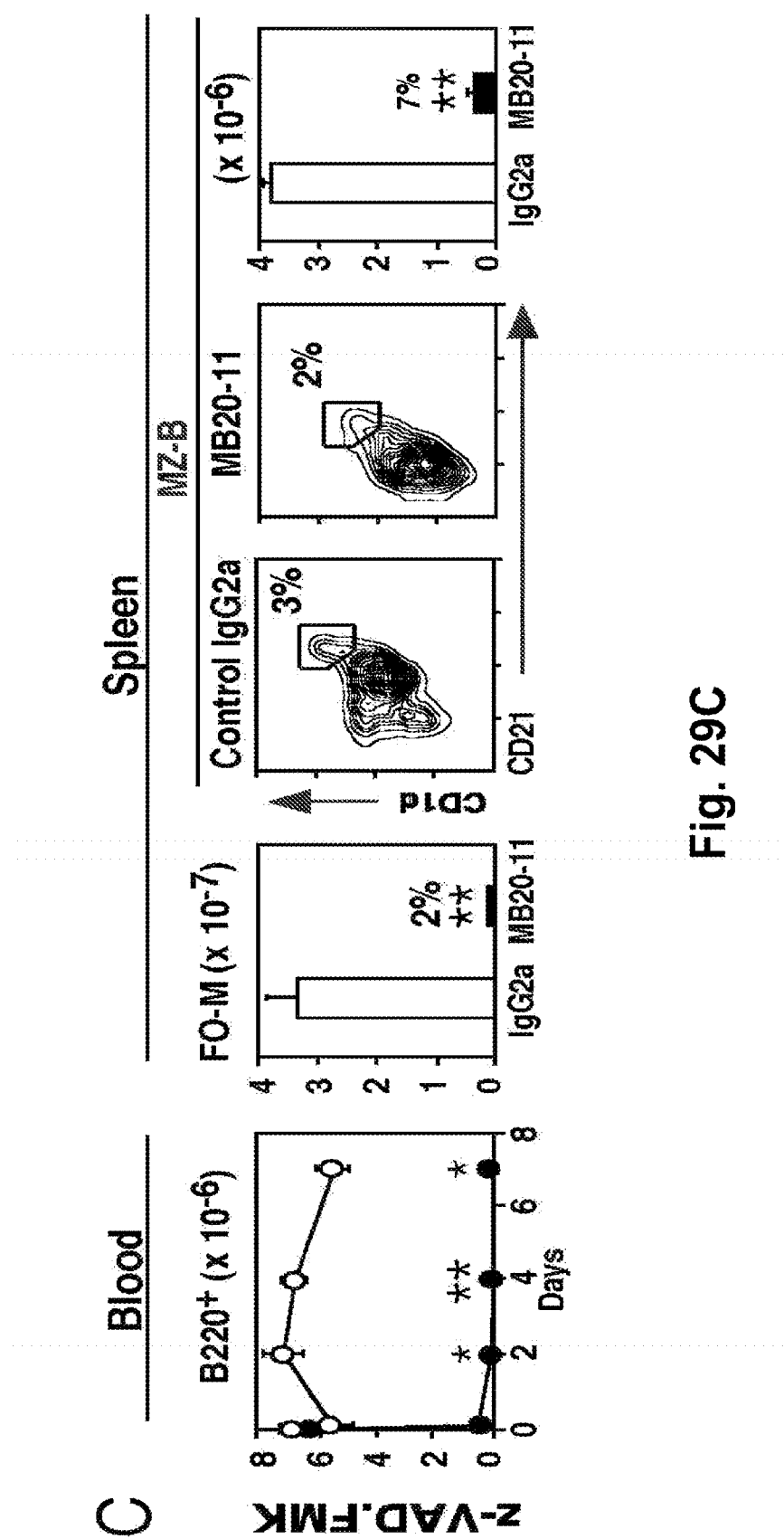

FIG. 29A-FIG. 29C. Caspase-dependent apoptosis pathway is not involved in CD20 mAb-mediated marginal zone B cell depletion. FIG. 29A) CD20 mAb alone did not induce B cell apoptosis in vitro. Purified splenic B cells from wild type mice cultured with control mAb (open triangles), MB20-11 mAb (open circles), anti-IgM F(ab')$_2$Ab (open squares) or MB20-11 mAb plus anti-IgM F(ab')$_2$Ab (filled circles). After 12, 24, 36, and 72 hours, the cells were harvested and apoptotic cells were identified by annexinV and PI staining followed by FACS analysis. Histograms represent the data obtained at 72 hours. These results are representative of three experiments. FIG. 29B-FIG. 29C) Blood and spleen FO-M and MZ-B cell numbers (±SEM) after MB20-11 (filled circles/bars) or isotype control (open circles/bars) mAb treatment (250 μg/mouse) in Bcl-2 TG (n=3), Bcl-X$_L$TG (n=4), B6$^{lpr/lpr}$ (=3), or TNFR$^{-/-}$ mice (n=5), or z-VAD.FMK-treated C57BL/6 mice (n=3). Significant differences between sample means are indicated (*, p<0.05; **, p<0.01).

Figure 30:
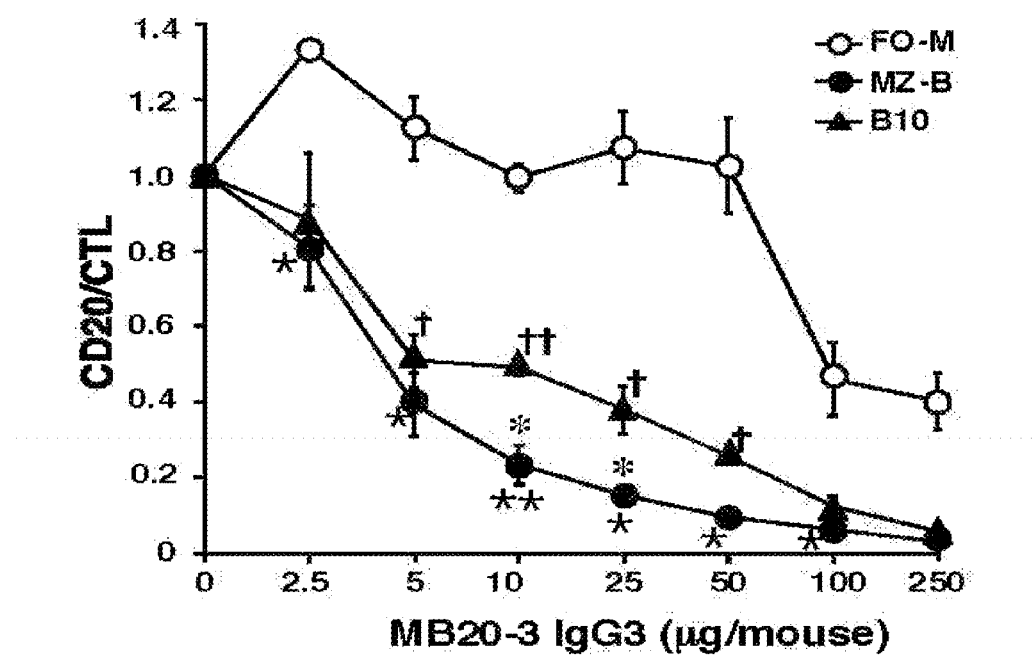

FIG. 30. Spleen FO-M, MZ-B and B10 cell (B220+ CD19+IL10+) numbers were determined 7 days after MB20-3 IgG3 mAb treatment at indicated Ab doses. Values (±SEM) represent the percentage of B cells present in mAb-treated mouse (n=3) relative to control mAb-treated littermates (n=3). Significant differences between sample means are indicated (*, p<0.05; **, p<0.01; †, p<0.05; ††, p<0.01).

FIG. 31A-FIG. 31B. FIG. 31A) Spleen FO-M and MZ-B cell numbers were determined in C57BL/6 mice 7 days after MB20-3 (black bars), MB20-13 (grey bars), MB20-18 (hatched bars), or control mAb (white bars) treatment (50 μg/mouse). FIG. 31B) Splenocytes from control, MB20-3, MB20-13, or MB20-18 mAb treated C57BL/6 mice were stimulated with LPS, PMA, ionomycin, and monensin for 5 hours. CD1d and CD5 expression on B220$^+$ cells (upper panel) and the frequencies of IL-10 producing B cells (lower panel) were determined by immunofluorescence staining. Bar graphs indicated mean (±SEM) percentages and numbers of B cells that produced IL-10 in one representative experiment with three mice per group. FIG. 31A-FIG. 31B) Significant differences between sample means are indicated (*, p<0.05; **, p<0.01).

Figures 32A, 32B:
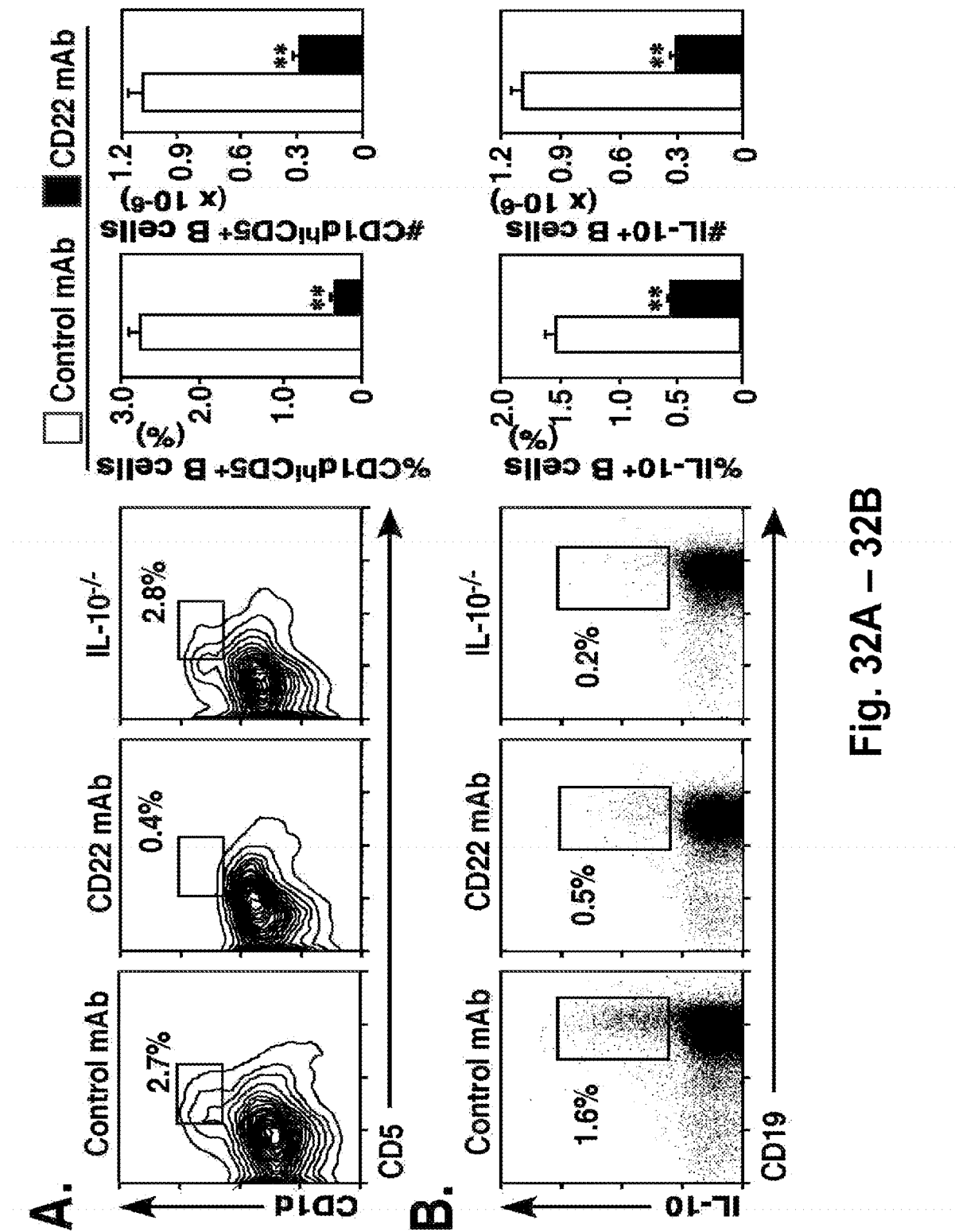

FIG. 32A-FIG. 32B. CD22 mAb depletes B10 cells. Eight week-old C57BL/6 mice were treated with CD22 mAb (MB22-10; 250 μg/mouse) or control mAb (B1; 250 μg/mouse) 7 days before analysis. (FIG. 32A) Representative CD1d and CD5 expression by CD19$_+$ B cells. Splenocytes were stained with CD1d, CD5, and CD19 mAbs with flow cytometry analysis of viable cells. Results represent one mouse indicating the frequency of CD1d$_{hi}$CD5$_+$ B cells among total B cells within the indicated gates. Bar graphs indicate mean (±SEM) percentages and numbers of CD1d$_{hi}$CD5$_+$ B cells in one of two independent experiments with three mice in each group. (FIG. 32B) IL-10 production by B cells. Splenocytes were cultured with LPS (10 µg/ml), PMA (50 ng/ml), ionomycin (500 ng/ml), and monensin (2 µM) for 5 h, then stained with B220 and CD19 mAb to identify B cells, permeabilized, and stained using IL-10 mAb with flow cytometry analysis of viable cells. Representative results demonstrate the frequency of IL-10-producing cells among total B220₊ B cells within the indicated gates. Bar graphs indicate mean (±SEM) percentages and numbers of B cells that produced IL-10 in one of two independent experiments with three mice in each group. Leukocytes from IL-10$_{-/-}$ mice served as negative controls to demonstrate specificity and to establish background IL-10 staining levels. (A, B) Significant differences between sample means are indicated: **, p<0.01.

5. DETAILED DESCRIPTION

The present invention relates to a phenotypically distinct CD1d$^{high}$CD5$^+$ B cell subset that regulates T cell mediated inflammatory and immune responses through secretion of IL-10. The invention also relates to harnessing this regulatory B cell subset for the manipulation of the immune and inflammatory responses, and for the treatment of diseases, disorders and conditions associated with altered IL-10 levels, including inflammatory and autoimmune diseases, as well as immunosuppression and cancer in humans and other mammals.

Cellular compositions enriched for the CD1d$^{high}$CD5$^+$ B cell subset, and methods for their preparation are described. These cellular compositions can be expanded and used in adoptive transfer therapies to treat conditions associated with diminished IL-10 production, e.g., inflammatory and/or autoimmune conditions or diseases. In an alternative approach, therapeutic regimens designed to expand the endogenous population of the CD1d$^{high}$CD5$^+$ B cell subset, or increase their production of IL-10 can be used to treat inflammatory and/or autoimmune conditions or diseases in subjects in need thereof. In this approach, antibodies that activate and/or stimulate expansion of the regulatory B cell subset, or increase their production of IL-10 can be used. Expansion can be accomplished in vivo (e.g., by direct administration of the antibody or receptor agonist) or ex vivo (e.g., by activating the cells obtained from the subject and returning the activated cells to the subject).

In another embodiment, methods are described for treating diseases, disorders and conditions associated with enhanced IL-10 production, e.g., conditions involving immunosuppression and certain cancers. These therapeutic approaches involve depleting or ablating the endogenous CD1d$^{high}$CD5$^+$ regulatory B cell subset, or inhibiting their production of IL-10 in subjects in need thereof. In this approach, antibodies that kill the regulatory B cell subset, or inhibit their proliferation or their production of IL-10 can be used.

In yet another embodiment, methods for identifying the regulatory B cell subset in patients and/or patient samples are described for diagnosing the immune status of affected individuals.

In another embodiment, a method for generating an antibody that preferentially or selectively depletes the regulatory B cell population is provided, the method comprising: (i) selecting an antibody that binds to a marker that is presently known or subsequently determined to be expressed by regulatory B cells including, e.g. CD5, CD19, CD20, CD21, CD22, CD24, CD40 and CD72; (ii) assaying the antibody for the ability to induce homotypic adhesion of B cells (Kansas G S, Wood G S, Tedder T F. Expression, distribution and biochemistry of human CD39: Role in activation-associated homotypic adhesion of lymphocytes. *J Immunol.* 1991; 146:2235-2244; Kansas G S, Tedder T F. Transmembrane signals generated through MHC class II, CD19, CD20, CD39 and CD40 antigens induce LFA-1-dependent and -independent adhesion in human B cells through a tyrosine kinase-dependent pathway. *J Immunol.* 1991; 147: 4094-4102.; Wagner N, Engel P, Vega M, Tedder T F. Ligation of MHC class I and class II molecules leads to heterologous desensitization of signal transduction pathways that regulate homotypic adhesion in human lymphocytes. *J Immunol.* 1994; 152:5275-5287.); (iii) assaying the antibody for the ability to deplete the regulatory B cell population; and (iv) if needed, modifying the Fc region of the antibody so that the mechanism of depletion of the regulatory B cell population by the antibody is independent of the antibody's Fc region.

5.1 the Regulatory B Cell Subset

The present invention relates to a regulatory subset of the normal B cell population characterized phenotypically as CD1d$^{high}$CD5$^+$, and functionally by its ability to produce IL-10. The invention also relates to therapeutic uses of this regulatory B cell population.

The regulatory B cell phenotype can be determined by antibody staining and flow cytometry, FACS, using antibodies to CD1d and CD5 and techniques known in the art, including but not limited to those described in the examples, infra. See, e.g., Section 6 et seq. The invention is based, in part, on the surprising discovery that cellular compositions enriched by selection for both CD1d$^{high}$ and CD5 cellular markers will contain a high percentage of IL-10 producing B cells than a population enriched with only one of these markers.

The ability of the cells to produce IL-10 can be assessed by measuring IL-10 production in naïve cells and in cultured cells stimulated with LPS (lipopolysaccharide), PMA (phorbol 12-myristate 13-acetate), ionomycin, CpG or comparable stimulatory Toll-like receptor agonists, or with an agonist of CD40 (e.g., using an antibody to CD40). Production of IL-10 by the cells can be assessed by assaying for IL-10 in the cell culture supernatant. In addition, production of IL-10 can be verified directly by intracellular cytokine staining. Standard immunoassays known in the art can be used for such purpose. Examples of assays for IL-10 production are described in Section 6, infra. While IL-10 is produced at low levels in the naïve CD1d$^{high}$CD5$^+$ B cell subset, IL-10 production is increased in response to stimulation.

5.1.1 Cellular Compositions Enriched in the Regulatory B Cell Subset

The enriched, isolated and/or purified regulatory B cell subset composition can comprise anywhere from 0.5% to 50%, at least 55%, at least 60%, at least 65%, at least 70%, at least 75%, at least 80%, at least 85%, at least 90%, at least 95%, at least 99%, or 100% regulatory B cells having the CD1d$^{high}$CD5$^+$ phenotype that produce IL-10 (as determined by the assays described above). In a preferred embodiment, the enriched/purified regulatory B cell subset comprises greater than 50% regulatory B cells having the CD1d$^{high}$CD5$^+$ phenotype. In a more preferred embodiment, the enriched/purified regulatory B cell subset comprises greater than 75% regulatory B cells having the CD1d$^{high}$CD5$^+$ phenotype. In a still more preferred embodiment, the enriched/purified regulatory B cell subset comprises greater than 90% regulatory B cells having the CD1d$^{high}$CD5$^+$ phenotype.

The enriched, isolated and/or purified CD1d$^{high}$CD5$^+$ regulatory B cells can be obtained from a mammalian subject, including but not limited to rodents, e.g. mice, rats; livestock, e.g. pigs, horses, cows, etc., pets, e.g. dogs, cats; and primates, e.g. humans. In one embodiment, the subject is an animal model of an IL-10 associated disease. The phenotypic markers described herein were identified in murine models; however, the invention contemplates that the cognate human regulatory B cell population will also produce IL-10, will be phenotypically distinct from other B cell populations, and will likely utilize the same transcription factors and display the same cell surface markers.

Alternatively, the regulatory B cells may be enriched/purified from any tissue where they reside including, but not limited to, blood (including blood collected by blood banks), spleen, bone marrow, tissues removed and/or exposed during surgical procedures, and tissues obtained via biopsy procedures. Tissues/organs from which the regulatory B cells are enriched, isolated, and/or purified may be isolated from both living and non-living subjects, wherein the non-living subjects are organ donors.

Methods for the isolation of the regulatory B cells are based on selecting cells having the CD1d$^{high}$CD5$^+$ cell-specific markers; however, additional markers can be included for selection, such as CD19$^{high}$. In a particular aspect of this embodiment, a population of regulatory B cells is enriched/purified by flow cytometry as demonstrated in the examples described in Section 6, infra. However, a variety of cell separation techniques known in the art can be used, including but not limited to magnetic separation using antibody-coated magnetic beads and/or particles, FACS, affinity chromatography, affinity column separation, "panning" with antibody attached to a solid matrix, density gradient centrifugation, and counter-flow centrifugal elutriation. (See, e.g., Kumar and Lykke, 1984, Pathology, 1:53-62).

According to these embodiments, a cellular composition enriched for the CD1d$^{high}$CD5$^+$ B cell subset that has been enriched by selection using both CD1d$^{high}$ and CD5 as cellular markers will contain a higher percentage of IL-10 producing B cells than one enriched using only one of these markers. The use of the CD1d$^{high}$ and CD5 markers to isolate/enrich/purify regulatory B cells that produce IL-10 has several advantages. Using these cell surface markers, as opposed to intracellular IL-10 as a marker, allows for the selection/sorting of the IL-10 producing B cell population without permeabilizing the cells, which would make them therapeutically useless.

Regulatory B cells can also be isolated by negatively selecting against cells that are not regulatory B cells. This can be accomplished by performing a lineage depletion, wherein cells are labeled with antibodies for particular lineages such as the T lineage, the macrophage/monocyte lineage, the dendritic cell lineage, the granulocyte lineages, the erythrocytes lineages, the megakaryocytes lineages, and the like. Cells labeled with one or more lineage specific antibodies can then be removed either by affinity column processing (where the lineage marker positive cells are retained on the column), by affinity magnetic beads or particles (where the lineage marker positive cells are attracted to the separating magnet), by "panning" (where the lineage marker positive cells remain attached to the secondary antibody coated surface), or by complement-mediated lysis (where the lineage marker positive cells are lysed in the presence of complement by virtue of the antibodies bound to their cell surface). Another lineage depletion strategy involves tetrameric complex formation. Cells are isolated using tetrameric anti-human antibody complexes (e.g., complexes specific for multiple markers on multiple cell types that are not markers of regulatory B cells, given in more detail infra) and magnetic colloid in conjunction with Stem-Sep columns (Stem Cell Technologies, Vancouver, Canada). The cells can then optionally be subjected to centrifugation to separate cells having tetrameric complexes bound thereto from all other cells.

In a certain embodiment, the enriched/purified population of regulatory B cells can be stored for a future use. In this regard, the regulatory B cell population can be stored by "cryopreservation." Cryopreservation is a process where cells or whole tissues are preserved by cooling to low sub-zero temperatures, such as 77 K or −196° C. in the presence of a cryoprotectant. At these low temperatures, any biological activity, including the biochemical reactions that would lead to cell death, is effectively stopped. Storage by cryopreservation includes, but is not limited to, storage in liquid nitrogen, storage in freezers maintained at a constant temperature of 0° C., storage in freezers maintained at a constant temperature of −20° C., storage in freezers maintained at a constant temperature of −80° C., and storage in freezers maintained at a constant temperature of lower than −80° C. In one aspect of this embodiment, the cells may be "flash-frozen," e.g., in ethanol/dry ice or in liquid nitrogen prior to storage. In another aspect of this embodiment, the cells can be preserved in medium comprising a cryprotectant including, but not limited to dimethyl sulfoxide (DMSO), glycerol, ethylene glycol, propylene glycol, sucrose, and trehalose. Other methods of storing biological matter are well known to those of skill in the art, such as "hibernation," wherein cells are stored at temperatures above freezing or by preservation of the cells in a "static" state, as described in U.S. patent application publication No. 2007/0078113, herein incorporated by reference in is entirety.

The population of regulatory B cells can be obtained from a subject in need of therapy or suffering from a disease associated with elevated or diminished levels of IL-10. Alternatively, the population of regulatory B cells can be obtained from a donor, preferably a histocompatibility matched donor. The regulatory B cell population may be harvested from the peripheral blood, bone marrow, spleen, or any other organ/tissue in which regulatory B cells reside in said subject or donor. In a further aspect, the regulatory B cells may be isolated from a pool of subjects and/or donors, or from pooled blood.

When the population of regulatory B cells is obtained from a donor distinct from the subject, the donor is preferably syngeneic, but can also be allogeneic, or even xenogeneic, provided the cells obtained are subject-compatible in that they can be introduced into the subject. Allogeneic donor cells are preferably human-leukocyte-antigen (HLA)-compatible, and are typically administered in conjunction with immunosuppressive therapy. To be rendered subject-compatible, xenogeneic cells may be subject to gamma irradiation or PEN110 treatment as described (Fast et al., 2004, Transfusion 44:282-5).

5.1.2. Enrichment of the Regulatory B Cell Subset

Regulatory B cells can be enriched by selecting cells having the CD1d$^{high}$CD5$^+$ surface markers and separating using automated cell sorting such as fluorescence-activated cell sorting (FACS), solid-phase magnetic beads, etc. as demonstrated in examples described in sections 6 and 7 infra. To enhance enrichment, positive selection may be combined with negative selection; i.e., by removing cells having surface markers specific to non-B cells and/or those specific to non-regulatory B cells. Non-limiting examples of methods of negative selection are described supra. Exemplary surface markers specific to non-regulatory B cells include CD3, CD4, CD7, CD8, CD15, CD16, CD34, CD56, CD57, CD64, CD94, CD116, CD134, CD157, CD163, CD208, F4/80, Gr-1, and TCR.

5.2 Expansion of the Regulatory B Cell Subset and/or Enhancing their Production of IL-10

In a particular embodiment, expansion of the regulatory B cell population is achieved by contacting the population of regulatory B cells with stimulatory composition sufficient to cause an increase in the number of regulatory B cells. This may be accomplished by contacting the enriched, isolated and/or purified B cell subset with a mitogen, cytokine, growth factor, or antibody. The regulatory B cells are preferably expanded at least 10-fold and preferably at least 50, 100, 200, 300, 500, 800, 1000, 10,000, or 100,000-fold. In a specific aspect of this embodiment, the expanded regulatory B cell population retains all of the genotypic, phenotypic, and functional characteristics of the original population. In another embodiment, one or more of the characteristics of the regulatory B cell population is lost or modified following expansion.

Levels of IL-10 produced by the regulatory B cell subset can be increased by administration of agonists to the B cell surface receptor CD40. Non-limiting examples of CD40 agonists include anti-CD40 antibodies and fragments thereof, the CD40 ligand and polypeptide fragments thereof, small molecules, synthetic drugs, peptides (including cyclic peptides), polypeptides, proteins, nucleic acids, synthetic or natural inorganic molecules, mimetic agents, and synthetic or natural organic molecules.

In a certain embodiment, the CD40 agonist is an anti-CD40 antibody. The anti-CD40 antibodies of the invention can be of any form, as disclosed above. Antibodies to CD40 are known in the art (see, e.g., Buhtoiarov et al., 2005, J. Immunol. 174:6013-22; Francisco et al., 2000, Cancer Res. 60:3225-31; Schwulst et al., 2006, 177:557-65, herein incorporated by reference in their entireties).

Expansion of IL-10 production by the regulatory B cell subset can be advantageously achieved ex vivo, i.e., by isolating the enriched $CD1d^{high}CD5^+$ population and contacting the cells with a CD40 agonist. In an aspect of this embodiment, the cells are contacted with a CD40 agonist and relevant antigen(s). In a specific aspect of this embodiment, the cells are contacted with both an anti-CD40 antibody and relevant antigen(s).

5.3 Ablation of the Regulatory B Cell Subset and/or Inhibiting their Production of IL-10

The regulatory B cell subset can be ablated by engaging the B cell surface receptor CD22. Non-limiting examples of compounds capable of engaging CD22 to ablate the regulatory B cell population include anti-CD22 antibodies and fragments thereof, the CD22 ligand and fragments thereof, CD22 ligand mimetics, small molecules, synthetic drugs, peptides (including cyclic peptides), polypeptides, proteins, nucleic acids, synthetic or natural inorganic molecules, mimetic agents, and synthetic or natural organic molecules. Antibodies to CD22 are known in the art (see, e.g., Tuscano et al., 2003, Blood 101:3641-7; US 2004/0001828 A1; and US 2007/0264360, incorporated by reference herein in their entireties).

Alternatively, a bispecific antibody for CD1d and CD5 may be used to target the regulatory B cell subset (these will be referred to herein as bispecific "anti-CD1d/CD5"). Bispecific antibodies can be prepared from anti-CD1d and anti-CD5 antibodies using techniques that are known in the art (see, e.g., U.S. Pat. Nos. 5,534,254, 5,837,242, 6,492,123; U.S. Patent application publication Nos. 20040058400 and 20030162709, which are all herein incorporated by reference in their entireties).

In order to kill or ablate the regulatory B cell subset, targeting antibodies (e.g., anti-CD22 or bispecific anti-CD1d/CD5) of an isotype that mediate ADCC (antibody-dependent and mediated toxicity) or CDC (complement-dependent cytotoxicity) can be used. Of the various human immunoglobulin classes, IgG1, IgG2, IgG3, IgG4 and IgM are known to activate complement. Human IgG1 and IgG3 are known to mediate ADCC.

Antibodies targeting the $CD1d^{high}CD5^+$ regulatory B cell subset can be further conjugated to a cytotoxic agent, using methods known in the art (see, e.g., DiJoseph et al., 2004, Clin. Cancer Res. 10:8620-9). This may be preferred when using antibodies or antibody fragments that do not mediate ADCC or CDC. Non-limiting examples of cytotoxic agents include antimetabolites (e.g., cytosine arabinoside, aminopterin, methotrexate, 6-mercaptopurine, 6-thioguanine, cytarabine, and 5-fluorouracil decarbazine); alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, cis-dichlorodiammine-platinum (II) (CDDP), and cisplatin); vinca alkaloid; anthracyclines (e.g., daunorubicin (formerly daunomycin) and doxorubicin); antibiotics (e.g., dactinomycin (formerly actinomycin), bleomycin, mithramycin, and anthramycin (AMC)); calicheamicin; CC-1065 and derivatives thereof; auristatin molecules (e.g., auristatin PHE, bryostatin-1, and dolastatin-10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun 266: 76-80 (1999), Mohammad, et al., Int. J. Oncol. 15:367-72 (1999), all of which are incorporated by reference herein in their entireties); DNA-repair enzyme inhibitors (e.g., etoposide or topotecan); kinase inhibitors (e.g., compound ST1571, imatinib mesylate (Kantarjian et al., Clin. Cancer Res. 8(7):2167-76 (2002)); demecolcine; and other cytotoxic agents (e.g., paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucorticoids, procaine, tetracaine, lidocaine, propranolol, and puromycin and analogs or homologues thereof and those compounds disclosed in U.S. Pat. Nos. 6,245,759, 6,399, 633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459, all of which are incorporated by reference herein in their entirety); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305, all of which are herein incorporated by reference in their entirety); topoisomerase inhibitors (e.g., camptothecin, irinotecan, SN-38, topotecan, 9-aminocamptothecin, GG211 (GI147211), DX-8951f, IST-622, rubitecan, pyrazoloacridine, XR5000, saintopin, UCE6, UCE1022, TAN-1518A, TAN 1518B, KT6006, KT6528, ED-110, NB-506, ED-110, NB-506, and rebeccamycin); bulgarein; DNA minor groove binders such as Hoechst dye 33342 and Hoechst dye 33258; nitidine; fagaronine; epiberberine; coralyne; beta-lapachone; BC-4-1; antisense oligonucleotides (e.g., those disclosed in the U.S. Pat. Nos. 6,277,832, 5,998,596, 5,885,834, 5,734,033, and 5,618,709, all of which are herein incorporated by reference in their entirety); adenosine deaminase inhibitors (e.g., fludarabine phosphate and 2-chlorodeoxyadenosine); and pharmaceutically acceptable salts, solvates, clathrates, and prodrugs thereof.

In another embodiment, the anti-CD22 or bispecific anti-CD1d/CD5 antibody can be conjugated to a radioactive metal ion, such as the alpha-emitters $^{211}$astatine, $^{212}$bismuth, $^{213}$bismuth; the beta-emitters $^{131}$iodine, $^{90}$yttrium, $^{177}$lutetium, $^{153}$samarium, and $^{109}$palladium; or macrocyclic chelators useful for conjugating radiometal ions, including but not limited to, $^{131}$indium, $^{131}$L, $^{131}$yttrium, $^{131}$holmium, $^{131}$samarium, to polypeptides or any of those listed supra. In certain embodiments, the macrocyclic chelator is 1,4,7,10-tetraazacyclododecane-N,N',N'',N'''-tetraacetic acid (DOTA), which can be attached to the antibody via a linker molecule. Such linker molecules are commonly known in the art and described in Denardo, et al., 1998, Clin Cancer Res 4(10):2483-90; Peterson, et al., 1999, Bioconjug Chem 10(4):553-7; and Zimmerman, et al., 1999, Nucl Med Biol 26(8):943-50, each incorporated by reference herein in their entireties.

In still another embodiment, the anti-CD22 antibody or bispecific anti-CD1d/CD5 antibody is conjugated to a proteinaceous agent that modifies a given biological response and leads to cytotoxicity. In one embodiment, the antibody is conjugated to a plant-, fungus-, or bacteria-derived toxin. Non-limiting examples of such toxins include A chain toxins, ribosome inactivating proteins, ricin A, deglycosylated ricin A chain, abrin, alpha sarcin, aspergillin, restrictocin, ribonucleases, diphtheria toxin, bacterial endotoxin, saporin toxin, Granzyme B or the lipid A moiety of bacterial endotoxin, cholera toxin, or *Pseudomonas* exotoxin and derivatives and variants thereof.

In another embodiment, an antagonist capable of engaging CD22 to ablate the regulatory B cell population is a synthetic CD22 ligand, such as that described in Collins et al., 2006, J. Immunol. 5:2994-3003, incorporated herein by reference in its entirety. In one aspect of this embodiment, the synthetic CD22 ligand may be further conjugated to a toxin, such as the saporin toxin.

Alternatively, a compound capable of engaging a marker or markers on the regulatory B cell subset can inhibit the production of IL-10 by the regulatory B cells. Non-limiting examples of such compounds include antibodies and fragments thereof, small molecules, synthetic drugs, peptides (including cyclic peptides), polypeptides, proteins, nucleic acids, synthetic or natural inorganic molecules, mimetic agents, and synthetic or natural organic molecules. In one embodiment, the compound engages CD22. In an aspect of this embodiment, the compound is an anti-CD22 antibody. In another aspect of this embodiment, the compound engages CD5. In an aspect of this embodiment, the compound is an anti-CD5 antibody. In another aspect of this embodiment, the compound engages CD1d. In an aspect of this embodiment, the compound is an anti-CD1d antibody. In still another aspect of this embodiment, the compound is a bispecific anti-CD1d/CD5 antibody. In yet another aspect of this embodiment, the compound engages CD19. In an aspect of this embodiment, the compound is an anti-CD19 antibody.

5.4 Production of Therapeutic Antibodies

Antibodies that target, activate, inhibit and/or kill the regulatory B cell CD1d$^{high}$CD5$^+$ subset and which can be used in the therapeutic regimens described herein can be made using techniques well known in the art. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Sambrook et al, 2001, Molecular Cloning: A Laboratory Manual, Cold Spring Harbor Laboratory Press, Cold Spring Harbor, N.Y.; Ausubel et al, Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al (eds.) (1999) Genome Analysis: A Laboratory Manual, Cold Spring Harbor Laboratory Press, each of which is incorporated by reference herein in its entirety.

Antibodies for use in the methods of the invention include, but are not limited to, synthetic antibodies, monoclonal antibodies (mAbs), recombinantly produced antibodies, multispecific antibodies (including bi-specific antibodies), human antibodies, humanized antibodies, chimeric antibodies, intrabodies, diabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies to be used in the methods of the invention include immunoglobulin molecules and immunologically active portions of immunoglobulin molecules, i.e., molecules that contain an antigen binding site that binds to a CD22 or CD40 antigen, or bispecifically to the CD1d and CD5 antigens. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody fragments that retain the ability to specifically bind to an epitope. In certain embodiments, fragments include Fab fragments; Fab'; F(ab')$_2$; a bispecific Fab; a single chain Fab chain comprising a variable region, also known as, a sFv; a disulfide-linked Fv, or dsFv; a camelized VH; a bispecific sFv; a diabody; and a triabody. Derivatives of antibodies also include one or more CDR sequences of an antibody combining site. In certain embodiments, the antibody to be used with the invention comprises a single-chain Fv ("scFv").

The antibodies used in the methods of the invention may be from any animal origin including birds and mammals (e.g., human, murine, donkey, sheep, rabbit, goat, guinea pig, camel, horse, or chicken).

In certain embodiments, the antibodies of the invention are monoclonal antibodies (mAbs). Monoclonal antibodies can be prepared using a wide variety of techniques known in the art including the use of hybridoma, recombinant, and phage display technologies, or a combination thereof. For example, mAbs can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981) (each of which is herein incorporated by reference in their entireties).

Antibodies can also be generated using various phage display methods. Examples of phage display methods that can be used to make the antibodies include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al, 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated by reference herein in its entirety.

In certain embodiments, the antibodies of the invention are chimeric antibodies or single chain antibodies. Techniques developed for the production of "chimeric antibodies" (Morrison et al., 1984, Proc Natl Acad Sci 81:851; Neuberger et al., 1984 Nature 312:604; Takeda et al., 1985, Nature 314:452, each incorporated by reference herein in its entirety) and single chain antibodies (U.S. Pat. No. 4,946,778; Bird, 1988, Science 242:423; Huston et al, 1988, Proc Natl Acad Sci USA 85:5879; and Ward et al, 1989, Nature 334:544, each incorporated by reference herein in its entirety) are well known in the art.

In a certain embodiment, antibodies used in the methods of the invention are humanized antibodies. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089, each of which is herein incorporated by reference in its entirety), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al, 1994, PNAS 91:969-973, each of which is incorporated by reference herein in its entirety), chain shuffling (U.S. Pat. No. 5,565,332, herein incorporated by reference in its entirety), and techniques disclosed in, e.g., U.S. Pat. No. 6,407,213, U.S. Pat. No. 5,766,886, WO 9317105, Tan et al., 2002, J. Immunol. 169:1119 25, Caldas et al., 2000 Protein Eng. 13(5):353-60, Morea et al., 2000, Methods 20(3):267 79, Baca et al., 1997, J. Biol. Chem. 272(16):10678-84, Roguska et al., 1996, Protein Eng. 9(10):895 904, Couto et al., 1995 Cancer Res. 55 (23 Supp):5973s-5977s, Couto et al., 1995, Cancer Res. 55(8):1717-22, Sandhu J S, 1994, Gene 150(2):409-10, and Pedersen et al., 1994, J. Mol. Biol. 235(3):959-73 U.S. Patent Pub. No. US 2005/0042664 A1 (Feb. 24, 2005), each of which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, each of which is incorporated by reference herein in its entirety).

Single domain antibodies can be produced by methods well-known in the art. (See, e.g., Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety).

Further, antibodies that bind to a desired antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438, herein incorporated by reference in their entireties).

Bispecific antibodies can be prepared using techniques that are known in the art. (See, e.g., U.S. Pat. Nos. 5,534,254, 5,837,242, 6,492,123; U.S. patent application publication Nos. 20040058400 and 20030162709, which are all herein incorporated by reference in their entireties.

The present invention contemplates the use of antibodies recombinantly fused or chemically conjugated (including both covalently and non-covalently conjugations) to a polypeptide. Fused or conjugated antibodies of the present invention may be used for ease in purification. For example, the antibodies or fragments thereof for use in present invention can be fused to marker sequences, such as a peptide to facilitate purification. See e.g., PCT publication WO 93/21232; EP 439,095; Naramura et al., 1994, Immunol Lett 39:91; U.S. Pat. No. 5,474,981; Gillies et al., 1992, Proc Natl Acad Sci USA 89:1428; Fell et al., 1991, J Immunol 146:2446, which are herein incorporated by reference in their entireties.

In certain aspects, the antibodies used in the present invention can be produced intracellularly, in the periplasmic space, or directly secreted into the medium. If the antibodies are produced intracellularly, as a first step, the particulate debris, either host cells or lysed fragments, may be removed, for example, by centrifugation or ultrafiltration.

Exemplary methods for the use of host cells and vectors in the production of antibody can be found in U.S. Pat. Nos. 4,816,567 and 6,331,415 to Cabilly et al., each of which is incorporated by reference herein in its entirety.

5.5 Therapeutic Applications of the B Cell Subset to Treat Diseases and Disorders Associated with Diminished IL-10 Levels Diseases or disorders associated with diminished levels of IL-10 and elevated immune/inflammatory responses (particularly inflammatory diseases and autoimmune diseases) can be treated in accordance with the invention using different therapeutic modalities designed to supply the regulatory B cell subset to an affected subject (e.g., by adoptive transfer/transplant); expand the endogenous regulatory B cell subset in an affected subject; and/or enhance production of IL-10 by the regulatory B cell subset (either adoptively transferred cells or the endogenous population) in the affected subject.

In one approach, a cellular composition enriched for the IL-10 producing $CD1d^{high}CD5^+$ regulatory B cell subset is administered to a subject in need thereof in amounts effective to increase IL-10. The cellular composition can be obtained from a histocompatibilty matched donor. Alternatively, lymphocytes may be obtained from the subject to be treated, enriched for the $CD1d^{high}CD5^+$ regulatory B cell subset and returned to the patient. In either case the enriched cells can be exposed to an antigen of interest prior to introduction into the subject to further fine-tune the regulation of the immune response.

Alternatively, an effective amount of a therapeutic agent capable of stimulating the proliferation of the endogenous regulatory B cell subset that produces IL-10, and/or increasing the amounts of IL-10 produced by the endogenous regulatory B cell subset can be administered to a subject in need thereof in amounts effective to increase IL-10 levels in said subject. These agents may be targets to the $CD1d^{high}CD5^+$ regulatory B cell subset.

5.5.1. Diseases and Disorders Associated with Reduced IL-10 Production that can be Treated Using the Regulatory B Cell Subset Diseases and conditions associated with diminished IL-10 levels can be treated in accordance with this aspect of the invention. Decreased levels of IL-10 have been demonstrated in autoimmune and inflammatory diseases including, but not limited to psoriasis (Asadullah et al., 1998, J. Clin. Investig. 101:783-94, Nickoloff et al., 1994, Clin. Immunol. Immunopathol., 73:63-8, Mussi et al. 1994, J. Biol. Regul. Homeostatic Agents), rheumatoid arthritis (Jenkins et al., 1994, Lymphokine Cytokine Res. 13:47-54; Cush et al., 1995, Arthritis Rheum. 38:96-104; Al Janadi et al., 1996, J. Clin. Immunol. 16:198-207), allergic contact dermatitis (Kondo et al., 1994, J. Investig. Dermatol. 103:811-14; Schwarz et al., 1994, J. Investig. Dermatol. 103:211-16), inflammatory bowel disease (Kuhn et al., 1993, Cell 75:263-74; Lindsay and Hodgson, 2001, Aliment. Pharmacol. Ther. 15:1709-16) and multiple sclerosis (Barrat et al., 2002, J. Exp. Med. 195:603-16; Cua et al., 2001, J. Immunol. 166: 602-8; Massey et al., 2002, Vet. Immunol. Immunopathol. 87:357-72; Link and Xiao, 2001, Immunol. Rev. 184:117-28).

Any type of autoimmune disease can be treated in accordance with this method of the invention. Non-limiting examples of autoimmune disorders include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteritis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein, some autoimmune disorders are associated with an inflammatory condition. Thus, there is overlap between what is considered an autoimmune disorder and an inflammatory disorder. Therefore, some autoimmune disorders may also be characterized as inflammatory disorders.

In an aspect of this embodiment, the methods of the invention can be used to treat inflammatory diseases associated with diminished IL-10 levels, but not autoimmune diseases.

In another aspect of this embodiment, the methods of the invention can be used to treat autoimmune diseases associated with diminished IL-10 levels, but not inflammatory diseases.

In yet another aspect of this embodiment, the methods of the invention can be used to treat autoimmune diseases associated with diminished IL-10 levels, wherein the autoimmune disease to be treated is not systemic lupus erythematosus.

Any type of inflammatory disease can be treated in accordance with this method of the invention. Non-limiting examples of inflammatory diseases include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In still another aspect of this embodiment, the methods of the invention encompass therapies that are aimed at treating diseases associated with a helper T (Th) 1-mediated inflammatory response but not diseases associated with a Th2-mediated inflammatory response.

In an alternative aspect of this embodiment, the methods of the invention encompass therapies that are aimed at treating diseases associated with a Th2-mediated inflammatory response but not diseases associated with a Th1-mediated inflammatory response.

IL-10 is capable of inhibiting ischemia/reperfusion injury (Deng et al., 2001, Kidney Int. 60:2118-28), graft-versus-disease, and transplant-related mortality (Baker et al., 1999, Bone Marrow Transplant 23:1123-9; Holler et al., 2000, Bone Marrow Transplant 25:237-41). As such, one embodiment of the present invention involves treating transplant-associated diseases/conditions by increasing the level of IL-10 in a patient in need thereof.

In another embodiment, the levels of endogenous IL-10 are increased in a subject receiving an organ transplant by administration of a regulatory B cell subset. In one aspect of this embodiment, the regulatory B cell population is isolated from the patient themselves, i.e., the subject is the donor. In another aspect of this embodiment, the regulatory B cell population is isolated from a donor that is not the subject. The donor of the regulatory B cells may be the same as the organ donor. In another embodiment, the regulatory B cell population is pooled from several donors.

5.5.2. Therapeutic Modalities

In one embodiment, a subject suffering from an autoimmune disease or an inflammatory disease associated with diminished levels of IL-10 is administered a population of regulatory B cells. In one aspect of this embodiment, the regulatory B cell population is isolated from the patient themselves, i.e., the subject is the donor. In another aspect of this embodiment, the regulatory B cell population is isolated from a donor that is not the subject. In an aspect of this embodiment, the regulatory B cell population is pooled from several donors. According to this embodiment, administration of a regulatory B cell population to a subject in need thereof results in an increased level of IL-10 production in the patient sufficient to control, reduce, or eliminate symptoms of the disease being treated.

In one aspect of this embodiment, the therapeutic agent is an antibody, in particular, an anti-CD40 antibody. In other aspects, the therapeutic agent is a small molecule, a polypeptide, DNA, or RNA that interacts with the B cell CD40 receptor.

In another embodiment, a subject suffering from an inflammatory or autoimmune disease associated with diminished levels of IL-10 is treated by administration of a therapeutic agent capable of causing an increase in IL-10 production by the regulatory B cells in the patient. In a specific aspect of this embodiment, the therapeutic agent targets the B cell CD40 receptor. In another aspect of this embodiment, the therapeutic agent is an anti-CD40 antibody, a small molecule, a polypeptide, DNA, or RNA that is capable of binding, targeting, and/or modulating CD40 so as to result in increase in IL-10 production by the regulatory B cells in the subject.

An antibody according to these embodiments can be any type of antibody or fragment thereof, as described above. According to this embodiment administration of an anti-CD40 antibody or fragment thereof to a subject with an autoimmune disease or an inflammatory disease associated with diminished levels of IL-10 results in an upregulation of IL-10 production by the endogenous regulatory B cell population in the subject.

In still another embodiment, a patient receiving a transplant is administered a therapeutic agent capable of increasing endogenous IL-10 production by the regulatory B cell subset of that patient to increase the patient's tolerance to the transplant. In yet another embodiment, a patient receiving a transplant is administered a regulatory B cell subset to increase the patient's tolerance to the transplant.

The subject is preferably a mammal such as non-primate (e.g., cows, pigs, horses, cats, dogs, rats, etc.) and a primate (e.g., monkey, such as a cynomolgous monkey and a human) In a preferred embodiment, the subject is a human.

5.5.2.1. Regulatory B Cells as Therapeutic Agents

In one embodiment, adoptive transfer of regulatory B cells can be effective to suppress a wide variety of diseases, including, but not limited to any of those described above, i.e., autoimmune diseases, inflammatory diseases, or any other disease which may be treated by introduction of a regulatory B cell population into a subject. Adoptive transfer of regulatory B cells can further be employed to minimize the immune/inflammatory response associated with transplant of cells and/or tissues.

In an exemplary adoptive cell transfer protocol, a mixed population of B cells is initially extracted from a target donor. The regulatory B cells isolated from the donor may be isolated from any location in the donor in which they reside including, but not limited to, the blood, spleen, lymph nodes, and/or bone marrow of the donor. Depending on the application, the B cells may be extracted from a healthy donor; a donor suffering from a disease that is in a period of remission or during active disease; or from the organs, blood, or tissues of a donor that has died. In the case of the latter, the donor is an organ donor. In yet another embodiment, the regulatory B cells can be obtained from the subject, expanded or activated and returned to the subject.

Harvested lymphocytes may be separated by flow cytometry or other cell separation techniques based on regulatory B cell markers such as described herein, and then transfused to a recipient. Alternatively, the cells may be stored for future use. In one aspect of this embodiment, the donor and the recipient are the same subject. In another aspect of this embodiment, the donor is a subject other than the recipient. In a further aspect of this embodiment, the "donor" comprises multiple donors other than the recipient, wherein the regulatory B cells from said multiple donors are pooled.

In another embodiment, the regulatory B cell population obtained from a donor can be expanded, enriched, or made to produce elevated levels of IL-10, as described in sections 5.1 and 5.2, supra, prior to being administered to a recipient.

In the adoptive transfer techniques contemplated herein, wherein the donor is a subject other than the recipient, the recipient and the donor are histocompatible. Histocompatibility is the property of having the same, or mostly the same, alleles of a set of genes called the major histocompatibility complex (MHC). These genes are expressed in most tissues as antigens, to which the immune system makes antibodies. When transplanted cells and/or tissues are rejected by a recipient, the bulk of the immune system response is to the MHC proteins. MHC proteins are involved in the presentation of foreign antigens to T-cells, and receptors on the surface of the T-cell are uniquely suited to recognition of proteins of this type. MHC are highly variable between individuals, and therefore the T-cells from the host recognize the foreign MHC with a very high frequency leading to powerful immune responses that cause rejection of transplanted tissue. As such, the chance of rejection of the regulatory B cell population by the recipient is minimized.

The amount of regulatory B cells which will be effective in the treatment and/or suppression of a disease or disorder which may be treated by introduction of a regulatory B cell population into a subject can be determined by standard clinical techniques. The dosage will depend on the type of disease to be treated, the severity and course of the disease, the purpose of introducing the regulatory B cell population, previous therapy the recipient has undertaken, the recipient's clinical history, and the discretion of the attending physician. The regulatory B cell population can be administered in treatment regimes consistent with the disease, e.g., a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Exemplary, non-limiting doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ regulatory B cells/m$^2$. In a certain embodiment, the dose used in the treatment of human subjects ranges from about $3.8 \times 10^9$ to about $3.8 \times 10^{10}$ regulatory B cells/m$^2$.

In another aspect of this embodiment, the regulatory B cells obtained from the donor can be introduced into a recipient at a desired location, so as to specifically target the therapeutic effects of the regulatory B cell population, i.e., IL-10 production. Such techniques can be accomplished using implantable immune modulation devices, e.g., virtual lymph nodes, such as those described in U.S. patent application publication No. 2003/0118630; WO1999/044583; and U.S. Pat. No. 6,645,500, which are incorporated by reference herein in their entireties. According to this embodiment, an IL-10 producing regulatory B cell population can be isolated from a donor as described above, added to an implantable immune modulation device, and said device then can be inplanted into a recipient at a location where the therapeutic effects of the regulatory B cell population, i.e., IL-10 production, are needed.

5.5.2.2. Antigen-Specific Regulatory B Cells

In another embodiment, the regulatory B cell population can be made responsive to a certain antigen involved in a specific disease. In an aspect of this embodiment, the regulatory B cell population, when sensitized with a certain antigen, will produce therapeutic amounts of IL-10 upon subsequent encounters with the antigen. In an aspect of this embodiment, such an antigen-specific regulatory B cell population may be used in an adoptive transfer technique, wherein a subject is or has previously been immunized with a certain antigen and the antigen-sensitized regulatory B cells from said subject are isolated and transplanted to the same or another subject. In still another aspect of this embodiment, a regulatory B cell population from a subject can be isolated and subsequently can be sensitized with a disease-specific antigen ex vivo or in vitro. The sensitized regulatory B cell population can then be transplanted into the original or another subject by any method known in the art. In still another aspect of this embodiment, the antigen-specific regulatory B cell population can be added to an implantable immune modulation device, as described above. According to this embodiment, the implanted regulatory B cell population will produce strategically localized IL-10 when encountering antigen in the host. In a further aspect, the regulatory B cell population and a disease-specific antigen can both be placed in an implantable immune modulation device, and said device then can be transplanted into a recipient at a location where the therapeutic effects of the regulatory B cell population, i.e., IL-10 production, are needed, thus resulting in an amplified response to the disease in vivo.

In another aspect, a certain disease-specific antigen can be administered in conjunction with a CD40 agonist. In a certain aspect of this embodiment, the therapeutic agent is an antibody, in particular, an anti-CD40 antibody. In other aspects, the therapeutic agent is a small molecule, a polypeptide, DNA, or RNA that interacts with the B cell CD40 receptor.

Any antigen from any disease, disorder, or condition may be used in accordance with the methods of the invention. Exemplary antigens include but are not limited to bacterial, viral, parasitic, allergens, autoantigens and tumor-associated antigens. If a DNA based vaccine is used the antigen will typically be encoded by a sequence of the administered DNA construct. Alternatively, if the antigen is administered as a conjugate the antigen will typically be a protein comprised in the administered conjugate. Particularly, the antigen can include protein antigens, peptides, whole inactivated organisms, and the like.

Specific examples of antigens that can be used in the invention include antigens from hepatitis A, B, C or D, influenza virus, *Listeria, Clostridium botulinum*, tuberculosis, tularemia, *Variola major* (smallpox), viral hemorrhagic fevers, *Yersinia pestis* (plague), HIV, herpes, pappilloma virus, and other antigens associated with infectious agents. Other antigens include antigens associated with autoimmune conditions, inflammatory conditions, allergy, and asthma. Non-limiting examples of autoimmune diseases and inflammatory diseases are provided, supra.

In an aspect of this embodiment, a regulatory B cell population sensitized with a disease-specific antigen can be administered alone or in conjunction with a CD40 agonist, in particular, an anti-CD40 antibody, for use as a therapeutic or prophylactic vaccine for conferring immunity against such disease conditions.

In another embodiment, a regulatory B cell subset may be sensitized with antigen from a prospective transplant donor, so as to increase the levels of IL-10 production by the regulatory B cells in a transplant recipient. In an aspect of this embodiment, the increased IL-10 production by the regulatory B cell subset in the transplant recipient results in a decreased immune/inflammatory response to the transplant in the transplant recipient. The role of regulatory B cells in transplants is described in section 5.5.2.3, infra.

5.5.2.3. Regulatory B Cells in Organ Transplant Patients

In another embodiment, the levels of endogenous IL-10 are increased in a subject receiving an organ transplant by administration of a regulatory B cell subset. In one aspect of this embodiment, the regulatory B cell population is isolated from the patient themselves, i.e., the subject is the donor. In another aspect of this embodiment, the regulatory B cell population is isolated from a donor that is not the subject. In an aspect of this embodiment, the regulatory B cell population is pooled from several donors. In another aspect of this embodiment, the regulatory B cell subset is isolated from a subject that has died, wherein said subject is an organ donor. In embodiments wherein the regulatory B cells are from a donor that is not the subject, the subject and the donor are histocompatible.

In one aspect of this embodiment, the regulatory B cell subset is administered prior to the transplant. According to this aspect, the therapeutic agent can be administered at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. Administration of the therapeutic agent can be by any method known to those of skill in the art.

In another aspect of this embodiment, the regulatory B cell subset is administered at the same time as the transplant.

In still another aspect of this embodiment, the regulatory B cell subset is administered following the transplant.

In a certain aspect, the regulatory B cell subset is administered before, during, and after the transplant. According to this aspect, when the regulatory B cell subset is administered after the transplant, it may be administered for at least 12 hours, at least 1 day, at least 2 days, at least 3 days, at least 4 days, at least 5 days, at least 6 days, at least 1 week, at least 2 weeks, at least 3 weeks, at least 4 weeks, least 1 month, or at least 1 year following the transplant or for the duration of the patient's life.

As described in section 5.5.2.2, supra, in one embodiment, a regulatory B cell subset administered to a patient that is receiving a transplant can be sensitized with antigens specific to the transplanted material. According to this embodiment, the transplant recipient will have a decreased immune/inflammatory response to the transplanted material and, as such, the likelihood of rejection of the transplanted material is minimized.

In another embodiment, the levels of endogenous IL-10 are increased in a subject receiving an organ transplant by administration of a therapeutic agent capable of causing an increase in IL-10 production by the regulatory B cells in the patient. The therapeutic agent can be administered in vivo or ex vivo; i.e., the regulatory B cell population can be isolated/enriched from the patient, contacted with the therapeutic agent ex vivo, and the "activated" population returned to the patient. In a specific aspect of this embodiment, the therapeutic agent targets the B cell CD40 receptor. In another aspect of this embodiment, the therapeutic agent is an anti-CD40 antibody, a small molecule, a polypeptide, DNA, or RNA that is capable of binding, targeting, and or modulating CD40 so as to result in increase in IL-10 production by the regulatory B cells in the subject.

In one aspect of this embodiment, the therapeutic agent capable of causing an increase in IL-10 production by the regulatory B cells in the patient is administered prior to the transplant. According to this aspect, the therapeutic agent can be administered at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. Administration of the therapeutic agent can be by any method known to those of skill in the art.

In another aspect of this embodiment, the therapeutic agent capable of causing an increase in IL-10 production by the regulatory B cells in the patient is administered at the same time as the transplant.

In still another aspect of this embodiment, the therapeutic agent capable of causing an increase in IL-10 production by the regulatory B cells in the patient is administered following the transplant.

In a certain aspect, the therapeutic agent capable of causing an increase in IL-10 production by the regulatory B cells in the patient is administered before, during, and after the transplant. According to this aspect, when the therapeutic agent capable of causing an increase in IL-10 production by the regulatory B cells in the patient is administered after the transplant, it may be administered for at least 12 hours, at least 1 day, at least 2 days, at least 3 days, at least 4 days, at least 5 days, at least 6 days, at least 1 week, at least 2 weeks, at least 3 weeks, at least 4 weeks, least 1 month, or at least 1 year following the transplant or for the duration of the patient's life.

According to these embodiments, administration of a therapeutic agent capable of causing an increase in IL-10 production by the regulatory B cells in the patient or administration of a regulatory B cell subset results in a decreased immune response in the patient receiving the transplant, wherein the decreased immune response results in an increased likelihood that the transplant will be accepted, an increased tolerance to the transplant, an increased duration of time in which the transplant is accepted, and/or an increased lifespan in the transplant recipient.

Any type of transplant can be performed according to these methods.

5.6 Therapeutic Targeting of the B Cell Subset to Treat Diseases and Disorders Associated with Enhanced IL-10 Levels In another embodiment, the invention provides methods for treating and/or managing a disease or disorder associated with a decreased/depressed/impaired immune/inflammatory response, particularly cancer, by administrating to a subject in need thereof a therapeutically or prophylactically effective amount of a therapeutic agent capable of ablating the population of regulatory B cells that produce IL-10 and/or the amounts of IL-10 being produced by the regulatory B cell subset. In another embodiment, the invention provides methods for the treatment of cancer by administrating to a subject in need thereof a therapeutically or prophylactically effective amount of a therapeutic agent capable of ablating the population of regulatory B cells that produce IL-10 and/or the amounts of IL-10 being produced by the regulatory B cell subset.

In an aspect of this embodiment, the therapeutic agent is an antibody that mediates CDC or ADCC and kills target cells, or an immunoconjugate that alters the function of or kills target cells is used. In particular, an anti-CD22 mAb that kills or inhibits the proliferation of the regulatory B cell subset can be used. Alternatively, a bispecific anti-CD1d/CD5 antibody can be used.

In another aspect of this embodiment, the therapeutic agent is an antibody that does not utilize CDC or ADCC to kill the target cells. In another aspect, the antibody does not kill the target cells by apoptosis.

In another aspect of this embodiment, the therapeutic agent is an antibody that does not utilize CDC, ADCC, or apoptosis as the primary mechanism for killing target cells, i.e., the majority of target cells are killed by a mechanism that is CDC-, ADCC-, and apoptosis-independent.

In another aspect of this embodiment, the therapeutic agent is a small molecule, a polypeptide, DNA, or RNA that interacts with the B cell CD22 receptor or with the CD1d or CD5 receptors.

The subject is preferably a mammal such as non-primate (e.g., cows, pigs, horses, cats, dogs, rats, etc.) and a primate (e.g., monkey, such as a cynomolgous monkey and a human). In a preferred embodiment, the subject is a human.

5.6.1 Diseases and Disorders Associated with Increased IL-10 Production

IL-10 has been shown to promote tumor growth and overexpression of IL-10 has been demonstrated in certain cancers (Matsuda et al., 1994, J. Exp. Med. 180:2371-6; Salazar-Onfray et al., 1997, J. Immunol. 159:3195-3202; Hagenbaugh et al. 1997, J. Exp. Med. 185:2101-110; Kruger-Kraskagakes et al. 1994, Br. J. Cancer 70:1182-5, Dummer et al., 1996, Int. J. Cancer 66:607-10; Kim et al., 1995, J. Immunol. 155:2240-47; Blay et al., 1993, Blood 82:2169-74; Asadullah et al., 2000, Exp. Dermatol. 9:71-6). As such, one embodiment of the present invention involves treating cancer by decreasing the level of IL-10 in a patient in need thereof by ablation of the IL-10 producing regulatory B cell subset and/or reducing the amount of IL-10 produced by the IL-10 producing regulatory B cell subset.

Any type of cancer can be treated in accordance with this method of the invention. Non-limiting examples of cancers include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al, 1985, Medicine, 2d Ed., J.B. Lippincott Co., Philadelphia and Murphy, 1997, Informed Decisions: The Complete Book of Cancer Diagnosis, Treatment, and Recovery, Viking Penguin, Penguin Books U.S.A., Inc., United States of America, incorporated by reference herein in its entirety).

Increased levels of IL-10 have been demonstrated in certain autoimmune and inflammatory diseases including, but not limited to systemic lupus erythematosus (Park et al., 1998, Clin. Exp. Rheumatol. 16:283-88; Llorente et al., 1995, J. Exp. Med. 181:839-44), systemic sclerosis (Hasegawa et al., 1997, J. Rheumatol. 24:328-32), Bullous Pemphigoid (Schmidt et al., 1996, Arch. Dermatol. Res. 228: 353-7; Giacalone et al., 1998, Exp. Dermatol. 7:157-61), and atopic dermatitis (Ohmen et al., 1995, J. Immunol. 154: 1956-63; Asadullah et al., 1996, J. Investig. Dermatol. 197:833-7). As such, one embodiment of the present invention involves treating an autoimmune or inflammatory by decreasing the level of IL-10 in a patient in need thereof by ablation of the IL-10 producing regulatory B cell subset and/or reducing the amount of IL-10 produced by the IL-10 producing regulatory B cell subset.

Any type of autoimmune disease that is accompanied by increased IL-10 production can be treated in accordance with this method of the invention. A non-limiting list of autoimmune disorders is provided above.

Any type of inflammatory disease that is accompanied by increased IL-10 production can be treated in accordance with this method of the invention. A non-limiting list of inflammatory diseases is provided above.

In an aspect of this embodiment, the methods of the invention can be used to treat inflammatory diseases associated with diminished IL-10 levels, but not autoimmune diseases.

In another aspect of this embodiment, the methods of the invention can be used to treat autoimmune diseases associated with diminished IL-10 levels, but not inflammatory diseases.

In yet another aspect of this embodiment, the methods of the invention can be used to treat autoimmune diseases associated with diminished IL-10 levels, wherein the autoimmune disease to be treated is not systemic lupus erythematosus.

In still another aspect of this embodiment, the methods of the invention encompass therapies that are aimed at treating diseases associated with a helper T (Th) 1-mediated inflammatory response but not diseases associated with a Th2-mediated inflammatory response.

In an alternative aspect of this embodiment, the methods of the invention encompass therapies that are aimed at treating diseases associated with a Th2-mediated inflammatory response but not diseases associated with a Th1-mediated inflammatory response.

5.6.2 Therapies

In one embodiment, a subject suffering from cancer who has elevated levels of IL-10 is treated by administration of a therapeutic agent capable of ablating the population of regulatory B cells in the patient and/or reducing the amount of IL-10 production produced by the regulatory B cell population. In a specific aspect of this embodiment, the therapeutic agent targets the B cell CD22 receptor. In another aspect of this embodiment, the therapeutic agent is an anti-CD22 antibody, a small molecule, a polypeptide, DNA, or RNA that is capable of binding, targeting, and or modulating CD22 so as to result in ablation of the regulatory B cell subset.

In another embodiment, a subject suffering from an immune deficiency disease associated with elevated levels of IL-10 is treated by administration of a therapeutic agent capable of ablating the population of regulatory B cells in the patient and thereby reducing the amount of IL-10 production produced by the regulatory B cell population. In a specific aspect of this embodiment, the therapeutic agent targets the B cell CD22 receptor. In another aspect of this embodiment, the therapeutic agent is an anti-CD22 antibody, a small molecule, a polypeptide, DNA, or RNA that is capable of binding, targeting, and or modulating CD22 so as to result in ablation of the regulatory B cell subset.

In an alternative embodiment, a subject suffering from cancer or an immune deficiency disease associated with elevated levels of IL-10 is treated by administration of a bispecific anti-CD1d/CD5 antibody capable of ablating the population of regulatory B cells in the patient and thereby reducing the amount of IL-10 produced.

In order to kill or ablate the regulatory B cell subset, targeting antibodies (e.g., anti-CD22 or bispecific anti-CD1d/CD5) of an isotype that mediate ADCC (antibody-dependent and mediated toxicity) or CDC (complement-dependent cytotoxicity) can be used. Of the various human immunoglobulin classes, IgG1, IgG2, IgG3, IgG4 and IgM are known to activate complement. Human IgG1 and IgG3 are known to mediate ADCC.

Antibodies targeting the $CD1d^{high}CD5^+$ regulatory B cell subset can be further conjugated to a cytotoxic agent, using methods known in the art (see, e.g., DiJoseph et al., 2004, Clin. Cancer Res. 10:8620-9). This may be preferred when using antibodies or antibody fragments that do not mediate ADCC or CDC. Non-limiting examples of cytotoxic agents include antimetabolites (e.g., cytosine arabinoside, aminopterin, methotrexate, 6-mercaptopurine, 6-thioguanine, cytarabine, and 5-fluorouracil decarbazine); alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, cis-dichlorodiammine-platinum (II) (CDDP), and cisplatin); vinca alkaloid; anthracyclines (e.g., daunorubicin (formerly daunomycin) and doxorubicin); antibiotics (e.g., dactinomycin (formerly actinomycin), bleomycin, mithramycin, and anthramycin (AMC)); calicheamicin; CC-1065 and derivatives thereof; auristatin molecules (e.g., auristatin PHE, bryostatin-1, and dolastatin-10; see Woyke et al., Antimicrob. Agents Chemother 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun 266: 76-80 (1999), Mohammad, et al., Int. J. Oncol. 15:367-72 (1999), all of which are incorporated by reference herein in their entireties); DNA-repair enzyme inhibitors (e.g., etoposide or topotecan); kinase inhibitors (e.g., compound ST1571, imatinib mesylate (Kantarjian et al., Clin. Cancer Res. 8(7):2167-76 (2002)); demecolcine; and other cytotoxic agents (e.g., paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucorticoids, procaine, tetracaine, lidocaine, propranolol, and puromycin and analogs or homologues thereof and those compounds disclosed in U.S. Pat. Nos. 6,245,759, 6,399, 633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459, all of which are incorporated by reference herein in their entirety); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305, all of which are herein incorporated by reference in their entirety); topoisomerase inhibitors (e.g., camptothecin, irinotecan, SN-38, topotecan, 9-aminocamptothecin, GG211 (GI147211), DX-8951f, IST-622, rubitecan, pyrazoloacridine, XR5000, saintopin, UCE6, UCE1022, TAN-1518A, TAN 1518B, KT6006, KT6528, ED-110, NB-506, ED-110, NB-506, and rebeccamycin); bulgarein; DNA minor groove binders such as Hoechst dye 33342 and Hoechst dye 33258; nitidine; fagaronine; epiberberine; coralyne; beta-lapachone; BC-4-1; antisense oligonucleotides (e.g., those disclosed in the U.S. Pat. Nos. 6,277,832, 5,998,596, 5,885,834, 5,734,033, and 5,618,709, all of which are herein incorporated by reference in their entirety); adenosine deaminase inhibitors (e.g., fludarabine phosphate and 2-chlorodeoxyadenosine); and pharmaceutically acceptable salts, solvates, clathrates, and prodrugs thereof.

In another embodiment, the antibody that targets the $CD1d^{high}CD5^+$ regulatory B cell population, the anti-CD22 or bispecific anti-CD1d/CD5 antibody can be conjugated to a radioactive metal ion, such as the alpha-emitters $^{211}$astatine, $^{212}$bismuth, $^{213}$bismuth; the beta-emitters $^{131}$iodine, $^{90}$yttrium, $^{177}$lutetium, $^{153}$samarium, and $^{109}$palladium; or macrocyclic chelators useful for conjugating radiometal ions, including but not limited to, $^{131}$indium, $^{131}$L, $^{131}$yttrium, $^{131}$holmium, $^{131}$samarium, to polypeptides or any of those listed supra. In certain embodiments, the macrocyclic chelator is 1,4,7,10-tetraazacyclododecane-N, N',N'',N'''-tetraacetic acid (DOTA), which can be attached to the antibody via a linker molecule. Such linker molecules are commonly known in the art and described in Denardo, et al., 1998, Clin Cancer Res 4(10):2483-90; Peterson, et al., 1999, Bioconjug Chem 10(4):553-7; and Zimmerman, et al., 1999, Nucl Med Biol 26(8):943-50, each incorporated by reference herein in their entireties.

In still another embodiment, the antibody that targets the $CD1d^{high}CD5^+$ regulatory B cell population, the anti-CD22 antibody, or bispecific anti-CD1d/CD5 antibody is conjugated to a proteinaceous agent that modifies a given biological response and leads to cytotoxicity. In one embodiment, the antibody is conjugated to a plant-, fungus-, or bacteria-derived toxin. Non-limiting examples of such toxins include A chain toxins, ribosome inactivating proteins, ricin A, deglycosylated ricin A chain, abrin, alpha sarcin, aspergillin, restrictocin, ribonucleases, diphtheria toxin, bacterial endotoxin, saporin toxin, Granzyme B or the lipid A moiety of bacterial endotoxin, cholera toxin, or *Pseudomonas* exotoxin and derivatives and variants thereof.

In another embodiment, an antagonist capable of engaging CD22 to ablate the regulatory B cell population is a synthetic CD22 ligand, such as that described in Collins et al., 2006, J. Immunol. 5:2994-3003, incorporated herein by reference in its entirety. In one aspect of this embodiment, the synthetic CD22 ligand may be further conjugated to a toxin, such as the saporin toxin.

In an alternative embodiment, a subject suffering from cancer or an immune deficiency disease associated with elevated levels of IL-10 is treated by administration of a compound capable of engaging a marker or markers on the regulatory B cell subset can inhibit the production of IL-10 by the regulatory B cells. Non-limiting examples of such compounds include antibodies and fragments thereof, small molecules, synthetic drugs, peptides (including cyclic peptides), polypeptides, proteins, nucleic acids, synthetic or natural inorganic molecules, mimetic agents, and synthetic or natural organic molecules. In one embodiment, the compound engages CD22. In an aspect of this embodiment, the compound is an anti-CD22 antibody. In another aspect of this embodiment, the compound engages CD5. In an aspect of this embodiment, the compound is an anti-CD5 antibody. In another aspect of this embodiment, the compound engages CD1d. In an aspect of this embodiment, the compound is an anti-CD1d antibody. In still another aspect of this embodiment, the compound is a bispecific anti-CD1d/CD5 antibody. In yet another aspect of this embodiment, the compound engages CD19. In an aspect of this embodiment, the compound is an anti-CD19 antibody.

An antibody according to these embodiments can be any type of antibody or fragment thereof, as described above. According to this embodiment, administration of an antibody that targets the CD1d$^{high}$CD5$^+$ regulatory B cell population or fragment thereof, including an anti-CD22 antibody or fragment thereof to a patient with cancer, an autoimmune disease, or an inflammatory disease associated with increased levels of IL-10 results in a downregulation of IL-10 production by the regulatory B cell population in the patient.

In another embodiment, a patient suffering from cancer or an immune deficiency disease associated with elevated levels of IL-10 is treated by administration of an antibody that binds to a B cell marker and selectively depletes the regulatory B cell population in the patient. According to this embodiment, the B cell marker can be any antigen that is presently known or subsequently determined to be expressed by regulatory B cells including, e.g. CD5, CD19, CD20, CD21, CD22, CD24, CD40 and CD72. In one aspect of this embodiment, the antibody that binds to a B cell marker and selectively depletes the regulatory B cell population in the patient does not cause depletion of the regulatory B cell population by an antibody-dependent cell-mediated cytotoxicity (ADCC) mechanism, by complement-dependent cytotoxicity (CDC), or by apoptosis. In another aspect, depletion of the regulatory B cell population by the antibody is independent of the antibody's Fc region. In another aspect of this embodiment, the antibody that binds to a B cell marker and selectively depletes the regulatory B cell population depletes splenic Marginal Zone B cells but does not substantially deplete splenic Follicular B cells. In a specific aspect, the antibody that binds to a B cell marker and selectively depletes the regulatory B cell population is an IgG2b or an IgG3 isotype.

In another embodiment, the antibody for use in treating a patient suffering from cancer or an immune deficiency disease associated with elevated levels of IL-10 that binds to a B cell marker and selectively depletes the regulatory B cell population comprises a human IgG isotype or Fc region that does not activate complement or lead to ADCC or kill cells by inducing apoptosis. Any human isotype or Fc region that does not activate complement or lead to ADCC or kill cells by inducing apoptosis can be used in accordance with this embodiment. In one aspect, the isotype is IgG4.

In a specific embodiment, a patient suffering from cancer is treated by administration of an anti-CD20 antibody that selectively depletes the regulatory B cell population in the patient, wherein the depletion of the regulatory B cell population by the anti-CD20 antibody is not caused by ADCC, CDC, or apoptosis. In another aspect, depletion of the regulatory B cell population by the antibody is independent of the antibody's Fc region. In an aspect of this embodiment, the anti-CD20 antibody depletes splenic Marginal Zone B cells but does not substantially deplete splenic Follicular B cells. In a specific aspect, the anti-CD20 is an IgG2b or an IgG3 isotype. In another aspect, the anti-CD20 antibody comprises a human IgG isotype or Fc region that does not activate complement or lead to ADCC or cells by inducing apoptosis. Any human isotype or Fc region that does not activate complement or lead to ADCC or kill cells by inducing apoptosis can be used in accordance with this embodiment. In one aspect, the isotype is IgG4.

In certain embodiments, the regulatory B cell population is depleted by at least 1%, at least 1% to 5%, at least 1% to 10%, at least 1% to 25%, at least 1% to 50%, at least 55%, at least 60%, at least 65%, at least 70%, at least 75%, at least 80%, at least 85%, at least 90%, at least 95%, at least 99%, or by 100% as measured by an assay known to one of skill in the art, e.g., immunofluorescence staining with flow cytometry analysis, ELISA assay for IL-10 secretion, or ELISpot analysis for determining numbers of IL-10-secreting cells.

In certain embodiments, the antibodies described herein are administered alone. In other embodiments, the antibodies described herein are administered to patients as a front-line therapy. In other embodiments, the antibodies described herein are administered to patients as a secondary therapy. In certain embodiments, the patient has not previously been treated for the cancer or the immune deficiency disease. In other embodiments, the patient is undergoing or has undergone treatment for the cancer or the immune deficiency disease. In yet other embodiments, the patient has failed treatment for the cancer or the immune deficiency disease.

In certain embodiments, the antibodies described herein are administered in combination with other therapeutic agents. Any therapy that is useful, has been used, or is currently being used for the prevention, treatment, and/or management of cancer or an immune deficiency disease can be used in compositions and methods of the invention. Such therapies include, but are not limited to, peptides, polypeptides, antibodies, conjugates, nucleic acid molecules, small molecules, mimetic agents, synthetic drugs, inorganic molecules, and organic molecules.

Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy including, but not limited to acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. US 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents"); vorozole; zanoterone; zeniplatin; zilascorb; and zinostatin stimalamer.

5.7 Vaccine Formulations

In another embodiment, a therapeutic agent capable of ablating the regulatory B cell subset can be administered in conjunction with a vaccine in order to increase the immune response associated with an infectious disease or cancer-associated target, e.g., a tumor or antigen. According to this embodiment, ablation of the regulatory B cell subset serves to decrease endogenous levels of IL-10 in the subject being vaccinated and to thereby boost the immune response directed to the infectious agent, infected cells, or tumor antigen. Any infectious disease or malignant cell can be vaccinated against according to this method of the invention.

A non-limiting list of FDA licensed vaccines (and associated disease) that could be administered in accordance with the methods of the invention includes: Acel-Immune (Diphtheria, tetanus, pertussis), ActHIB (*Haemophilus influenzae* type b), Anthrax vaccine, Attenuvax (Measles), Biavax II (Rubella, Mumps), Botox (Botulism), Chickenpox vaccine, Cholera vaccine, Comvax (*Haemophilus influenzae* type b, Hepatitis B), DTP (Diphtheria, Tetanus, Pertussis), Diphtheria vaccine, Engerix-B (Hepatitis B), Influenza vaccine, Fluvirin (Influenza), German Measles vaccine, Havrix (Hepatitis A), HBIG (Hepatitis B), Hepatitis A vaccine, Hepatitis B vaccine, Heptavax (Hepatitis B), HibTITER (*Haemophilus influenzae* type b, Diphtheria), Imovax Rabies vaccine, Infanrix (Diphtheria, Tetanus, Pertussis), Ipol (Polio), JE-Vax (Japanese Encephalitis Virus), Pedvax-HIB (*Haemophilus influenzae* type b, Meningitis), Meningococcal polysaccharide vaccine (Meningitis), Menomune-A/C/Y/W-135 (Meningitis), Meruvax-II (Rubella), M-M-R II (Measles, Mumps, Rubella), M-R-VAX II (Measles, Mumps, Rubella), Mumpsvax (Mumps), OmniHIB (*Haemophilus influenzae* type b, Diphtheria), Orimune (Polio), Paratyphoid vaccine (Typhoid), Pertussis vaccine, Plague vaccine, Pneumococcal vaccine (Pneumonia), Pneumovax 23 (Pneumonia), Pne-Imune 23 (Pneumonia), Polio vaccine, Recombivax HB (Hepatitis B), RhoGAM (Rhesus), Rocky Mountain Spotted Fever vaccine, Rubella vaccine, Rubeola vaccine, Smallpox vaccine, Tetanus vaccine, Tetramune (Diphtheria, Tetanus, Pertussis, *Haemophilus influenzae* type b), Tice BCG USP (*Mycobacterium Bovis* Infection), Tri-Immunol (Diphtheria, Tetanus, Pertussis), Tripedia (Diphtheria, Tetanus, Pertussis), Typhim Vi (Typhoid), Typhoid vaccine, Typhus vaccine, Vaqta (Hepatitis A), Varicella vaccine, Varivax (Varicella), Vivotif Berna (Typhoid), and Yellow Fever vaccine.

In one aspect of this embodiment, the therapeutic agent capable of ablating the regulatory B cell subset and the vaccine are administered concurrently. In another aspect of this embodiment, the therapeutic agent capable of ablating the regulatory B cell subset is administered prior to administration of the vaccine. Alternatively, the therapeutic agent capable of ablating the regulatory B cell subset can be administered following the administration of the vaccine.

In another aspect of this embodiment, the therapeutic agent capable of ablating the regulatory B cell subset and the vaccine are administered in conjunction with an adjuvant. A non-limiting list of adjuvants administered in accordance with the methods of the invention includes: alum (e.g., aluminum hydroxide, aluminum phosphate); Montanide ISA 720; MF-59; PROVAX; immunostimulatory nucleic acids, such as CpG oligodeoxynucleotides; saponins purified from the bark of the *Q. saponaria* tree, such as QS21; poly[di(carboxylatophen-oxy)phosphazene, derivatives of lipopolysaccharides (LPS), such as monophosphoryl lipid A, muramyl dipeptide (MDP; Ribi) andthreonyl-muramyl dipeptide (t-MDP; Ribi); OM-174; *Leishmania* elongation factor; ISCOMs; SB-AS2; SB-AS4; non-ionic block copolymers that form micelles such as CRL 1005; Syntex Adjuvant Formulation CpG nucleic acids; Bacterial toxins, e.g., Cholera toxin (CT), CT derivatives including but not limited to CT B subunit (CTB); *Zonula occludens* toxin, zot; *Escherichia coli* heat-labile enterotoxin; Labile Toxin (LT), LT derivatives including but not limited to LT B subunit (LTB); Pertussis toxin, PT; toxin derivatives; Lipid A derivatives (e.g., monophosphoryl lipid A, MPL); bacterial outer membrane proteins (e.g., outer surface protein A (OspA) lipoprotein of *Borrelia burgdorferi*, outer membrane protein of *Neisseria meningitidis*).

5.8 Diagnostics

In another embodiment, methods are provided for diagnosing a subject suffering from a disease that is associated with elevated or diminished levels of IL-10 production. In another embodiment, a subject with a predisposition to a certain disease can be diagnosed. In an aspect of these embodiments, regulatory B cells are isolated from the subject and assayed for specificity to a certain disease-specific antigen.

The regulatory B cells to be analyzed may be collected from any location in which they reside in the subject including, but not limited to, blood, spleen, thymus, lymph nodes, and bone marrow. The isolated regulatory B cells may be analyzed intact, or lysates may be prepared for analysis.

Methods for the quantitation of cells and detection of antigenic specificity are known in the art, and may include pre-labeling the sample directly or indirectly; adding a second stage antibody that binds to the antibodies or to an indirect label, e.g., labeled goat anti-human serum, rat anti-mouse, and the like. For example, see U.S. Pat. No. 5,635,363. Generally, assays will include various negative and positive controls, as known in the art.

Various methods are used to determine the antigenic specificity profile from a patient sample. The comparison of a binding pattern obtained from a patient sample and a binding pattern obtained from a control, or reference, sample is accomplished by the use of suitable deduction protocols including, but not limited to, AI systems, statistical comparisons, and pattern recognition algorithms Typically a data matrix is generated, where each point of the data matrix corresponds to a readout from a specific epitope. The information from reference patterns can be used in analytical methods to determine relative abundance, changes over time, and any other factors relevant to analysis.

Any disease can be diagnosed according to these embodiments. In particular, diseases associated with diminished levels of endogenous IL-10, i.e., immune and inflammatory diseases, and diseases associated with elevated levels of endogenous IL-10, i.e., cancer can be diagnosed based on isolation of regulatory B cells in a subject with disease-specific antigen specificity.

In another embodiment, a subject diagnosed with a given disease can be monitored for disease progression. Formats for patient sampling include time courses that follow the progression of disease, comparisons of different patients at similar disease stages, e.g., early onset, acute stages, recovery stages; and tracking a patient during the course of response to therapy. In an aspect of this embodiment, the numbers of regulatory B cells having specificity to a certain disease-specific antigen can be monitored over the course of a given therapy. As a non-limiting example, a therapy designed to expand the endogenous population of regulatory B cells that respond to a given disease should result in an increase in the numbers of regulatory B cells with specificity to a certain antigen associated with said disease relative to the general population of regulatory B cells.

6. EXAMPLE 1: A Regulatory B Cell Subset with a Unique CD1D$^{HIGH}$CD5$^+$ Phenotype Controls T Cell-Dependent Inflammatory Responses B cells mediate multiple functions that influence immune and inflammatory responses. In this study, T cell-mediated inflammation was exaggerated in CD19-deficient mice and mice depleted of CD20$^+$ B cells, while inflammation was significantly reduced in mice with hyperactivated B cells due to CD19 overexpression (hCD19Tg). These inflammatory responses were negatively regulated by a unique spleen CD1d$^{high}$CD5$^+$ B cell subset that was absent in CD19$^{-/-}$ mice, represented only 1-2% of spleen B220$^+$ cells in wild type mice, but was expanded to ~10% of B220$^+$ cells in hCD19Tg mice. Adoptive transfer of these spleen CD1d$^{high}$CD5$^+$ B cells normalized the exacerbated inflammation observed in wild type mice depleted of CD20$^+$ B cells and in CD19$^{-/-}$ mice. Remarkably, IL-10 production was restricted to this CD1d$^{high}$CD5$^+$ B cell subset, with IL-10 production diminished in CD19$^{-/-}$ mice, yet increased in hCD19TG mice. Thereby, CD1d$^{high}$CD5$^+$ B cells represent a novel and potent subset of regulatory B cells.

6.1 Materials and Materials 6.1.1 Abs and Immunofluorescence Analysis

Mouse CD20-specific mouse mAb MB20-11 (IgG2c) was used as described (Uchida et al., 2004, J. Exp. Med. 199: 1659-69). The mouse anti-human CD19 (hCD19) mAb FMC63 (IgG2a, provided by Dr. Heddy Zola, Child Health Research Inst., Adelaide, South Australia) was used as described (Yazawa et al., 2005, Proc. Natl. Acad. Sci. USA 102:15178-83). Other mAbs included: B220 mAb RA3-6B2 (provided by Dr. Robert Coffman, DNAX Corp., Palo, Alto, Calif.); CD19 (1D3), CD5 (53-7.3), CD1d (1B1), CD21/35 (7G6), CD23 (B3B4), CD24 (M1/69), CD25 (PC61), CD43 (S7), and CD11b (M1/70) from BD PharMingen (San Diego, Calif.); IgM (11/41) from eBioscience (San Diego, Calif.); and IgD (11-26) from Southern Biotechnology Associates (Birmingham, Ala.). Intracellular staining for Foxp3 (FJK-16s, eBioscience) used the Cytofix/Cytoperm kit (BD PharMingen). Single cell suspensions of spleen, peripheral lymph node (cervical, paired axillary and inguinal), and mesenteric lymph node were generated by gentle dissection. To isolate peritoneal cavity leukocytes, 10 ml of cold (4° C.) PBS was injected into the peritoneum of sacrificed mice followed by gentle massage of the abdomen. Intestinal Peyer's patches were isolated as described (Venturi et al., 2003, Immunity 19:713-24). Peripheral blood mononuclear cells were isolated from heparinized blood after centrifugation over a discontinuous Lymphoprep (Axis-Shield PoC As, Oslo, Norway) gradient. Viable cells were counted using a hemocytometer, with relative lymphocyte percentages determined by flow cytometry analysis. Single-cell leukocyte suspensions were stained on ice using predetermined optimal concentrations of each antibody for 20-60 min, and fixed as described (Sato et al., 1996, J. Immunol. 157:4371-8). Cells with the light scatter properties of lymphocytes were analyzed by 2-4 color immunofluorescence staining and FACScan or FACSCalibur flow cytometers (Becton Dickinson, San Jose, Calif.). Background staining was determined using unreactive isotype-matched control mAbs (Caltag Laboratories, San Francisco, Calif.) with gates positioned to exclude ≥98% of unreactive cells.

6.1.2 Mice and Immunotherapy

Wild-type C57BL/6 and IL-10$^{-/-}$ (B6.129P2-Il10$^{tm1Cgnn}$/J) mice (Kuhn et al., 1993, Cell 75:263-74) were from The Jackson Laboratory (Bar Harbor, Me.). CD20$^{-/-}$, CD19$^{-/-}$, and hCD19Tg (h19-1 line) mice were as described (Sato et al., 1996, J. Immunol. 157:4371-8; Sato et al., 1997, J. Immunol. 158:4662-9; Uchida et al., 2004, Int. Immunol. 16:119-29). Specifically, CD19$^{-/-}$ and hCD19Tg mice were backcrossed with C57BL/6 mice for 14 and 7 generations, respectively.

To deplete B cells, sterile CD20, hCD19, and isotype-matched control mAbs (250 µg) were injected in 200 µl PBS through lateral tail veins. All mice were bred in a specific pathogen-free barrier facility and used at 8-12 wks of age.

6.1.3 Contact Hypersensitivity Reaction

CHS reactions were induced using oxazolone as described (Tedder et al., 1995, J. Exp. Med. 181:2259-64). Briefly, mice were sensitized with 25 µl of a solution consisting of oxazolone (100 mg/ml, 4-ethyoxymethylene-2-phenyloxazolone; Sigma, St. Louis, Mo.) in acetone/olive oil (4:1 v/v) applied evenly for two consecutive days on a shaved hind flank. On day 5, sensitized mice were challenged by applying 10 µl of oxazolone solution (10 mg/me in acetone/olive oil (4:1) to the right ear (5 µl on the dorsal side and 5 µl on the ventral side). In certain experiments, 25 µl of 0.5% 2,4-dinitrofluorobenzene (DNFB, Sigma) was used as the sensitization agent. An identical amount of acetone/olive oil (4:1) was administered to the left ear. In some experiments, mice were treated with 250 µg anti-IL-10 receptor (1B1.3a; BD PharMingen) or isotype control mAb 1 hour before and 47 hours after oxazolone challenge. The thickness of the central portion of each ear lobe was measured at 24, 48, 72, and 96 hours after challenge using a constant force, calibrated digital thickness gage (Mitsutoyo Corp., Tokyo, Japan). Each ear lobe was measured three times at each time interval in a blinded fashion, with the mean of these values used for analysis.

6.1.4 B Cell Isolation and Stimulation

B220- or CD19-mAb coated microbeads (Miltenyi Biotech, Auburn, Calif.) were used to purify B cells by positive selection following the manufacturer's instructions. When necessary, the cells were enriched a second time using a fresh MACS column to obtain >95% purities.

For cytokine production, $4 \times 10^5$ purified B cells were cultured either with LPS (10 µg/ml, *Escherichia coli* serotype 0111: B4, Sigma) or with goat F(ab')$_2$ anti-mouse IgM antibody (20 µg/ml, Cappel, Aurora, Ohio) plus CD40 mAb (1 µg/ml, HM40-3; BD PharMingen) in 0.2 ml of complete medium (RPMI 1640 media containing 10% FCS, 200 µg/ml penicillin, 200 U/ml streptomycin, 4 mM L-Glutamine, and $5 \times 10^{-5}$ M 2-mercaptoethanol; all from Gibco, Carlsbad, Calif.) in a 96-well flat-bottom plate for 48 h. Culture supernatant fluid was collected after 48 hours to assess cytokine production.

6.1.5 Cytokine Analysis Using ELISA and Luminex Assays

Cytokines were measured in culture supernatant fluid using the Fluorokine MAP multiplex kit (R&D Systems, Minneapolis, Minn.) with Luminex® 100™ dual laser, flow-based sorting and detection (Luminex Corporation, Austin, Tex.) allowing simultaneous quantification of the following cytokines in single samples: IL-1β, IL-4, IL-5, IL-6, IL-10 IL-12, IL-13, IL-17, TNF-α, IFN-γ, and GM-CSF. Cytokine concentrations in culture supernatant fluid were also quantified using IL-10 OptEIA ELISA kits (BD PharMingen), IL-23 (p19/p40) ELISA Ready-SET-Go kits (eBioscience), and TGF-β1 DuoSet kits (R&D Systems) following the manufacturer's protocols. All assays were carried out on triplicate samples.

6.1.6 ELISPOT

The frequency of IL-10-producing B cells was determined using ELISPOT assays as described (Morris et al., 1994, J. Immunol. 152:1047-56). Briefly, Immobilon-P Multiscreen 96-well plates (Millipore, Billerica, Mass.) were precoated with 100 µl of capture mAb (JESS-2A5, 5 µg/ml) at 4° C. overnight. After three PBS washes, plates were blocked with complete medium (200 µl/ml) for 2 hours at room temperature. Purified B cells in 100 µl complete medium containing LPS (10 µg/ml) were cultured in the coated plates in duplicate at 37° C. in a humidified $CO_2$ incubator for 24 h. After washing, biotinylated detection mAb (SXC-1, 2 µg/ml, BD PharMingen) was added to the wells (100 µl/well). After incubation for 2 hours at room temperature, the plates were washed, streptavidine-HRP (BD PharMingen) was added to the wells, and the plates were incubated for 1 hour at room temperature. After washing, the plates were developed using 3-amino-9-ethylcarbazone and $H_2O_2$ (BD PharMingen).

6.1.7 Flow Cytometric Analysis of Intracellular IL-10 Synthesis

Intracellular cytokine analysis was as described (Openshaw et al., 1995, J. Exp. Med., 182:1357-67). Briefly, isolated leukocytes or purified cells were resuspended ($1 \times 10^6$ cells/ml) with LPS (10 µg/ml), PMA (50 ng/ml; Sigma), ionomycin (500 ng/ml; Sigma), and monensin (2 µM; eBioscience) for 5 h. For IL-10 detection, Fc receptors were blocked with anti-mouse Fc receptor mAb (2.4G2; BD PharMingen) before cell surface staining, and then fixed and permeabilized using the Cytofix/Cytoperm kit (BD PharMingen) according to the manufacturer's instructions. Permeabilized cells were stained with phycoerythrin-conjugated anti-IL-10 mAb (JESS-16E3; BD PharMingen). Leukocytes from IL-10$^{-/-}$ mice served as negative controls to demonstrate specificity and to establish background-staining levels.

6.1.8 Isolation of Total RNA and Real-Time Reverse Transcription PCR

B cells were purified (>95% purity) using B220 mAb-coated magnetic beads. Total RNA was extracted using TRIzol (Invitrogen, Carlsbad, Calif.). Random hexamer primers (Promega, Madison, Wis.) and Superscript II RNase H Reverse Transcriptase (Invitrogen, Carlsbad, Calif.) were used to generate cDNA as described (Engel et al., 1993, J. Immunol. 150:4719-32). IL-10 transcripts were quantified by real-time PCR analysis using SYBR Green as the detection agent as described (Ponomarev et al., 2004, J. Immunol. 173:1587-95). The PCR was performed with the iCycler iQ system (Bio-Rad, Hercules, Calif.). All components of the PCR mix were purchased from Bio-Rad and used according to the manufacturer's instructions. Cycler conditions were one amplification cycle of denaturation at 95° C. for 3 min followed by 40 cycles of 95° C. for 10 s, 59° C. for 1 min, and 95° C. for 1 min Specificity of the RT-PCR was controlled by the generation of melting curves. IL-10 expression threshold values were normalized to GAPDH expression using standard curves generated for each sample by a series of four consecutive 10-fold dilutions of the cDNA template. For all reactions, each condition was performed in triplicate. Data analysis was performed using iQ Cycler analysis software. The sense IL-10 primer was 5'-GGTTGCCAAGCCTTATCGGA-3' (SEQ ID NO: 1) and the antisense primer was 5'-ACCTGCTCCACTGCCTTGCT-3' (SEQ ID NO: 2). The sense GAPDH primer was 5'-TTCACCACCA TGGAGAAGGC-3' (SEQ ID NO: 3) and the antisense primer was 5'-GGCATGGACTGTGGTCATGA-3' (SEQ ID NO: 4)(Ponomarev et al., 2004, J. Immunol. 173:1587-95).

6.1.9 Microarray Expression Profiling

For microarray analysis, viable IL-10 secreting B cells were detected after 5 hours of LPS, PMA, and ionomycin stimulation using an IL-10 secretion detection kit (Miltenyi Biotech) before cell sorting. RNAs from purified B cell subsets were prepared as above and processed for use on Affymetrix Mouse Genome 430 2.0 GeneChips (Affymetrix, Santa Clara, Calif.). All quality parameters for the arrays were confirmed to be in the range recommended by the manufacturer.

6.1.10 Cell Sorting and Adoptive Transfers

Splenic B cells were purified using CD19 mAb-coupled microbeads (Miltenyi Biotech). In addition, CD1d$^{high}$CD5$^+$ B cells were selected using a FACSVantage SE flow cytometer (Becton-Dickinson, San Jose, Calif.) with purities of ~85%-95%. After isolation, 2×10$^6$ CD1d$^{high}$CD5$^+$ or non-CD1d$^{high}$CD5$^+$ B cells were immediately transferred i.v. into CD19$^{-/-}$ or B cell-depleted recipient mice before CHS induction.

6.1.11 Statistical Analysis

All data are shown as means±SEM. The significance of differences between sample means was determined using the Student's t test.

6.2 Results

6.2.1 Mice with Altered B Cells Differentially Regulate Inflammation

To assess T cell-mediated inflammation responses in mice with altered B cell signaling, CD19$^{-/-}$, hCD19Tg, and their wild type littermates were sensitized and challenged with oxazolone. B cells from hCD19Tg mice are hyper-responsive to transmembrane signals, proliferate at higher levels to certain mitogens, generate elevated humoral immune responses to T-dependent antigens, and spontaneously produce increasing amounts of IgG subclass auto-Abs as they age (Inaoki et al., 1997, J. Exp. Med. 186:1923-31). Thus, CD19 functions as a general 'rheostat' that defines signaling thresholds critical for expansion of the peripheral B cell pool (Tedder, 1998, Semin Immunol. 10:259-65). Ear inflammation was measured before and every 24 hours after challenge. In wild type mice, ear inflammation peaked at 24 hours after challenge, then decreased gradually (FIG. 1A). Ear swelling was significantly diminished in hCD19Tg mice compared with wild type littermates throughout the observation period (39±13%, 48 h, p<0.05). By contrast, ear swelling was enhanced and prolonged in CD19$^{-/-}$ mice (58±8%, 48 h, p<0.05) as reported (Watanabe et al., 2007, Am. J. Pathol. 171:560-70). Despite this, blood, spleen, and lymph node regulatory CD25$^+$Foxp3$^+$CD4$^+$ T cell numbers were identical in wild type, hCD19Tg, and CD19$^{-/-}$ mice. Thus, enhanced or reduced B cell function inversely paralleled T cell-mediated inflammatory responses.

6.2.2 B Cell Depletion Enhances CHS Responses

To determine whether B cells were directly responsible for decreased T cell-mediated inflammatory responses in hCD19Tg mice, B cells were depleted in hCD19Tg mice by using anti-human CD19 mAb as described (Yazawa et al., 2005, Proc. Natl. Acad. Sci. USA 102:15178-83). CD19 mAbs depleted the vast majority of circulating B cells within 1 hour of treatment, with >95% depletion of spleen and lymph node B cells within 2 days. Mice were treated with a single injection of hCD19 mAb 7 days before or 2 days after primary oxazolone sensitization. Mice treated with hCD19 mAb 7 days before primary sensitization showed significantly enhanced CHS responses compared with control mAb-treated littermates (p<0.01, FIG. 1B). Mice treated with hCD19 mAb 2 days after primary oxazolone sensitization had comparable CHS responses with control mAb-treated mice at 24 hours following oxazolone elicitation, but developed augmented CHS responses by 48 hours after elicitation. Ear swelling 48 hours after oxazolone challenge in mice treated with hCD19 mAb 7 days before or 2 days after primary oxazolone sensitization was increased by 102±8% or 89±12%, respectively. Thus, B cell depletion in hCD19Tg mice restored CHS responses to levels observed in wild type littermates.

To examine whether normal B cells regulate T cell-mediated inflammatory responses in wild type mice, B cells were depleted from mice with intact immune systems using CD20 mAb. Mature CD20$^+$ B cells in wild type mice are eliminated within 2 days after a single treatment with CD20 mAb (Uchida et al., 2004, J. Exp. Med. 199:1659-69). Mice depleted of B cells 7 days before or 2 days following primary oxazolone sensitization exhibited significantly enhanced CHS responses when compared with control mAb-treated littermates: 91±10% and 72±11% increase, respectively at 48 hours after oxazolone challenge (FIG. 1C). Thus, B cell depletion augmented T cell-mediated inflammatory responses in both wild type and hCD19Tg mice.

To determine whether CD19-deficiency completely eliminates B cell negative regulation, CD19$^{-/-}$ mice were also depleted of B cells using CD20 mAb. B cell depletion further increased CHS severity in CD19$^{-/-}$ mice, but the difference was not statistically different from control mAb-treated littermates (FIG. 1D). This suggests that some regulatory B cells still exist in CD19$^{-/-}$ mice, but at levels below those found in wild type and hCD19Tg mice. Moreover, anti-human CD19 as well as anti-mouse CD20 mAbs do not eliminate all peritoneal cavity B cells in these short-term experiments (Hamaguchi et al., 2005, J. Immunol. 7:4389-99; Yazawa et al., 2005, Proc. Natl. Acad. Sci. USA 102: 15178-83). Furthermore, CD20 mAb treatment does not reduce serum or natural Ab levels (DiLillo et al., 2008, J. Immunol. 180:361-71). Thereby, induced B cell depletion eliminates most B cell negative regulation, but does not eliminate the peritoneal B-1 cell population that also appears important for CHS initiation (Itakura et al., 2005, J. Immunol. 175:7170-8).

6.2.3 B Cell Cytokine Expression in Wild Type, hCD19Tg, and CD19$^{-/-}$ Mice B cells produce multiple cytokines that can act as growth and differentiation factors and influence immune responses (Harris et al., 2000, Nat. Immunol. 1:475-82). Therefore, B cells were purified from wild type, hCD19Tg, and CD19$^{-/-}$ mice (FIG. 2A) with cytokine production quantified and compared with T cell-mediated inflammatory responses observed in each mouse strain. While B cells cultured without mitogens did not produce cytokines, lipopolysaccharide (LPS)-stimulated B cells from wild type, hCD19Tg, and CD19$^{-/-}$ mice produced significant levels of TNF-α, IL-1β, IL-10, and IL-6 protein as determined using Luminex assays (FIG. 2B). Anti-IgM antibody plus CD40 mAb stimulation also induced the production of these cytokines, but at lower levels than induced by LPS stimulation. Only wild type B cells secreted TGF-β1, but only at very low levels after anti-IgM antibody plus CD40 mAb stimulation. Neither LPS nor anti-IgM antibody plus CD40 mAb stimulation induced detectable IL-4, -5, -12, -13, -17, or -23 secretion. Nonetheless, increased and decreased IL-10 production by B cells was the only cytokine change that paralleled the decreased and increased inflammatory responses of hCD19Tg and CD19$^{-/-}$ mice, respectively. In Luminex and standard ELISAs, B cells from hCD19Tg mice showed increased IL-10 levels compared with wild type mice (LPS stimulation 1.8-fold; p<0.01), while B cells from CD19$^{-/-}$ mice exhibited reduced IL-10 levels (65% of wild type, p<0.05; FIG. 2B-C). Using ELISPOT assays, IL-10-producing B cell frequencies were 2.7-fold higher in hCD19Tg mice than wild type mice (p<0.01), but 74% lower in CD19$^{-/-}$ mice than in wild type mice (p<0.01; FIG. 2D). Thus, increased and decreased frequencies of IL-10-producing B cells paralleled the decreased and increased inflammatory responses of hCD19Tg and CD19$^{-/-}$ mice, respectively.

6.2.4 IL-10-Producing B Cells Localize in the Spleen and Peritoneal Cavity

Reciprocal IL-10 production by B cells from hCD19Tg and CD19$^{-/-}$ mice was verified directly by intracellular cytokine staining. Cytoplasmic IL-10 production was not detected in resting B cells from wild type, hCD19Tg, or CD19$^{-/-}$ mice (FIG. 3A). After stimulation with LPS, PMA, and ionomycin for 5 h, the frequencies of spleen IL-10-producing B cells was 7.4-fold higher in hCD19Tg mice than in wild type mice (p<0.01), whereas the frequency of IL-10-producing B cells was 85% lower in CD19$^{-/-}$ mice than in wild type mice (p<0.01; FIG. 3B). Interestingly, IL-10 production by non-B cells after LPS, PMA, and ionomycin stimulation was also increased in hCD19Tg mice (FIG. 4). In addition, constitutive CD19 overexpression by B cells since birth can affect T cell activation independent of immunization (Stohl et al., 2005, Clin. Immunol. 116:257-64), suggesting additional inhibitory mechanisms in these mice as a potential result of B cell hyperactivity. Peritoneal IL-10-producing B cell frequencies were 3-fold higher in hCD19Tg mice than in wild type mice (p<0.01), but 80% lower in CD19$^{-/-}$ mice (p<0.01; FIG. 3C). Even though both CD19$^{-/-}$ and hCD19Tg mice have significantly reduced numbers of splenic B cells compared with wild type mice (Haas et al., 2005, Immunity 23:7-18; Sato et al., 1997, J. Immunol. 158:4662-9; Sato et al., 1995, J. Immunol. 157:4371-8), the numbers of IL-10-producing splenic and peritoneal B cells were 2.1-fold and 3.1-fold higher in hCD19Tg mice than in wild type mice, respectively (p<0.01). Splenic and peritoneal IL-10-producing B cell numbers were 80% and 78% lower in CD19$^{-/-}$ mice than in wild type mice, respectively (p<0.01). By contrast, naïve or stimulated B cells from blood, peripheral and mesenteric lymph nodes, and Peyer's patches exhibited little, if any, IL-10 production in wild type, hCD19Tg, or CD19$^{-/-}$ mice (FIG. 3D-F). Intracellular staining of B cells from IL-10$^{-/-}$ mice served as background controls. Thus, IL-10-producing B cells represent a distinct subset that was dramatically reduced in CD19$^{-/-}$ mice, but preferentially expanded in hCD19Tg mouse spleen and peritoneal cavity.

6.2.5 Cytokine Gene Expression by IL-10 Producing B Cells

Figure 3H:
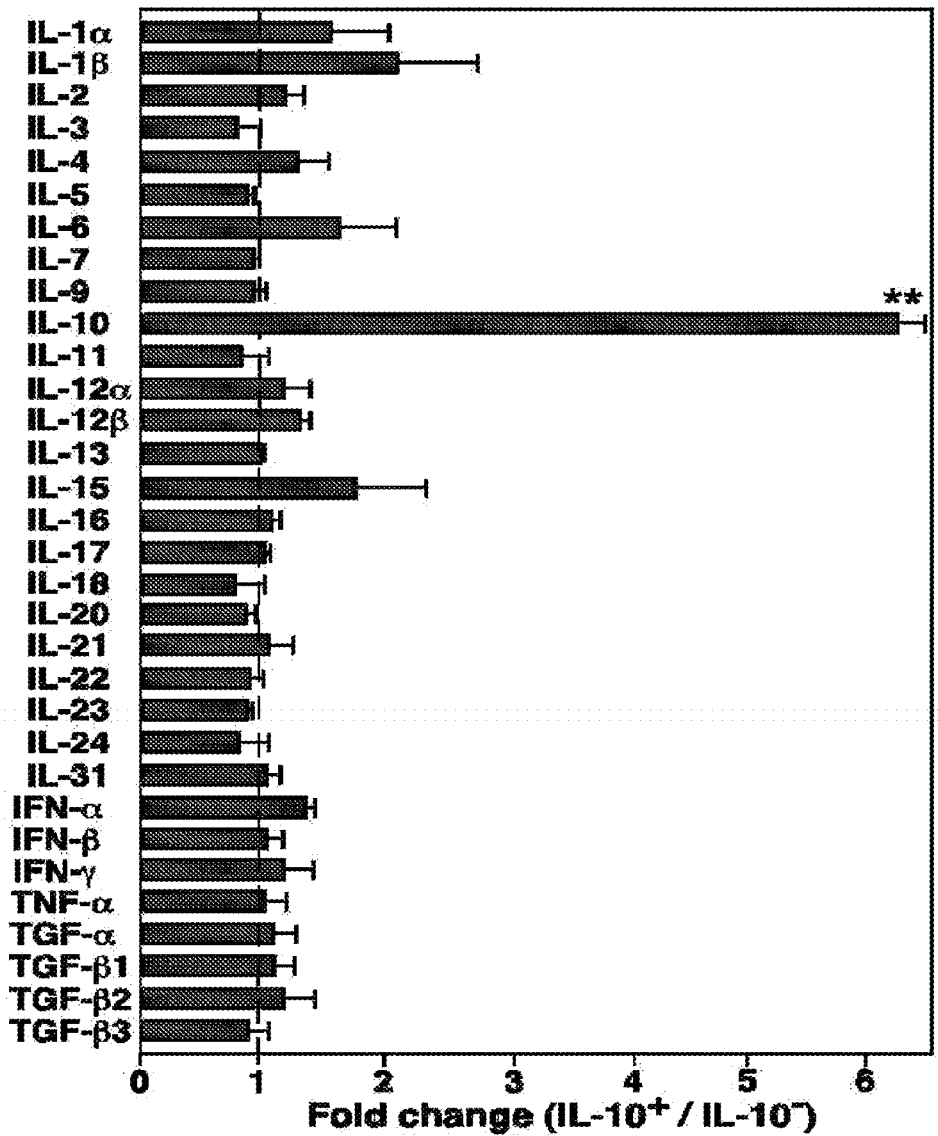

Whether IL-10-producing B cells preferentially generated other cytokine transcripts was examined by microarray analysis of purified IL-10-secreting B cells relative to other spleen B cells from hCD19Tg mice (FIG. 3G). IL-10-secreting B cells exhibited 6-fold higher levels of IL-10 transcripts when compared with other B cells, whereas transcript levels were not significantly different for all other cytokines (FIG. 3H). Thus, IL-10-secreting B cells were unique in their cytokine production capability.

6.2.6 Spleen IL-10-Producing B Cells are CD1d$^{high}$CD5$^+$

Figures 5A, 5B, 5C, 5D:
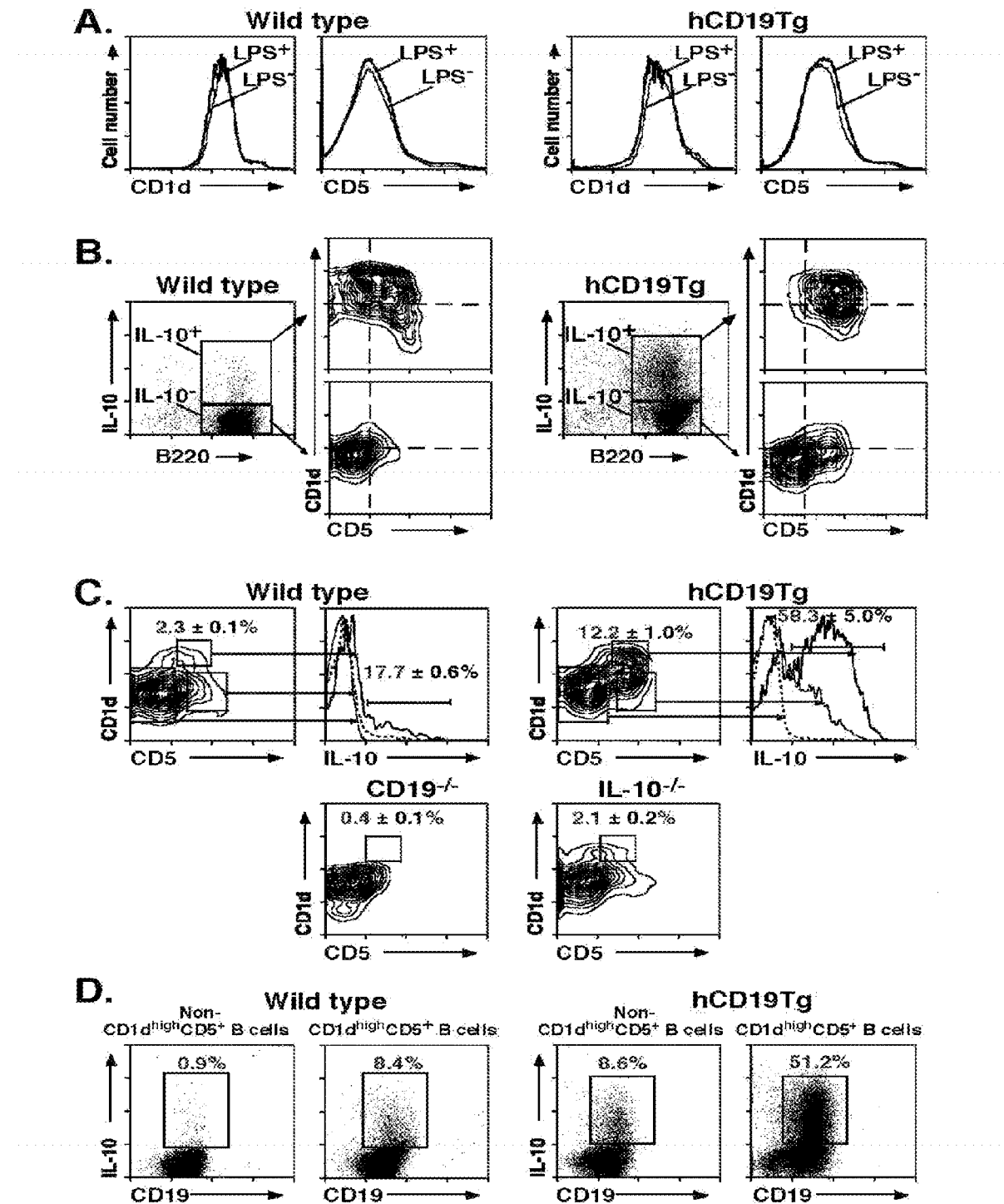
Figures 6A, 6B, 6C, 6D, 6E:
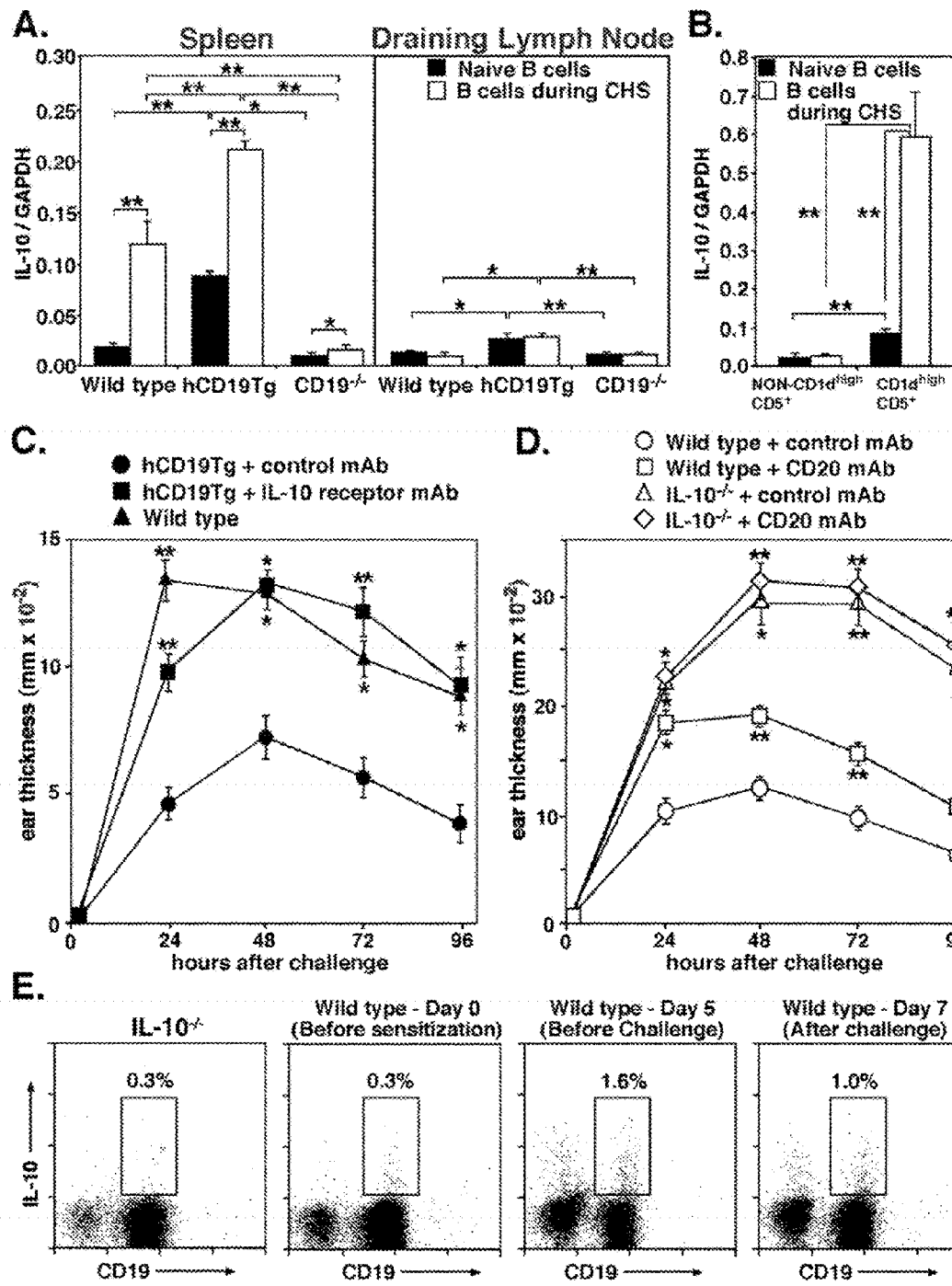

Whether IL-10-producing B cells represent a known B cell subset was determined by immunofluorescence staining with flow cytometry analysis. Since B cell cytoplasmic IL-10 was only visualized after combined LPS, PMA, ionomycin, and monensin treatment for 5 hours (FIG. 3), the effect of this treatment and cell permeabilization on phenotypes was determined. In all cases, untreated, treated, or permeabilized B cells from wild type and hCD19Tg mice expressed identical IgM, IgD, CD19, CD5, CD1d, CD21, CD24, CD23, CD11b, CD43, and B220 densities (FIG. 5A). It was therefore possible to use these cell surface molecules to categorize IL-10-producing B cells. Spleen IL-10-producing B cells in wild type and hCD19Tg mice were part of a mouse CD19$^{high}$ subset (FIG. 3B-C). Furthermore, spleen IL-10-producing B cells exhibited the CD5$^+$CD19$^{high}$ phenotype characteristic of B-1a cells, but unexpectedly expressed high CD1d levels in both wild type and hCD19Tg mice (FIG. 5B). By contrast, CD19$^{-/-}$ mice did not have detectable spleen CD1d$^{high}$CD5$^+$ or IL-10-producing B cells (FIGS. 3B and 5C, Table I). On average, B cells with a CD1d$^{high}$CD5$^+$ phenotype represented 2.3% and 12.2% of spleen B220$^+$ cells in wild type and hCD19Tg mice, respectively (FIG. 6C). The number of CD1d$^{high}$CD5$^+$ splenic B cells was 38% higher in hCD19Tg mice than in wild type mice (Table I). CD1d$^{low}$CD5$^+$ B cells did not express IL-10 at significant frequencies (FIG. 6C). Within the CD1d$^{high}$CD5$^+$ B cell subset, an average of 18% and 58% expressed IL-10 in wild type and hCD19Tg mice, respectively. When CD1d$^{high}$CD5$^+$ or the remaining spleen B cells were purified and then stimulated, the vast majority of IL-10 producing B cells were found within the CD1d$^{high}$CD5$^+$ subset of B cells from wild type and hCD19Tg mice (FIG. 6D), further excluding the possibility that LPS, PMA, and ionomycin treatment induced their phenotype as well as IL-10 production.

Figure 5E:
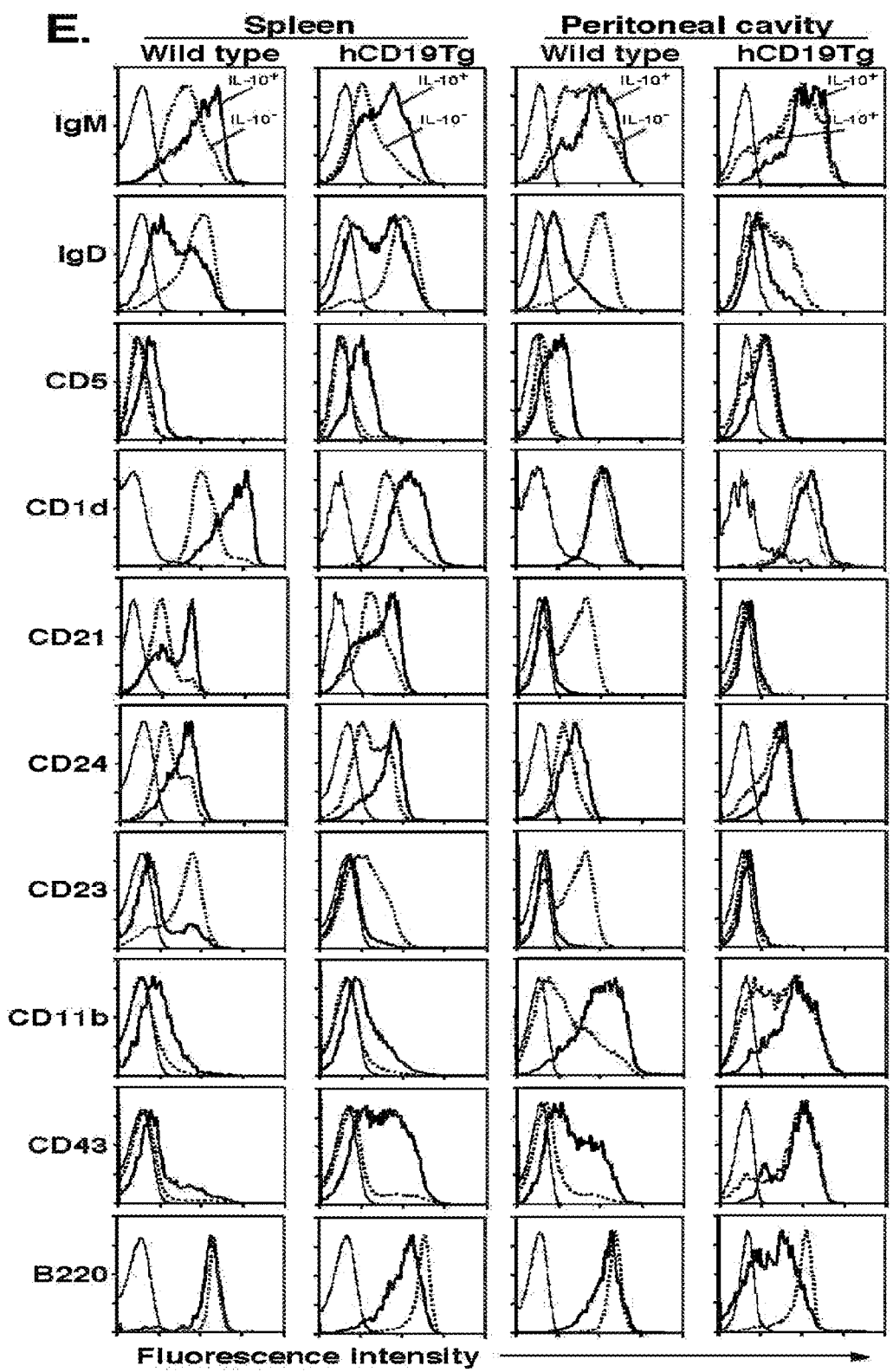

To further verify the phenotype of IL-10-producing spleen B cells, the phenotype of the IL-10$^+$ and IL-10$^-$ populations was determined Most splenic IL-10-producing B cells expressed IgM, CD1d, CD19, and CD24 at high levels (FIG. 5B, 5E). Approximately half of splenic IL-10-producing B cells expressed high density CD21 (44.3±2.6% and 54.8±1.6% in wild type and hCD19Tg mice, respectively). Peritoneal cavity IL-10-producing B cells were CD19$^{high}$ IgM$^{high}$ IgD$^{low}$ CD5$^+$ CD23$^-$ CD11b$^+$ CD43$^+$ B220$^{low}$, a phenotype consistent with B-1a cells. Thus, splenic IL-10-producing B cells shared features common to marginal zone (MZ), T2-MZ precursors, and B-1a B cells, but were localized within a unique CD1d$^{high}$CD5$^+$ subset.

6.2.7 Increased B Cell IL-10 Expression During T Cell-Mediated Responses

To determine whether B cell IL-10 production might contribute to regulation of T cell-mediated inflammation, IL-10 production by B cells was assessed during CHS responses in wild type, hCD19Tg, or CD19$^{-/-}$ mice. Spleen and draining axillary and inguinal lymph node B cells were purified two days after ear challenge with oxazolone, with IL-10 mRNA levels quantified by real-time PCR analysis. Relative IL-10 transcript levels in B cells from spleen and peripheral lymph nodes of unchallenged hCD19Tg mice were significantly increased relative to B cells from wild type mice (spleen 4.5-fold, p<0.01, lymph node 1.5-fold, p<0.05; FIG. 6A). During CHS responses, spleen B cells from both wild type and hCD19Tg mice exhibited significantly higher IL-10 transcript levels than naïve B cells (6-fold, p<0.01 and 2.2-fold, p<0.01, respectively), and hCD19Tg B cells produced significantly higher IL-10 transcripts than wild type B cells (1.8-fold, p<0.01; FIG. 6A, left panel). IL-10 transcript levels in spleen B cells from challenged CD19$^{-/-}$ mice increased significantly during CHS responses but only up to 16% of levels from wild type B cells (p<0.01). By contrast, B cell IL-10 mRNA levels in draining lymph nodes did not change during CHS responses (FIG. 6A, right panel). In similar experiments, IL-10 transcripts produced by the spleen CD1d$^{high}$CD5$^+$ B cell subset were increased 7.1-fold during CHS responses in comparison with naïve CD1d$^{high}$CD5$^+$ B cells, while IL-10 transcript levels were significantly lower in non-CD1d$^{high}$CD5$^+$ B cells with or without sensitization and challenge (FIG. 6B). Thus, B cell IL-10 production in the spleen but not lymph nodes was increased during CHS responses and the level of IL-10 production by B cells inversely paralleled the severity of inflammatory responses.

6.2.8 IL-10 Inhibits T Cell-Mediated Inflammatory Responses in hCD19Tg and Wild Type Mice Blocking IL-10 function in vivo using an anti-IL-10 receptor mAb enhances CHS responses in wild type mice (Ferguson et al., 1994, J. Exp. Med. 179:1597-1604). Therefore, whether the enhanced CHS responses observed in hCD19Tg mice were dependent on IL-10 was assessed using a function-blocking mAb reactive with the IL-10 receptor (Barrat et al., 2002, J. Exp. Med. 195:603-16). Anti-IL-10 receptor mAb treatment 1 hour before oxazolone challenge significantly augmented CHS responses in hCD19Tg mice when compared with control mAb-treated littermates (FIG. 6C, $p<0.05$ at 48 h). In fact, anti-IL-10 receptor mAb treatment restored CHS responses to levels normally observed in wild type littermates. Thus, the suppression of T cell-mediated inflammation observed in hCD19Tg mice was IL-10 dependent.

The relative contribution of wild type IL-10-producing B cells to CHS suppression was assessed by comparing the effects of CD20 mAb-induced B cell depletion in wild type and IL-10$^{-/-}$ mice. B cell depletion significantly augmented CHS responses in wild type mice (FIG. 6D). Remarkably, CHS responses were increased similarly by B cell depletion and IL-10-deficiency after 24 hours after challenge. Subsequently, CHS responses were higher in IL-10$^{-/-}$ mice, suggesting that B cell IL-10 production contributed most significantly to early inhibition of CHS responses, while IL-10 production by the remaining peritoneal B cells or other IL-10 producing subsets regulated later stages of the CHS response. Equally important was that CD20 mAb-induced B cell depletion did not affect CHS severity in IL-10$^{-/-}$ mice, arguing that the inhibitory role of B cells in CHS regulation is solely due to IL-10 production. Thus, B cells suppressed T cell-mediated inflammation in an IL-10-dependent manner, with a more significant contribution early during inflammation.

IL-10-production by blood B cells was also assessed to determine whether IL-10-producing B cells enter the circulation during CHS responses. IL-10-producing B cells were not observed in IL-10$^{-/-}$ or naïve mice before oxazolone-sensitization (FIGS. 3D and 6E). However, circulating IL-10-producing B cells were found in the blood after sensitization, with the percentage of circulating IL-10-producing B cells peaking before challenge and gradually decreasing after challenge (FIG. 6E). Thus, IL-10-producing B cells enter the circulation during CHS responses.

6.2.9 Adoptive Transfer of CD1d$^{high}$CD5$^+$ B Cells Inhibit T Cell-Mediated Inflammatory Responses The ability of CD1d$^{high}$CD5$^+$ B cells to regulate CHS responses was assessed using adoptive transfer experiments. Splenic CD1d$^{high}$CD5$^+$ B cells and non-CD1d$^{high}$CD5$^+$ B cells were purified from either oxazolone-sensitized (5 days after primary sensitization) wild type mice or their unsensitized littermates (FIG. 7A, left panels). Purified B cells were then transferred into oxazolone-sensitized CD19$^{-/-}$ mice that were challenged with oxazolone 48 hours after the transfer. Sensitized CD1d$^{high}$CD5$^+$ B cells transferred into CD19$^{-/-}$ mice significantly reduced (43% at 48 h, $p<0.05$) ear swelling (FIG. 7A, middle panel). Ear swelling was not inhibited in recipients given CD1d$^{high}$CD5$^+$ B cells from non-sensitized mice or non-CD1d$^{high}$CD5$^+$ B cells from sensitized mice. Likewise, splenic CD1d$^{high}$CD5$^+$ B cells purified from oxazolone-sensitized IL-10$^{-/-}$ mice did not affect ear swelling in CD19$^{-/-}$ recipients (FIG. 7A, right panel). Thus, sensitized splenic CD1d$^{high}$CD5$^+$ B cells inhibited CHS responses in an IL-10-dependent manner and likely in an antigen-specific manner.

To assess whether IL-10-producing CD1d$^{high}$CD5$^+$ B cells also played a role in CHS responses in wild type mice, spleen CD1d$^{high}$CD5$^+$ B cells were purified from oxazolone sensitized CD20$^{-/-}$ mice (FIG. 7B, left panels) and transferred into wild type recipient mice that had been depleted of B cells using CD20 mAb. CD20$^{-/-}$ mice do not express CD20 and are therefore resistant to B cell depletion. CD20$^{-/-}$ mice had normal numbers of CD1d$^{high}$CD5$^+$ IL-10-producing B cells compared to wild type mice. When B cells were depleted in wild type mice, CHS responses were increased significantly. However, the adoptive transfer of sensitized CD1d$^{high}$CD5$^+$CD20$^{-/-}$ B cells just before challenge normalized CHS responses in B cell-depleted mice (FIG. 7B, middle panel). The adoptive transfer of naïve CD1d$^{high}$CD5$^+$CD20$^{-/-}$ B cells into B cell-depleted mice 2 days before oxazolone sensitization and then ear challenge had the same effect (FIG. 7B, right panel). By contrast, the transfer of non-CD1d$^{high}$CD5$^+$CD20$^{-/-}$ B cells from naïve or sensitized mice into recipients before sensitization or challenge, respectively, did not reduce oxazolone-induced ear swelling. Thus, IL-10 secretion by CD1d$^{high}$CD5$^+$ B cells regulated T cell-mediated inflammatory responses in vivo.

Whether IL-10 secretion by CD1d$^{high}$CD5$^+$ B cells was induced by inflammation or was antigen-specific was addressed by the adoptive transfer of splenic CD1d$^{high}$CD5$^+$ B cells purified from DNFB-sensitized mice (FIG. 7C, left panels). When transferred into oxazolone-sensitized CD19$^{-/-}$ recipients, neither CD1d$^{high}$CD5$^+$ nor non-CD1d$^{high}$CD5$^+$ B cells purified from DNFB-sensitized mice affected ear swelling in CD19$^{-/-}$ recipients (FIG. 7C, right panel). These findings suggest that IL-10 producing CD1d$^{high}$CD5$^+$ B cells function is antigen-specific rather than a result of inflammatory stimuli.

TABLE I

Spleen B lymphocyte subsets in wild type, hCD19Tg, CD19$^{-/-}$, and IL-10$^{-/-}$ mice[a]

| Mouse genotype | B cell subset numbers ($\times 10^{-5}$) | | | |
| --- | --- | --- | --- | --- |
| | CD1d$^{high}$CD5$^+$ | B-1a | MZ | Follicular |
| hCD19Tg | 18 ± 2* | 32 ± 4 | 16 ± 1** | 68 ± 4* |
| Wild type | 13 ± 1 | 30 ± 3 | 42 ± 3 | 362 ± 42 |
| IL-10$^{-/-}$ | 12 ± 1 | 31 ± 2 | 42 ± 1 | 324 ± 17 |
| CD19$^{-/-}$ | 0.4 ± 0.1** | 8 ± 1** | 12 ± 1** | 148 ± 6* |

[a]B cell subsets were: CD1d$^{high}$CD5$^+$, B-1a (CD5$^+$B220$^{low}$), MZ (CD1d$^{high}$CD21$^{high}$B220$^{high}$), and follicular (CD21$^{int}$CD23$^+$B220$^{high}$).
[b]Values (±SEM, n ≥ 4 mice) were significantly different from those of wild type mice,
*p < 0.05,
**p < 0.01.

6.3 Discussion

This study demonstrates that a phenotypically distinct CD1d$^{high}$CD5$^+$CD19$^{high}$ B cell subset (FIG. 5) regulates T cell-mediated inflammatory responses through the secretion of IL-10. For convenience, splenic IL-10-producing CD1d$^{high}$CD5$^+$ B cells as "B10 cells" are designated. These rare IL-10-producing B cells represented only 1-2% of spleen B220$^+$ cells and 7-8% of peritoneal B cells in wild type mice, but were not normally detectable in blood or lymph nodes (FIG. 3). However, IL-10-producing CD1d$^{high}$CD5$^+$ B cells were expanded significantly in the spleen (~10% of B220+ cells) and peritoneal cavity (~25%) but not blood or lymph nodes of hCD19Tg mice, and was collapsed in CD19$^{-/-}$ mice (FIGS. 3 and 5C, Table I). In parallel, the abilities of B cells from hCD19Tg, wild type, and CD19$^{-/-}$ mice to modify CHS responses (FIGS. 1 and 3) inversely paralleled their capacity to secrete IL-10 (FIGS. 2 and 3). Similarly, B cell depletion increased CHS responses in wild type mice to the levels observed in CD19$^{-/-}$ mice, and normalized CHS responses in hCD19Tg mice (FIG. 1). B cell depletion in CD19$^{-/-}$ mice did not reduce CHS severity excluding the possibility that CD19$^{-/-}$ B cells abnormally produce pro-inflammatory mediators during CHS responses (FIG. 1D). Spleen and blood B cell IL-10 expression was also enhanced in wild type and hCD19Tg mice during CHS responses, but not in CD19$^{-/-}$ mice (FIGS. 6A and E). Furthermore, blocking IL-10 receptor function normalized CHS responses in hCD19Tg mice (FIG. 6C). The adoptive transfer of spleen CD1d$^{high}$CD5+ B cells from wild type and CD20$^{-/-}$ mice normalized CHS responses in CD19$^{-/-}$ mice and CD20 mAb-treated mice, respectively, while spleen CD1d$^{high}$CD5+ B cells from IL-10$^{-/-}$ mice were without effect (FIG. 7A-B). Thus, CD1d$^{high}$CD5+ B cell production of IL-10 regulated T cell-dependent CHS responses.

That B10 cells were found exclusively within the relatively rare spleen CD1d$^{high}$CD5+CD19$^{high}$ B cell subset distinguishes the current results from previous studies (Mizoguchi and Bhan, 2006, J. Immunol. 176:705-10), but also unifies most of the current studies regarding IL-10 production by B cells. Some spleen B cells and peritoneal CD5+ B-1a cells are known to produce IL-10 (Brummel and Lenert, 2005, J. Immunol. 174:2429-34; Evans et al., 2007, J. Immunol. 178:7868-78; Fillatreau et al., 2002, Nat. Immunol. 3:944-50; Gray et al., 2007, Proc. Natl. Acad. Sci. USA 104:14080-5; Harris et al., 2000, Nat. Immunol. 1:475-82; Mauri et al., 2003, J. Exp. Med. 197:489-501; Spencer and Daynes, 1997, Int. Immunol. 9:745-54). Specifically, spleen B cells with a CD21+CD23− "MZ" phenotype can produce IL-10 in response to CpG (Brummel and Lenert, 2005, J. Immunol. 174:2429-34) or apoptotic cell (Gray et al., 2007, Proc. Natl. Acad. Sci. USA 104:14080-5) stimulation. Spleen CD1d+CD21+CD23+ B cells with a "T2-MZ precursor" phenotype also produce IL-10 and can inhibit collagen-induced arthritis (Evans et al., 2007, J. Immunol. 178:7868-78). Spleen CD5+ B cells also produce IL-10 following IL-12 stimulation, while CD5− B cells do not (Spencer and Daynes, 1997, Int. Immunol. 9:745-54). Thus, spleen B10 cells share some phenotypic markers with both CD1d$^{high}$CD21$^{high}$ MZ B cells and CD5+CD19$^{high}$B220$^{low}$ B-1a cells. However, the frequency of spleen CD1d$^{high}$CD5+ B cells in wild type mice (2.3±0.1%) was significantly lower than the frequencies of spleen B-1a (6.2±0.3%, p<0.01) and MZ (6.9±0.4%, p<0.01) B cells. Moreover, IL-10 secretion was predominantly localized within the spleen CD1d$^{high}$CD5+ B cell subset in wild type mice, while other spleen B cells including B-1a and follicular B cells did not secrete IL-10 at significant frequencies (FIG. 5C). Since fractionating such small B cell subsets with absolute purity remains technically difficult, it is possible that some IL-10 producing B cells exist that are not CD1d$^{high}$CD5+, although these cells may also represent B10 cells at different states of maturation. Alternatively, it is possible that B10 cells may represent an "activated" MZ or B-1a subset, although B10 cells did not selectively produce other cytokines (FIG. 3H). Thus, the CD1d$^{high}$CD5+CD19$^{high}$ spleen subset as currently identified represents a relatively rare but functionally potent population of IL-10-producing regulatory B cells.

IL-10 production likely explains the potent ability of B10 cells to regulate T cell-mediated inflammatory responses. The adoptive transfer of only 2×10$^6$ wild type CD1d$^{high}$CD5+ B cells normalized the CHS responses of both CD19$^{-/-}$ mice and mice depleted of B cells (FIG. 7). This is remarkable since not all CD1d$^{high}$CD5+ B cells produced IL-10 following LPS stimulation (FIG. 5). Moreover, B10 cells may be antigen-specific since the adoptive transfer of CD1d$^{high}$CD5+ B cells from antigen-sensitized mice into CD19$^{-/-}$ recipients inhibited CHS responses, while CD1d$^{high}$CD5+ B cells from unsensitized mice or from mice sensitized with a different antigen were without effect (FIG. 7A, C). It is not known whether splenic or peritoneal IL-10-producing B cells affect immune responses centrally or this depends on B10 cell migration into draining lymph nodes or peripheral tissues. However, IL-10 transcripts were not significantly increased in B cells from lymph nodes draining the sites of antigen challenge (FIG. 5A). Furthermore, B cell infiltration is not observed in the challenged ears of wild type and CD19$^{-/-}$ mice during CHS responses (Watanabe et al., 2007, Am. J. Pathol. 171:560-70). Nonetheless, B10 cells entered the circulation during CHS responses (FIG. 6E) and may thereby migrate in small numbers to local sites of inflammation. B cell depletion in tight skin mice, a genetic model for human systemic sclerosis, reduces IL-10, IL-4, IL-6, and TGF-β production in the skin, while B cell transcripts are not found in the lesional skin (Hasegawa et al., 2006, Am. J. Pathol. 169:954-66). Similarly, B cell-deficient and CD19$^{-/-}$ mice exhibit augmented EAE responses (Fillatreau et al., 2002, Nat. Immunol. 3:944-50; Matsushita et al., 2006, Am. J. Pathol. 168:812-21), although central nervous system B cells are rare during EAE (McGeachy et al., 2005, J. Immunol. 3025-32). Thus, splenic and peritoneal IL-10-producing B cells may alter the peripheral production of IL-10 and other cytokines by non-B cells circulating through draining lymph nodes or peripheral tissue, thereby influencing systemic as well as local inflammatory responses.

Functional and lineage relationships between spleen B10, B-1a, and MZ B cells, and peritoneal B-1a, B-1b, and peritoneal IL-10-producing B cells are possible. However, their only common features identified thus far are shared phenotypic markers. Since B10 and B-1a cell frequencies are increased in hCD19Tg mice (Table I), while B10 and B-1a cells are rare in CD19$^{-/-}$ mice (Haas et al., 2005, Immunity 23:7-18; Sato et al., 1996, J. Immunol. 157:4371-8), it is possible that B10 cells and B-1a cells represent different branches of a common lineage. By contrast, B-1b cell frequencies are increased in CD19$^{-/-}$ mice (Haas et al., 2005, Immunity 23:7-18), while B10 cells were significantly reduced (Table I). Phenotypically- and histologically-defined MZ B cells are also reduced in CD19$^{-/-}$ mice, while organized marginal zones are equally difficult to identify in hCD19Tg mice by immunohistochemistry staining (Haas et al., 2005, Immunity 23:7-18). Likewise, spleen B cells with a CD1d$^{high}$CD21$^{high}$B220+"MZ phenotype" were reduced in hCD19Tg mice, while CD1d$^{high}$CD5+ B cells numbers were increased relative to wild type mice (Table I). Moreover, only ~50% of B10 cells exhibited the CD21$^{high}$ phenotype of MZ B cells. Nonetheless, increased numbers of splenic IL-10-producing B cells and an expanded population of "MZ-like" CD1d$^{high}$ B cells that express CD5 have been identified in mouse lupus models (Duan et al., 2007, Lab. Invest. 87:14-28). Thus, B10 cells might be important in regulating autoimmune disease since hCD19Tg mice develop autoimmunity with age (Sato et al., 1996, J. Immunol. 157:4371-8). Notably, IL-10 production was not required for CD1d$^{high}$CD5$^+$ B cell generation since this subset was present in IL-10$^{-/-}$ mice (FIG. 5C, Table I). Regardless, it is exciting to speculate that each B cell subset has different functions, with B10 cells producing IL-10 and thereby regulating T cell function, while B-1a cells produce natural and autoantibodies, B-1b cells produce adaptive immune responses to T cell-independent antigens (Haas et al., 2005, Immunity 23:7-18), and MZ B cells provide protection early during pathogen challenge (Martin et al., 2001, Immunity 14:617-29).

That B10 cells represent a unique subset with regulatory functions in vivo provides new insight into potential regulatory roles for B cells during immune responses and autoimmune disease. B cell depletion in mice resulted in significantly enhanced CHS responses, suggesting that B10 cells regulate T cell responses (FIG. 1). B cell depletion also significantly delays the onset of collagen-induced arthritis in DBA/1J mice (Yanaba et al., 2007, J. Immunol. 179:1369-80), skin sclerosis in tight skin mice (a model of systemic sclerosis) (Hasegawa et al., 2006, Am. J. Pathol. 169:954-66), Sjogren's-like disease in Id3-deficient mice (Hayakawa et al., 2007, Immunology 122:73-9), and diabetes in non-obese diabetic mice (Xiu et al., 2008, J. Immunol. 180:2863-75). By contrast, we have found that B cell depletion early in the course of disease worsens EAE, whereas B cell depletion at the height of disease ameliorates EAE. This suggests the dominance of different B cell functions during disease progression, which may involve B10 cells. Similarly, B cell depletion in humans using a chimeric anti-human CD20 mAb, was recently found to exacerbate ulcerative colitis (Goetz et al., 2007, Inflamm Bowel Dis. 13:1365-8) and may contribute to the development of psoriasis (Dass et al., 2007, Arthritis Rheum. 56:2715-8). By contrast, B cell depletion using a chimeric anti-human CD20 mAb may benefit rheumatoid arthritis, systemic lupus erythematosus, idiopathic thrombocytopenic purpura, and pemphigus vulgaris patients (Edwards and Cambridge, 2006, Nat. Rev. Immunol. 6:394-403; El Tal et al., 2006, J. Am. Acad. Dermatol. 55:449-59). Thereby, the benefit of B cell depletion therapy is likely to vary according to disease and the relative involvement of different B and T cell subsets. Thus, the B10 cell subset that is included in a phenotypically defined CD1d$^{high}$CD5$^+$ B cell population may represent relatively rare but functionally potent regulatory cells. Regardless, further defining the role of B10 cells and other B cell subsets in disease and regulatory function in vivo may provide new insights and therapeutic approaches for treating inflammatory and organ-specific autoimmunity in addition to other diseases.

7. EXAMPLE 2: A role for CD1D$^{HIGH}$CD5$^+$ Regulatory B Cells inExperimental Autoimmune Encephalomyelitis (EAE)

EAE is a T lymphocyte-mediated autoimmune disease of the CNS that models human multiple sclerosis. This example shows that B lymphocytes significantly influence EAE disease initiation and progression using mice depleted of mature B cells but with otherwise intact immune systems. Unexpectedly, B cell depletion before EAE induction significantly exacerbated disease symptoms and increased encephalitogenic T cell influx into the CNS. This resulted from the depletion of a rare splenic IL-10-producing CD1d$^{high}$CD5$^+$ regulatory B cell subset since the adoptive transfer of these cells normalized EAE in B cell-deficient mice. By contrast, B cells were also required for CNS-autoantigen specific-CD4$^+$ T cell generation during EAE development. Thereby, B cell depletion during EAE progression dramatically suppressed disease symptoms, impaired CNS-autoantigen specific-CD4$^+$ T cell expansion, and reduced encephalitogenic T cell entry into the CNS. These results demonstrate reciprocal regulatory roles for B cells during EAE immunopathogenesis.

7.1 Materials and Methods 7.1.1 Cell Preparation and Immunofluorescence Analysis Single-cell leukocyte suspensions from spleens, peripheral lymph nodes (paired axillary and inguinal), and bone marrow (bilateral femurs) were generated by gentle dissection. Mononuclear cells from the CNS were isolated after cardiac perfusion with PBS, as described (Zeine and Owens, 1992, J. Neuroimmunol. 40:57-69). Briefly, CNS tissues were digested with collagenase D (2.5 mg/ml, Roche Diagnostics, Mannheim, Germany) and DNaseI (1 mg/ml, Roche Diagnostics) at 37° C. for 45 min. Mononuclear cells were isolated by passing the tissue through 70-µm cell strainers (BD Biosciences, San Diego, Calif.), followed by percoll gradient (70%/37%) centrifugation. Lymphocytes were collected from the 37:70% interface and washed.

Mouse CD20-specific mAb MB20-11 was used as described (Uchida et al., 2004, J. Exp. Med. 199:1659-69). FITC-, PE- or PE-Cy5-conjugated CD1d (1B1), CD3 (17A2), CD4 (H129.19), CD5 (53-7.3), CD8 (53-6.7), CD19 (1D3), CD25 (PC61), CD44 (IM7), B220 (H1.2F3), Thy1.2 (53-2.1), and T cell antigen receptor Vβ11-specific (RR3-15) mAbs were from BD Biosciences (San Diego, Calif.); anti-IgM mAb (11/41) was from eBioscience (San Diego, Calif.). FITC-conjugated mAb reactive with L-selectin (CD62L; clone LAM1-116) was as described (Steeber et al., 1997, J. Immunol. 159:952-63). Intracellular staining used mAbs reactive with IFN-γ (XMG1.2), IL-17A (eBiol7B7), and Foxp3 (FJK-16s) (all from eBioscience) and the Cytofix/Cytoperm kit (BD Biosciences). For intracellular cytokine staining, lymphocytes were stimulated in vitro with phorbol 12-myristate 13-acetate (10 ng/ml; Sigma, St. Louis, Mo.) and ionomycin (1 µg/ml; Sigma), in the presence of monensin (1 µl/ml; eBioscience) for 4 hours before staining. MOG$_{38-49}$/IAb tetramer and control tetramer (CLIP/IAb) were constructed and supplied by the NIH Tetramer Core Facility (Atlanta, Ga.). Background staining was assessed using non-reactive, isotype-matched control mAbs (Caltag Laboratories, San Francisco, Calif.). For two- or three-color immunofluorescence analysis, single cell suspensions (10$^6$ cells) were stained at 4° C. using predetermined optimal concentrations of mAb for 20 minutes as described (Zhou et al., 1994, Mol. Cell. Biol. 14:3884-94). For tetramer staining, lymphocytes were stained for 3 hours at 37° C. as described (Falta et al., 2005, Arth. Rheum. 52:1885-96). Blood erythrocytes were lysed after staining using FACS™ Lysing Solution (Becton Dickinson, San Jose, Calif.). Cells with the forward and side light scatter properties of lymphocytes were analyzed using a FACScan flow cytometer (Becton Dickinson).

7.1.2 Mice

Female C57BL/6 (B6) mice were obtained from The Jackson Laboratory (Bar Harbor, Me.). CD20$^{-/-}$ mice were as described (Uchida et al., 2004, Int. Immunol. 16:119-29). TCR$^{MOG}$ transgenic mice whose CD4$^+$ T cells respond to MOG$_{35-55}$ peptide (Bettelli et al., 2003, J. Exp. Med. 197:1073-81) were provided by Dr. V. K. Kuchroo (Harvard Medical School, Boston, Mass.). Mice were housed in a specific pathogen-free barrier facility.

7.1.3 EAE Induction and Immunotherapy

Active EAE was induced in female B6 (six- to eight-week-old) mice by subcutaneous immunization with 100 µg of MOG$_{35-55}$ peptide (MEVGWYRSPFSRVVHLYRNGK; NeoMPS, San Diego, Calif. (SEQ ID NO: 5)) emulsified in CFA containing 1 mg/ml of heat-killed *Mycobacterium tuberculosis* H37RA (Sigma-Aldrich, St. Louis, Mo.) on day 0. Additionally, mice received 200 ng of pertussis toxin (List Biological Laboratories, Campbell, Calif.) intraperitoneally in 0.5 ml of PBS on days 0 and 2. Clinical signs of EAE were assessed daily with a 0-6 scoring system (0, no signs; 1, flaccid tail; 2, impaired righting reflex and/or gait; 3, partial hind limb paralysis; 4, total hind limb paralysis; 5, hind limb paralysis with partial fore limb paralysis; 6, moribund state) (Fillatreau et al., 2002, Nat. Immunol. 3:944-50). To deplete B cells in vivo, sterile CD20 (MB20-11, IgG2c) or isotype-matched control mAbs (250 µg) were injected in 200 µl PBS through lateral tail veins (Uchida et al., 2004, Int. Immunol. 16:119-29).

7.1.4 Histology

Following an initial perfusion with PBS, animals were perfused transcardially with 4% paraformaldehyde and spinal cords were removed. Tissues were processed and blocked in paraffin wax. Transverse spinal cord sections were stained with H&E for assessment of inflammation and with Luxol Fast Blue for demyelination. Sections were assessed as follows: inflammation: 0, none; 1, a few inflammatory cells; 2, organization of perivascular infiltrates; and 3, increasing severity of perivascular cuffing with extension into adjacent tissues. For demyelination: 0, none; 1, rare foci; 2, a few areas of demyelination; 3, large (confluent) areas of demyelination (Calida et al., 2001, J. Immunol. 166:723-6).

7.1.5 Serological Evaluation of MOG Peptide-Specific Ab Production

To evaluate MOG peptide-specific Ab production, 96 well microtiter plates (Costar, Cambridge, Mass.) were coated with 10 µg/ml of MOG peptide. Plates were incubated with serum samples diluted 1:100, with bound antibody detected using alkaline phosphatase-conjugated goat anti-mouse IgG or IgM Abs (Southern Biotechnology Associates, Inc., Birmingham, Ala.).

7.1.6 Adoptive Transfer Experiments

CD4$^+$ T cells were isolated from pooled spleens and lymph nodes of TCR$^{MOG}$ transgenic mice using an isolation kit from Miltenyi Biotech (Auburn, Calif.). TCR$^{MOG}$ CD4$^+$ T cells were then labeled with CFSE Vybrant™ CFDA SE fluorescent dye (5 µM; CFSE; Invitrogen-Molecular Probes, Carlsbad, Calif.) as described (Quah et al., 2007, Nat. Protoc. 2:2049-56). Labeled TCR$^{MOG}$ CD4$^+$ T cells (5×10$^6$) were then transferred i.v. into mice. Four days after adoptive transfer, T cells were stained for CD4 and Vβ11 expression with proliferation assessed by flow cytometry.

Splenic B cells were purified from CD20$^{-/-}$ mice using CD19 mAb-coupled microbeads (Miltenyi Biotech). In addition, CD1d$^{high}$CD5$^+$ B cells were isolated using a FACSVantage SE flow cytometer (Becton Dickinson) with purities of 95-98%. After isolation, 2×10$^6$ CD1d$^{high}$CD5$^+$ or non-CD1d$^{high}$CD5$^+$ B cells were immediately transferred i.v. into B cell-depleted recipient mice 2 days before EAE induction.

7.1.7 Statistical Analysis

All data are shown as means±SEM. The significance of differences between sample means was determined using the Student's t test.

7.2 Results 7.2.1 B Cells are Capable of Inhibiting and Augmenting EAE

To assess the contributions of B cells during EAE induction or progression, mice were given CD20 mAb either 7 days before EAE induction (day −7) or when EAE symptoms were present on day 14. The CD20-specific mAb was mouse antibody MB20-11 and was used as described (Uchida et al., 2004, J. Exp. Med. 199:1659-69). In both cases, CD20 mAb significantly depleted the majority of mature B cells in the bone marrow, blood, spleen, and peripheral lymph nodes by day 18 after EAE induction, while control mAb treatment was without effect (FIG. 8 and Table II). Peritoneal cavity B cells are more resistant to CD20 mAb-mediated depletion (Hamaguchi et al., 2005, J. Immunol. 4389-99), which explains their less complete depletion 4 days after day 14 CD20 mAb injection. Nonetheless, MOG immunization did not significantly affect B cell subset depletion when compared with unimmunized mice (Yanaba et al., 2007, J. Immunol. 179:1369-80; DiLillo et al., 2008, J. Immunol. 180:361-71).

In mice treated with CD20 or control mAb, EAE symptoms first appeared around day 12 with similar disease incidence (93-100%, FIG. 9A and Table III). However, mice depleted of B cells before MOG immunization exhibited significantly worse disease. This included a more severe peak in disease symptom severity and disease persisting longer when compared with control mAb-treated mice ($p<0.05$, FIG. 9A left panel and Table III). By contrast, B cell depletion during EAE development dramatically reduced disease severity at all time points when compared with control mAb-treated mice ($p<0.05$, FIG. 9A right panel and Table III). Microscopic examination of CNS tissues collected from each group of mice on day 18 revealed that B cell depletion before EAE induction resulted in more robust leukocyte infiltration into the CNS and more significant demyelination when compared with control mAb-treated mice ($p<0.05$, FIG. 9B). B cell depletion during EAE development resulted in reduced leukocyte infiltration and significantly less demyelination when compared with control mAb-treated mice ($p<0.05$). Thus, the presence of B cells had profound effects on disease course and CNS leukocyte infiltration that was dependent on whether B cells were depleted before disease induction or after symptoms developed.

TABLE II

Tissue B cell depletion following EAE induction and CD20 mAb treatment[a]

| | | Treated day −7[c] (% Depletion) | | Treated day 14 (% Depletion) | |
|---|---|---|---|---|---|
| Tissue | B subset[b] | Control mAb | CD20 mAb | Control mAb | CD20 mAb |
| Bone marrow: | Pro/pre | 0.10 ± 0.04 | 0.11 ± 0.05 (0) | 0.09 ± 0.03 | 0.09 ± 0.05 (0) |
| | Immature | 0.16 ± 0.10 | 0.04 ± 0.02 (72) | 0.16 ± 0.04 | 0.04 ± 0.02 (72) |
| | Mature | 0.48 ± 0.16 | 0.01 ± 0.01 (99*) | 0.51 ± 0.14 | 0.01 ± 0.01 (97*) |
| Blood: | B220$^+$ | 3.2 ± 0.9 | 0.03 ± 0.01 (99*) | 3.0 ± 0.7 | 0.05 ± 0.02 (98*) |
| Spleen: | B220$^+$ | 20.0 ± 6.5 | 0.07 ± 0.02 (99*) | 19.6 ± 1.3 | 1.8 ± 0.6 (91*) |
| | Mature | 11.4 ± 4.3 | 0.02 ± 0.02 (99**) | 12.6 ± 1.3 | 0.68 ± 0.31 (95*) |

TABLE II-continued

Tissue B cell depletion following EAE induction and CD20 mAb treatment[a]

| Tissue | B subset[b] | Treated day −7[c] (% Depletion) | | Treated day 14 (% Depletion) | |
|---|---|---|---|---|---|
| | | Control mAb | CD20 mAb | Control mAb | CD20 mAb |
| | T1 | 1.5 ± 0.6 | 0.02 ± 0.02 (99*) | 1.4 ± 0.5 | 0.18 ± 0.07 (87*) |
| | T2 | 1.2 ± 0.5 | 0.01 ± 0.01 (99*) | 1.3 ± 0.4 | 0.01 ± 0.01 (99*) |
| | Marginal zone | 1.9 ± 0.7 | 0.01 ± 0.02 (99*) | 1.9 ± 0.4 | 0.01 ± 0.01 (99*) |
| Peripheral LN: | B220+ | 1.2 ± 0.4 | 0.05 ± 0.02 (95*) | 1.2 ± 0.3 | 0.43 ± 0.08 (65*) |
| Peritoneum: | B220+ | 1.2 ± 0.2 | 0.01 ± 0.01 (99**) | 1.3 ± 0.1 | 0.14 ± 0.08 (89*) |
| | B1a | 0.11 ± 0.03 | 0.01 ± 0.01 (95*) | 0.13 ± 0.03 | 0.05 ± 0.01 (62) |
| | B1b | 0.12 ± 0.04 | 0.01 ± 0.01 (95*) | 0.12 ± 0.01 | 0.05 ± 0.02 (63) |
| | B2 | 1.0 ± 0.4 | 0.01 ± 0.01 (99*) | 1.14 ± 0.37 | 0.13 ± 0.08 (90*) |

[a]Mice were treated with mAb (250 μg) 7 days before or 14 days after MOG immunization. Tissue B cell numbers were determined on day 18 (n ≥ 4 mice per value).
[b]B cell subsets were: bone marrow pro/pre (IgM−B220$^{low}$), immature (IgM+B220$^{low}$), mature (IgM+B220$^{high}$); spleen mature (CD24+CD21+B220+), T1 (CD24$^{high}$CD21−B220+), T2 (CD24$^{high}$CD21+B220+), and marginal zone (CD21$^{high}$CD1d+B220+); peritoneal B-1a (CD5+CD11b+IgM$^{high}$B220$^{low}$), B-1b (CD5−CD11b+IgM$^{high}$B220$^{low}$) and B2 (CD5−IgM$^{low}$B220$^{high}$). LN, lymph node.
[c]Values (±SEM) indicate cell numbers (×10$^{−6}$) present in each tissue. Blood results are shown as cells/ml. Significant differences between CD20 versus control mAb-treated mice are indicated;
*p < 0.05,
**p < 0.01.

TABLE III

EAE clinical scores following CD20 mAb treatment[a]

| Group | Incidence[c] | Mean day of onset | Mean maximum score |
|---|---|---|---|
| Untreated[b] | 9/10 (90%) | 13.1 ± 0.5 | 2.6 ± 0.8 |
| Day −7 control mAb | 13/14 (93%) | 13.0 ± 0.5 | 2.8 ± 0.6 |
| Day −7 CD20 mAb | 14/14 (100%) | 12.9 ± 0.5 | 4.3 ± 0.4** |
| Day 14 control mAb | 14/15 (93%) | 12.9 ± 0.4 | 2.9 ± 0.7 |
| Day 14 CD20 mAb | 14/15 (93%) | 12.9 ± 0.3 | 1.5 ± 0.4* |

[a]Mice were treated with CD20 or control mAb (250 μg) 7 days before or 14 days after MOG immunization.
[b]The untreated group was not treated with mAb.
[c]Assessment of clinical EAE includes the number of mice that developed disease, the mean day of disease onset ± SEM among mice with EAE, and the mean maximum clinical score ± SEM of each treatment group. The mean maximum clinical score was obtained for the group over the entire observation period. Significant differences between CD20 versus control mAb-treated mice are indicated;
*p < 0.005,
**p < 0.0005.

7.2.2 Depletion of B Cells Abrogates MOG-Specific Antibody Production

The effect of B cell depletion on serum antibody responses was assessed since MOG-specific antibodies enhance CNS demyelination and inflammation, and increase EAE severity (Linington et al., 1988, Am. J. Pathol. 130: 443-54; Lyons et al., 1999, Eur. J. Immunol. 29:3432-9). Control mAb-treated mice produced significant IgM and IgG MOG-specific antibody responses by day 18 after immunization when compared with unimmunized littermates (FIG. 9C, p<0.001). MOG-specific IgG antibody levels increased in parallel with disease progression, while MOG-specific IgM antibody levels decreased significantly after day 18 (p<0.05). B cell depletion before MOG immunization completely abrogated MOG-specific IgM and IgG antibody production. B cell depletion after disease initiation significantly inhibited both MOG-specific IgM and IgG antibody production at the peak of disease (p<0.001 and p<0.01, respectively) and IgG production during the recovery phase (p<0.01), consistent with results obtained using other immunogens (DiLillo et al., 2008, J. Immunol. 180: 361-71). Thus, B cell depletion before EAE induction and during EAE development significantly attenuated autoantibody production, which did not correlate with increased EAE severity following early B cell depletion.

7.2.3 Depletion of B Cells During EAE Development Reduces Antigen-Specific T Cell Proliferation B cells are important for encephalitogenic T cell activation (Bettelli et al., 2006, J. Clin. Invest. 116:2393-402; Krishnamoorthy et al., 2006, J. Clin. Invest. 116:2385-92) and for antigen-specific T cell proliferation in diabetes and arthritis models (Bouaziz et al., 2007, Proc. Natl. Acad. Sci. USA 20882-7; Xiu et al. 2008, J. Immunol. 180:2863-75). Therefore, the effects of B cell depletion on antigen-specific T cell proliferation in EAE mice was assessed by the adoptive transfer of CFSE-labeled CD4+ T cells from TCR$^{MOG}$ mice (Bettelli et al., 2003, J. Exp. Med. 197:1073-81) on day 17. Four days after adoptive transfer, CFSE dilution as a marker for cell division was assessed by flow cytometry. The frequencies and numbers of dividing TCR$^{MOG}$ CD4+ T cells within lymph nodes were comparable between mice treated with CD20 or control mAb before EAE induction (FIG. 10A). However, B cell depletion during EAE development significantly inhibited TCR-$^{MOG}$ T cell proliferation (p<0.001, FIG. 10A). Therefore, B cell depletion during EAE development but not before EAE induction, significantly reduced MOG-specific CD4+ T cell expansion in vivo.

Following B cell depletion on days −7 or 14, spleen CD4+ and CD8+ T cell numbers were not changed 18 days after EAE induction (FIG. 10B and Table IV). Numbers of naïve CD44−CD62L+, activated CD44+CD62L+, memory CD44+ CD62L−, and regulatory CD25+FoxP3+ (T-reg) CD4+ T cells were not changed following CD20 mAb treatment either before and after EAE induction (FIGS. 10B-C and Table IV). Likewise, CD20 mAb treatment either before EAE induction or during EAE development did not affect lymph node T cell numbers, subsets, or phenotypes when compared with control mAb-treated littermates. Thus, B cell depletion did not have global effects on T cell numbers or phenotypes, but appeared to selectively affect antigen-specific T cell expansion late in the course of disease.

TABLE IV

Spleen T cell populations following EAE induction and CD20 mAb treatment[a]

| T subset | Treated day −7[b] | | Treated day 14 | |
| --- | --- | --- | --- | --- |
| | Control mAb | CD20 mAb | Control mAb | CD20 mAb |
| $CD4^+CD3^+$ | 5.6 ± 0.3 | 5.3 ± 0.8 | 5.0 ± 0.7 | 5.4 ± 0.8 |
| $CD8^+CD3^+$ | 5.4 ± 0.3 | 5.9 ± 0.8 | 5.4 ± 0.8 | 4.8 ± 0.6 |
| $CD44^-CD62L^+CD4^+$ | 2.2 ± 0.1 | 2.9 ± 0.3 | 2.1 ± 0.1 | 2.5 ± 0.3 |
| $CD44^+CD62L^+CD4^+$ | 0.46 ± 0.07 | 0.39 ± 0.09 | 0.43 ± 0.06 | 0.38 ± 0.05 |
| $CD44^+CD62L^-CD4^+$ | 1.3 ± 0.2 | 0.9 ± 0.2 | 1.3 ± 0.2 | 1.2 ± 0.2 |
| $CD25^+FoxP3^+CD4^+$ | 0.48 ± 0.12 | 0.33 ± 0.08 | 0.47 ± 0.22 | 0.50 ± 0.24 |

[a]Mice were treated with mAb (250 μg) 7 days before or 14 days after MOG immunization, both T cell numbers determined on day 18 (n ≥ 4 mice per value).
[b]Values (±SEM) indicate cell numbers (×10$^{-6}$).

7.2.4 B Cell Depletion Modifies Encephalitogenic T Cells within the CNS

To assess whether CNS-infiltrating T cells are affected by B cell depletion, the frequencies of MOG-specific T-effector and T-reg cells were quantified on day 18 using $MOG_{38-49}$/IAb tetramers. MOG-specific T cells preferentially accumulated within the CNS, but were only detected at very low frequencies in spleen and lymph nodes (FIG. 11A). B cell depletion before EAE induction resulted in significantly expanded MOG-specific T-effector cell numbers in the CNS when compared with control mAb-treated littermates ($p<0.05$). The number of MOG-specific T-reg cells in B cell-depleted mice was not changed, which resulted in a significantly higher ratio of T-effector/T-reg cells ($p<0.01$). Conversely, MOG-specific T-effector and T-reg cell numbers within the CNS were significantly reduced in mice depleted of B cells during EAE development ($p<0.05$).

Since IFN-γ and IL-17 play critical roles in EAE development (Kuchroo et al., 1993, J. Immunol. 151:4371-82; Baron et al., 1993, J. Exp. Med. 177:57-68; Park et al., 2005, Nat. Immunol. 6:1133-41; Bettelli et al., 2006, Nature 235-8), their expression by CNS-infiltrating CD4$^+$ T cells was assessed 18 days after MOG immunization. B cell depletion before EAE induction significantly increased the numbers of IFN-γ and IL-17 producing CD4$^+$ T cells within the CNS as analyzed by intracellular cytokine staining ($p<0.05$, FIG. 11B). Conversely, B cell depletion during EAE development resulted in significantly reduced numbers of IFN-γ and IL-17 producing CD4$^+$ T cells ($p<0.05$). Thus, B cell depletion before EAE induction increased encephalitogenic CD4$^+$ T cell expansion within the CNS, whereas B cell depletion during EAE development reduced the influx of encephalitogenic CD4$^+$ T cells.

7.2.5 CD1d$^{high}$CD5$^+$ Regulatory B Cells Inhibit EAE

As described in Example 1, we have identified a population of B cells that can inhibit T cell-mediated inflammation through IL-10 production. These regulatory IL-10-producing B cells are found within a rare CD1d$^{high}$CD5$^+$ subset and can inhibit the induction of antigen-specific inflammatory reactions. Therefore, whether EAE exacerbation following B cell depletion resulted from the lack of CD1d$^{high}$CD5$^+$ regulatory B cells was assessed through adoptive transfer experiments. Splenic CD1d$^{high}$CD5$^+$ B cells and non-CD1d$^{high}$CD5$^+$ B cells were purified from CD20$^{-/-}$ mice (FIG. 12A) and transferred into wild type mice that had been depleted of B cells using CD20 mAb before EAE induction. CD20$^{-/-}$ B cells are resistant to CD20 mAb-mediated B cell depletion (Uchida et al., 2004, J. Exp. Med. 199:1659-69). Adoptive transfer of only 2×10$^6$ CD1d$^{high}$CD5$^+$ B cells completely normalized disease in B cell-deficient mice, while total B cell depletion exacerbated EAE in wild type mice (FIG. 12B). By contrast, the adoptive transfer of non-CD1d$^{high}$CD5$^+$ B cells into B cell depleted mice did not affect EAE severity. Thus, regulatory CD1d$^{high}$CD5$^+$ B cells play a protective role during EAE initiation.

7.3 Discussion

These studies show that B cells play critical positive and negative regulatory roles in EAE immunopathogenesis. Consequently, B cell depletion had two opposing effects on disease. B cell depletion before EAE induction resulted in the increased influx or expansion of encephalitogenic T cells within the CNS (FIG. 11), which significantly exacerbated disease symptoms (FIG. 9A-B). Since the adoptive transfer of regulatory B cells within the CD1d$^{high}$CD5$^+$ subset, but not other B cells, normalized EAE (FIG. 12), we propose that increased EAE severity following B cell depletion results from the effective depletion of this B cell subset (FIG. 8). Conversely, B cell depletion during EAE development impaired MOG-specific T cell expansion (FIG. 10C) and significantly inhibited the influx or expansion of encephalitogenic T cells within the CNS (FIG. 11), which dramatically suppressed disease symptoms (FIG. 9A-B). Thereby, B cells were also essential for generating optimal pathogenic CD4$^+$ T cell responses following MOG immunization. The reciprocal positive and negative regulatory roles of B cells are likely to overlap during the course of disease, with the balance of these two opposing influences shaping the normal course of EAE immunopathogenesis. This is likely to also occur in other T cell-mediated autoimmune diseases.

The current findings resolve previously unexplained contradictions between previous studies showing the importance of B cells in EAE. Exacerbated disease after early CD20 mAb treatment can be explained by the depletion of IL-10-producing regulatory CD1d$^{high}$CD5$^+$ B cells (FIGS. 8 and 12). B cells have been previously shown to suppress EAE through IL-10 production (Fillatreau et al., 2002, Nat. Immunol. 3:944-50). IL-10-producing B cells can also down-regulate other autoimmune and inflammatory diseases, such as collagen-induced arthritis, inflammatory bowel disease, and contact hypersensitivity (Mauri et al., 2003, J. Exp. Med. 197:489-501; Mizoguchi et al., 2002, Immunity 16:219-30). That B cell depletion enhanced EAE severity in the absence of MOG-specific autoantibodies (FIG. 9C) also argues that B cells and their antibody products are not required for EAE induction. Ameliorated disease progression following B cell depletion after EAE symptom onset (FIG. 9A) can be explained by inhibition of CD4$^+$ T cell activation (FIGS. 10, 11). That B cells may serve as antigen presenting cells to prime MOG-specific T cells (Lyons et al., 1999, Eur. J. Immunol. 29:3432-9; Bettelli et al., 2006, J. Clin. Invest. 116:2393-402; Krishnamoorthy et al., 2006, J. Clin. Invest. 116:2385-92) provides a mechanistic explanation for this observation. A role for B cells in early antigen presentation and CD4+ T cell activation is also possible, but this may be obscured by the use of a potent adjuvant during MOG immunization. Alternatively, B cells may play a more critical role in antigen presentation or CD4+ T cell activation after disease initiation with dendritic cells and other antigen presenting cells more important for disease initiation. Mice genetically deficient for B cells develop EAE normally but fail to resolve the disease (Wolf et al., 1996, J. Exp. Med. 184:2271-8; Fillatreau et al., 2002, Nat. Immunol. 3:944-50). By contrast, early B cell depletion in mice with otherwise normal immune systems exacerbated not only the recovery phase of EAE but also the peak phase of EAE induction (FIG. 9A). This apparent contradiction may reflect the observation that immune system development and T cell priming are abnormal in mice lacking B cells since birth (AbuAttieh et al., 2007, J. Immunol. 178:2950-60; Chiu et al., 2001, Diabetes 50:763-70). Thereby, an absence of regulatory B cells combined with abnormal T cell activation due to the total absence of B cells may explain normal EAE induction in congenitally B cell-deficient mice. Regardless, the lack of disease resolution in both models suggests that regulatory B cells are likely to be critical for not only regulating disease induction but also for resolving disease.

That B cell depletion after the onset of EAE symptoms ameliorated disease progression (FIG. 9A) makes this strategy applicable for treating human MS after disease onset. However, adverse disease following B cell depletion before EAE induction in the current study suggests that B cell depletion may promote the occurrence of MS symptoms in some undiagnosed cases. Nonetheless, B cell depletion during EAE development reduced EAE severity both clinically and histologically (FIG. 9A-B), and was accompanied by significantly reduced autoantibody levels (FIG. 9C). Reduced autoantibody production may be clinically important since plasma exchange can reduce clinical disease activity in a subset of MS patients (Kieseier and Hartung, 2003, Semin Neurol. 23:133-46; Weinshenker et al., 1999, Ann Neurol. 46:878-86). However, CD20 mAb treatment does not lead to the depletion of long-lived plasma cells in mice (DiLillo et al., 2008, J. Immunol. 180:361-71) so CD20+ B cell depletion may be most beneficial when carried out before the long-lived plasma cell pool is established. Similarly, B cell depletion significantly attenuates early foreign- and autoantigen-specific CD4+ T cell proliferation in vivo (Bouaziz et al., 2007, Proc. Natl. Acad. Sci. USA 104:20882-7). Also, B cell depletion early in the course of diabetes in NOD mice (Xiu et al., 2008, J. Immunol. 180:2863-75), collagen-induced arthritis in DBA-1 mice (Yanaba et al., 2007, J. Immunol. 179:1369-80), Sjogren's-like disease in Id3-deficient mice (Hayakawa et al., 2007, Immunology 122:73-9), and systemic sclerosis-like disease in tight skin mice (Hasegawa et al., 2006, Am. J. Pathol. 169:954-66) has maximal benefit. However, in these cases, it was not possible to reverse T cell expansion or disease progression once inflammatory disease was initiated. Thereby, B cell depletion shortly after diagnosis may offer the most optimal strategy for disease management.

As shown in the studies described in Section 6, supra, IL-10-producing CD1d$^{high}$CD5+ B cells regulate T cell-mediated inflammatory responses in a contact hypersensitivity model. Thereby, B cells can be divided into two functionally distinct subsets in autoimmunity: regulatory B cells and B cells that can activate CD4+ T cells. The therapeutic effect of B cell depletion likely depends on the contributions and the timing of these B cell subsets during the course of each autoimmune disease. The current studies suggest that the selective depletion of mature B cells while sparing IL-10-producing B cells may offer a potent therapeutic approach. Moreover, the in vivo or in vitro expansion of IL-10-producing regulatory B cells may also offer a new strategy for treating patients with MS and other autoimmune or inflammatory diseases.

8. EXAMPLE 3: Identification of a Human Regulatory B Cell Population

A population of IL-10 producing human B cells was identified. Peripheral blood mononuclear cells (PBMC) were isolated from four healthy human donors and activated in vitro in RPMI 1640 media containing 10% fetal bovine serum (FBS), 10 μg/ml of LPS, 50 ng/ml of PMA, 500 ng/ml of ionomycin, and monensin for 5 hours. IL-10+ and IL-10− B cells were examined by immunofluorescence staining with flow cytometry analysis using cytoplasmic IL-10 expression and cell surface CD19 expression as markers for identifying the cells. A population of CD19+ B cells that produce IL-10 was identified in each of the four subjects (FIG. 14). These IL-10 producing B cells represented between 0.25 and 0.63 percent of the overall B cell population across the four donors and likely represent the human regulatory B cell counterpart to the regulatory B cell subset identified in mice, as described above.

9. EXAMPLE 4: Expansion of the IL-10 Producing B Cell Population by CD40 Ligation Human and murine B cell IL-10 production was measured following stimulation with anti-CD40 mAb. Peripheral blood mononuclear cells from mice and healthy human volunteers were isolated from heparinized blood after centrifugation over a discontinuous Lymphoprep (Axis-Shield PoC As, Oslo, Norway) gradient. Viable cells were counted using a hemocytometer, with relative lymphocyte percentages determined by flow cytometry analysis. Subsequently, isolated cells were resuspended ($2 \times 10^6$ cells/me in complete medium (RPMI 1640 media containing 10% FCS, 200 μg/ml penicillin, 200 U/ml streptomycin, 4 mM L-Glutamine, and $5 \times 10^{-5}$ M 2-mercaptoethanol; all from Gibco, Carlsbad, Calif.) with LPS (10 μg/ml, Escherichia coli serotype 0111: B4, Sigma), PMA (50 ng/ml; Sigma), ionomycin (500 ng/ml; Sigma), and monensin (2 μM; eBioscience, San Diego, Calif.) for 5 h, in 24-well flat-bottom plates. In some cases, the cells were cultured with anti-human CD40 mAb for 48 hours with PMA, ionomycin, and monensin added during the final for 5 hours of culture.

Single cell suspensions of cultured cells were incubated with anti-mouse Fc receptor mAb (2.4G2; BD PharMingen) to block Fc receptors, before cell surface staining on ice using predetermined optimal concentrations of each antibody. The cells were washed, fixed, and permeabilized using the Cytofix/Cytoperm kit (BD PharMingen) according to the manufacturer's instructions. For cytoplasmic IL-10 detection, permeabilized cells were stained with phycoerythrin-conjugated anti-human-IL-10 mAb (JES3-9D7, eBioscience). Cells with the light scatter properties of lymphocytes were analyzed by 2-4 color immunofluorescence staining with analysis using FACScan or FACSCalibur flow cytometers (Becton Dickinson, San Jose, Calif.). Background staining was determined using unreactive isotype-matched control mAbs (Caltag Laboratories, San Francisco, Calif.) with gates positioned to exclude ≥98% of unreactive cells.

Anti-human CD40 mAb stimulation of blood B cells from healthy human volunteers for 48 hours with LPS, PMA and ionomycin stimulation during the last 5 hours of culture induced significantly higher levels of IL-10-producing B cells (0.7±0.2% p<0.05), when compared with blood B cells cultured with LPS, PMA, and ionomycin stimulation alone for 5 hours (FIG. 13). Parallel results with circulating mouse cells are shown as controls. Therefore, human blood contains IL-10 competent B cells, with prolonged CD40 stimulation enhancing the numbers of circulating human blood B cells that can be induced to express cytoplasmic IL-10.

10. EXAMPLE 5: Determination of a role for Regulatory B Cells in Cancer

To understand the role that B cells play in tumor-specific immune responses, we have adapted and developed an in vivo murine tumor model to understand whether B cells play a significant role in the immune system's natural defenses against tumor growth. We utilized a primary cutaneous melanoma model in which mice were injected subcutaneously with B16 melanoma tumor cells one week after treatment with either CD20 or control mAb. Tumor growth was measured in terms of tumor volume on days 7 and 14 after tumor injection. Remarkably, tumor growth was significantly enhanced in B cell-depleted mice, as their tumors were approximately twice the volume of tumors from control mice (FIG. 15). We have also exploited a lung metastasis melanoma tumor model. Mice were treated with either control or CD20 mAb seven days before intravenous administration of B16 melanoma cells. As in the primary cutaneous tumor model, tumor growth and metastasis was significantly enhanced in B cell-depleted mice. These mice contained approximately twice the number of metastasis spots on their lungs, and the sizes of these spots were increased compared to control mice (FIG. 15). The augmented growth of tumors in B cell-depleted mice is likely due to impaired $CD4^+$ and $CD8^+$ T cell activation in the absence of B cells. Therefore, B cells are required for the host to mount a normal immune response to melanoma.

In addition, we have developed a new mouse lymphoma model using primary $CD20^+$ tumor cells from a C57BL/6 Eµ-cMyc transgenic mouse. CD20 mAb treatment of syngeneic mice with adoptively transferred lymphomas prevents tumor development or significantly prolongs mouse survival depending on tumor volume, mAb dose, and treatment timing. By contrast, when $CD20^{-/-}$ mice that are resistant to B cell depletion with CD20 mAbs were implanted with these CD20 mAb-susceptible $CD20^+$ lymphoma cells, there was no difference in survival between mice receiving control or CD20 mAbs (FIG. 16). This indicates that the host immune system's ability to control tumor cell growth is impaired when B cells are present. Thereby, when host B cells are ablated, anti-tumor immunity is enhanced. Therefore, these data suggest an important role for regulatory B cells in lymphoma tumor immunity.

The results observed in EAE, contact hypersensitivity, and lymphoma mouse models indicate that IL-10-producing B10 cells play a significant negative role in the regulation of immune responses. Thus, it is likely that regulatory B cells can impair a host's ability to mount maximally effective natural and vaccine-induced anti-tumor immune responses. Further, the specific depletion of B10 cells may enhance both natural and vaccine-induced anti-tumor immune responses, thereby leading to increased tumor rejection and prolonged host survival.

11. EXAMPLE 6: The Development and Function of $CD1D^{HIGH}CD5^+$ Regulatory B Cells (B10 Cells) Requires Antigen Receptor Diversity and TLR Signals Autoimmunity and inflammation are controlled in part by regulatory B cells, including a recently identified IL-10-competent $CD1d^{hi}CD5^+$ B cell subset termed B10 cells that represents 1-3% of adult mouse spleen B cells. In this study, pathways that influence B10 cell generation and IL-10 production were identified and compared with previously described regulatory B cells. IL-10-competent B cells were predominantly $CD1d^{hi}CD5^+$ in adult spleen and were the prevalent source of IL-10 but not other cytokines. B10 cell development and/or maturation in vivo required Ag receptor diversity and intact signaling pathways, but not T cells, gut-associated flora, or environmental pathogens. Spleen B10 cell frequencies were significantly expanded in aged mice and mice predisposed to autoimmunity, but were significantly decreased in mouse strains that are susceptible to exogenous autoantigen-induced autoimmunity. LPS, PMA, plus ionomycin stimulation in vitro for 5 hours induced B10 cells to express cytoplasmic IL-10. However, prolonged LPS or CD40 stimulation (48 h) induced additional adult spleen $CD1d^{hi}CD5^+$ B cells to express IL-10 following PMA+ionomycin stimulation. Prolonged LPS or CD40 stimulation of newborn spleen and adult blood or lymph node $CD1d^{lo}$ and/or $CD5^-$ B cells also induced cytoplasmic IL-10 competence in rare B cells, with CD40 ligation uniformly inducing CD5 expression. IL-10 secretion was induced by LPS signaling through MyD88-dependent pathways, but not following CD40 ligation. LPS stimulation also induced rapid B10 cell clonal expansion when compared with other spleen B cells. Thereby, both adaptive and innate signals regulate B10 cell development, maturation, CD5 expression, and competence for IL-10 production.

11.1 Materials and Methods 11.1.1 Mice

Wild type C57BL/6 (B6), $IL-10^{-/-}$ (B6.129P2-Il10$^{tm1Cgn}$/J), NOD (NOD/Lt), DBA/1J, SJL/J, NZB/W F1 (NZBWF1/J), $CD40^{-/-}$ (B6.129P2-CD40$^{tm1Kik}$/J), MRL/lpr (MRL/MpJ-Fas$^{lpr}$/J), MD4 (C57BL/6-Tg(TghelMD4)4Ccg/J) that express IgM and IgD specific for HEL (Goodnow, et al. 1988. A *Nature* 334:676-682), and nude (C57BL/6-Hfh11$^{nu}$) mice were from the Jackson Laboratory (Bar Harbor, Me.). $MHC-I/II^{-/-}$ (B6.129-H2-Ab1$^{tm1Gru}$B2m$^{tm1Jae}$N17 from Taconic Farms, Inc., Hudson, N.Y.) mice were as described (Grusby, et al. 1993. *Proc. Natl. Acad. Sci. USA* 90:3913-3917) and were provided by Y. Zhuang (Duke University, Durham, N.C.). $MyD88^{-/-}$ mice (Adachi, et al. 1998. *Immunity* 9:143-150) were provided by Y. Yang (Duke University) with the permission of S. Akira (Osaka University, Osaka Japan). $CD22^{-/-}$, $CD21^{-/-}$, $CD19^{-/-}$, and hCD19Tg (h19-1 line) mice on a B6 genetic background were as described (Poe, et al. 2004. *Nat. Immunol.* 5:1078-1087; Sato, et al. 1996. *J. Immunol.* 157:4371-4378; Sato, et al. 1997. *J. Immunol.* 158:4662-4669; Haas, et alr. 2002. *Immunity* 17:713-723). CD40L/BTg mice with B cells expressing cell surface CD40L were as described (Higuchi, et al. 2002. *J. Immunol.* 168:9-12). $CD40L/BTg/CD22^{-/-}$ double mutant mice were generated by crossing CD40L/BTg mice with $CD22^{-/-}$ mice. B6 neonates were 3 to 10 days old. All mice were housed in a specific pathogen-free barrier facility and used at 12-16 wk of age, unless otherwise specified. All studies were approved by the Duke University Animal Care and Use Committee. Tissues from 6 mo-old gnotobiotic and specific-pathogen-free 129S6/SvEv mice were generously provided by Dr. Scott Plevy and the Univ. of North Carolina at Chapel Hill Center for Gastrointestinal Biology & Disease Gnotobiotic Core.

11.1.2 Antibodies

Anti-mouse mAbs included: B220 mAb RA3-6B2 (provided by Dr. Robert Coffman, DNAX Corp., Palo, Alto, Calif.); and CD19 (1D3), CD5 (53-7.3), CD1d (1B1), CD40 (HM40-3), CD21/35 (7G6), CD23 (B3B4), CD24 (M1/69), CD43 (S7), and CD93 (AA4.1) mAbs from BD PharMingen (San Diego, Calif.). Anti-mouse IgM Ab was from Jackson ImmunoResearch Laboratories, Inc. (West Grove, Pa.). Phycoerythrin-conjugated anti-mouse IL-10 mAb (JESS-16E3) was from eBioscience (San Diego, Calif.).

11.1.3 B Cell Isolation, Immunofluorescence Analysis and Cell Sorting

Blood mononuclear cells were isolated from heparinized blood after centrifugation over a discontinuous Lymphoprep (Axis-Shield PoC As, Oslo, Norway) gradient. Single cell splenocyte suspensions were generated by gentle dissection with >90% cell viability as determined by trypan blue exclusion. Cell numbers were quantified using a hemocytometer, with relative lymphocyte percentages among viable cells (based on scatter properties) determined by flow cytometry analysis. B220- or CD19-mAb coated microbeads (Miltenyi Biotech) were used to purify spleen B cells by positive selection following the manufacturer's instructions. When necessary, the cells were enriched a second time using a fresh MACS column to obtain >99% purities.

Single cell leukocyte suspensions were stained on ice using predetermined optimal concentrations of each Ab for 20-60 min, and fixed as described (Sato, et al. 1996. *J. Immunol.* 157:4371-4378). Cells with the light scatter properties of lymphocytes were analyzed by 2-4 color immunofluorescence staining and FACScan or FACSCalibur flow cytometers (Becton Dickinson, San Jose, Calif.). Dead cells were excluded from the analysis based on their forward- and side-light scatter properties and the use of LIVE/DEAD Fixable Dead Cell Stain Kits (Invitrogen-Molecular Probes, Carlsbad, Calif.). All histograms are shown on a 4 decade logarithmic scale, with gates shown to indicate background isotype-matched control mAb staining set with <2% of the cells being positive. Background staining was determined using unreactive isotype-matched control mAbs (Caltag Laboratories, San Francisco, Calif.) with gates positioned to exclude ≥98% of unreactive cells. Spleen $CD1d^{hi}CD5^+$, $CD1d^{int}CD5^-$, $CD1d^{lo}CD5^-$ B cells were isolated using a FACSVantage SE flow cytometer (Becton Dickinson, San Jose, Calif.) with ~75%-95% purities.

11.1.4 Analysis of IL-10 Production

Intracellular IL-10 analysis by flow cytometry was as described (Yanaba, et al. 2008. *Immunity* 28:639-650). Briefly, isolated leukocytes or purified cells were resuspended ($2\times10^6$ cells/ml) in complete medium [RPMI 1640 media containing 10% FCS, 200 µg/ml penicillin, 200 U/ml streptomycin, 4 mM L-Glutamine, and $5\times10^{-5}$ M 2-mercaptoethanol (all from Gibco, Carlsbad, Calif.)] with LPS (10 µg/ml, *Escherichia coli* serotype 0111: B4, Sigma), PMA (50 ng/ml; Sigma), ionomycin (500 ng/ml; Sigma), and monensin (2 µM; eBioscience) for 5 h, in 24-well flat-bottom plates. In some experiments, the cells were incubated for 48 hours with LPS (10 µg/ml) and/or anti-mouse CD40 mAb (1 µg/ml), and/or anti-mouse IgM Ab (10 µg/ml, Jackson ImmunoResearch Laboratories, Inc, West Grove, Pa.). For analysis of cell proliferation, leukocytes were stained with CFSE Vybrant™ CFDA SE fluorescent dye (0.1 µM; CFSE; Invitrogen-Molecular Probes) according to the manufacturer's instructions. For IL-10 detection, Fc receptors were blocked with mouse Fc receptor mAb (2.4G2; BD PharMingen) with dead cells detected by using a LIVE/DEAD® Fixable Green Dead Cell Stain Kit (Invitrogen-Molecular Probes) before cell surface staining. Stained cells were fixed and permeabilized using a Cytofix/Cytoperm kit (BD PharMingen) according to the manufacturer's instructions and stained with phycoerythrin-conjugated mouse anti-IL-10 mAb. Leukocytes from $IL-10^{-/-}$ mice served as negative controls to demonstrate specificity and to establish background IL-10 staining levels.

Secreted IL-10 was quantified by ELISA. Purified B cells ($4\times10^5$) were cultured in 0.2 ml of complete medium in a 96-well flat-bottom tissue culture plates. Culture supernatant fluid IL-10 concentrations were quantified using IL-10 OptEIA ELISA kits (BD PharMingen) following the manufacturer's protocols. All assays were carried out using triplicate samples.

11.1.5 B Cell Cytokine Transcript Expression Analysis

Purified spleen B cells were cultured for 5 hours with LPS+PMA+ionomycin (L+PI). IL-10-secreting spleen B cells were identified using an IL-10 secretion detection kit (Miltenyi Biotech, Auburn, Calif.) with subsequent staining for CD19 expression before cell sorting into $IL-10^+CD19^+$ and $IL-10^-CD19^+$ populations. Total RNA was extracted from the purified B cells using TRIzol (Invitrogen-Molecular Probes), with relative cytokine transcripts quantified by GeneChip analysis (Affymetrix Mouse Genome 430 2.0 GeneChips; Affymetrix, Santa Clara, Calif.). All quality parameters for the arrays were confirmed to be in the range recommended by the manufacturer.

11.1.6 Statistical Analysis

All data are shown as means (±SEM). Significant differences between sample means were determined using the Student's t test.

11.2 Results 11.2.1 IL-10-Producing B Cells Preferentially Secrete IL-10

IL-10-Producing B Cells Preferentially Secrete IL-10

Spleen B cells that are competent to express cytoplasmic IL-10 following 5 hours of L+PIM stimulation were predominantly found within the $CD1d^{hi}CD5^+CD19^+$ subset in wild type B6 mice (FIG. 17A), as described (Yanaba, et al. 2008. *Immunity* 28:639-650). By contrast, IL-10 expressing B cells were significantly less common within the $CD1d^{hi}CD5^-$, $CD1d^{lo}CD5^+$, or $CD1d^{lo}CD5^-$ B cell subsets ($p<0.01$), with B cells from $IL-10^{-/-}$ mice used as negative controls for background IL-10 staining. We have previously shown that 5 hour L+PIM stimulation does not influence the phenotype of these B cell subsets (Yanaba, et al. 2008. *Immunity* 28:639-650; Matsushita, et al. 2008. *J. Clin. Invest.* 118:3420-3430). $IL-10^+CD19^+$ B10 cells were predominantly $CD21^{int/hi}$, $CD23^{lo}$, $CD24^{hi}$, $CD43^{+/-}$, and $CD93^-$ (AA4.1) (FIG. 17B). Thereby, spleen B10 cells are relatively rare and share some overlapping phenotypic markers with the B-1a, MZ, and T2-MZ precursor B cell subsets, but are nonetheless phenotypically distinct, (Yanaba, et al. 2008. *Immunity* 28:639-650; Matsushita, et al. 2008. *J. Clin. Invest.* 118:3420-3430).

Determining whether spleen B10 cells purified from wild type mice produce only Il-10 was problematic due to inherent technical difficulties when purifying such low-frequency cells and the predominantly low level induction of most cytokines by B cells. However, spleen B10 cell frequencies and numbers are expanded in mice expressing a human CD19 transgene (hCD19Tg, FIG. 17C) (Yanaba, et al. 2008. *Immunity* 28:639-650). Within the CD1d$^{hi}$CD5$^+$ B cell subset in hCD19Tg mice, 58% of the cells were induced to express cytoplasmic IL-10 following L+PIM stimulation for 5 h, but were significantly less common within the CD1d$^{hi}$CD5$^-$, CD1d$^{lo}$CD5$^+$, or CD1d$^{lo}$CD5$^-$ B cell subsets ($p<0.01$). Whether IL-10-competent B cells represent a heterogeneous population capable of producing other cytokines was therefore examined by purifying IL-10-secreting CD19$^+$ B cells from hCD19Tg mice (FIG. 17D). IL-10 transcripts were expressed at ~6-fold higher frequencies in IL-10-secreting B cells when compared with B cells that did not secrete detectable IL-10 (FIG. 17E). Furthermore, IL-10$^+$ B cells did not produce transcripts for 31 additional cytokines at levels higher than IL-10$^-$ B cells under these culture conditions. Thus, the IL-10-secreting CD1d$^{hi}$CD5$^+$ B10 cell subset was phenotypically and functionally unique.

11.2.2 B10 Cell Numbers During Development

To characterize B10 cell development, the frequencies and numbers of spleen CD1d$^{hi}$CD5$^+$ B cells and IL-10-producing B cells were assessed in neonatal, 2-mo-old, and 6-mo-old wild type B6 mice. CD1d$^{hi}$CD5$^+$ B cells were virtually absent in neonatal spleen, with 5-fold lower frequencies than in 2-mo-old mice (FIG. 18A). Remarkably, neonatal spleen had 6.8-fold higher frequencies of IL-10-producing B cells than the 1-2% frequency induced in 2-mo-old wild type spleen B cells following 5 hour L+PIM stimulation (FIG. 18B). Nonetheless, the majority of IL-10$^+$ B cells in neonates had a CD1d$^{lo}$CD5$^+$ phenotype, with 6.5-fold higher CD5 expression levels than IL-10$^-$ B cells ($p<0.001$, FIG. 18C). Conversely, the frequencies and numbers of CD1d$^{hi}$CD5$^+$ B cells were 1.4- and 1.8-fold higher in 6-mo-old mice than in 2-mo-old mice. IL-10$^+$ B cell frequencies and numbers were also 1.8- and 1.6-fold higher, respectively, in 6-mo-old mice compared with 2-mo-old mice ($p<0.05$). Spleen IL-10$^+$ B cells from 2- and 6-mo-old mice were predominantly CD1d$^{hi}$CD5$^+$. Thus, neonatal IL-10-producing CD1d$^{lo}$CD5$^+$ B cells were present at relatively high frequencies and numbers, while CD1d$^{hi}$CD5$^+$ B10 cells expanded with age in the spleens of adult mice.

11.2.3 B10 Cell Development is T Cell and Pathogen Independent

Figures 19D, 19E, 19F:
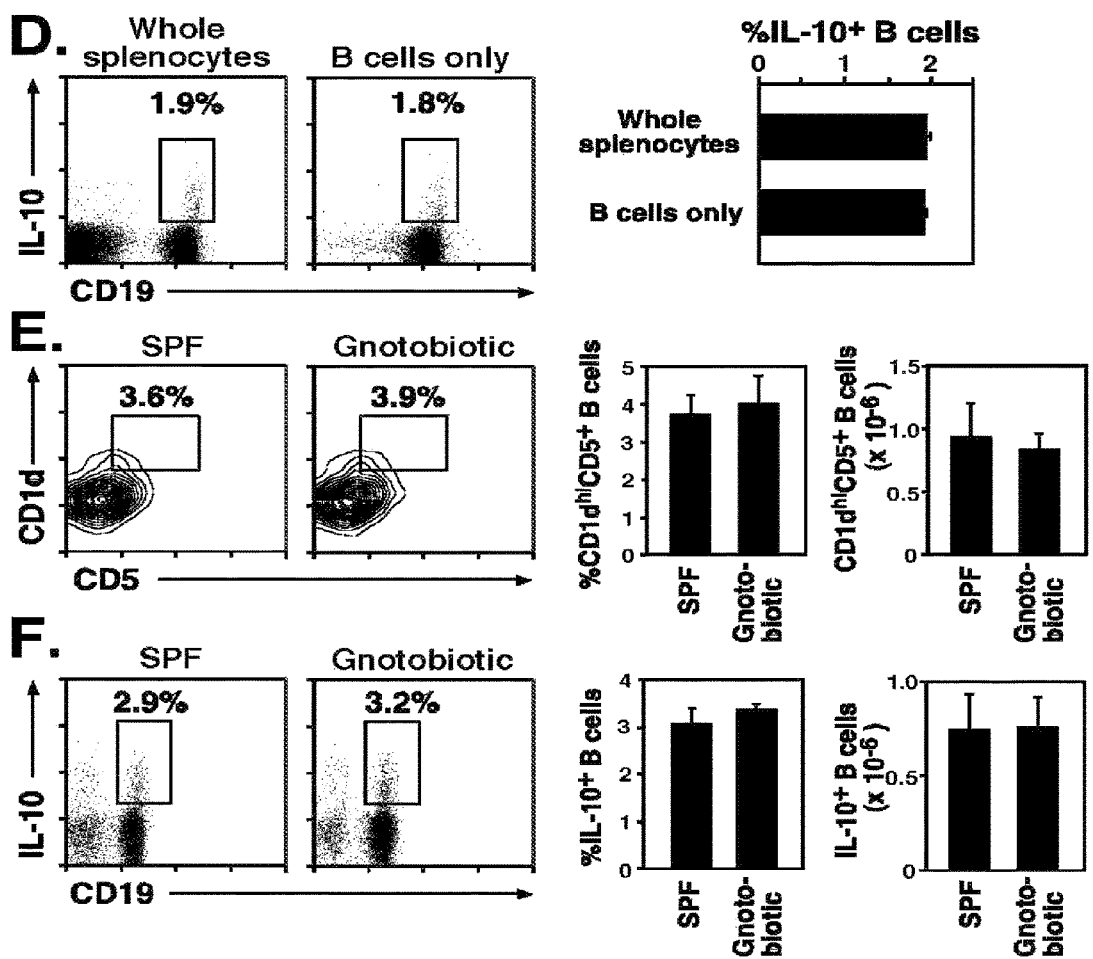

To identify factors that influence B10 cell development, CD1d$^{hi}$CD5$^+$ and IL-10-producing B cells were assessed in T cell-deficient nude mice and in gnotobiotic mice. CD1d$^{hi}$CD5$^+$ B cell frequencies and numbers were ~5-fold higher in adult nude mice than in age-matched wild type mice ($p<0.05$; FIG. 19A). Cytoplasmic IL-10$^+$ B cell frequencies and numbers were also ~4.5-fold higher in L+PIM-stimulated splenocytes from nude mice when compared with wild type mice ($p<0.05$; FIG. 19B). The majority of IL-10$^+$ B cells in nude and wild type mice had a CD1d$^{hi}$CD5$^+$ phenotype, while IL-10$^-$ B cells were CD1d$^{lo}$CD5$^-$ (FIG. 19C). Whether B cell IL-10 production in vitro was influenced by the presence of T cells was also assessed by culturing whole splenocytes or purified B cells alone with L+PIM for 5 h. The frequency of B cells that expressed cytoplasmic IL-10 among all B cells was comparable in both cultures (FIG. 19D). Thus, spleen B10 cell development does not require the presence of T cells in nude mice.

To determine whether environmental factors influence B10 cell development, germ-free mice were assessed. CD1d$^{hi}$CD5$^+$ B cell frequencies and numbers were similar, if not identical, in age-matched mice reared in gnotobiotic and specific pathogen-free colonies (FIG. 19E). Cytoplasmic IL-10$^+$ B cell frequencies and numbers were also similar (FIG. 19F) and the majority of IL-10$^+$ B cells had a CD1d$^{hi}$CD5$^+$ phenotype. Thus, environmental flora and gut-associated bacteria are not required for spleen B10 cell development.

11.2.4 Autoimmunity Promotes B10 Cell Development

The influence of autoimmunity on B10 cell development was assessed in the NOD, NZB/W F1, MRL/lpr, DBA/1, and SJL mouse strains. NOD mice are a spontaneous model of type 1 diabetes (Anderson, et al. 2005. *Annu. Rev. Immunol.* 23:447-485). DBA/1 mice develop CIA after collagen immunization (Courtenay, et al. 1980. *Nature*. 283:666-668). SJL mice are susceptible to EAE after myelin proteolipid protein immunization (Dal Canto, et al. 1995. *Microsc. Res. Tech.* 32:215-229). MRL/lpr and NZB/W mice spontaneously develop lupus-like disease (Theofilopoulos, A. N., ed. 1992. Murine models of lupus. Churchill Livingston, Edinburgh). Most B cells in NOD (85±2%, n>3), MRL/lpr (80±12%, n=3), and SJL (94±1% n=3) mice expressed cell surface CD5 at levels that were significantly higher than background control mAb staining in comparison with B cells from B6 (25±2%, n>3), NZB/W (28±1%, n=3), and DBA/1 (14±1%, n=3) mice in side-by-side comparisons (FIG. 20A). Nonetheless, the frequency of CD1d$^{hi}$CD5$^+$ B cells was limited, but 3- to 9-fold higher in NZB/W, MRL/lpr, NOD, and SJL mice than in 2-mo-old B6 mice. CD1d$^{hi}$CD5$^+$ B cell numbers were also 3.8- to 5.9-fold increased in NZB/W, MRL/lpr, and NOD mice. Thus, the CD1d$^{hi}$CD5$^+$ B cell subset increased in frequency in mice predisposed to autoimmunity.

The numbers of cytoplasmic IL-10$^+$ B cells were 2- to 4-fold higher in NZB/W, MRL/lpr, and NOD mice than in B6 wild type mice after L+PIM-stimulation (FIG. 20B). By contrast, IL-10-producing B cell numbers were 49% and 55% lower in DBA/1 and SJL mice, respectively, relative to wild type mice ($p<0.01$). In all cases, the majority of cytoplasmic IL-10$^+$ B cells also retained a CD1d$^{hi}$CD5$^+$ phenotype (FIG. 20C). Thus, B10 cell numbers were significantly higher in diabetes- and lupus-prone mice, but significantly below wild type levels in DBA/1 and SJL mice that are susceptible to exogenous autoantigen-induced autoimmune disease.

11.2.5 Receptors that Regulate B10 Cell Development In Vivo

B cell development is regulated through the BCR and other molecules that inform B cells of their extracellular microenvironment, including CD19, CD21, CD22, and CD40 (Tedder. 1998. *Semin. Immunol.* 10:259-265). Whether cell surface signals influence B10 cell development was determined by assessing CD1d$^{hi}$CD5$^+$ and IL-10 producing B cell development in IL-10$^{-/-}$, MD4, CD19$^{-/-}$, CD21$^{-/-}$, CD40$^{-/-}$, hCD19Tg, CD22$^{-/-}$, CD40L/BTg, and CD40L/BTg/CD22$^{-/-}$ mice. MD4 transgenic mice have a fixed BCR specific for hen egg lysozyme (Goodnow, et al. 1988. A *Nature* 334:676-682). MHC-I/II$^{-/-}$ mice are deficient in cell surface MHC class II, and most MHC class I and CD1 molecules due to combined disruption of the H2-Abl and β2-microglobulin genes (Grusby, et al. 1993. *Proc. Natl. Acad. Sci. USA* 90:3913-3917; Brutkiewicz, et al. 1995. *J. Exp. Med.* 182:1913-1919). B cells from CD40L/BTg mice express ectopic cell surface CD40L constitutively, with some mice developing lupus-like disease (Higuchi, et al. 2002. *J. Immunol.* 168:9-12).

CD1d$^{hi}$CD5$^+$ B cells were present at similar frequencies and numbers in IL-10$^{-/-}$, wild type, and MD4 mice (FIG. 21A). However, both the frequencies (65% decrease, $p<0.01$) and numbers (90% decrease, $p<0.01$) of L+PIM-induced cytoplasmic IL-10$^+$ B cells were reduced in MD4 mice when compared with wild type mice (FIG. 21B). In CD19$^{-/-}$ mice, the frequency and number of CD1d$^{hi}$CD5$^+$ B cells was 87-92% lower than in wild type littermates, while L+PIM-induced IL-10$^+$ B cell frequencies and numbers were 73% and 89% lower, respectively (p<0.01). By contrast, CD21- or CD40-deficiencies did not affect the frequencies or numbers of CD1d$^{hi}$CD5$^+$ or IL-10 producing B cells. CD1d$^{hi}$CD5$^+$ B cell frequencies could not be assessed in MHCI/II$^{-/-}$ mice that do not express CD1d, but IL-10 producing spleen B cell frequencies and numbers were normal. Spleen CD1d$^{hi}$CD5$^+$ B cell frequencies and numbers were normal in MyD88$^{-/-}$ mice (FIG. 21A), while L+PIM-induced cytoplasmic IL-10$^+$ B cell frequencies and numbers were reduced by 40% and 46%, respectively, in 5 hour assays (FIG. 21B). Thus, BCR diversity, and CD19- and MyD88-generated signals were critical for normal IL-10 producing CD1d$^{hi}$CD5$^+$ B10 cell development and/or peripheral expansion in vivo, or visualization in vitro.

The frequencies and numbers of CD1d$^{hi}$CD5$^+$ B cells were 5.8- and 1.5-fold higher in hCD19Tg mice than in wild type littermates, respectively (FIG. 21A). IL-10-producing B cell frequencies and numbers were 7.9- and 2.1-fold higher in hCD19Tg mice, respectively (FIG. 21B). Similarly, the frequency and number of CD1d$^{hi}$CD5$^+$ B cells was 2.7- and 1.9-fold higher in CD22$^{-/-}$ mice than in wild type mice, while the frequency and number of IL-10-producing B cells was 4.1- and 2.8-fold higher, respectively. The frequency and number of CD1d$^{hi}$CD5$^+$ B cells was 1.4- and 3.9-fold higher in CD40L/BTg mice than in wild type mice, while the frequency and number of IL-10-producing B cells was 1.4- and 3.7-fold higher, respectively. Thus, CD19 overexpression, CD22-deficiency, and ectopic CD40L expression on B cells significantly enhanced B10 cell numbers in vivo.

Combined CD22-deficiency and CD40L expression dramatically expanded the B10 cell subset in CD40L/BTg/CD22$^{-/-}$ mice (FIG. 21). The frequency and number of CD1d$^{hi}$CD5$^+$ B cells was 7.0- and 16-fold higher in CD40L/BTg/CD22$^{-/-}$ mice, while the frequency and number of IL-10-producing B cells was 11- and 26-fold higher in CD40L/BTg/CD22$^{-/-}$ mice than in wild type mice, respectively (p<0.01). Thus, the absence of CD22 regulation combined with CD40L expression by B cells dramatically increased B10 cell numbers in vivo. In all mouse lines except MHC-I/II$^{-/-}$ mice, L+PIM-induced IL-10$^+$ B cells maintained a CD1d$^{hi}$CD5$^+$ phenotype when present. Thus, spleen B10 cell development or expansion in vivo is not intrinsic, but depends in part on transmembrane signals.

Figure 22A:
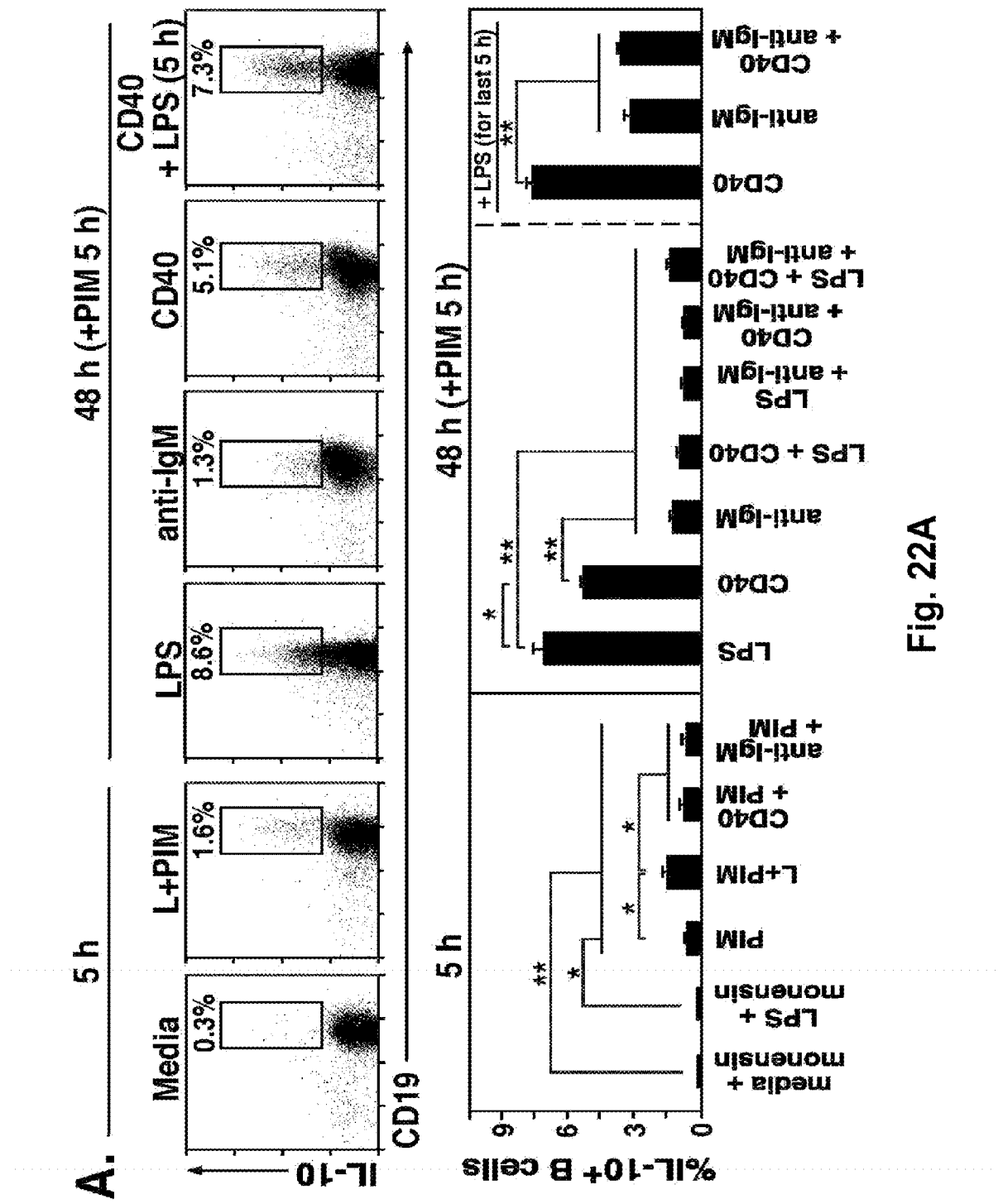

11.2.6 LPS and CD40 Stimulation Induce B Cell Cytoplasmic IL-10 Production In Vitro Signals that regulate B cell IL-10 production were assessed by culturing wild type spleen B cells with LPS, agonistic CD40 mAb, or mitogenic anti-IgM Ab at predetermined optimal concentrations. PMA, ionomycin, and monensin (PIM)-stimulation for 5 hours induced cytoplasmic IL-10 expression by 0.5-2% of B cells, which was 8 to 13-fold higher than for media alone and >5-fold higher than for LPS alone (FIG. 22A). The addition of CD40 mAb or anti-IgM Ab to PIM-stimulated cultures did not significantly increase IL-10$^+$ B cell frequencies. However, L+PIM-stimulation for 5 hours induced >2-fold higher frequencies of IL-10$^+$ B cells than PIM, or CD40 mAb plus PIM, or anti-IgM Ab plus PIM (p<0.01). Thus, L+PIM stimulation induced optimal B cell cytoplasmic IL-10 expression in 5 hour assays.

Culturing B cells with LPS or CD40 mAb for 48 hours with PIM added during the last 5 hours of culture induced significantly higher frequencies of cytoplasmic IL-10$^+$ B cells than anti-IgM Ab with PIM added during the last 5 hours of culture (FIG. 22A). LPS stimulation was also significantly more robust than CD40 mAb stimulation. Unexpectedly however, the combination of LPS plus CD40 mAb for 48 h, or anti-IgM Ab plus either LPS or CD40 mAb, or all three together with PIM stimulation during the last 5 hours did not increase IL-10$^+$ B cell frequencies significantly beyond what was normally observed with 5 hour PIM stimulation alone. Thus, culturing B cells with LPS or CD40 mAb for 48 hours before PIM stimulation induced the highest numbers of B cells with cytoplasmic IL-10 expression.

Spleen B cells stimulated with CD40 mAb for 48 hours plus L+PIM for 5 hours did not induce significantly higher numbers of cytoplasmic IL-10$^+$ B cells than LPS for 48 hours plus PIM for 5 hours (FIG. 22A). However, this sequential combination of stimuli induced the most robust levels of cytoplasmic IL-10 expression when compared with independent LPS or CD40 mAb stimulation. By contrast, adding L+PIM during the last 5 hours of anti-IgM Ab, or CD40 mAb plus anti-IgM Ab cultures only induced 2-fold higher numbers of IL-10$^+$ B cells than anti-IgM Ab or CD40 mAb alone. Thus, CD40 ligation with subsequent 5 hour L+PIM stimulation was the most potent strategy for inducing the highest numbers of cytoplasmic IL-10$^+$ B cells with the highest levels of cytoplasmic IL-10.

11.2.7 LPS but not BCR or CD40 Ligation Induces B Cell IL-10 Secretion In Vitro

Figures 22B, 22C, 22D:
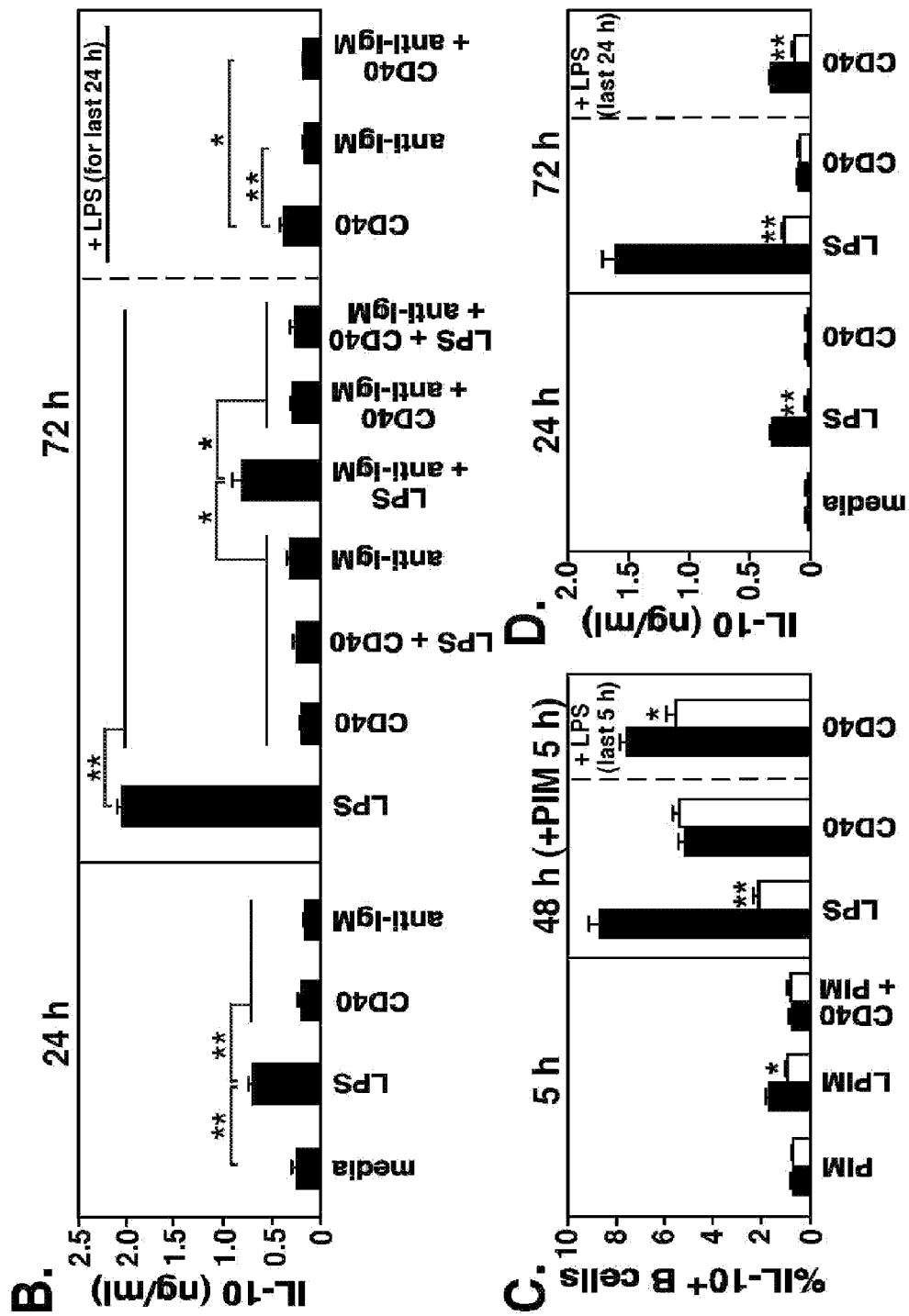

Signals that regulate B cell IL-10 secretion were assessed by culturing spleen B cells with LPS, agonistic CD40 mAb, or mitogenic anti-IgM Ab, with culture supernatant fluid IL-10 levels determined by ELISA. LPS stimulation of spleen B cells for 24 hours induced 3.5- to 3.8-fold more IL-10 than unstimulated cells, or cells cultured with CD40 mAb or anti-IgM Ab (p<0.01; FIG. 22B). LPS stimulation alone for 72 hours induced significant B cell IL-10 secretion in contrast to CD40 mAb, anti-IgM Ab, or CD40 mAb plus anti-IgM Ab (p<0.01). In fact, simultaneous CD40 mAb or anti-IgM Ab treatment reduced LPS-induced IL-10 secretion by >68%. Furthermore, B cells cultured with CD40 mAb, anti-IgM Ab, and CD40 mAb plus anti-IgM Ab did not secrete significantly more IL-10 when LPS was added during the last 24 hours of culture. Thus, LPS was the most potent stimulus for inducing both IL-10 production and secretion, while CD40-generated signals promoted cytoplasmic IL-10 generation but inhibited its secretion.

11.2.8 Normal B10 Cell Development in MyD88$^{-/-}$ Mice

L+PIM-induced cytoplasmic IL-10$^+$ B cell frequencies and numbers were reduced in MyD88$^{-/-}$ mice (FIG. 21B). Whether this represented a developmental defect in vivo or reflected the absence of LPS-induced IL-10 production was therefore assessed in vitro. The frequency of cytoplasmic IL-10$^+$ MyD88$^{-/-}$ spleen B cells was also significantly reduced after 48 hours of LPS stimulation relative to wild type B cells (FIG. 22C). By contrast, the frequency of CD40 mAb-induced cytoplasmic IL-10$^+$ B cells was equivalent in MyD88$^{-/-}$ and wild type littermates. Adding LPS to MyD88$^{-/-}$ B cell cultures during the last 5 hours did not increase the frequency of CD40 mAb-induced cytoplasmic IL-10$^+$ B cells. IL-10 secretion was also significantly reduced in LPS-stimulated cultures of MyD88$^{-/-}$ B cells (FIG. 22D). Therefore, MyD88 expression was not required for normal B10 cell development and/or expansion in vivo, but MyD88 was required for optimal IL-10 production and secretion following LPS stimulation.

11.2.9 LPS and CD40 Stimulation Promotes B Cell Competence for Cytoplasmic IL-10 Production Although CD5$^+$ B cells predominate in the spleens of neonatal wild type mice (FIG. 18), IL-10 production was not constitutive since culturing neonatal spleen B cells with monensin alone did not result in detectable cytoplasmic IL-10 staining. Nonetheless, relatively high frequencies of IL-10-producing B cells were generated after 5 hours of L+PIM stimulation (FIGS. 18 and 7A). Whether additional neonatal B cells could be induced to produce IL-10 was therefore assessed by culturing spleen B cells with LPS or agonistic CD40 mAb for 48 h. IL-10$^+$ B cells were 40% more frequent after prolonged LPS stimulation ($p<0.05$) despite lower level cytoplasmic IL-10 staining (FIG. 23A). Culturing neonatal splenocytes with CD40 mAb induced significantly fewer IL-10$^+$ B cells ($p<0.05$). The combination of CD40 mAb for 48 hours with L+PIM stimulation during the last 5 hours of culture generated similar numbers of IL-10$^+$ B cells as in the 48 hour LPS cultures, but the overall intensity of cytoplasmic IL-10 staining was highest. Therefore, the majority of CD5$^+$ neonatal B cells were already competent for L+PIM-induced IL-10 production, with additional in vitro stimulation increasing B10 cell numbers significantly.

CD1d$^{hi}$CD5$^+$ or IL-10-competent B cells are not commonly observed in the blood or peripheral lymph nodes of naïve wild type mice, even after 5 hours of L+PIM stimulation in vitro (FIG. 23B). Whether prolonged LPS or CD40 stimulation could induce B cell competence for IL-10 production was therefore examined. LPS or agonistic CD40 mAb stimulation induced 6-9-fold higher frequencies of cytoplasmic IL-10$^+$ B cells in 48 hour cultures than in 5 hour L+PIM cultures ($p<0.01$; FIG. 23B). The combination of CD40 mAb for 48 hours with L+PIM stimulation during the last 5 hours of culture also generated high numbers of IL-10$^+$ B cells with the highest intensity of cytoplasmic IL-10 staining. Similar results were obtained using peripheral lymph node B cells. These results suggest that prolonged LPS or CD40 stimulation can promote the maturation of CD5$^-$ progenitor B10 cells into an IL-10 competent state.

Whether LPS or CD40 generated signals induce B cells to express a CD1d$^{hi}$CD5$^+$ phenotype was therefore assessed. Neonatal spleen, and adult blood and spleen B cells were cultured with LPS or agonistic CD40 mAb for 48 hours and examined for CD1d and CD5 expression by immunofluorescence staining. CD40 mAb but not LPS stimulation induced markedly higher CD5 expression on most B cells (FIG. 23C). By contrast, B cell CD1d expression was not induced or changed by LPS or CD40 mAb stimulation or the combination of both treatments for 48 h. Thus, CD5 was an induced marker for CD40-stimulated B10 cells.

11.2.10 IL-10 Production by Adult Spleen B Cells is Restricted to the CD1d$^{hi}$CD5$^+$ B Cell Subset Splenic B10 cells that express cytoplasmic IL-10 after L+PIM stimulation localize primarily within the CD1d$^{hi}$CD5$^+$ subset (FIG. 17A). It was therefore determined whether the increased frequency of IL-10$^+$ B cells in LPS or CD40 stimulated cultures results from the maturation of B10 cell progenitor cells within the CD1d$^{hi}$CD5$^+$ subset or other B cell populations. Spleen CD1d$^{hi}$CD5$^+$ or non-CD1d$^{hi}$CD5$^+$ B cells from wild type mice were purified and cultured with LPS for 48 h, or with agonistic CD40 mAb for 48 hours with LPS added during the last 5 hours of culture. The CD1d$^{hi}$CD5$^+$ B cell subset from B6 mice normally contains ~9-18% IL-10$^+$ B cells after 5 hours of L+PIM stimulation (FIG. 17A). However, 33-43% of the CD1d$^{hi}$CD5$^+$ B cells expressed cytoplasmic IL-10 after 48 hour LPS or CD40 mAb stimulation, whereas <3% of CD1d$^{lo}$CD5$^-$ B cells produced IL-10 (FIG. 24A). Thus, splenic B cells capable of producing IL-10 after prolonged LPS or CD40 mAb stimulation predominantly derive from the CD1d$^{hi}$CD5$^+$ subset.

To determine whether the increased frequency of IL-10$^+$ B cells after LPS or CD40 stimulation results from the clonal expansion of existing IL-10-competent B cells or maturation of progenitor B10 cells, IL-10$^+$ B cell proliferation was assessed by labeling purified spleen B cells with CFSE before LPS or CD40 mAb stimulation in vitro. LPS stimulation for 48 hours induced IL-10$^+$ and IL-10$^-$ B cell proliferation, although IL-10$^+$ B cells proliferated more than IL-10$^-$ B cells as measured by reduced CFSE staining (FIG. 24B). By contrast, CD40 mAb stimulation for 48 hours plus LPS treatment for the last 5 hours of culture only induced modest IL-10$^+$ or IL-10$^-$ B cell proliferation during these 48 hour cultures. CD40 mAb stimulation predominantly induces B cell clonal expansion between 72-96 hours as described (Poe, et al. 2004. *Nat. Immunol.* 5:1078-1087; Brutkiewicz, et al. 1995. *J. Exp. Med.* 182:1913-1919). Thus, LPS stimulation induces and expands the IL-10$^+$ B cell subset during 48 hour cultures, while CD40 ligation induces B cell competence for cytoplasmic IL-10 production (FIG. 24C).

11.3 Discussion

The majority of adult spleen B cells that were competent for IL-10 production after 5 hour L+PIM stimulation were found within the CD1d$^{hi}$CD5$^+$ subset (FIG. 17A). IL-10$^+$ B10 cells preferentially produced IL-10 transcripts relative to other B cells, but did not appear to preferentially produce other known cytokines (FIG. 17E). IL-10-competent B cells were also found within the CD1d$^{hi}$CD5$^-$ and CD1d$^{int}$CD5$^+$ subsets, but at significantly lower ($p<0.05$) frequencies and numbers than in the CD1d$^{hi}$CD5$^+$ subset. Spleen CD1d$^{hi}$CD5$^+$ B cells also exist that could acquire IL-10 competence in vitro after 48 hour stimulation with LPS or agonistic CD40 mAb (FIGS. 22A and 24A), potentially reflecting their maturation. By contrast, spleen CD1d$^{lo}$CD5$^-$ B cells were not rendered IL-10 competent after 48 hour stimulation with LPS or agonistic CD40 mAb (FIG. 24A). Progenitor B10 cells may also exist that do not express CD5 or CD1d, yet can be induced to express IL-10 in vitro. Specifically, the vast majority of blood and lymph node B cells in adult mice were CD1d$^{lo}$CD5$^-$ and did not express IL-10 after 5 hour L+PIM stimulation (FIG. 23B). However, a small subset of blood and lymph node B cells acquired IL-10 competence after 48 hour CD40 ligation and/or LPS exposure. Neonatal spleen B cells predominantly expressed CD5 and were almost exclusively CD1d$^{lo}$, but ~14% were induced to express cytoplasmic IL-10 after 5 hour L+PIM exposure (FIG. 18). Consistent with this, neonatal and adult B cells uniformly upregulated CD5 expression after CD40 ligation in vitro (FIG. 23C). Thereby, L+PIM stimulation may induce IL-10 production in small subsets of B cells that have received appropriate competence-inducing signals in vivo or in vitro regardless of their maturation. Alternatively, CD1d$^{lo}$CD5$^-$ progenitor B10 cells may be induced to mature, express CD5, and acquire competence for activation-induced cytoplasmic IL-10 production as proposed in the maturation scheme outlined in FIG. 24C. Factors that regulate or induce CD1d expression by some spleen B cells are unknown. Thus, IL-10 competence and the CD1d$^{hi}$CD5$^+$ phenotype define the spleen B10 cell subset, but may also reflect their maturation, activation status, subset commitment, and/or tissue localization.

Development, maturation, and/or expansion of the spleen B10 cell subset required specific external signals. BCR specificity significantly influenced B10 cell development, with B10 cell numbers reduced by 90% in transgenic mice expressing a fixed Ag-receptor (FIG. 21B). In contrast, B10 cell development did not require the presence of T or NKT cells (FIG. 19). Furthermore, CD1, MHC class I and class II, CD21, or CD40 expression were not required for normal B10 cell development or IL-10 induction (FIG. 21). Nonetheless, CD40 ligation induced cytoplasmic IL-10 production by B cells in vitro (FIG. 22) and ectopic CD154 expression by B cells in CD40L/BTg mice increased B10 cell numbers by 3- to 4-fold (FIG. 21). Thereby, CD40: CD154 interactions may facilitate B10 cell maturation under some conditions, but were not required for B10 cell acquisition of IL-10-competence in vivo. TLR signaling was also critical for B10 cell effector function since LPS induced B10 cells to both produce and secrete IL-10 in vitro, while CD40 ligation only induced cytoplasmic IL-10 production (FIG. 22). B10 cell development was normal in MyD88$^{-/-}$ mice (FIG. 22 C-D), but LPS-induced IL-10 production and secretion were significantly reduced in MyD88$^{-/-}$ B cells (FIG. 22D). A need for MyD88 in LPS-induced B10 cell function may explain why mice containing only MyD88$^{-/-}$ B cells develop chronic EAE (Lampropoulou, et al. 2008. *J. Immunol.* 180:4763-4773). Thus, intertwined innate and adaptive signals may regulate B10 cell maturation and effector function rather than independently regulating distinct follicular, MZ, and B-1a regulatory B cell subsets.

The B10 cell subset expanded significantly in response to enhanced B cell signaling in vivo, while retaining their CD1d$^{hi}$CD5$^+$ phenotype. B10 cell numbers were significantly expanded in hCD19Tg mice, but were dramatically reduced in CD19$^{-/-}$ mice (FIG. 21). B10 cell numbers were also increased 2- to 3-fold in CD22$^{-/-}$ mice (FIG. 21). CD19 regulates a Lyn kinase amplification loop (Fujimoto, et al. 1999. *Immunity* 11:191-200; Fujimoto, et al. 2000. *Immunity* 13:47-57) that enhances transmembrane signals (Yazawa, et al. 2003. *Blood* 102:1374-1380; Poe, et al. 2001. *Int. Rev. Immunol.* 20:739-762; Tedder, et al. 2005. *Curr. Dir. Autoimmunity* 8:55-90), while CD22 dampens B cell and CD19 signal transduction through the recruitment of SHP-1 and SHIP phosphatases (Fujimoto, et al. 1999. *Immunity* 11:191-200; Poe, et al. 2001. *Int. Rev. Immunol.* 20:739-762), resulting in elevated cell surface CD5 expression by B cells in CD22$^{-/-}$ B6 mice (Poe, et al. 2004. *J. Immunol.* 172: 2100-2110). Spleen B10 cells were also significantly expanded in CD40L/BTg mice, with a 26-fold increase in CD22$^{-/-}$CD40L/BTg mice where up to 20% of spleen B cells were B10 cells (FIG. 21). Since CD22 negatively regulates CD40 signaling (Poe, et al. 2004. *Nat. Immunol.* 5:1078-1087; Poe, et al. 2004. *J. Immunol.* 172:2100-2110), enhanced CD40 function may drive B10 cell expansion and/or survival in CD22$^{-/-}$CD40L/BTg mice (Higuchi, et al. 2002. *J. Immunol.* 168:9-12; van Kooten, et al. 2000. *J. Leukoc. Biol.* 67:2-17). Although spleen B1a cells were also expanded in hCD19Tg (3-fold), CD40L/BTg (4.2-fold), and CD22$^{-/-}$CD40L/BTg (3-fold) mice, these frequencies did not parallel B10 cell expansion. Thus, the B10 cell subset responds significantly to transmembrane signals in vivo.

Spleen B10 cell numbers were increased in mice predisposed to develop autoimmunity. B10 cell numbers expanded significantly in the NZB/W F1 and MRL/lpr mouse models of lupus and the NOD model of diabetes even before obvious autoantibodies and signs of disease were apparent (FIG. 20, data now shown). B10 cell numbers are significantly expanded in CD40L/BTg mice (FIG. 21), although some develop lupus-like disease (Higuchi, et al. 2002. *J. Immunol.* 168:9-12). Spleen B10 cell numbers were also significantly higher in 6 mo-old C57BL/6 mice relative to 2 mo-old mice (FIG. 18), which may combat the development of autoimmunity with age. By contrast, B10 cell numbers were significantly lower in the DBA/1 and SJL mouse models of autoantigen-inducible autoimmunity, where the relative paucity of B10 cells may prevent effective tolerance induction. Thereby, B10 cell expansion may suppress autoimmunity, in contrast to B1a cells that contribute to autoimmune disease (Hayakawa, et al. 1986. *Eur. J. Immunol.* 16:450-456). As a result, these autoimmune diseases may be worse in the absence of B10 cells as occurs when all B cells are depleted during CHS and EAE (Yanaba, et al. 2008. *Immunity* 28:639-650; Matsushita, et al. 2008. *J. Clin. Invest.* 118:3420-3430). Since B10 cell numbers are dynamic, change during development, and increase with age and autoimmunity, alterations in the balance between B10 cell negative regulation and B cell positive contributions to immune responses are likely to vary in different diseases and during the course of disease (Bouaziz, et al. 2008. *Immunol. Rev.* 224:201-214).

Spleen B10 cells and their potential progenitors (FIG. 24C) can account for many of the in vivo activities previously attributed to regulatory B cells (Bouaziz, et al. 2008. *Immunol. Rev.* 224:201-214; Yanaba, et al. 2008. *Immunity* 28:639-650; Matsushita, et al. 2008. *J. Clin. Invest.* 118: 3420-3430). Specifically, BCR and CD40 engagement are required for regulatory B cell functions in CIA, CHS, and EAE models (Fillatreau, et al. 2002. *Nat. Immunol.* 3:944-950; Evans, et al. 2007. *J. Immunol.* 178:7868-7878; Yanaba, et al. 2008. *Immunity* 28:639-650; Matsushita, et al. 2008. *J. Clin. Invest.* 118:3420-3430), and functional B10 cells required diverse BCRs (FIG. 21) and in vivo Ag sensitization (Yanaba, et al. 2008. *Immunity* 28:639-650; Matsushita, et al. 2008. *J. Clin. Invest.* 118:3420-3430) for their generation. Stimulating naïve or autoimmune spleen B cells in vitro with LPS or agonistic CD40 mAb also gives rise to regulatory B cells that inhibit or prevent autoimmunity (Mauri, et al. 2003. *J. Exp. Med.* 197:489-501; Tian, et al. 2001. *J. Immunol.* 167:1081-1089). That CD40 ligation induced IL-10-competence in both CD1d$^{hi}$CD5$^+$ and some CD1d$^{int}$CD5$^-$ B cells (FIG. 22) may also explain how agonistic CD40 mAbs reduce inflammation in the CIA model of rheumatoid arthritis (Mauri, et al. 2000. *Nat. Med.* 6:673-679). LPS induction of B10 cell competence for IL-10 production and secretion (FIG. 22C) may also explain why LPS pretreatment modulates the course of disease in EAE (Buenafe, et al. 2007. *J. Neuroimmunol.* 182:32-40) Similarly, B cells activated with LPS in vitro can protect NOD mice in vivo, although this effect was not attributed to B cell IL-10 production (Tian, et al. 2001. *J. Immunol.* 167:1081-1089). Thus, B10 cells and regulatory B cells identified in previous studies were similar in their responses to polyclonal stimuli such as LPS and CD40.

That BCR diversity was required for B10 cell development in vivo (FIG. 21) supports observations that B10 cell and regulatory B cell function is Ag-specific (Fillatreau, et al. 2002. *Nat. Immunol.* 3:944-950; Yanaba, et al. 2008. *Immunity* 28:639-650; Matsushita, et al. 2008. *J. Clin. Invest.* 118:3420-3430). The activation of arthritogenic splenocytes with collagen alone (Evans, et al. 2007. *J. Immunol.* 178:7868-7878) or collagen plus agonistic CD40 mAb in vitro gives rise to IL-10 producing B cells that prevent arthritis (Mauri, et al. 2003. *J. Exp. Med.* 197:489-501). Autoreactive B cell production of IL-10 during EAE also requires simultaneous autoantigen and CD40 stimulation (Fillatreau, et al. 2002. *Nat. Immunol.* 3:944-950). Transfusions of BCR-activated B cells also protects NOD mice from type 1 diabetes in an IL-10-dependent manner (Hussain, et al. 2007. *J. Immunol.* 179:7225-7232). However, BCR ligation using mitogenic Ab in vitro negatively regulated cytoplasmic and secreted IL-10 production when combined with LPS or CD40 mAb during in vitro cultures, although BCR ligation alone induced some B cells to express IL-10 at higher than background levels (FIG. 22). These results contrast with the findings of others that BCR ligation using anti-Igκ Ab does not affect simultaneous LPS-induced IL-10 secretion by splenic transitional, follicular, and marginal zone B cells, B1 B cells from the peritoneal cavity, or lymph node B cells (Lampropoulou, et al. 2008. *J. Immunol.* 180:4763-4773). However, the strength, nature, or timing of BCR generated signals required for evoking B10 cell development or function may be specifically regulated in vivo. For example, BCR engagement by potent foreign Ags may inhibit B10 cell clonal expansion or divert B10 progenitor cells along a distinct functional pathway, while BCR signals generated by self Ags may promote their expansion. Thereby, LPS or other signals may optimally induce B10 cell effector function (IL-10 secretion) after Ag-selection or CD40-induced maturation in vivo.

It remains difficult to distinguish the relationships between spleen B10, B-1a, and MZ B cells due to their shared phenotypic markers and potentially overlapping developmental pathways. For example, microbial colonization and conventional T cells were not required for spleen B10, B-1a, or $CD1d^{hi}$ MZ B cell development, and all three subsets require CD19 expression (FIGS. 19 and 21). However, spleen $CD5^+$ and IL-10-competent B cells were present at high frequencies in newborns, while the splenic $CD1d^{hi}$ subset was not detectable in newborns (FIGS. 17-18) but develops between 3-7 wks after birth (Makowska, et al. 1999. *Eur. J. Immunol.* 29:3285-3294). Spleen B10 cell proliferation was also more robust following LPS stimulation than for IL-10⁻ B cells (FIG. 24B). MZ B cells also expand and provide protection early during pathogen challenge (Martin, et al. 2001. *Immunity* 14:617-629). Furthermore, some IL-10 producing cells can be induced within the spleen $CD1d^{hi}CD5^-$ and $CD1d^{lo}CD5^+$ subsets (FIG. 17A), but it is hard to discern whether these cells represent contaminating B10 cells or are progenitor B10 cells that have not fully upregulated CD1d or CD5 expression (FIG. 24C). Therefore, it is likely that spleen B-1a and MZ B cells represent subsets of mixed origins, with B10 cells representing either a distinct subset with shared phenotypic markers, or a subset representing different branches of a common lineage.

These studies address the ambiguity regarding a major B cell subset that regulates inflammation and autoimmune disease. Evidence for the existence of a distinct natural B10 cell subset that generally suppresses immune responses was not uncovered. Rather, the current data indicate that BCR and other signals are central to B10 cell generation and that polyclonal signals such as CD40 and LPS can induce their maturation and/or regulatory functions. Thereby, immature $CD5^{+/-}$ progenitor B10 cells may be induced to mature and express CD5 and CD1d through Ag selection, potentially involving CD40 signals that induced CD5 expression (FIG. 23C). BCR ligation is also well characterized to induce CD5 expression (Cong, et al. 1991. *Int. Immunol.* 3:467). That CD40 ligation induces cytoplasmic IL-10 production but not significant cytokine secretion is likely to represent another critical regulatory checkpoint in B10 cell function. Although regulatory B cells and B10 cells have been predominantly described in mouse models where autoantigen plus TLR-agonist-containing adjuvants induce autoimmunity, B10 cells also significantly influence CHS inflammation, where disease is independent of adjuvant challenge (Yanaba, et al. 2008. *Immunity* 28:639-650). Thus, stimuli in addition to LPS are likely to also regulate IL-10 secretion by B10 cells. Although B10 cell development and tolerance regulation are undoubtedly more complex, the current results provide a potential framework (FIG. 24C) for further characterizing B10 cell development.

12. EXAMPLE 7: Regulatory B Lymphocyte Elimination Enhances Lymphoma Depletion during CD20 Immunotherapy Non-Hodgkin's lymphoma therapy commonly involves the use of CD20 monoclonal antibody (mAb) to deplete tumor cells. Herein, the depletion of a rare $CD1d^{high}CD5^+$ regulatory B cell subset (B10 cells), but not conventional B cells, significantly influenced lymphoma depletion through IL-10-dependent mechanisms. Thus, CD20 mAb-sensitive regulatory B cells are potent negative regulators of tumor depletion in vivo and may represent a new therapeutic target for treating lymphoma and other cancers.

12.1 Materials and Methods 12.1.1 Mice

C57BL/6 and IL-10⁻/⁻ (B6.129P2-Il10$^{tm1Cgn}$/J) were from NCI-Frederick Laboratory (Frederick, Md.). CD20⁻/⁻ mice were as described (Uchida, et al. Int. Immunol. 16, 119-129 (2004)). Mice were housed in a specific pathogen-free barrier facility and first used at 6-10 weeks of age. The Duke University Animal Care and Use Committee approved all studies.

12.1.2 Cell Isolation and Immunofluorescence Analysis

CD20 expression was visualized using biotin-conjugated mouse CD20 (MB20-11) mAbs (Uchida, et al. Int. Immunol. 16, 119-129 (2004)) plus phycoerythrin-Cy5 (PE-Cy5) streptavidin (eBioscience, San Diego, Calif.). Other mAbs included: B220 (RA3-6B2), CD5 (53-7.3), CD1d (1B1), CD19 (1D3), and CD154 (MR1) from BD Biosciences (San Diego, Calif.). CD11b (M1/70), CD86 (GL1), F4/80 (BM8), and IL-10 (JESS-16E3) mAbs were from eBioscience. Anti-mouse IgM (1B4B1) antibody was from Southern Biotechnology Associates (Birmingham, Ala.). For immunofluorescence analysis, single cell suspensions ($10^6$ cells) were stained at 4° C. using predetermined optimal concentrations of mAb for 30 minutes as described (Sato, et al. J. Immunol. 157, 4371-4378 (1996)). Single-cell suspensions of spleen were generated by gentle dissection. Blood erythrocytes were lysed after staining using FACS™ Lysing Solution (Becton Dickinson, San Jose, Calif.). Cells with the light scatter properties of lymphoma cells or lymphocytes were analyzed by immunofluorescence staining with flow cytometry gating on live lymphoma cells or lymphocytes as identified by forward/side light scatter. For IL-10 detection, spleen or BL3750 cells were resuspended ($2 \times 10^6$ cells/ml) in complete medium [RPMI 1640 media (Cellgro, Herndon, Va.) containing 10% FCS (Sigma, St. Louis, Mo.), 200 μg/ml penicillin, 200 U/ml streptomycin, 4 mM L-Glutamine (all Cellgro), and 55 μM 2-mercaptoethanol (Invitrogen, Carlsbad, Calif.)] with LPS (10 μg/ml, *Escherichia coli* serotype 0111: B4, Sigma), PMA (50 ng/ml; Sigma), ionomycin (500 ng/ml; Sigma), and monensin (2 μM; eBioscience) for 5 h. Before cell surface staining, Fc receptors were blocked using anti-mouse Fc receptor mAb (2.4G2; BD PharMingen), and dead cells were labeled using a LIVE/DEAD® Fixable Green Dead Cell Stain Kit (Invitrogen- Molecular Probes). Stained cells were fixed and permeabilized using a Cytofix/Cytoperm kit (BD PharMingen) according to the manufacturer's instructions and stained with phycoerythrin-conjugated mouse anti-IL-10 mAb. Splenocytes from IL-10$^{-/-}$ mice served as negative controls to demonstrate specificity and to establish background IL-10 staining levels.

12.1.3 Lymphoma Model

BL3750 lymphoma cells were as previously described (Minard-Colin, et al. Blood 112, 1205-1213 (2008)). Briefly, BL3750 cells were isolated from lymph nodes of a single C57BL/6 cMycTG$^{+/-}$ mouse and cultured for 7 days before freezing in aliquots at −70° C. For each experiment, tumor cells were thawed and expanded for 24-48 hours in complete medium (RPMI 1640 media containing 20% fetal bovine serum, 100 U/ml penicillin, 100 μg/ml streptomycin, 2 mM L-glutamine, and 55 μM 2-mercaptoethanol). BL3750 cells in 250 μl PBS were injected subcutaneously into the dorsal skin of recipient mice on day 0. Mice were then given purified mAb in 250 μl of PBS intravenously, and were monitored daily starting at day 7 for tumor development and progression, and mortality. Tumor size was measured tri-weekly using a calibrated micrometer. For tumor measurements, the greatest longitudinal diameter was designated as L, and the greatest transverse diameter designated as W. The two chosen measurements were perpendicular to each other and in a plane tangential with the body wall. Tumor volumes (TV) was calculated as follow: TV=[(W)$^2$×L]/2. All mice were euthanized when exhibiting distress or tumor volumes exceeding 2.0 cm$^3$ with the date of euthanasia recorded as the date of death from disease.

12.1.4 CD20 Immunotherapy

Sterile mouse anti-mouse CD20 mAb (MB20-11, IgG2c) and unreactive mouse control IgG2a mAb were produced in vitro (Uchida, et al. Int. Immunol. 16, 119-129 (2004)) and purified by protein A affinity chromatography (Amersham, Arlington Heights, Ill.). All mAbs were endotoxin free (Pyrogent Plus test kit, sensitivity of 0.06 EU/mL, Cambrex Bio Science, Walkersville, Md.).

12.1.5 Cell Sorting and Adoptive Transfer Experiments

Naïve CD20$^{-/-}$ or IL-10$^{-/-}$CD20$^{-/-}$ mice were used as B cell donors. Splenic B cells were first enriched using CD19 mAb-coated microbeads kits (Miltenyi Biotech, Auburn, Calif.) according to the manufacturer's instructions. In addition, CD1d$^{high}$CD5$^+$ and CD1d$^{low}$CD5$^-$ B cells were isolated using a FACSVantage SE flow cytometer (Becton Dickinson) with purities of 95-98%. After purification, 2×10$^6$ cells were immediately transferred intravenously into C57BL/6 mice. In some experiments, mice were used that had survived for 30-45 days after tumor challenge (10$^5$ BL3750 cells on day 0) and CD20 mAb treatment (250 μg on day 1). Similar results were obtained when the donor B cells were isolated from naïve mice or mice that has survived BL3750 challenge so all results were pooled.

12.1.6 Statistical Analysis

Statistical comparisons of survival using the Log-Rank test and the generation of Kaplan-Meier cumulative survival plots used Prism software (version 4.0; GraphPad Software, San Diego, Calif.).

12.2 Results

Figures 25A, 25B, 25C:
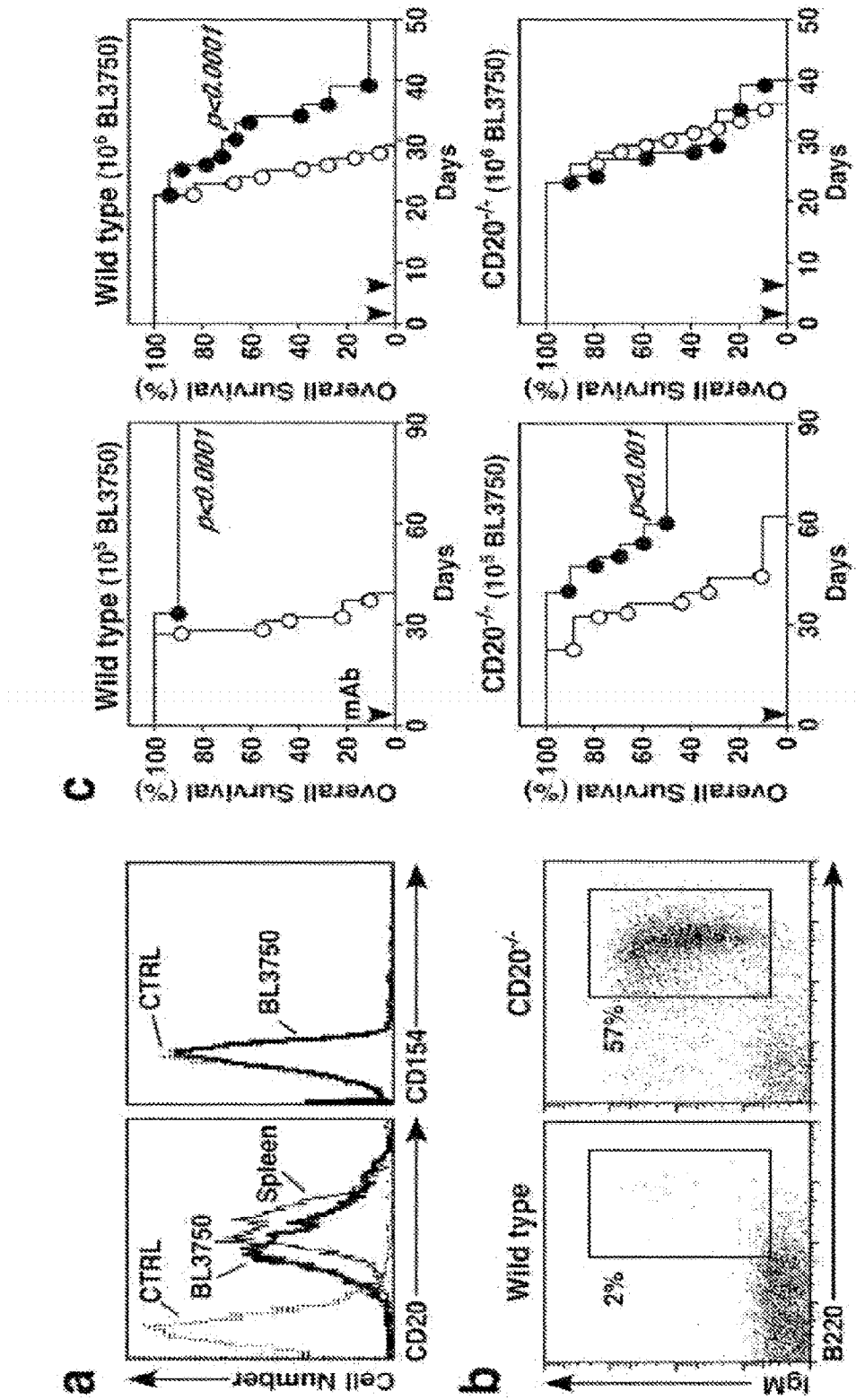

The role of B cells during lymphoma depletion was examined in mice with intact immunity using primary CD20$^+$ BL3750 lymphoma cells (FIG. 25a) isolated from a Eμ-cMycTG$^{+/-}$ mouse as described (Minard-Colin, et al. Blood 112, 1205-1213 (2008)). BL3750 cells provide a syngeneic mouse model for quantifying the response of Burkitt's-like lymphoma cells to CD20 immunotherapy in vivo (Uchida, et al. J. Exp. Med. 199, 1659-1669 (2004)). A single dose of mouse anti-mouse CD20 mAb but not control mAb (250 μg/mouse) depletes >95% of mature B cells after 2 days in wild type mice, with the effect lasting up to 8 weeks (FIG. 25b) (Uchida, et al. Int. Immunol. 16, 119-129 (2004); Hamaguchi, et al. J. Immunol. 174, 4389-4399 (2005)). Wild type mice given 10$^5$ BL3750 cells on day 0 developed detectable tumors at the site of injection by 12-19 days, with a median survival of 31 days (range 27-39, FIG. 25c). CD20 mAb given 1 day after BL3750 cell transfer depleted normal B cells and had a significant therapeutic effect on tumor growth, with 89% of mice remaining disease free for ≥60 days (p<0.0001). Transplantation of 10$^6$ BL3750 cells resulted in death of all control mAb-treated mice (median 25 days, range 21-29), with CD20 mAb treatment on days 1 and 7 delaying tumor growth (FIG. 25d) and extending median survival to 34 days (p<0.0001; FIG. 25c). This homologous tumor model was therefore used to determine whether endogenous normal B cells influence CD20 mAb-induced anti-tumor responses.

Figures 25D, 25E:
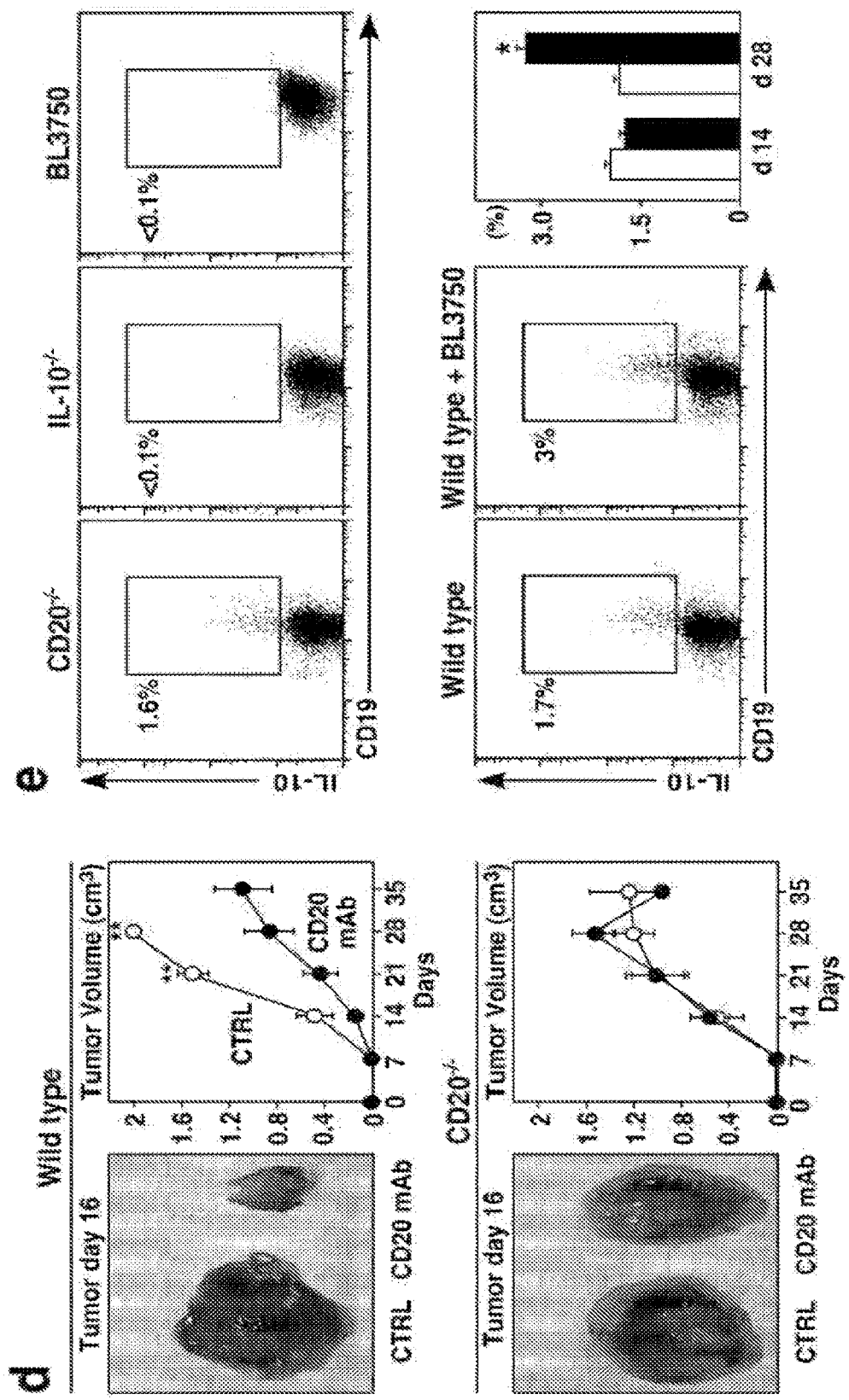

CD20 mAb does not deplete blood or tissue B cells in CD20$^{-/-}$ mice (FIG. 25b), which have normal B cell and immune system development (Uchida, et al. Int. Immunol. 16, 119-129 (2004)). Nonetheless, CD20 mAb had a therapeutic benefit in CD20$^{-/-}$ mice given 10$^5$ CD20$^+$ BL3750 cells, with 50% of mice remaining disease free for up to 60 days (p<0.001; FIG. 25c). However, this anti-tumor response was less effective than in wild type littermates. Moreover, tumor growth and the survival of CD20$^{-/-}$ mice given 10$^6$ BL3750 cells were equivalent after control (median 31 days, range 23-36) or CD20 (median 28 days, range 23-40) mAb treatments (FIG. 25c-d). Reduced tumor clearance in CD20$^{-/-}$ mice was not expected since circulating CD20 mAb levels persist longer in CD20$^{-/-}$ mice than in wild type littermates (Hamaguchi, et al. J. Immunol. 174, 4389-4399 (2005)). In addition, lymphoma and normal B cell depletion in vivo is mediated by monocytes through antibody dependent cellular cytotoxicity, and CD20$^{-/-}$ mice have normal monocyte numbers (Minard-Colin, et al. Blood 112, 1205-1213 (2008); Uchida, et al. J. Exp. Med. 199, 1659-1669 (2004)). Thus, the persistence of endogenous B cells inhibited the anti-tumor effects of CD20 mAb in vivo.

To determine whether regulatory B10 cells could inhibit the anti-tumor effects of CD20 mAb in vivo, the effect of lymphoma progression on B10 cell frequencies was examined using published methods (Yanaba, et al Immunity 28, 639-650 (2008); Matsushita, et al. J. Clin. Invest. 118, 3420-3430 (2008)). B10 cells represent a small IL-10-competent subset within the rare CD1d$^{high}$CD5$^+$ subset of spleen B cells (FIG. 25e). IL-10$^{-/-}$ B cells served as negative controls for IL-10 staining and BL3750 cells did not produce detectable IL-10. Remarkably, IL-10-producing B10 cell frequencies increased 2-fold in tumor-bearing wild type (day 28) mice in comparison to wild type littermates or CD20$^{-/-}$ mice without tumors. The effect of adoptively transferred B10 cells on monocyte activation was also examined in vivo since macrophages express IL-10 receptors at high-levels (Moore, et al. Annu. Rev. Immunol. 19, 683-765 (2001)) and mediate the depletion of CD20 mAb-coated B cells and tumor cells through antibody-dependent cellular cytotoxicity (ADCC) (Minard-Colin, et al. Blood 112, 1205-1213 (2008); Uchida, et al. J. Exp. Med. 199, 1659-1669 (2004)). Spleen CD1d$^{high}$CD5$^+$ B cells were purified from CD20$^{-/-}$ mice and transferred into wild type mice that were given CD20 mAb one day later to induce monocyte-mediated ADCC. Within the CD1d$^{hi}$CD5$^+$ B cell subset of wild type and CD20$^{-/-}$ mice, 9-11% of the cells were cytoplasmic IL-10 competent, while few CD1d$^{lo}$CD5$^-$ B cells expressed IL-10 (p<0.01; FIG. 26a). Forty-eight hours after CD20 mAb treatment, CD11b$^+$F4/80$^+$ macrophage expression of major histocompatibility (MHC) class II molecules and CD86 was significantly higher (p<0.05, FIG. 26b). However, activation marker expression was significantly reduced in mice given CD20$^{-/-}$CD1d$^{high}$CD5$^+$ B cells prior to CD20 mAb treatment when compared with littermates given CD20 mAb alone (FIG. 26b). Thereby, CD20 mAb-induced monocyte activation was significantly reduced in the presence of CD1d$^{hi}$CD5$^+$ B cells.

Since B10 cell numbers increased with tumor progression and B10 cells inhibited macrophage activation in vivo, the effect of B10 cells on tumor killing was assessed using adoptive transfer experiments. CD1d$^{high}$CD5$^+$ B cells or conventional non-CD1d$^{high}$CD5$^+$ B cells from CD20$^{-/-}$ mice were transferred into wild type recipients given BL3750 cells one day later (day 0), followed by CD20 or control mAb treatment on days 1 and 7. CD20 mAb treatment of wild type mice delayed tumor growth and prolonged survival (median 34 days, range 21-39; p<0.0001; FIG. 26c upper panels). However, the adoptive transfer of CD20$^{-/-}$CD1d$^{high}$CD5$^+$ B cells into wild type mice eliminated the therapeutic benefit of CD20 mAb treatment (median 24 days, range 21-26), while CD1d$^{high}$CD5$^+$ B cells purified from IL-10$^{-/-}$ CD20$^{-/-}$ mice were without effect (FIG. 26c lower panels). Tumor growth and mouse survival were not affected by the adoptive transfer of CD1d$^{low}$CD5$^-$ B cells from CD20$^{-/-}$ or IL-10$^{-/-}$ CD20$^{-/-}$ mice (FIG. 26c). Thus, B10 cells negatively regulated lymphoma depletion through IL-10 production.

12.3 Discussion

The current study demonstrates that B10 cells are potent negative regulators of tumor depletion by CD20 mAb in vivo through IL-10 production. In addition, lymphoma progression induced B10 cell expansion, potentially through antigen-specific pathways as occurs in inflammation and autoimmunity (Yanaba, et al Immunity 28, 639-650 (2008); Matsushita, et al. J. Clin. Invest. 118, 3420-3430 (2008)). Thereby, CD20 mAb induces lymphoma depletion through at least two mechanisms; direct mAb targeting of lymphoma cells for depletion, and through the removal of host B10 cells. That B10 cells inhibited macrophage activation provides one explanation for reduced lymphoma depletion, but B10 cells may also negatively regulate anti-tumor immunity. Enhanced immunity and resistance to diverse syngeneic tumors has also been reported in studies using congenitally B cell-deficient μMT mice (Qin, et al. Nat Med 4, 627-630 (1998); Shah, et al. Int J Cancer 117, 574-586 (2005); Inoue, et al. Cancer Res. 66, 7741-7747 (2006)). Although the absence of B cells during μMT mouse development results in significant quantitative and qualitative abnormalities within the immune system, increased tumor resistance has been attributed to enhanced anti-tumor Th1 cytokines, augmented cytolytic T cell responses, or CD40 ligand (CD154) expressed by tumor cells interacting with CD40 expressed by B cells (Qin, et al. Nat Med 4, 627-630 (1998); Shah, et al. Int J Cancer 117, 574-586 (2005); Inoue, et al. Cancer Res. 66, 7741-7747 (2006)). Since BL3750 cells did not express CD154 (FIG. 25a), a role for B10 cells in mAb-mediated tumor depletion provides an additional explanation for these previous studies and identifies an unanticipated mechanism through which CD20 mAb-directed therapies may work in lymphoma patients. Moreover, selective B10 cell depletion may represent a powerful new therapeutic approach for augmenting anti-tumor responses for the treatment of lymphoma and potentially other cancers.

13. EXAMPLE 8: Generation of Antibodies that Selectively Deplete B10 Cells

A panel of twelve anti-mouse-CD20 mAbs (Uchida et al., 2004, Int. Immunol. 16:119-29) was analyzed for the ability of individual mAbs to induce homotypic adhesion of splenic B cells using methods known in the art (Kansas G S, Wood G S, Tedder T F. Expression, distribution and biochemistry of human CD39: Role in activation-associated homotypic adhesion of lymphocytes. *J Immunol.* 1991; 146:2235-2244; Kansas G S, Tedder T F. Transmembrane signals generated through MHC class II, CD19, CD20, CD39 and CD40 antigens induce LFA-1-dependent and -independent adhesion in human B cells through a tyrosine kinase-dependent pathway. *J Immunol.* 1991; 147: 4094-4102.; Wagner N, Engel P, Vega M, Tedder T F. Ligation of MHC class I and class II molecules leads to heterologous desensitization of signal transduction pathways that regulate homotypic adhesion in human lymphocytes. *J Immunol.* 1994; 152:5275-5287.) Antibodies that induced homotypic adhesion were then found to preferentially deplete splenic marginal zone B cells, which includes a significant fraction of the regulatory B10 subset of B cells, relative to the follicular B cell population (FIG. 27A). Furthermore, the CD20 mAbs that selectively deplete both marginal zone B cells and the regulatory B cell population do so by mechanisms that are ADCC- (FIG. 27B), CDC- (FIG. 28), and apoptosis- (FIG. 29) independent. Moreover, this mechanism is independent of the B cell FcγRIIB receptor (FIG. 27C). Likewise, the MB20-3 CD20 mAb that induces robust homotypic adhesion but does not efficiently engage most Fcγ receptors due to its IgG3 isotype deplete B10 and marginal zone B cells, but did not deplete follicular B cells except at high mAb concentrations (FIG. 30). Therefore, IgG3 or IgG2b CD20 mAbs with Fc regions that do not efficiently engage most Fcγ receptors but induce robust homotypic adhesion (MB20-3 and MB20-18) were compared with the IgG3 MB20-13 CD20 mAb that does not induce homotypic adhesion for the ability to deplete B10 cells and marginal zone B cells relative to follicular B cells. The MB20-3 and MB20-18 mAbs preferentially induced the depletion of marginal zone B cells (FIG. 31A) and B10 cells (FIG. 31B), but not follicular B cells (FIG. 31A). Furthermore, CD20 mAbs that were capable of preferentially depleting B10 and marginal zone B cells could be modified or switched to isotypes that would not initiate ADCC, resulting in antibodies that selectively deplete splenic B10 cells and marginal zone B cells, but not splenic follicular B cells.

14. EXAMPLE 9: ANTI-CD22 Antibodies Deplete the Regulatory B Cell Population

Administration of CD22 mAbs to mice results in depletion of the regulatory B cell population as evidenced by a decrease in CD1d$^{high}$CD5$^+$ B cells (FIG. 32A) and a decrease in B cell IL-10 production (FIG. 32B).

Various publications are cited herein, the disclosures of which are incorporated by reference in their entireties.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

What is claimed is:

1. A method comprising: (a) selecting B lymphocytes in a sample from a mammalian subject; (b) contacting the B lymphocytes with a CD5 antibody and a CD1d antibody; and (c) selecting the B lymphocytes expressing both CD5 and CD1d$^{high}$ to generate a B10 cellular composition comprising CD5$^+$, CD1d$^{high}$ B lymphocytes.

2. The method of claim 1, wherein at least 65% of the cells in the B10 cellular composition are CD5$^+$, CD1d$^{high}$ B lymphocytes.

3. The method of claim 1, wherein at least 75% of the cells in the B10 cellular composition are CD5$^+$, CD1d$^{high}$ B lymphocytes.

4. The method of claim 1, further comprising selecting the B lymphocytes for expression of at least one marker selected from the group consisting of MHC class II, CD19, CD20, CD21, CD22, CD24, CD40, CD72 and B220.

5. The method of claim 1, further comprising selecting the B lymphocytes to be negative for at least one marker selected from the group consisting of CD3, CD4, CD7, CD8, CD15, CD16, CD34, CD56, CD57, CD64, CD94, CD116, CD134, CD157, CD163, CD208, F4/80, Gr-1, and TCR.

6. The method of claim 1, wherein the B lymphocytes are from a healthy unstimulated donor.

7. The method of claim 1, wherein the B lymphocytes are antigen-specific.

8. The method of claim 1, further comprising contacting the B10 cellular composition with at least one agent selected from the group consisting of lipopolysaccharide phorbol 12-myristate 13-acetate (PMA), ionomycin, a Toll-like receptor agonist and a CD40 agonist.

9. The method of claim 8, wherein the cells are contacted with the CD40 agonist or CpG in combination with PMA and ionomycin.

10. The method of claim 9, wherein the stimulation is for between 5 and 48 hours.

11. The method of claim 9, wherein the cells are stimulated for 48 hours with a CD40 agonist and PMA and ionomycin are added for the last 5 hours.

12. The method of claim 8, wherein at least 55% of the cells in the B10 cellular composition are characterized by the ability to produce IL-10.

13. The method of claim 8, wherein at least 75% of the cells in the B10 cellular composition are characterized by the ability to produce IL-10.

14. The method of claim 1, further comprising administering the B10 cellular composition to a subject in need thereof.

15. The method of claim 14, wherein the subject is in need of treatment for an autoimmune or inflammatory condition.

16. The method of claim 14, wherein the cells were obtained from a histocompatibility matched donor.

17. The method of claim 14, wherein the B10 cellular composition was exposed to an antigen prior to administration to the subject.

18. The method of claim 8, farther comprising administering the B10 cellular composition to a subject in need thereof.

19. The method of claim 18, wherein the subject is in need of treatment for an autoimmune or inflammatory condition.

20. The method of claim 18, wherein the B10 cellular composition was exposed to an antigen prior to administration to the subject.

* * * * *